(12) United States Patent
Levey et al.

(10) Patent No.: US 10,568,948 B2
(45) Date of Patent: Feb. 25, 2020

(54) VACCINES FOR TREATMENT AND PREVENTION OF CANCER

(71) Applicant: Agenus Inc., Lexington, MA (US)

(72) Inventors: Daniel Lewis Levey, Boston, MA (US); John Christopher Castle, Mainz (DE)

(73) Assignee: AGENUS INC., Lexington, MA (US)

( * ) Notice: Subject to any disclaimer, the term of this patent is extended or adjusted under 35 U.S.C. 154(b) by 346 days.

(21) Appl. No.: 15/154,543

(22) Filed: May 13, 2016

(65) Prior Publication Data

US 2016/0331821 A1    Nov. 17, 2016

Related U.S. Application Data

(60) Provisional application No. 62/307,592, filed on Mar. 14, 2016, provisional application No. 62/257,458, filed on Nov. 19, 2015, provisional application No. 62/205,591, filed on Aug. 14, 2015, provisional application No. 62/161,053, filed on May 13, 2015.

(51) Int. Cl.
| | |
|---|---|
| *A61K 39/00* | (2006.01) |
| *A61K 39/39* | (2006.01) |
| *C07K 14/47* | (2006.01) |
| *C07K 14/74* | (2006.01) |
| *C12Q 1/6886* | (2018.01) |

(52) U.S. Cl.
CPC .......... *A61K 39/0011* (2013.01); *A61K 39/39* (2013.01); *C07K 14/4748* (2013.01); *C07K 14/70539* (2013.01); *C12Q 1/6886* (2013.01); *A61K 2039/545* (2013.01); *A61K 2039/55511* (2013.01); *A61K 2039/55516* (2013.01); *A61K 2039/55533* (2013.01); *A61K 2039/55577* (2013.01); *A61K 2039/575* (2013.01); *C07K 2319/33* (2013.01)

(58) Field of Classification Search
CPC ............ C07K 2319/33; C07K 2319/01; C07K 14/4748; C07K 14/70539; A61K 2039/01
See application file for complete search history.

(56) References Cited

U.S. PATENT DOCUMENTS

| | | | |
|---|---|---|---|
| 4,690,915 A | 9/1987 | Rosenberg et al. |
| 4,761,470 A | 8/1988 | Emini et al. |
| 5,188,964 A | 2/1993 | Mcguire et al. |
| 5,232,833 A | 8/1993 | Sanders et al. |
| 5,288,639 A | 2/1994 | Burnie et al. |
| 5,348,945 A | 9/1994 | Berberian et al. |
| 5,652,115 A | 7/1997 | Marks et al. |
| 5,750,119 A | 5/1998 | Srivastava et al. |
| 5,830,464 A | 11/1998 | Srivastava et al. |
| 5,837,251 A | 11/1998 | Srivastava et al. |
| 5,935,576 A | 8/1999 | Srivastava et al. |
| 5,948,646 A | 9/1999 | Srivastava et al. |
| 5,961,979 A | 10/1999 | Srivastava et al. |
| 5,985,270 A | 11/1999 | Srivastava et al. |
| 5,997,873 A | 12/1999 | Srivastava et al. |
| 6,007,821 A | 12/1999 | Srivastava et al. |
| 6,017,540 A | 1/2000 | Srivastava et al. |
| 6,030,618 A | 2/2000 | Srivastava et al. |
| 6,037,135 A | 3/2000 | Kubo et al. |
| 6,231,859 B1 | 5/2001 | Kensil et al. |
| 6,383,494 B1 | 5/2002 | Srivastava et al. |
| 6,387,374 B1 | 5/2002 | Srivastava et al. |
| 6,406,700 B1 | 6/2002 | Srivastava et al. |
| 6,410,026 B1 | 6/2002 | Srivastava et al. |
| 6,410,027 B1 | 6/2002 | Srivastava et al. |
| 6,410,509 B1 | 6/2002 | Triebel et al. |
| 6,436,404 B1 | 8/2002 | Srivastava et al. |
| 6,451,316 B1 | 9/2002 | Srivastava et al. |
| 6,475,490 B1 | 11/2002 | Srivastava et al. |
| 6,572,860 B1 | 6/2003 | Zimmerman et al. |
| 6,645,495 B1 | 11/2003 | Kensil et al. |
| 6,663,868 B1 | 12/2003 | Rothman et al. |
| 6,984,389 B2 | 1/2006 | Li et al. |
| 7,105,162 B1 | 9/2006 | Schmidt et al. |
| 7,132,109 B1 | 11/2006 | Srivastava et al. |
| 7,186,515 B1 | 3/2007 | Srivastava et al. |
| 7,309,491 B2 | 12/2007 | Slusarewicz et al. |
| 7,420,037 B2 | 9/2008 | Slusarewicz et al. |
| 7,601,359 B1 | 10/2009 | Srivastava et al. |
| 7,666,581 B2 | 2/2010 | Srivastava et al. |
| 7,811,828 B2 | 10/2010 | Lemmel et al. |
| 7,998,486 B2 | 8/2011 | Mautino et al. |
| 8,029,808 B2 | 10/2011 | Srivastava et al. |
| 8,140,270 B2 | 3/2012 | Kingsmore et al. |
| 8,349,558 B2 | 1/2013 | Fatho et al. |
| 8,372,393 B2 | 2/2013 | Kündig et al. |
| 8,541,002 B2 | 9/2013 | Truneh et al. |
| 8,591,890 B2 | 11/2013 | Srivastava et al. |
| 8,877,204 B2 | 11/2014 | Srivastava et al. |
| 9,115,402 B2 | 8/2015 | Hacohen et al. |
| 9,186,418 B2 | 11/2015 | Cohen et al. |
| 9,248,172 B2 | 2/2016 | Srivastava et al. |
| 9,352,019 B2 | 5/2016 | Srivastava et al. |
| 9,783,849 B2 | 10/2017 | Weinschenk et al. |
| 9,791,443 B2 | 10/2017 | Weinschenk et al. |

(Continued)

FOREIGN PATENT DOCUMENTS

| | | |
|---|---|---|
| DE | 19602985 A1 | 7/1997 |
| EP | 0859631 B1 | 8/1998 |

(Continued)

OTHER PUBLICATIONS

Petersen et al, Journal of Molecular Medicine, 2009, vol. 87, pp. 1045-1051 (Year: 2009).*

(Continued)

*Primary Examiner* — Karen A. Canella
(74) *Attorney, Agent, or Firm* — Lathrop GPM LLP; Andrew T. Wilkins; Rebecca L. Wright

(57) ABSTRACT

Provided are compositions useful as therapeutic vaccines (e.g., cancer vaccines), and methods of producing such compositions. The compositions disclosed herein generally employ a stress protein and at least one synthetic peptide, which may be a phosphopeptide or phosphopeptide mimetic, comprising a cancer-specific mutation present in a patient's cancer.

21 Claims, 20 Drawing Sheets

Specification includes a Sequence Listing.

(56) References Cited

U.S. PATENT DOCUMENTS

| | | |
|---|---|---|
| 2001/0034042 A1 | 10/2001 | Srivastava et al. |
| 2002/0044948 A1 | 4/2002 | Khleif et al. |
| 2006/0079458 A1 | 4/2006 | Srivastava et al. |
| 2006/0093612 A1 | 5/2006 | Srivastava et al. |
| 2009/0208450 A1 | 8/2009 | Yang et al. |
| 2009/0280511 A1 | 11/2009 | Yahara et al. |
| 2011/0287057 A1 | 11/2011 | Podack et al. |
| 2012/0059670 A1 | 3/2012 | Sanborn et al. |
| 2012/0100173 A1 | 4/2012 | Leclair et al. |
| 2012/0142894 A1 | 6/2012 | Kosmatopoulos et al. |
| 2012/0208706 A1 | 8/2012 | Downing et al. |
| 2014/0105854 A1 | 4/2014 | Truneh et al. |
| 2014/0178438 A1 | 6/2014 | Sahin et al. |
| 2015/0079119 A1 | 3/2015 | Johnston et al. |
| 2015/0110821 A1 | 4/2015 | Saint-remy et al. |
| 2015/0140041 A1 | 5/2015 | Vitiello et al. |
| 2015/0178445 A1 | 6/2015 | Cibulskis et al. |
| 2015/0205911 A1 | 7/2015 | Aswad et al. |
| 2015/0232525 A1 | 8/2015 | Durrant et al. |
| 2015/0252427 A1 | 9/2015 | Srivastava et al. |
| 2015/0315247 A1 | 11/2015 | Binder et al. |
| 2015/0320848 A1 | 11/2015 | Rammensee et al. |
| 2016/0045594 A1 | 2/2016 | Geraghty et al. |
| 2016/0132631 A1 | 5/2016 | Bremel et al. |

FOREIGN PATENT DOCUMENTS

| | | | |
|---|---|---|---|
| EP | | 1117421 B2 | 7/2001 |
| EP | | 1126872 B1 | 8/2001 |
| EP | | 1787654 B1 | 5/2007 |
| EP | | 1879612 B1 | 1/2008 |
| EP | | 2111867 B1 | 10/2009 |
| EP | | 2129389 B1 | 12/2009 |
| EP | | 2374814 A2 | 10/2011 |
| EP | | 2752198 A1 | 7/2014 |
| WO | WO 1997/006685 A1 | | 2/1997 |
| WO | WO 1997/010000 A1 | | 3/1997 |
| WO | WO 1997/030721 A1 | | 8/1997 |
| WO | WO 1998/014207 A1 | | 4/1998 |
| WO | WO 1999/022761 A1 | | 5/1999 |
| WO | WO 1999/047641 A1 | | 9/1999 |
| WO | WO 2000/009159 A1 | | 2/2000 |
| WO | WO 2001/063278 A2 | | 8/2001 |
| WO | WO 2001/078655 A2 | | 10/2001 |
| WO | WO 2001/078772 A1 | | 10/2001 |
| WO | WO 2001/079259 A1 | | 10/2001 |
| WO | WO 2001/091787 A1 | | 12/2001 |
| WO | WO 2003/015712 A2 | | 2/2003 |
| WO | WO 2003/062262 A2 | | 7/2003 |
| WO | WO 2003/072595 A2 | | 9/2003 |
| WO | WO 2003/090686 A2 | | 11/2003 |
| WO | WO 2004/033657 A2 | | 4/2004 |
| WO | WO 2004/071457 A2 | | 8/2004 |
| WO | WO 2004/075636 A1 | | 9/2004 |
| WO | WO 2004/091493 A2 | | 10/2004 |
| WO | WO 2005/028496 A2 | | 3/2005 |
| WO | WO 2007/101227 A3 | | 9/2007 |
| WO | WO 2008/031126 A1 | | 3/2008 |
| WO | WO 2008/035350 A1 | | 3/2008 |
| WO | WO 2010/115118 A3 | | 10/2010 |
| WO | WO 2011/149909 A2 | | 12/2011 |
| WO | WO 2012/159643 A1 | | 11/2012 |
| WO | WO-2012159754 A2 * | 11/2012 | ......... A61K 39/0011 |
| WO | WO 2013/074058 A1 | | 5/2013 |
| WO | WO 2013/158611 A1 | | 10/2013 |
| WO | WO 2013/177593 A2 | | 11/2013 |
| WO | WO 2014/039675 A2 | | 3/2014 |
| WO | WO 2014/093855 A1 | | 3/2014 |
| WO | WO 2014/036562 A2 | | 6/2014 |
| WO | WO 2014/082729 A9 | | 6/2014 |
| WO | WO 2014/168874 A2 | | 10/2014 |
| WO | WO 2014/180490 A1 | | 11/2014 |
| WO | WO 2015/013461 A2 | | 1/2015 |
| WO | WO 2015/014375 A1 | | 2/2015 |
| WO | WO 2015/085233 A1 | | 6/2015 |
| WO | WO 2015/095811 A2 | | 6/2015 |
| WO | WO 2015/103037 A2 | | 7/2015 |
| WO | WO 2016/040110 A1 | | 3/2016 |
| WO | WO 2016/040900 A1 | | 3/2016 |
| WO | WO 2017/091333 A1 | | 6/2017 |

OTHER PUBLICATIONS

Kershaw et al, Clinical & Translational Immunology, 2014, vol. 3, p. e16, 7 pages (Year: 2014).*
Abstract of Van de Roemer et al, Immunology, Sep. 2012, vol. 137, suppl.1, p. 715, abstract No. P1737 (Year: 2012).*
Croft and Purcell, Expert Review of Vaccines, 2011, vol. 10, pp. 211-226 (Year: 2011).*
[No Author Listed] (2005) "Abstracts from the IV International Conference on heat shock proteins in immune response. Farmington, Connecticut, USA. Oct. 10-13, 2004," Immunology 114(1):141-54.
"Agenus Vaccine Shows Significant Reduction in Viral Burden after HerpV Generated Immune Activation," Agenus Press Release issued Jun. 26, 2014 (last accessed Mar. 28, 2018 at investor.agenusbio.com/2014-06-20-Agenus-Vaccine-Shows-Significant-Reduction-in-Viral-Burden-after-HerpV-Generated-Immune-Activation).
"Cell Genesys Crushed on Latest GVAX Failure; Seeking Options" published online by BioWorld on Oct. 17, 2008 (last accessed Mar. 22, 2018 at www.bioworld.com/content/cell-genesys-crushed-latest-gvax-failure-seeking-options).
"GSK's candidate shingles vaccine demonstrates 90% efficacy against shingles in people 70 years of age and over," GSK news release from Oct. 27, 2015 (last accessed on Mar. 23, 2018 at www.gsk.com/en-gb/media/press-releases/gsk-s-candidate-shingles-vaccine-demonstrates-90-efficacy-against-shingles-in-people-70-years-of-age-and-over/).
"Agenus acquires PhosImmune with a novel class of cancer neoantigens," Agenus press release issued Dec. 23, 2015 (last accessed on Mar. 29, 2018 at investor.agenusbio.com/2015-12-23-Agenus-Acquires-PhosImmune-with-a-Novel-Class-of-Cancer-Neoantigens).
"Agenus announces Phase 2 checkpoint inhibitor combination trial with Prophage cancer vaccine for melanoma," Press Release issued Jan. 14, 2014 (last accessed Mar. 28, 2018 at investor.agenusbio.com/2014-01-14-Agenus-Announces-Phase-2-Checkpoint-inhibitor-Combination-Trial-with-Prophage-Cancer-Vaccine-for-Melanoma).
"Agenus brain cancer vaccine shows extended survival in Phase 2 Final Data Analysis," Agenus Press Release Issued Jul. 1, 2014 (last accessed Mar. 28, 2018 at investor.agenusbio.com/2014-07-01-Agenus-Brain-Cancer-Vaccine-Shows-Extended-Survival-in-Phase-2-Final-Data-Analysis).
"Disappointing Results for Melacine" online publication by PharmaLetter on Oct. 7, 1994 (last accessed Mar. 22, 2018 at www.thepharmaletter.com/article/dissapointing-results-for-melacine).
"GlaxoSmithKline shutters lung cancer vaccine study on latest MAGE-A3 setback", published online Apr. 2, 2014 by FierceBiotech (last accessed Mar. 22, 2018 at www.fiercebiotech.com/r-d/glaxosmithkline-shutters-lung-cancer-vaccine-study-on-latest-mage-a3-setback).
"GSK's malaria vaccine phase 3 study containing Agenus' QS-21 published in The Lancet," Agenus Press Release issued Apr. 24, 2015 (last accessed Mar. 28, 2018 at investor.agenusbio.com/2015-04-24-GSK-s-Malaria-Vaccine-Phase-3-Study-Containing-Agenus-QS-21-Published-in-The-Lancet).
"Positive outcome of phase 3 study of GSK shingles vaccine containing Agenus adjuvant," Agenus Press Release issued Dec. 18, 2014 (last accessed Mar. 28, 2018 at investor.agenusbio.com/2014-12-18-Positive-Outcome-of-Phase-3-Study-of-GSK-Shingles-Vaccine-Containing-Agenus-Adjuvant).
Agenus Presentation [Untitled] given at Rodman & Renshaw Annual Global Investment Conference, New York City, NY, on Sep. 8-10, 2015.
Agenus Presentation, "A Comprehensive Immuno-oncology Ecosystem," given at Cowen and Co. 36th Annual Health Care Conference on Mar. 7, 2016.

(56) References Cited

OTHER PUBLICATIONS

Agenus Presentation, "Agenus R&D Day" given in New York City, NY on Nov. 19, 2015.
Agenus Presentation, "Agenus R&D Day," given on May 14, 2015.
Agenus Presentation, "Antibodies in Drug Discovery," given in Cambridge, UK on Feb. 10, 2016.
Agenus Presentation, "Corporate Presentation," given Feb. 2014.
Agenus Presentation, "Emerging Leader in Immuno-oncology", given on Jan. 6, 2016.
Agenus Presentation, "Individualized Cancer Immunotherapies," given on Jan. 20, 2016.
Agenus Presentation, "Integrated Approach to Immuno-Oncology" given in New York City, NY on Mar. 31, 2016.
Agenus Presentation, "Integrated Solutions in Immuno-Oncology," given to Jefferies on Apr. 7, 2016.
Agenus Presentation, "Spotlight on effective antigens for immune education," given at World Vaccine Congress on Apr. 8, 2015.
Agnandji et al. (2011) "First Results of Phase 3 Trial of RTS,S/AS01 Malaria Vaccine in African Children," N Engl J Med 365(20):1863-75.
Arnold et al. (1997) "Influences of Transporter Associated with Antigen Processing (TAP) on the Repertoire of Peptides Associated with the Endoplasmic Reticulum-resident Stress Protein gp96," J Exp Med 186(3):461-6.
Auger et al. (1996) "HLA-DR4 and HLA-DR10 motifs that carry susceptibility to rheumatoid arthritis bind 70-kD heat shock proteins," Nat. Med. 2(3):306-10.
Barrios et al. (1992) "Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming," Eur. J. Immunol. 22(6):1365-72.
Bartkowiak et al. (2015) "Unique potential of 4-1BB agonist antibody to promote durable regression of HPV+ tumors when combined with an E6/E7 peptide vaccine," Proc Natl Acad Sci U S A 112(38):E5290-9.
Basu et al. (1999) "Calreticulin, a peptide-binding chaperone of the endoplasmic reticulum, elicits tumor- and peptide-specific immunity," J. Exp. Med. 189(5):797-802.
Basu et al. (2000) "Necrotic but not apoptic cell death releases heat shock proteins, which deliver a partial maturation signal to dendritic cells and activate the NF-xB pathway" Int Immunol. 12:1539-1546.
Basu et al. (2001) "CD91 Is a Common Receptor for Heat Shock Proteins gp96, hsp90, hsp70, and Calreticulin" Immunity 14:303-313.
Bekri et al. "Preclinical study of a mutations based-vaccine for multiple myeloma immunotherapy," abstract to poster for Multiple Myeloma Workshop, Boston, MA, published on May 5, 2016.
Bekri et al. "Preclinical study of a mutations based-vaccine for multiple myeloma immunotherapy," poster presented at Multiple Myeloma Workshop, Boston, MA on May 5, 2016.
Bensaude et al. (1983) "Spontaneous high expression of heat-shock proteins in mouse embryonal carcinoma cells and ectoderm from day 8 mouse embryo," EMBO J. 2:173-177.
Berd et al. (2004) "Immunopharmacologic Analysis of an Autologous, Hapten-Modified Human Melanoma Vaccine" J Clin Oncol 22:403-415.
Binder et al. (2001) "Heat Shock Protein-chaperoned Peptides but Not Free Peptides Introduced into the Cytosol Are Presented Efficiently by Major Histocompatibility Complex I Molecules," J Biol Chem 276(20):17163-71.
Binder et al. (2005) "Peptides chaperoned by heat-shock proteins are a necessary and sufficient source of antigen in the cross-priming of CD8+ T cells," Nat Immunol 6(6):593-9.
Binder et al. (2014) "Functions of Heat Shock Proteins in Pathways of the Innate and Adaptive Immune System," J Immunol 193:5765-5771.
Blachere et al. (1993) "Heat shock protein vaccines against cancer," J Immunotherapy 14:352-356.

Blachere et al. (1993) "Immunization with GP96 heat shock proteins isolated from tumors or influenza virus infected cells elicits MHC-restricted, antigen-specific cytotoxic T lymphocytes against the corresponding cells/antigens," J Cell Biochem. 17D:124 Abstract NZ 502.
Blachere et al. (1997) "Heat Shock Protein-Peptide Complexes, Reconstituted In Vitro, Elicit Peptide-specific Cytotoxic T Lymphocyte Response and Tumor Immunity," J Exp Med. 186(8):1315-22.
Boegel et al. (2014) "A catalog of HLA type, HLA expression. and neoepitope candidates in human cancer cell lines" Oncoimmunology 3(8):e954893, p. 2, left-hand column, paragraph 2; and p. 10, left-hand column, paragraph 2.
Boon (1992) "Toward a genetic analysis of tumor rejection antigens," Adv. in Cancer Res. 58:177-210.
Buckwalter et al. (2008) "It is the antigen(s), stupid and other lessons from over a decade of vaccitherapy of human cancer," Semin Immunol 20(5):296-300.
Buczynski et al. (2001) "Characterization of a Lidless Form of the Molecular Chaperone DnaK," J Biol Chem 276:27231-27236.
Bukau et al. (1998) "The Hsp70 and Hsp60 Chaperone Machines" Cell 92:351-366.
Burkholder et al. (1996) "Mutations in the C-terminal fragment of DnaK affecting peptide binding," Proc Natl Acad Sci U S A. 93(20):10632-7.
Carreno et al. (2015) "A dendritic cell vaccine increases the breadth and diversity of melanoma neoantigen-specific T cells," Science 348(6236):803-8.
Castellino et al. (2000) "Receptor-mediated Uptake of Antigen/Heat Shock Protein Complexes Results in Major Histocompatibility Complex Class I Antigen Presentation via Two Distinct Processing Pathways," J Exp Med 91(11):1957-64.
Castle et al. (2012) "Exploiting the Mutanome for Tumor Vaccination," Cancer Res. 72(5):1081-91.
Castle et al. (2014) "Immunomic, genomic and transcriptomic characterization of CT26 colorectal carcinoma," BMC Genomics 15:190.
Castle et al. (2014) "Mutated tumor alleles are expressed according to their DNA frequency," Sci Rep 4:4743.
Ciupitu et al (1998) "Immunization with a Lymphocytic Choriomeningitis Virus Peptide Mixed with Heat Shock Protein 70 Results in Protective Antiviral Immunity and Specific Cytotoxic T Lymphocytes," J Exp Med 187:685-691.
Clarke et al. (1988) "Purification of complexes of nuclear oncogene p53 with rat and *Escherichia coli* heat shock proteins: in vitro dissociation of hsc70 and dnaK from murine p53 by ATP," Mol. Cell Biol. 8(3):12061215.
Cobbold et al. (2013) "MHC Class I—Associated Phosphopeptides Are the Targets of Memory-like Immunity in Leukemia," Sci Transl Med 5:203ra125.
Cohen (1993) "Cancer Vaccines Get a Shot in the Arm," Science 262:841-843.
Craig (1993) "Chaperones: helpers along the pathways to protein folding," Science 260(5116):1902-3.
Dahlstrom et al. (2003) "Human Papillomavirus Type 16 Infection and Squamous Cell Carcinoma of the Head and Neck in Never-Smokers: A Matched Pair Analysis1," Clin Can. Res 9:2620-2626.
Davidoff et al. (1992) "Immune response to p53 is dependent upon p53/HSP70 complexes in breast cancers," Proc. Natl. Acad. Sci. USA 89(8):3439-3442.
Dendouga et al. (2012) "Cell-mediated immune responses to a varicella-zoster virus glycoprotein E vaccine using both a TLR agonist and QS21 in mice," Vaccine 30:3126-3135 (Abstract Only).
Didierlaurent et al. (2014) "Enhancement of Adaptive Immunity by the Human Vaccine Adjuvant AS01 Depends on Activated Dendritic Cells," J Immunol 193:1920-30.
Diken et al. (2015) "Current Developments in Actively Personalized Cancer Vaccination with a Focus on RNA as the Drug Format," Prog. Tumor Res (Basel) 42:44-54.
Duan et al. (2014) "Genomic and bioinformatic profiling of mutational neoepitopes reveals new rules to predict anticancer immunogenicity" J Exp Med. 211(11):2231-48.

(56) References Cited

OTHER PUBLICATIONS

Duraiswamy et al. (2013) "Dual Blockade of PD-1 and CTLA-4 Combined with Tumor Vaccine Effectively Restores T-Cell Rejection Function in Tumors," Cancer Res 73:3591-3603.
Ebert et al. (2012) "A Cancer Vaccine Induces Expansion of NY-ESO-1-Specific Regulatory T Cells in Patients with Advanced Melanoma," PLoS One 7(10):e48424.
Elliot et al. (1990) "Naturally processed peptides," Nature 348:195-197.
Falk et al. (1990) "Cellular peptide composition governed by major histocompatibility complex class I Molecules," Nature 348:248-251.
Falk et al. (1991) "Allele-specific motifs revealed by sequencing of self-peptides eluted from mhc molecules," Nature 351:290-296.
Feldweg et al. (1993) "Evidence for biochemical heterogeneity of gp96 heat shock protein/tumor rejecion antigen," J Cell Biochem., Suppl. 17D:108.
Filipazzi et al. (2008) "Adjuvant multipeptide vaccination in high-risk early melanoma patients" Journal of Clinical Oncology, 2008 ASCO Annual Meeting Proceedings (Post-Meeting Edition). vol. 26, No. 15S (May 20 Supplement).
Flechtner et al. (2006) "High-Affinity Interactions between Peptides and Heat Shock Protein 70 Augment CD8+ T Lymphocyte Immune Responses," J Immunol 177:1017-1027.
Flynn et al. (1989) "Peptide binding and release by proteins implicated as catalysts of protein assembly," Science 245(4916):385-90.
Flynn et al. (1991) "Peptide-binding specificity of the molecular chaperone BiP," Nature 353:726-730.
Francois et al. (2009) "The CD4+ T-Cell Response of Melanoma Patients to a MAGE-A3 Peptide Vaccine Involves Potential Regulatory T Cells," Cancer Res 69(10):4335-45.
Franklin (1993) "Making vaccines fit the cancer," New Scientist 140:17.
Fritsch et al. (2014) "HLA-Binding Properties of Tumor Neoepitopes in Humans," Cancer Immunol Res 2:522-529.
Garcia-Murillas et al. (2015) "Mutation tracking in circulating tumor DNA predicts relapse in early breast cancer," Sci Transl Med 7:302ra133.
Garcon et al. (2011) "Recent clinical experience with vaccines using MPL- and QS-21-containing Adjuvant Systems," Expert Rev. Vaccines 10:471-486.
Geng et al. (2006) "HSP70 vaccine in combination with gene therapy with plasmid DNA encoding sPD-1 overcomes immune resistance and suppresses the progression of pulmonary metastatic melanoma.," Int J Cancer 118:2657-2664 (Abstract Only).
Gething et al. (1992) "Protein folding in the cell," Nature 355(6355):33-45.
Gragerov et al. (1994) "Different peptide binding specificities of hsp70 family members," J Mol Biol. 241(2):133-5.
Gragerov et al. (1994) "Specificity of DnaK-peptide binding," J Mol Biol 235(3):848-54.
Gubin et al. (2014) "Checkpoint blockade cancer immunotherapy targets tumour-specific mutant antigens," Nature 515:577-581.
Gullo et al. (2004) "Heat shock proteins: to present or not, that is the question," Immunol. Lett. 94(1-2):1-10.
Haberthur et al. (2011) "CD4 T Cell Immunity Is Critical for the Control of Simian Varicella Virus Infection in a Nonhuman Primate Model of VZV Infection," PLOS Pathogens, 7(11):e1002367, pp. 1-16.
Halevy et al. (1990) "Different tumor-derived p53 mutants exhibit distinct biological activities," Science 250(4977):113-116.
Henderson et al (2010) "Caught with their PAMPs down? The extracellular signaling actions of molecular chaperones are not due to microbial contaminants," Cell Stress and Chaperones 15:123-141.
Hinds et al. (1987) "Immunological evidence for the association of p53 with a heat shock protein, hsc70, in p53-plus-ras-transformed cell lines," Mol. Cell. Biol. 7(8):2863-2869.

Hinds et al. (1990) "Mutant p53 DNA clones from human colon carcinomas cooperate with ran in transforming primary rat cells: a comparison of the "hot spot" mutant phenotypes," Cell Growth Differ. 1(12):571-580.
Hoos et al. (2003) "Vaccination with Heat Shock Protein-Peptide Complexes: From Basic Science to Clinical Applications." Expert Rev. Vaccines 2:369-379.
International Search Report with Written Opinion corresponding to International Patent Application No. PCT/US2016/032465, dated Sep. 13, 2016, 17 pages.
Ishii et al. (1999) "Isolation of MHC Class I-Restricted Tumor Antigen Peptide and Its Precursors Associated with Heat Shock Proteins hsp70, hsp90, and gp96," J Immunol 162:1303-1309.
Jakob et al. (1993) "Small heat shock proteins are molecular chaperones," J. Biol. Chem. 268(3):1517-1520.
Jardetsky et al. (1991) "Identification of self peptides bound to purified HLA-B27," Nature 353:326-329.
Jindal et al. (1992) "Vaccinia virus infection induces a stress response that leads to association of Hsp70 with viral proteins," J. Virol. 66(9):5357-62.
Jing. et al. (2012) "Cross-presentation and genome-wide screening reveal candidate T cells antigens for a herpes simplex virus type 1 vaccine," J Clin Invest. 1-20.
Jocham et al. (2004) "Adjuvant autologous renal tumour cell vaccine and risk of tumour progression in patients with renal-cell carcinoma after radical nephrectomy: phase III, randomised controlled trial," Lancet 363:594-599.
Johnston. et al. (2011) "HSV-2: in pursuit of a vaccine," J Clin Investigation, 121(12):4600-4609.
Kocsis et al. (2002) "Antibodies against the human heat shock proteni hsp70 in pateints with severe coronary artery disease," Immunol Invest 31:219-231.
Kovalchin et al. (2001) "Determinants of efficacy of immunotherapy with tumor-derived heat shock protein gp96," Cancer Immun 1:7.
Kreiter et al. (2015) "Mutant MHC class II epitopes drive therapeutic immune responses to cancer," Nature 520:692-696 with Erratum Kreiter et al. (2015) Nature 523:370.
Kumaraguru et al. (2002) "Immunization with Chaperone-Peptide Complex Induces Low-Avidity Cytotoxic T Lymphocytes Providing Transient Protection Against Herpes Simplex Virus Infection"; Journal of Virology, Jan. 2002, p. 136-141.
Kumaraguru et al. (2004) "Concomitant Helper Response Recues Otherwise Low Avidity CD8+ Memory CTLs to Become Efficient Effectors In Vivo," J Immunol 172:3719-3724.
Lakey et al. (1987) "Identification of a peptide binding protein that plays a role in antigen presentation," Proc. Natl. Acad. Sci. USA 84:1659-1663.
Lammert et al. (1997) "Protein disulfide isomerase is the dominant acceptor for peptides translocated into the endoplasmic reticulum," Eur J Immunol 27: 1685-1690.
Lennerz et al. (2005) "The response of autologous T cells to a human melanoma is dominated by mutated neoantigens," Proc Natl Acad Sci U S A 102(44):16013-8.
Levy (1991) "ATP is required for in vitro assembly of mhc class I antigens but not for transfer of peptides across the membrane," Cell 67:265-274.
Li et al. (1993) "Tumor rejection antigen gp96/grp94 is an ATPase: implications for protein folding and antigen presentation," EMBO J. 12(8):3143-51.
Lin et al. (1993) "The 170-kDa glucose-regulated stress protein is an endoplasmic reticulum protein that binds immunoglobulin," Mol. Biol. Cell 4(11):1109-19.
Lindquist (1986) "The Heat-Shock Response," Ann Rev Biochem 55:1151-91.
Lindquist et al. (1988) "The heat-shock proteins," Annu. Rev. Genet. 22:631-77.
Luescher et al. (1991) "Specific binding of antigenic peptides to cell-associated mhc class I molecules," Nature 351:72-77.
Lukacs et al. (1993) "Tumor cells transfected with a bacterial heat-shock gene lose tumorigenicity and induce protection against tumors," J. Exp. Med. 178:343-348.
Lussow et al. (1991) "Mycobacterial heat-shock proteins as carrier molecules," Eur. J. Immunol. 21:2297-2302.

(56) References Cited

OTHER PUBLICATIONS

Lyngaa et al. (2014) "T-cell Responses to Oncogenic Merkel Cell Polyomavirus Proteins Distinguish Patients with Merkel Cell Carcinoma from Healthy Donors," Clin Cancer Res 20(7):1768-1778.
Macary et al. (2004) "HSP70 Peptide Binding Mutants Separate Antigen Delivery from Dendritic Cell Stimulation," Immunity 20(1):95-106.
Macejak et al. (1992) "Association of heat shock protein 70 with enterovirus capsid precursor P1 in infected human cells," J. Virol. 66(3):1520-7.
Madden et al. (1991) "The structure of hla-b27 reveals nonamer self-peptides bound in an extended conformation," Nature 353:321-325.
Maki (1991) "The Human Homologue of the Mouse Tumor Rejection Antigen GP96," Ph.D. thesis, Cornell University.
Maki et al. (1990) "Human homologue of murine tumor rejection antigen gp96: 5'-Regulatory and coding regions and relationship to stress-induced proteins," Proc. Natl. Acad. Sci. USA 87(15):5658-5663.
Maki et al. (1993) "Mapping of the Genes for Human Endoplasmic Reticular Heat Shock Protein gp96/grp94," Somatic Cell Mol. Genetics 19(1):73-81.
Marty-Roix et al. "Identification of QS-21 as an Inflammasome-activating Molecular Component of Saponin Adjuvants," (2016) J Biol Chem 291(3):1123-36.
Mateo et al. (1999) "An HLA-A2 Polyepitope Vaccine for Melanoma Immunotherapy," J Immunol 163:4058-4063.
McCall et al. (1989) "Biotherapy: A New Dimension in Cancer Treatment," Biotechnology 7:231-240.
McGeoch et al. (1987) "DNA sequence and genetic content of the HindIII I region in the short unique component of the herpes simplex virus type 2 genome: identification of the gene encoding glycoprotein G, and evolutionary comparisons," J Gen Virol 68:19-38.
Melief et al. "Effective therapeutic anticancer vaccines based on precision guiding of cytolytic T lymphocytes," (2002) Immunol Rev 188:177-82.
Mo et al. (2011) "A Heat Shock Protein Based Polyvalent Vaccine Targeting HSV-2: CD4+ and CD8+ Cellular Immunity and Protective Efficacy" Vaccine 29; 8350-8541.
Mohammed et al. (2008) "Phosphorylation-dependent interaction between antigenic peptides and MHC class I: a molecular basis for presentation of transformed self," Nat Immunol 9(11): 1236-1243.
Moroi et al. (2000) "Induction of cellular immunity by immunization with novel hybrid peptides complexed to heat shock protein 70," Proc. Natl. Acad. Sci. U. S. A. 97(7):3485-90.
Nelson et al. (1992) "The translation machinery and 70 kd heat shock protein cooperate in protein synthesis," Cell 71:97-105.
Nieland et al. (1996) "Isolation of an immunodominant viral peptide that is endogenously bound to the stress protein GP96/GRP94," Proc. Natl. Acad. Sci. USA 93:6135-6139.
Noguchi et al. (2008) "Immunologic and clinical effects of personalized selection of peptide vaccines in HLA-A2 positive patients with advanced cancer," Journal of Clinical Oncology, 2008 ASCO Annual Meeting Proceedings (Post-Meeting Edition). vol. 26, No. 15S (May 20 Supplement), 2008: 3031.
Obara et al. (2010) "Phase I/II study of novel HLA-A24 restricted DEPDC1 and MPHOSPH1 peptide vaccine for bladder cancer," Journal of Clinical Oncology, 2010 ASCO Annual Meeting Abstracts, vol. 28, No. 15_suppl (May 20 Supplement).
Pack et al. (2008) "An intranasal heat shock protein based vaccination strategy confers protection against mucosal challenge with herpes simplex virus," Human Vaccines 4:360-364.
Peng et al. (1997) "Purification of immunogenic heat shock protein 70-peptide complexes by ADP-affinity chromatography," J. Immunol. Methods 204(1):13-21.

Phase I clinical trial NCT00683670 for Dendritic Cells (White Blood Cells) Vaccination for Advanced Melanoma by U. Penn. (published May 2008 and completed Jun. 2016) (last accessed on Mar. 22, 2018 at clinicaltrials.gov/ct2/show/NCT00683670?term=NCT00683670&rank=1).
Phase I clinical trial NCT01970358 for Personalized NeoAntigen Cancer Vaccine in Melanoma by Dana-Farber (last accessed on Mar. 22, 2018 at clinicaltrials.gov/ct2/show/NCT01970358?term=NCT01970358&rank=1).
Phase I clinical trial NCT02035956 for IVAC Mutanome by Biontech RNA Pharma (last accessed on Mar. 22, 2018 at clinicaltrials.gov/ct2/show/NCT02035956?term=NCT02035956&rank=1).
Phase I clinical trial NCT02149225 for GAPVAC Phase I Trial in Newly Diagnosed Glioblastoma Patients by Immatics Biotech. (first posted 2014) (last accessed on Mar. 22, 2018 at clinicaltrials.gov/ct2/show/NCT02149225?term=NCT02149225&rank=1).
Phase I clinical trial NCT02316457 for A-Immunotherapy of IVAC_W_bre1_uID and IVAC_M_uID (TNBC-MERIT) by Biontech AG (first posted Dec. 15, 2014) (last accessed on Mar. 22, 2018 at clinicaltrials.gov/ct2/show/NCT02316457?term=NCT02316457&rank=1).
Phase II clinical trial NCT02129075 for CDX-1401 and Poly-ICLC Vaccine Therapy With or Without CDX-301 in Treating Patients With Stage IIB-IV Melanoma by National Cancer Institute (published May 2, 2014) (last accessed on Mar. 22, 2018 at clinicaltrials.gov/ct2/show/NCT02129075?term=NCI+Phase+II+clinical+trial+for+stage+IIB-IV+melanoma+using+CDX-1401).
Pinhashi-Kimhi (1986) "Specific interaction between the p53 cellular tumour antigen and major heat shock proteins," Nature 320(6058):182-184.
Pockley et al. (1998) "Detection of heat shock protein 70 (HSP70) and anti-HSP70 antibodies in the serum of normal individuals," Immunol Invest 27(6):367-77.
Pol et al. (2015) "Trial Watch: Peptide-based anticancer vaccines," OncoImmunology 4:e974411.
Postow et al. (2015) "Immune Checkpoint Blockade in Cancer Therapy," J Clin Oncol 33(17):1974-82.
Rapidis et al. (2009) "Immunotherapy of Head and Neck Cancer: Current and Future Considerations," J Oncol Article ID 346345.
Rea et al. (2001) "Serum heat shock protein and anti-heat shock protein antibody levels in aging," Exp Gerontol 36:341-352.
Robert et al. (2001) "Phylogenetic conservation of the molecular and immunological properties of the chaperones gp96 and hsp70," Eur J Immunol 31:186-195 (Abstract Only).
Rotzschke et al. (1990) "Isolation and analysis of naturally processed viral peptides as recognized by Cytotoxic T cells", Nature 348:252-254.
Rudensky et al. (1991) "Sequence analysis of peptides bound to MHC class II molecules," Nature 353:622-627.
Salimu et al. (2015) "Cross-Presentation of the Oncofetal Tumor Antigen 5T4 from Irradiated Prostate Cancer Cells—A Key Role for Heat-Shock Protein 70 and Receptor CD91," Cancer Immunol Res 3:678-688.
Salk et al. (1993) "A strategy for prophylactic vaccination against HIV," Science 260:1270-1272.
Sato et al. (2001) "Immunotherapy using heat-shock protein preparations of leukemia cells after syngeneic bone marrow transplantation in mice," Blood 98:1852-1857.
Sawai et al. (1989) "Association of a cellular heat shock protein with simian virus 40 large T antigen in transformed cells," J. Virol. 63(9):3961-73.
Schadendorf et al. (2015) "Pooled Analysis of Long-Term Survival Data From Phase II and Phase III Trials of Ipilimumab in Unresectable or Metastatic Melanoma," J Clin Oncol 33:1889-1894.
Schlosser et al. (2007) "A novel cytosolic class I antigen-processing pathway for endoplasmic-reticulum-targeted proteins," EMBO Rep 8:945-951.
Schreiber et al. (2012) "T Cell Costimulation by TNFR Superfamily Vaccination (TNFRSF)4 and TNFRSF25 in the Context of Vaccination," J Immunol 189:3311-3318.
Schumacher et al. (1991) "Peptide selection by mhc class I molecules," Nature 350:703-706.

(56) References Cited

OTHER PUBLICATIONS

Schuster et al. (2011) "Vaccination With Patient-Specific Tumor-Derived Antigen in First Remission Improves Disease-Free Survival in Follicular Lymphoma," J Clin Oncol 29:2787-2794.

Singh-Jasuja et al. (2007) "Correlation of T-cell response, clinical activity and regulatory T-cell levels in renal cell carcinoma patients treated with IMA901, a novel multi-peptide vaccine," J Clin Oncol 2007 ASCO Annual Meeting Proceedings (Post-Meeting Edition) (Abstract).

Snyder et al. (2014) "Genetic basis for clinical response to CTLA-4 blockade in melanoma," N Engl J Med 371(23):2189-2199.

Somersan et al. (2001) "Primary Tumor Tissue Lysates Are Enriched in Heat Shock Proteins and Induce the Maturation of Human Dendritic Cells1," J Immunol 4844-4852.

Srivastava (1991) "Protein tumor antigens," Curr. Opin. Immunol. 3:654-658.

Srivastava (1993) "Peptide-binding heat shock proteins in the endoplasmic reticulum: role in immune response to cancer and in antigen presentation," Adv. Cancer Res. 62:153-77.

Srivastava (1994) "Heat shock proteins in immune response to cancer: the fourth paradigm," Experientia. 50(11-12):1054-60.

Srivastava (2002) "Roles of heat-shock proteins in innate and adaptive immunity," Nat Rev Immunol. 2:185-194.

Srivastava et al. (1986) "Tumor rejection antigens of chemically induced sarcomas of inbred mice," Proc. Natl. Acad. Sci. U. S. A. 83(10):3407-11.

Srivastava et al. (1986) "Tumor-specific immunogenicity of stress-induced proteins: Convergence of two evolutionary pathways of antigen presentation?," Seminars in Immunol. 3:57-64.

Srivastava et al. (1987) "5'-Structural analysis of genes encoding polymorphic antigens of chemically induced tumors," Proc. Natl. Acad. Sci. USA 84:3807-3811.

Srivastava et al. (1988) "Chromosomal assignment of the gene encoding the mouse tumor rejection antigen gp96," Immunogenetics 28(3):205-7.

Srivastava et al. (1988) "Individually distinct transplantation antigens of chemically induced mouse tumors," Immunol. Today 9(3):78-83.

Srivastava et al. (1989) "Gp96 Molecules: Recognition Elements in Tumor Immunity," Human Tumor Antigens and Specific Tumor Therapy, pp. 63-71.

Srivastava et al. (1989) "Identification of a Human Homologue of the Murine Tumor Rejection Antigen GP96," Cancer Res. 49:1341-1343.

Srivastava et al. (1990) "Immunization with Soluble Gp96 Antigens Elicits Tumor-Specific Cellular Immunity," Cellular Immunity and the Immunotherapy of Cancer, pp. 307-314.

Srivastava et al. (1991) "Stress-induced proteins in immune response to cancer," Curr. Top. Microbiol. Immunol. 167:109-23.

Srivastava et al. (1993) "Evidence for peptide-chaperoning by the endoplasmic reticular heat shock protein GP96: implications for vaccination against cancer and infectious diseases," J. Cell. Biochem. Suppl. 17D:94, Abstract NZ014.

Srivastava et al. (1994) "Heat shock protein-peptide complexes in cancer immunotherapy," Curr. Opin. Immunol. 6(5):728-32.

Srivastava et al. (1994) "Heat shock proteins transfer peptides during antigen processing and CTL priming," Immunogenetics 39:93-98.

Srivastava et al. (2009) "Treating human cancers with heat shock protein-peptide complexes: the road ahead," Expert Opin Biol Ther 9: 179-186.

Stevens et al. (2003) "The solution structure of the bacterial HSP70 chaperone protein domain DnaK(393-507) in complex with the peptide NRLLLTG," Protein Sci. 12:2588-2596.

Stratton (2011) "Exploring the Genomes of Cancer Cells: Progress and Promise," Science 331:1553-1558.

Supplementary European Search Report for EP 04809742.2 dated Sep. 17, 2007 (5 pgs.).

Surquin et al. (2010) "Rapid, enhanced, and persistent protection of patients with renal insufficiency by AS02V-adjuvanted hepatitis B vaccine," Kidney Int 77:247-255.

Susumu et al. (2008) "Cross-presentation of NY-ESO-1 cytotoxic T lymphocyte epitope fused to human heat shock cognate protein by dendritic cells".

Suto et al. (1995) "A mechanism for the specific immunogenicity of heat shock protein-chaperoned peptides," Science 269(5230):1585-1588.

Tamura et al. (1997) "Immunotherapy of Tumors with Autologous Tumor-Derived Heat Shock Protein Preparations," Science 278:117-120.

Terasaki et al. (2008) J Clin Oncol, 2008 ASCO Annual Meeting Proceedings (Post-Meeting Edition) vol. 26, No. 15S (May 20 Supplement) (Abstract).

Testori et al. (2008) "Phase III Comparison of Vitespen, an Autologous Tumor-Derived Heat Shock Protein gp96 Peptide Complex Vaccine, With Physician's Choice of Treatment for Stage IV Melanoma: The C-100-21 Study Group," J Clin Oncol 26:955-962.

Thomas et al. (1982) "Molecular and cellular effects of heat shock and related treatments of mammalian tissue-culture cells," Cold Spring Habor Symp. Quant. Biol. 46:985-996.

Tischer et al. (2011) "Heat shock protein 70/peptide complexes: potent mediators for the generation of antiviral T cells particularly with regard to low precursor frequencies," J Transl. Med. 9:175.

Udono (1993) "Heat shock proteins HSP70, HSP90 and GP96 elicit tumor specific immunity to the tumors from which they are isolated," J. Cell. Biochem. Suppl. 17D:113, Abstract NZ225.

Udono et al. (1993) "Heat shock protein 70-associated peptides elicit specific cancer immunity," J. Exp. Med. 178(4):1391-6.

Udono et al. (1994) "Comparison of tumor-specific immunogenicities of stress-induced proteins gp96, hsp90, and hsp70," J. Immunol. 152(11):5398-403.

Udono et al. (1994) "Cellular requirements for tumor-specific immunity elicited by heat shock proteins: Tumor rejection antigen gp96 primes CD8+ T cells in vivo," Proc Natl Acad Sci USA 91:3077-3081.

Ullrich et al. (1986) "A mouse tumor-specific transplantation antigen is a heat shock-related protein," Proc. Natl. Acad. Sci. U. S. A. 83(10):3121-5.

Van Allen et al. (2015) "Genomic correlates of response to CTLA4 blockade in metastatic melanoma," Science 350:207-211.

Van Den Enyde et al. (1991) "The gene coding for a major tumor rejection antigen of tumor P815 is identical to the normal gene of synergistic DBA/2 mice," J. Exp. Med. 173:1373-1384.

Van Rooij et al. (2013) "Tumor Exome Analysis Reveals Neoantigen-Specific T-Cell Reactivity in an Ipilimumab-Responsive Melanoma," J Clin Oncol 31:e439-e442.

Vanbuskirk et al. (1989) "A peptide binding protein having a role in antigen presentation is a member of the hsp70 heat shock family," J. Exp. Med. 170:1799-1809.

Varnavski et al. (2005) "Effective Induction of CD8 T-Cell Memory Response by Noncovalent Complex of Ileat Shock Protein 70 and Herpes Simplex Virus (11SV) Antigenic Peptide—Implication for HSV-2 Peptide Vaccine Development," Immunology 114:14 1-154 (Abstract No. R16).

Vermorken et al. (1999) "Active specific immunotherapy for stage II and stage III human colon cancer: a randomised trial" Lancet 353:345-350.

Wald et al. (2011) "Safety and immunogenicity of long HSV-2 peptides complexed with rhHsc70 in HSV-2 seropositive persons" Vaccine 29:8520-8529.

Wang et al. (2001) "Characterization of heat shock protein 110 and glucose-regulated protein 170 as cancer vaccines and the effect of fever-range hyperthermia on vaccine activity," J. Immunol. 166(1):490-7.

Warren et al. (2010) "A census of predicted mutational epitopes suitable for immunologic cancer control" Hum Immunol. Mar. 2010;71(3):245-54, left-hand column, last paragraph.

Welch (1993) "How cells respond to stress," Sci. Am. 268(5):56-64.

Welch et al. (1982) "Purification of the major mammalian heat shock proteins," J. Biol. Chem. 257:14949-14959.

(56) References Cited

OTHER PUBLICATIONS

Welch et al. (1985) "Rapid purification of mammalian 70,000-dalton stress proteins: affinity of the proteins for nucleotides," Mol. Cell. Biol. 5:1229-1237.
White et al. (1988) "Differential Distribution of the Adenovirus E1A Proteins and Colocalization of E1A a with the 70-Kilodalton Cellular Heat Shock Protein in Infected Cells," J. Virol. 62(11):4153-4166.
Wilson et al. (2012) "ISCOMATRIX vaccines mediate CD8+ T-cell cross-priming by a MyD88-dependent signaling pathway" Immunol Cell Biol 90:540-552.
Wood et al. (2008) "An adjuvant autologous therapeutic vaccine (HSPPC-96; vitespen) versus observation alone for patients at high risk of recurrence after nephrectomy for renal cell carcinoma: a multicentre, open-label, randomised phase III trial" Lancet 372(9633):145-54.
Yadav et al. (2014) "Predicting immunogenic tumour mutations by combining mass spectrometry and exome sequencing" (2014) Nature 515:572-576.
Yan et al. (2011) "Regulatory T-cell depletion synergizes with gp96-mediated cellular responses and antitumor activity." Cancer Immunol Immunother 60:1763-1774.
Yedavelli et al. (1999) "Preventive and therapeutic effect of tumor derived heat shock protein, gp96, in an experimental prostate cancer model." Int J Mol Med 4:243-248 (Abstract Only).
Young (1990) "Stress proteins and immunology," Annu. Rev. Immunol. 8:401-20.
Zarling et al. (2014) "MHC-Restricted Phosphopeptides from Insulin Receptor Substrate-2 and CDC25b Offer Broad-Based Immunotherapeutic Agents for Cancer" Cancer Res 74:6784-6795.
Zhang et al. (1998) "Interactions of peptides with DnaK and C-terminal DnaK fragments studied using fluorescent and radioactive peptides," Arch Biochem Biophys 356(2):177-86.
Zhang et al. (2014) "Crystal Structure of the Stress-Inducible Human Heat Shock Protein 70 Substrate-Binding Domain in Complex with Peptide Substrate" (2014) PLoS ONE 9:e103518.
Zhu et al. (1996) "Structural analysis of substrate binding by the molecular chaperone DnaK," Science 272(5268):1606-14.
Aalamian, M. et al. (2006) "Autologous renal cell cancer vaccines using heat shock protein-peptide complexes," Urologic Oncology. 24(5):425-433.
Agenus Roadshow Slide Deck dated May 15, 2015.
Agenus Slide Deck for Immunotherapy Conference Talk (NY) dated Mar. 31, 2016.
Agenus Slide Deck for RBS Immunotherapy Conference Talk (NY) dated Mar. 27, 2014.
Altmeyer, A. et al. (1996) "Tumor-specific cell surface expression of the-KDEL containing, endoplasmic reticular heat shock protein gp96," Int J Cancer. 69(4):340-9.
Anderson, KM (2000) "Heat, heat shock, heat shock proteins and death: a central link in innate and adaptive immune responses," Immunol Lett. 74(1):35-9.
Anderson, S. et al. (1994) "The endoplasmic reticular heat shock protein gp96 is transcriptionally upregulated in interferon-treated cells," J. Exp. Med. 1980:1565-1569.
Basu, S. (2003) "Fever-like temperature induces maturation of dendritic cells through induction of hsp90," Int Immunol. 15(9):1053-61.
Basu, S. et al. (2000) "Heat shock proteins: the fountainhead of innate and adaptive immune responses," Cell Stress Chaperones. 5(5):443-51.
Binder, RJ (2000) "Saturation, competition, and specificity in interaction of heat shock proteins (hsp) gp96, hsp90, and hsp70 with CD11b+ cells," J Immunol. 165(5):2582-7.
Binder, RJ (2004) "Essential role of CD91 in re-presentation of gp96-chaperoned peptides," Proc Natl Acad Sci U.S.A. 101(16):6128-33.
Binder, RJ et al. (2000) "CD91: a receptor for heat shock protein gp96," Nat Immunol. 1(2):151-5.
Binder, RJ et al. (2000) "Cutting edge: heat shock protein gp96 induces maturation and migration of CD11c+ cells in vivo," J Immunol. 165(11):6029-35.
Binder, RJ et al. (2001) "Adjuvanticity of alpha 2-macroglobulin, an independent ligand for the heat shock protein receptor CD91," J Immunol. 166(8):4968-72.
Binder, RJ et al. (2002) "Naturally formed or artificially reconstituted non-covalent alpha2-macroglobulin-peptide complexes elicit CD91-dependent cellular immunity," Cancer Immunology Research. 2(1):1-9.
Binder, RJ et al. (2007) "Specific immunogenicity of heat shock protein gp96 derives from chaperoned antigenic peptides and not from contaminating proteins," J Immunol. 179(11):7254-61.
Blachere, NE et al. (1995) "Heat shock protein-based cancer vaccines and related thoughts on immunogenicity of human tumors," Semin Cancer Biol. 6(6):349-55.
Blachere, NE et al. (1997) "Heat shock protein-peptide complexes, reconstituted in vitro, elicit peptide-specific cytotoxic T lymphocyte response and tumor immunity," J Exp Med. 186(8):1315-22.
Callahan, MK (2006) "Heat shock up-regulates Imp2 and Imp7 and enhances presentation of immunoproteasome-dependent epitopes," Immunol. 177(12):8393-9.
Callahan, MK et al. (2008) "Heat-shock protein 90 associates with N-terminal extended peptides and is required for direct and indirect antigen presentation," Proc Natl Acad Sci U.S.A. 105(5):1662-7.
Castelli, C. (2004) "Heat shock proteins: biological functions and clinical application as personalized vaccines for human cancer," Cancer Immunol Immunother. 53(3):227-33.
Chandawarkar, RY (2004) "Immune modulation with high-dose heat-shock protein gp96: therapy of murine autoimmune diabetes and encephalomyelitis," Int Immunol. 16(4):615-24.
Feldweg, AM et al. (1995) "Molecular heterogeneity of tumor rejection antigen/heat shock protein GP96," Int J Cancer. 63(2):310-4.
Grizenkova, J. et al. (2012) "Overexpression of the Hspa13 (Stch) gene reduces prion disease incubation time in mice," Proc Natl Acad Sci U.S.A. 109(34):13722-7.
Janetzki, S. (1998) "Generation of tumor-specific cytotoxic T lymphocytes and memory T cells by immunization with tumor-derived heat shock protein gp96," J Immunother. 21(4):269-76.
Janetzki, S. (2000) "Immunization of cancer patients with autologous cancer-derived heat shock protein gp96 preparations: a pilot study," Int J Cancer. 88(2):232-8.
Kensil, CR et al. (2004) "Current vaccine adjuvants: an overview of a diverse class," Front Biosci. 9:2972-88.
Kovalchin, J. et al. (2001) "Determinants of efficacy of immunotherapy with tumor-derived heat shock protein gp96," Cancer Immunology Research. 1(1):7.
Kovalchin, JT et al. (2006) "In vivo delivery of heat shock protein 70 accelerates wound healing by up-regulating macrophage-mediated phagocytosis," Wound Repair Regen. 14(2):129-37.
Kovalchin, JT et al. (2006) "In vivo treatment of mice with heat shock protein, gp 96, improves survival of skin grafts with minor and major antigenic disparity," Transpl Immunol. 15(3):179-85.
Srivastava, PK (1997) "Purification of heat shock protein-peptide complexes for use in vaccination against cancers and intracellular pathogens," Methods. 12(2):165-71.
Li, C. et al. (2012) "Dendritic cells sequester antigenic epitopes for prolonged periods in the absence of antigen-encoding genetic information," Proc Natl Acad Sci U.S.A. 109(43):17543-8.
Li, Z. et al. (1994) "A critical contemplation on the role of heat shock proteins in transfer of antigenic peptides during antigen presentation," Behring Inst Mitt.(94):37-47.
Maki, RG et al. (2007) "A phase I pilot study of autologous heat shock protein vaccine HSPPC-96 in patients with resected pancreatic adenocarcinoma," Dig Dis Sci. 52(8):1964-72.
Martin, J. et al. (1993) "The reaction cycle of GroEL and GroES in chaperonin-assisted protein folding," Nature. 366(6452):228-33.
Mazzaferro, V. (2003) "Vaccination with autologous tumor-derived heat-shock protein gp96 after liver resection for metastatic colorectal cancer," Clin Cancer Res. 9(9):3235-45.

(56) References Cited

OTHER PUBLICATIONS

Ménoret A. (1999) "Association of peptides with heat shock protein gp96 occurs in vivo and not after cell lysis," Biochem Biophys Res Commun. 262(3):813-8.

Ménoret, A. et al. (2000) "Natural autoantibodies against heat-shock proteins hsp70 and gp96: implications for immunotherapy using heat-shock proteins," Immunology. 101(3):364-70.

Mo, A. et al. (2011) "A heat shock protein based polyvalent vaccine targeting HSV-2: CD4(+) and CD8(+) cellular immunity and protective efficacy," Vaccine. 29(47):8530-41.

Oki, Y. (2007) "Experience with heat shock protein-peptide complex 96 vaccine therapy in patients with indolent non-Hodgkin lymphoma," Cancer. 109(1):77-83.

Panjwani, NN (2002) "Heat shock proteins gp96 and hsp70 activate the release of nitric oxide by APCs," J Immunol. 168(6):2997-3003.

Parmiani, G. et al. (2004) "Heat Shock Proteins and Their Use as Anticancer Vaccines," Clinical Cancer Research. 10(24):8142-8146.

Peng, P. (1997) "Purification of immunogenic heat shock protein 70-peptide complexes by ADP-affinity chromatography," J Immunol Methods. 204(1):13-21.

Przepiorka, D. (1998) "Heat shock protein-peptide complexes as immunotherapy for human cancer," Mol Med Today. 4(11):478-84.

Rivoltini, L. (2003) "Human tumor-derived heat shock protein 96 mediates in vitro activation and in vivo expansion of melanoma- and colon carcinoma-specific T cells," J Immunol. 171(7):3467-74.

Robert, J. et al. (2001) "Immunological properties of heat shock proteins are phylogenetically conserved," Adv Exp Med Biol. 484:237-49.

Sengupta, D. et al. (2004) "Heat shock protein-mediated cross-presentation of exogenous HIV antigen on HLA class I and class II," J Immunol. 173(3):1987-93.

Sondermann, H. et al. (2000) "Characterization of a receptor for heat shock protein 70 on macrophages and monocytes," Biol Chem. 381(12):1165-74.

Srivastava, PK (2000) "Heat shock protein-based novel immunotherapies," Drug News Perspect. 13(9):517-22.

Srivastava, PK (2000) "Immunotherapy of human cancer: lessons from mice," Nature Immunology. 1:363-366.

Srivastava, PK (2001) "A central role for heat shock proteins in host deficiency," Adv Exp Med Biol. 495:121-6.

Srivastava, PK (2005) "Immunotherapy for human cancer using heat shock protein-peptide complexes," Curr Oncol Rep. 7(2):104-8.

Srivastava, PK (2008) "New jobs for ancient chaperones," Sci Am. 299(1):50-5.

Srivastava, PK (2012) "Identification of chaperones as essential components of the tumor rejection moieties of cancers," Cancer Immunology Research. 12(1):1-5.

Srivastava, PK et al. (1998) "Heat shock proteins come of age: primitive functions acquire new roles in an adaptive world," Immunity. 8(6):657-65.

Srivastava, PK et al. (2001) "Heat shock proteins: the 'Swiss Army Knife' vaccines against cancers and infectious agents," Vaccine. 19(17-19):2590-7.

Testori, A. et al. (2008) "Phase III comparison of vitespen, an autologous tumor-derived heat shock protein gp96 peptide complex vaccine, with physician's choice of treatment for stage IV melanoma: the C-100-21 Study Group," J Clin Oncol. 26(6):955-62.

Vatner, RE et al. (2010) "The tailless complex polypeptide-1 ring complex of the heat shock protein 60 family facilitates cross-priming of CD8 responses specific for chaperoned peptides," J Immunol. 185(11):6765-73.

Wald, A. et al. (2011) "Safety and immunogenicity of long HSV-2 peptides complexed with rhHsc70 in HSV-2 seropositive persons," Vaccine. 29(47):8520-9.

Wang, R. et al. (2006) "Exogenous heat shock protein 70 binds macrophage lipid raft microdomain and stimulates phagocytosis, processing, and MHC-II presentation of antigens," Blood. 107(4):1636-42.

Wang, R. et al. (2006) "HSP70 enhances macrophage phagocytosis by interaction with lipid raft-associated TLR-7 and upregulating p38 MAPK and PI3K pathways," J Surg Res. 136(1):58-69.

Yang, Y. et al. (2006) "Heat Shock Protein gp96 Is a Master Chaperone for Toll-like Receptors and Is Important in the Innate Function of Macrophages," Immunity. 26(2)215-216.

* cited by examiner

SEQUENCE LISTING

```
<160> NUMBER OF SEQ ID NOS: 478

<210> SEQ ID NO 1
<211> LENGTH: 9
<212> TYPE: PRT
<213> ORGANISM: Homo sapiens

<400> SEQUENCE: 1

Ala Leu Leu Asp Tyr Ser Val Pro Val
1               5

<210> SEQ ID NO 2
<211> LENGTH: 9
<212> TYPE: PRT
<213> ORGANISM: Homo sapiens

<400> SEQUENCE: 2

Phe Leu Ala Glu Val Pro His Arg Leu
1               5

<210> SEQ ID NO 3
<211> LENGTH: 9
<212> TYPE: PRT
<213> ORGANISM: Homo sapiens

<400> SEQUENCE: 3

Met Leu Leu Ser Lys Tyr Val Pro Val
1               5

<210> SEQ ID NO 4
<211> LENGTH: 9
<212> TYPE: PRT
<213> ORGANISM: Homo sapiens

<400> SEQUENCE: 4

Met Leu Leu Ser Thr Ser Val Pro Val
1               5

<210> SEQ ID NO 5
<211> LENGTH: 9
<212> TYPE: PRT
<213> ORGANISM: Homo sapiens

<400> SEQUENCE: 5

Arg Leu Gly Glu His Ile Ile Glu Val
1               5

<210> SEQ ID NO 6
<211> LENGTH: 9
<212> TYPE: PRT
<213> ORGANISM: Homo sapiens

<400> SEQUENCE: 6

Leu Leu Phe Glu Phe Leu Phe Leu Ile
1               5

<210> SEQ ID NO 7
<211> LENGTH: 9
<212> TYPE: PRT
<213> ORGANISM: Homo sapiens
```

```
<400> SEQUENCE: 7

Ala Leu Leu Asp Ile Ser Phe Phe Ala
1               5

<210> SEQ ID NO 8
<211> LENGTH: 9
<212> TYPE: PRT
<213> ORGANISM: Homo sapiens

<400> SEQUENCE: 8

Asn Leu Trp Gln Leu Phe Phe Tyr Val
1               5

<210> SEQ ID NO 9
<211> LENGTH: 9
<212> TYPE: PRT
<213> ORGANISM: Homo sapiens

<400> SEQUENCE: 9

Tyr Met Cys Ser Val Leu Phe Asn Leu
1               5

<210> SEQ ID NO 10
<211> LENGTH: 9
<212> TYPE: PRT
<213> ORGANISM: Homo sapiens

<400> SEQUENCE: 10

Arg Met Ala Asp Pro Leu Trp Ala Leu
1               5

<210> SEQ ID NO 11
<211> LENGTH: 9
<212> TYPE: PRT
<213> ORGANISM: Homo sapiens

<400> SEQUENCE: 11

Leu Leu Phe Asp Cys Met Trp Glu Thr
1               5

<210> SEQ ID NO 12
<211> LENGTH: 9
<212> TYPE: PRT
<213> ORGANISM: Homo sapiens

<400> SEQUENCE: 12

Met Ile Leu Gly Ser Leu Ile Tyr Val
1               5

<210> SEQ ID NO 13
<211> LENGTH: 9
<212> TYPE: PRT
<213> ORGANISM: Homo sapiens

<400> SEQUENCE: 13

Val Leu Ala Asp Ala Phe Tyr Ser Ile
1               5

<210> SEQ ID NO 14
<211> LENGTH: 9
<212> TYPE: PRT
<213> ORGANISM: Homo sapiens

<400> SEQUENCE: 14
```

```
Tyr Leu Val Ala Gly Val Thr Thr Val
1               5

<210> SEQ ID NO 15
<211> LENGTH: 9
<212> TYPE: PRT
<213> ORGANISM: Homo sapiens

<400> SEQUENCE: 15

Ser Leu Met Ser Met Trp Val Thr Val
1               5

<210> SEQ ID NO 16
<211> LENGTH: 9
<212> TYPE: PRT
<213> ORGANISM: Homo sapiens

<400> SEQUENCE: 16

Leu Met Ile Lys Asp Leu Ile Glu Val
1               5

<210> SEQ ID NO 17
<211> LENGTH: 9
<212> TYPE: PRT
<213> ORGANISM: Homo sapiens

<400> SEQUENCE: 17

Tyr Leu Leu Arg His Ser Glu Ser Val
1               5

<210> SEQ ID NO 18
<211> LENGTH: 9
<212> TYPE: PRT
<213> ORGANISM: Homo sapiens

<400> SEQUENCE: 18

Phe Met Asn Ser Phe Val Asn Val Val
1               5

<210> SEQ ID NO 19
<211> LENGTH: 9
<212> TYPE: PRT
<213> ORGANISM: Homo sapiens

<400> SEQUENCE: 19

Phe Leu Met Glu Ala Asp Leu Gly Met
1               5

<210> SEQ ID NO 20
<211> LENGTH: 9
<212> TYPE: PRT
<213> ORGANISM: Homo sapiens

<400> SEQUENCE: 20

Met Leu Asn Ser Leu Ile Tyr Ser Leu
1               5

<210> SEQ ID NO 21
<211> LENGTH: 9
<212> TYPE: PRT
<213> ORGANISM: Homo sapiens

<400> SEQUENCE: 21

Tyr Met Ala Gly Leu Phe Leu Gly Ile
1               5
```

```
<210> SEQ ID NO 22
<211> LENGTH: 9
<212> TYPE: PRT
<213> ORGANISM: Homo sapiens

<400> SEQUENCE: 22

Phe Val Trp Phe Ser Val Ala Gly Val
1               5

<210> SEQ ID NO 23
<211> LENGTH: 9
<212> TYPE: PRT
<213> ORGANISM: Homo sapiens

<400> SEQUENCE: 23

Gly Leu Leu Ala Met Ala Phe Leu Val
1               5

<210> SEQ ID NO 24
<211> LENGTH: 9
<212> TYPE: PRT
<213> ORGANISM: Homo sapiens

<400> SEQUENCE: 24

Lys Leu Ala Lys Leu Thr Phe Trp Leu
1               5

<210> SEQ ID NO 25
<211> LENGTH: 9
<212> TYPE: PRT
<213> ORGANISM: Homo sapiens

<400> SEQUENCE: 25

Phe Leu Ala Gln Glu Leu Leu Pro Leu
1               5

<210> SEQ ID NO 26
<211> LENGTH: 9
<212> TYPE: PRT
<213> ORGANISM: Homo sapiens

<400> SEQUENCE: 26

Ile Leu Met Lys Cys Phe Leu Ser Val
1               5

<210> SEQ ID NO 27
<211> LENGTH: 9
<212> TYPE: PRT
<213> ORGANISM: Homo sapiens

<400> SEQUENCE: 27

Thr Leu Leu Asp Ala Leu Tyr Val Ile
1               5

<210> SEQ ID NO 28
<211> LENGTH: 9
<212> TYPE: PRT
<213> ORGANISM: Homo sapiens

<400> SEQUENCE: 28

Ala Leu Phe Pro His Pro Gln His Val
1               5
```

```
<210> SEQ ID NO 29
<211> LENGTH: 9
<212> TYPE: PRT
<213> ORGANISM: Homo sapiens

<400> SEQUENCE: 29

Phe Leu Ile His Val Ala Ala Tyr Ala
1               5

<210> SEQ ID NO 30
<211> LENGTH: 9
<212> TYPE: PRT
<213> ORGANISM: Homo sapiens

<400> SEQUENCE: 30

Gly Met Met Met Gly Ala Trp Trp Leu
1               5

<210> SEQ ID NO 31
<211> LENGTH: 9
<212> TYPE: PRT
<213> ORGANISM: Homo sapiens

<400> SEQUENCE: 31

Tyr Leu Ile Ser Leu Phe Pro Ile Ile
1               5

<210> SEQ ID NO 32
<211> LENGTH: 9
<212> TYPE: PRT
<213> ORGANISM: Homo sapiens

<400> SEQUENCE: 32

Leu Leu Tyr Ser Leu Val Ala Gly Val
1               5

<210> SEQ ID NO 33
<211> LENGTH: 9
<212> TYPE: PRT
<213> ORGANISM: Homo sapiens

<400> SEQUENCE: 33

Leu Leu Pro Tyr Tyr Val Phe Glu Ile
1               5

<210> SEQ ID NO 34
<211> LENGTH: 9
<212> TYPE: PRT
<213> ORGANISM: Homo sapiens

<400> SEQUENCE: 34

Arg Leu Phe Asp Leu Leu Ser Thr Leu
1               5

<210> SEQ ID NO 35
<211> LENGTH: 9
<212> TYPE: PRT
<213> ORGANISM: Homo sapiens

<400> SEQUENCE: 35

Leu Leu Leu Gln Gly Leu Phe Val Val
1               5

<210> SEQ ID NO 36
<211> LENGTH: 9
```

```
<212> TYPE: PRT
<213> ORGANISM: Homo sapiens

<400> SEQUENCE: 36

Met Met Phe Asp Glu Tyr Gln Gly Leu
1               5

<210> SEQ ID NO 37
<211> LENGTH: 9
<212> TYPE: PRT
<213> ORGANISM: Homo sapiens

<400> SEQUENCE: 37

Leu Leu Phe Ala Asn Leu Tyr Leu Leu
1               5

<210> SEQ ID NO 38
<211> LENGTH: 9
<212> TYPE: PRT
<213> ORGANISM: Homo sapiens

<400> SEQUENCE: 38

Gly Leu Gln Glu Tyr Ser Pro Glu Ile
1               5

<210> SEQ ID NO 39
<211> LENGTH: 9
<212> TYPE: PRT
<213> ORGANISM: Homo sapiens

<400> SEQUENCE: 39

Ser Leu Val Ala Ile Ser Pro Ser Val
1               5

<210> SEQ ID NO 40
<211> LENGTH: 9
<212> TYPE: PRT
<213> ORGANISM: Homo sapiens

<400> SEQUENCE: 40

Leu Leu Ala Glu Met Gly Tyr Lys Val
1               5

<210> SEQ ID NO 41
<211> LENGTH: 9
<212> TYPE: PRT
<213> ORGANISM: Homo sapiens

<400> SEQUENCE: 41

Ala Leu Phe Trp Ser Phe Ala Pro Leu
1               5

<210> SEQ ID NO 42
<211> LENGTH: 9
<212> TYPE: PRT
<213> ORGANISM: Homo sapiens

<400> SEQUENCE: 42

Phe Val Leu Ile Val Leu Tyr Tyr Val
1               5

<210> SEQ ID NO 43
<211> LENGTH: 9
<212> TYPE: PRT
<213> ORGANISM: Homo sapiens
```

<400> SEQUENCE: 43

Gln Leu Phe Phe Phe Thr Trp Ser Leu
1               5

<210> SEQ ID NO 44
<211> LENGTH: 9
<212> TYPE: PRT
<213> ORGANISM: Homo sapiens

<400> SEQUENCE: 44

Lys Leu Leu Gln Ser Leu Thr Pro Leu
1               5

<210> SEQ ID NO 45
<211> LENGTH: 9
<212> TYPE: PRT
<213> ORGANISM: Homo sapiens

<400> SEQUENCE: 45

Val Leu Asp Glu Cys Phe Ser Arg Val
1               5

<210> SEQ ID NO 46
<211> LENGTH: 9
<212> TYPE: PRT
<213> ORGANISM: Homo sapiens

<400> SEQUENCE: 46

Ser Leu Leu Asp Gln Gly Asp Tyr Val
1               5

<210> SEQ ID NO 47
<211> LENGTH: 9
<212> TYPE: PRT
<213> ORGANISM: Homo sapiens

<400> SEQUENCE: 47

Lys Leu Thr Phe Trp Leu Leu Ala Val
1               5

<210> SEQ ID NO 48
<211> LENGTH: 9
<212> TYPE: PRT
<213> ORGANISM: Homo sapiens

<400> SEQUENCE: 48

Phe Leu Phe Leu Val Leu Leu Phe Val
1               5

<210> SEQ ID NO 49
<211> LENGTH: 9
<212> TYPE: PRT
<213> ORGANISM: Homo sapiens

<400> SEQUENCE: 49

Phe Ile Asn Glu Met Val Leu Phe Ile
1               5

<210> SEQ ID NO 50
<211> LENGTH: 9
<212> TYPE: PRT
<213> ORGANISM: Homo sapiens

<400> SEQUENCE: 50

Val Leu Phe Lys Val Ile Glu Ala Val
1               5

<210> SEQ ID NO 51
<211> LENGTH: 9
<212> TYPE: PRT
<213> ORGANISM: Homo sapiens

<400> SEQUENCE: 51

Ser Met Gln Asp Cys Gly Phe Pro Leu
1               5

<210> SEQ ID NO 52
<211> LENGTH: 9
<212> TYPE: PRT
<213> ORGANISM: Homo sapiens

<400> SEQUENCE: 52

His Ile Tyr Asp Glu Val Phe Glu Leu
1               5

<210> SEQ ID NO 53
<211> LENGTH: 9
<212> TYPE: PRT
<213> ORGANISM: Homo sapiens

<400> SEQUENCE: 53

Val Met Met Ser Gln Tyr Leu Glu Leu
1               5

<210> SEQ ID NO 54
<211> LENGTH: 9
<212> TYPE: PRT
<213> ORGANISM: Homo sapiens

<400> SEQUENCE: 54

Ala Leu Leu Thr Phe Asp Pro Leu Val
1               5

<210> SEQ ID NO 55
<211> LENGTH: 9
<212> TYPE: PRT
<213> ORGANISM: Homo sapiens

<400> SEQUENCE: 55

Thr Met Leu Asn Gln Leu Tyr His Leu
1               5

<210> SEQ ID NO 56
<211> LENGTH: 9
<212> TYPE: PRT
<213> ORGANISM: Homo sapiens

<400> SEQUENCE: 56

Leu Leu Leu Cys Tyr Ala Phe Arg Ala
1               5

<210> SEQ ID NO 57
<211> LENGTH: 9
<212> TYPE: PRT
<213> ORGANISM: Homo sapiens

<400> SEQUENCE: 57

Ala Leu Ala His Leu Pro Ala Leu Val

```
1               5

<210> SEQ ID NO 58
<211> LENGTH: 9
<212> TYPE: PRT
<213> ORGANISM: Homo sapiens

<400> SEQUENCE: 58

Phe Leu Phe Ser Ile Glu Leu Leu Ile
1               5

<210> SEQ ID NO 59
<211> LENGTH: 9
<212> TYPE: PRT
<213> ORGANISM: Homo sapiens

<400> SEQUENCE: 59

Ser Leu Cys Glu Phe Ser Asn Phe Leu
1               5

<210> SEQ ID NO 60
<211> LENGTH: 9
<212> TYPE: PRT
<213> ORGANISM: Homo sapiens

<400> SEQUENCE: 60

Ala Leu Thr Tyr Leu Leu His Leu Val
1               5

<210> SEQ ID NO 61
<211> LENGTH: 9
<212> TYPE: PRT
<213> ORGANISM: Homo sapiens

<400> SEQUENCE: 61

Val Leu Met Glu Ser Val Cys Asn Met
1               5

<210> SEQ ID NO 62
<211> LENGTH: 9
<212> TYPE: PRT
<213> ORGANISM: Homo sapiens

<400> SEQUENCE: 62

Leu Met Met Phe Arg Asp Val Ala Val
1               5

<210> SEQ ID NO 63
<211> LENGTH: 9
<212> TYPE: PRT
<213> ORGANISM: Homo sapiens

<400> SEQUENCE: 63

Ala Ser Met Glu Cys Ile Ser Pro Val
1               5

<210> SEQ ID NO 64
<211> LENGTH: 9
<212> TYPE: PRT
<213> ORGANISM: Homo sapiens

<400> SEQUENCE: 64

His Met Val Asp Glu Leu Glu Ala Val
1               5
```

-continued

```
<210> SEQ ID NO 65
<211> LENGTH: 9
<212> TYPE: PRT
<213> ORGANISM: Homo sapiens

<400> SEQUENCE: 65

Leu Val Ser Ser Ser Leu Trp Leu Val
1               5

<210> SEQ ID NO 66
<211> LENGTH: 9
<212> TYPE: PRT
<213> ORGANISM: Homo sapiens

<400> SEQUENCE: 66

Ser Leu Phe Ser Tyr Asp Cys Trp Leu
1               5

<210> SEQ ID NO 67
<211> LENGTH: 9
<212> TYPE: PRT
<213> ORGANISM: Homo sapiens

<400> SEQUENCE: 67

Asn Leu Leu Gly Leu Thr Phe Arg Ile
1               5

<210> SEQ ID NO 68
<211> LENGTH: 9
<212> TYPE: PRT
<213> ORGANISM: Homo sapiens

<400> SEQUENCE: 68

Ala Ile Val Gly Phe Thr Ser Pro Val
1               5

<210> SEQ ID NO 69
<211> LENGTH: 9
<212> TYPE: PRT
<213> ORGANISM: Homo sapiens

<400> SEQUENCE: 69

Val Leu Ser Trp Leu Ser Phe Trp Ile
1               5

<210> SEQ ID NO 70
<211> LENGTH: 9
<212> TYPE: PRT
<213> ORGANISM: Homo sapiens

<400> SEQUENCE: 70

Ile Ile Met Arg Val Asp Phe Asn Val
1               5

<210> SEQ ID NO 71
<211> LENGTH: 9
<212> TYPE: PRT
<213> ORGANISM: Homo sapiens

<400> SEQUENCE: 71

Ala Leu Trp Asn Leu Val Gln Phe Ala
1               5

<210> SEQ ID NO 72
```

```
<211> LENGTH: 9
<212> TYPE: PRT
<213> ORGANISM: Homo sapiens

<400> SEQUENCE: 72

Tyr Leu Ile Ser Leu Leu Leu Ile Ile
1               5

<210> SEQ ID NO 73
<211> LENGTH: 9
<212> TYPE: PRT
<213> ORGANISM: Homo sapiens

<400> SEQUENCE: 73

Tyr Leu Asn Pro Tyr Gln Leu Asn Ala
1               5

<210> SEQ ID NO 74
<211> LENGTH: 9
<212> TYPE: PRT
<213> ORGANISM: Homo sapiens

<400> SEQUENCE: 74

Phe Thr Phe Ser Leu Ala Met Phe Leu
1               5

<210> SEQ ID NO 75
<211> LENGTH: 9
<212> TYPE: PRT
<213> ORGANISM: Homo sapiens

<400> SEQUENCE: 75

Met Leu Tyr Gly Gln Ile Gly Tyr Ile
1               5

<210> SEQ ID NO 76
<211> LENGTH: 9
<212> TYPE: PRT
<213> ORGANISM: Homo sapiens

<400> SEQUENCE: 76

Ile Leu Ile Ala Ala Met Leu Glu Leu
1               5

<210> SEQ ID NO 77
<211> LENGTH: 9
<212> TYPE: PRT
<213> ORGANISM: Homo sapiens

<400> SEQUENCE: 77

Phe Leu Leu Pro Phe Ala Asn Glu Thr
1               5

<210> SEQ ID NO 78
<211> LENGTH: 9
<212> TYPE: PRT
<213> ORGANISM: Homo sapiens

<400> SEQUENCE: 78

Phe Leu Leu Ala Lys Val Ile Asn Thr
1               5

<210> SEQ ID NO 79
<211> LENGTH: 9
<212> TYPE: PRT
```

<213> ORGANISM: Homo sapiens

<400> SEQUENCE: 79

Gln Leu Ala Tyr Leu Asp Tyr Tyr Leu
1               5

<210> SEQ ID NO 80
<211> LENGTH: 9
<212> TYPE: PRT
<213> ORGANISM: Homo sapiens

<400> SEQUENCE: 80

Cys Leu Ala Asn Gln Ile Pro Phe Ile
1               5

<210> SEQ ID NO 81
<211> LENGTH: 9
<212> TYPE: PRT
<213> ORGANISM: Homo sapiens

<400> SEQUENCE: 81

Ser Leu Gly Ser Leu Leu Ser His Val
1               5

<210> SEQ ID NO 82
<211> LENGTH: 9
<212> TYPE: PRT
<213> ORGANISM: Homo sapiens

<400> SEQUENCE: 82

Phe Leu Phe Leu Ile Tyr Leu Leu Val
1               5

<210> SEQ ID NO 83
<211> LENGTH: 9
<212> TYPE: PRT
<213> ORGANISM: Homo sapiens

<400> SEQUENCE: 83

Ser Met Val Asp Gly Met Trp Gln Thr
1               5

<210> SEQ ID NO 84
<211> LENGTH: 9
<212> TYPE: PRT
<213> ORGANISM: Homo sapiens

<400> SEQUENCE: 84

Arg Ile Val Glu Phe Tyr Phe Met Leu
1               5

<210> SEQ ID NO 85
<211> LENGTH: 9
<212> TYPE: PRT
<213> ORGANISM: Homo sapiens

<400> SEQUENCE: 85

Asn Ile Phe Ala Ile Leu Glu Ser Val
1               5

<210> SEQ ID NO 86
<211> LENGTH: 9
<212> TYPE: PRT
<213> ORGANISM: Homo sapiens

```
<400> SEQUENCE: 86

Leu Met Leu Arg Cys Thr Glu Ser Val
1               5

<210> SEQ ID NO 87
<211> LENGTH: 9
<212> TYPE: PRT
<213> ORGANISM: Homo sapiens

<400> SEQUENCE: 87

Ile Leu Ser Gly Leu Val Asn Met Val
1               5

<210> SEQ ID NO 88
<211> LENGTH: 9
<212> TYPE: PRT
<213> ORGANISM: Homo sapiens

<400> SEQUENCE: 88

Ser Met His Trp Gln Asn Tyr Ser Val
1               5

<210> SEQ ID NO 89
<211> LENGTH: 9
<212> TYPE: PRT
<213> ORGANISM: Homo sapiens

<400> SEQUENCE: 89

Leu Leu Leu Gln Ala Asn Phe Ile Val
1               5

<210> SEQ ID NO 90
<211> LENGTH: 9
<212> TYPE: PRT
<213> ORGANISM: Homo sapiens

<400> SEQUENCE: 90

Thr Leu Met Ser Pro Leu Leu Gly Leu
1               5

<210> SEQ ID NO 91
<211> LENGTH: 9
<212> TYPE: PRT
<213> ORGANISM: Homo sapiens

<400> SEQUENCE: 91

Ser Ile Met Lys Gly Met Ile Pro Leu
1               5

<210> SEQ ID NO 92
<211> LENGTH: 9
<212> TYPE: PRT
<213> ORGANISM: Homo sapiens

<400> SEQUENCE: 92

Leu Leu Phe Gly Ile Asn Gln Ala Leu
1               5

<210> SEQ ID NO 93
<211> LENGTH: 9
<212> TYPE: PRT
<213> ORGANISM: Homo sapiens

<400> SEQUENCE: 93
```

Phe Thr Leu Cys Leu Ser Leu Met Val
1               5

<210> SEQ ID NO 94
<211> LENGTH: 9
<212> TYPE: PRT
<213> ORGANISM: Homo sapiens

<400> SEQUENCE: 94

Trp Leu Leu Thr Arg Pro Ile Phe Leu
1               5

<210> SEQ ID NO 95
<211> LENGTH: 9
<212> TYPE: PRT
<213> ORGANISM: Homo sapiens

<400> SEQUENCE: 95

Cys Met Leu Asp Met Phe Val Leu Ile
1               5

<210> SEQ ID NO 96
<211> LENGTH: 9
<212> TYPE: PRT
<213> ORGANISM: Homo sapiens

<400> SEQUENCE: 96

Ile Val Trp Glu Val Leu Phe Val Leu
1               5

<210> SEQ ID NO 97
<211> LENGTH: 9
<212> TYPE: PRT
<213> ORGANISM: Homo sapiens

<400> SEQUENCE: 97

Phe Leu Gln Thr Cys Asn Leu Pro Ile
1               5

<210> SEQ ID NO 98
<211> LENGTH: 9
<212> TYPE: PRT
<213> ORGANISM: Homo sapiens

<400> SEQUENCE: 98

Phe Leu Phe Gln Asp Leu Ala Val Thr
1               5

<210> SEQ ID NO 99
<211> LENGTH: 9
<212> TYPE: PRT
<213> ORGANISM: Homo sapiens

<400> SEQUENCE: 99

Asn Leu Phe Lys Gly Phe Tyr Thr Ala
1               5

<210> SEQ ID NO 100
<211> LENGTH: 9
<212> TYPE: PRT
<213> ORGANISM: Homo sapiens

<400> SEQUENCE: 100

Tyr Leu Tyr Thr Thr Asp Thr Gly Leu
1               5

<210> SEQ ID NO 101
<211> LENGTH: 9
<212> TYPE: PRT
<213> ORGANISM: Homo sapiens

<400> SEQUENCE: 101

Leu Leu Ser Pro Lys Asp Trp Gly Leu
1               5

<210> SEQ ID NO 102
<211> LENGTH: 9
<212> TYPE: PRT
<213> ORGANISM: Homo sapiens

<400> SEQUENCE: 102

Thr Met Ser Leu Asn Leu Ile Thr Val
1               5

<210> SEQ ID NO 103
<211> LENGTH: 9
<212> TYPE: PRT
<213> ORGANISM: Homo sapiens

<400> SEQUENCE: 103

Gly Leu Ala Asp Phe Ala Asp Ser Leu
1               5

<210> SEQ ID NO 104
<211> LENGTH: 9
<212> TYPE: PRT
<213> ORGANISM: Homo sapiens

<400> SEQUENCE: 104

Ile Leu Leu Pro Ile Pro Val Leu Leu
1               5

<210> SEQ ID NO 105
<211> LENGTH: 9
<212> TYPE: PRT
<213> ORGANISM: Homo sapiens

<400> SEQUENCE: 105

Leu Leu Thr Arg Pro Ile Phe Leu Val
1               5

<210> SEQ ID NO 106
<211> LENGTH: 9
<212> TYPE: PRT
<213> ORGANISM: Homo sapiens

<400> SEQUENCE: 106

Phe Leu Val Leu Leu Phe Val Ala Val
1               5

<210> SEQ ID NO 107
<211> LENGTH: 9
<212> TYPE: PRT
<213> ORGANISM: Homo sapiens

<400> SEQUENCE: 107

Phe Met Met Ser Tyr Glu Arg Ser Met
1               5

```
<210> SEQ ID NO 108
<211> LENGTH: 9
<212> TYPE: PRT
<213> ORGANISM: Homo sapiens

<400> SEQUENCE: 108

Met Leu Cys Asn Gly Leu Val Leu Leu
1               5

<210> SEQ ID NO 109
<211> LENGTH: 9
<212> TYPE: PRT
<213> ORGANISM: Homo sapiens

<400> SEQUENCE: 109

Leu Ile Ala Ala Met Leu Glu Leu Val
1               5

<210> SEQ ID NO 110
<211> LENGTH: 9
<212> TYPE: PRT
<213> ORGANISM: Homo sapiens

<400> SEQUENCE: 110

Leu Met Ala Asn Arg Phe Asp Asn Val
1               5

<210> SEQ ID NO 111
<211> LENGTH: 9
<212> TYPE: PRT
<213> ORGANISM: Homo sapiens

<400> SEQUENCE: 111

Leu Leu Asp Ile Ser Phe Phe Ala Leu
1               5

<210> SEQ ID NO 112
<211> LENGTH: 9
<212> TYPE: PRT
<213> ORGANISM: Homo sapiens

<400> SEQUENCE: 112

Gln Leu Leu Asp Gly Lys Val Thr Val
1               5

<210> SEQ ID NO 113
<211> LENGTH: 9
<212> TYPE: PRT
<213> ORGANISM: Homo sapiens

<400> SEQUENCE: 113

Ala Leu Ile Gln Val Gln Thr Thr Val
1               5

<210> SEQ ID NO 114
<211> LENGTH: 9
<212> TYPE: PRT
<213> ORGANISM: Homo sapiens

<400> SEQUENCE: 114

Phe Leu Val Trp Asn Asn Val Leu Leu
1               5

<210> SEQ ID NO 115
<211> LENGTH: 9
```

```
<212> TYPE: PRT
<213> ORGANISM: Homo sapiens

<400> SEQUENCE: 115

Leu Ile Ile Asp Ser Asn Leu Glu Val
1               5

<210> SEQ ID NO 116
<211> LENGTH: 9
<212> TYPE: PRT
<213> ORGANISM: Homo sapiens

<400> SEQUENCE: 116

Tyr Leu His Ser Ile Trp His Val Ile
1               5

<210> SEQ ID NO 117
<211> LENGTH: 9
<212> TYPE: PRT
<213> ORGANISM: Homo sapiens

<400> SEQUENCE: 117

Thr Ile Ile Leu Ala Leu Met Tyr Val
1               5

<210> SEQ ID NO 118
<211> LENGTH: 9
<212> TYPE: PRT
<213> ORGANISM: Homo sapiens

<400> SEQUENCE: 118

Val Leu Thr Ser Leu Pro Ala Leu Val
1               5

<210> SEQ ID NO 119
<211> LENGTH: 9
<212> TYPE: PRT
<213> ORGANISM: Homo sapiens

<400> SEQUENCE: 119

Ile Leu Ser Asn Arg Thr Val Leu Val
1               5

<210> SEQ ID NO 120
<211> LENGTH: 9
<212> TYPE: PRT
<213> ORGANISM: Homo sapiens

<400> SEQUENCE: 120

Lys Leu Cys Cys Ala Ser Ile Lys Val
1               5

<210> SEQ ID NO 121
<211> LENGTH: 9
<212> TYPE: PRT
<213> ORGANISM: Homo sapiens

<400> SEQUENCE: 121

Met Leu Pro Gly Phe Pro His Arg Leu
1               5

<210> SEQ ID NO 122
<211> LENGTH: 9
<212> TYPE: PRT
<213> ORGANISM: Homo sapiens
```

```
<400> SEQUENCE: 122

Ser Leu His Thr Ala Val Ala Glu Val
1               5

<210> SEQ ID NO 123
<211> LENGTH: 9
<212> TYPE: PRT
<213> ORGANISM: Homo sapiens

<400> SEQUENCE: 123

His Leu Phe Leu His Leu Pro Lys Leu
1               5

<210> SEQ ID NO 124
<211> LENGTH: 9
<212> TYPE: PRT
<213> ORGANISM: Homo sapiens

<400> SEQUENCE: 124

Gln Leu Ile Ala Gly Ile Leu Tyr Ala
1               5

<210> SEQ ID NO 125
<211> LENGTH: 9
<212> TYPE: PRT
<213> ORGANISM: Homo sapiens

<400> SEQUENCE: 125

Lys Leu Val Asn Gln Ser Tyr Met Ile
1               5

<210> SEQ ID NO 126
<211> LENGTH: 9
<212> TYPE: PRT
<213> ORGANISM: Homo sapiens

<400> SEQUENCE: 126

Ser Ile Ser Cys Ala Val Trp Phe Ala
1               5

<210> SEQ ID NO 127
<211> LENGTH: 9
<212> TYPE: PRT
<213> ORGANISM: Homo sapiens

<400> SEQUENCE: 127

Met Leu Leu Glu Gly Leu Tyr Leu Phe
1               5

<210> SEQ ID NO 128
<211> LENGTH: 9
<212> TYPE: PRT
<213> ORGANISM: Homo sapiens

<400> SEQUENCE: 128

Phe Val Leu Gln Ala Asn Phe Ile Val
1               5

<210> SEQ ID NO 129
<211> LENGTH: 9
<212> TYPE: PRT
<213> ORGANISM: Homo sapiens

<400> SEQUENCE: 129
```

Met Leu Asp Arg Leu Leu Ser Ala Ile
1               5

<210> SEQ ID NO 130
<211> LENGTH: 9
<212> TYPE: PRT
<213> ORGANISM: Homo sapiens

<400> SEQUENCE: 130

Tyr Ile Leu His Gln Lys Pro Phe Val
1               5

<210> SEQ ID NO 131
<211> LENGTH: 9
<212> TYPE: PRT
<213> ORGANISM: Homo sapiens

<400> SEQUENCE: 131

Asn Met Asn Gln Cys Thr Tyr Val Val
1               5

<210> SEQ ID NO 132
<211> LENGTH: 9
<212> TYPE: PRT
<213> ORGANISM: Homo sapiens

<400> SEQUENCE: 132

Phe Ala Met Tyr Asp Glu Thr Phe Val
1               5

<210> SEQ ID NO 133
<211> LENGTH: 9
<212> TYPE: PRT
<213> ORGANISM: Homo sapiens

<400> SEQUENCE: 133

Ser Val Ile Tyr Ile Ile Glu Ala Val
1               5

<210> SEQ ID NO 134
<211> LENGTH: 9
<212> TYPE: PRT
<213> ORGANISM: Homo sapiens

<400> SEQUENCE: 134

Ala Leu Leu Pro Ser Thr Thr Asp Val
1               5

<210> SEQ ID NO 135
<211> LENGTH: 9
<212> TYPE: PRT
<213> ORGANISM: Homo sapiens

<400> SEQUENCE: 135

Val Leu Leu Gln Phe Ser Thr Gly Leu
1               5

<210> SEQ ID NO 136
<211> LENGTH: 9
<212> TYPE: PRT
<213> ORGANISM: Homo sapiens

<400> SEQUENCE: 136

Ala Leu Gln Ala Gly Thr Val Gly Val

```
1               5

<210> SEQ ID NO 137
<211> LENGTH: 9
<212> TYPE: PRT
<213> ORGANISM: Homo sapiens

<400> SEQUENCE: 137

Gln Val Val Lys Tyr Pro Phe Tyr Val
1               5

<210> SEQ ID NO 138
<211> LENGTH: 9
<212> TYPE: PRT
<213> ORGANISM: Homo sapiens

<400> SEQUENCE: 138

Lys Val Leu Phe Ile Pro Phe Arg Val
1               5

<210> SEQ ID NO 139
<211> LENGTH: 9
<212> TYPE: PRT
<213> ORGANISM: Homo sapiens

<400> SEQUENCE: 139

Trp Gln Leu Phe Phe Tyr Val Thr Val
1               5

<210> SEQ ID NO 140
<211> LENGTH: 9
<212> TYPE: PRT
<213> ORGANISM: Homo sapiens

<400> SEQUENCE: 140

Tyr Leu Gln Ile Ile Thr Gln Leu Ile
1               5

<210> SEQ ID NO 141
<211> LENGTH: 9
<212> TYPE: PRT
<213> ORGANISM: Homo sapiens

<400> SEQUENCE: 141

Ile Leu His Glu Met Met Asp Glu Ile
1               5

<210> SEQ ID NO 142
<211> LENGTH: 9
<212> TYPE: PRT
<213> ORGANISM: Homo sapiens

<400> SEQUENCE: 142

Ser Thr Ile Ser Ser Ser Phe Leu Val
1               5

<210> SEQ ID NO 143
<211> LENGTH: 9
<212> TYPE: PRT
<213> ORGANISM: Homo sapiens

<400> SEQUENCE: 143

Ser Val Leu Glu Asn Gly Trp Glu Ile
1               5
```

```
<210> SEQ ID NO 144
<211> LENGTH: 9
<212> TYPE: PRT
<213> ORGANISM: Homo sapiens

<400> SEQUENCE: 144

Thr Leu Met Pro Asn Thr Ser Asn Leu
1               5

<210> SEQ ID NO 145
<211> LENGTH: 9
<212> TYPE: PRT
<213> ORGANISM: Homo sapiens

<400> SEQUENCE: 145

Gly Ile Tyr Gln Gln Cys Trp Leu Val
1               5

<210> SEQ ID NO 146
<211> LENGTH: 9
<212> TYPE: PRT
<213> ORGANISM: Homo sapiens

<400> SEQUENCE: 146

Tyr Leu Lys Phe Asn Ile Tyr Leu Ala
1               5

<210> SEQ ID NO 147
<211> LENGTH: 9
<212> TYPE: PRT
<213> ORGANISM: Homo sapiens

<400> SEQUENCE: 147

Leu Leu Gln Asp Phe Glu Ala Thr Leu
1               5

<210> SEQ ID NO 148
<211> LENGTH: 9
<212> TYPE: PRT
<213> ORGANISM: Homo sapiens

<400> SEQUENCE: 148

Lys Val Phe Asn Thr Ile Tyr Ser Leu
1               5

<210> SEQ ID NO 149
<211> LENGTH: 9
<212> TYPE: PRT
<213> ORGANISM: Homo sapiens

<400> SEQUENCE: 149

Trp Met Ser Ser Val Glu Glu Ala Val
1               5

<210> SEQ ID NO 150
<211> LENGTH: 9
<212> TYPE: PRT
<213> ORGANISM: Homo sapiens

<400> SEQUENCE: 150

Thr Leu Asn Ile Asn Leu Phe Pro Ala
1               5

<210> SEQ ID NO 151
```

```
<211> LENGTH: 9
<212> TYPE: PRT
<213> ORGANISM: Homo sapiens

<400> SEQUENCE: 151

His Leu Val Pro Tyr Ile Ile Asp Leu
1               5

<210> SEQ ID NO 152
<211> LENGTH: 9
<212> TYPE: PRT
<213> ORGANISM: Homo sapiens

<400> SEQUENCE: 152

Met Leu Phe Pro Glu Thr Lys Gly Ile
1               5

<210> SEQ ID NO 153
<211> LENGTH: 9
<212> TYPE: PRT
<213> ORGANISM: Homo sapiens

<400> SEQUENCE: 153

Val Met Leu Glu Ile Glu Glu Pro Ala
1               5

<210> SEQ ID NO 154
<211> LENGTH: 9
<212> TYPE: PRT
<213> ORGANISM: Homo sapiens

<400> SEQUENCE: 154

Phe Ile Leu Leu Lys Leu Leu Lys Val
1               5

<210> SEQ ID NO 155
<211> LENGTH: 9
<212> TYPE: PRT
<213> ORGANISM: Homo sapiens

<400> SEQUENCE: 155

Ser Leu Val Ala Gly Val Pro Val Leu
1               5

<210> SEQ ID NO 156
<211> LENGTH: 9
<212> TYPE: PRT
<213> ORGANISM: Homo sapiens

<400> SEQUENCE: 156

Val Thr Trp Leu Ile Ser Phe Gly Val
1               5

<210> SEQ ID NO 157
<211> LENGTH: 9
<212> TYPE: PRT
<213> ORGANISM: Homo sapiens

<400> SEQUENCE: 157

Arg Leu Tyr Ser Thr Val Cys Ala Leu
1               5

<210> SEQ ID NO 158
<211> LENGTH: 9
<212> TYPE: PRT
```

<213> ORGANISM: Homo sapiens

<400> SEQUENCE: 158

Val Met Ala Gln Thr Glu Pro Thr Val
1               5

<210> SEQ ID NO 159
<211> LENGTH: 9
<212> TYPE: PRT
<213> ORGANISM: Homo sapiens

<400> SEQUENCE: 159

Leu Leu Phe Glu Tyr Leu Ala Leu Phe
1               5

<210> SEQ ID NO 160
<211> LENGTH: 9
<212> TYPE: PRT
<213> ORGANISM: Homo sapiens

<400> SEQUENCE: 160

Gly Leu Phe Val Val Leu Ile Leu Val
1               5

<210> SEQ ID NO 161
<211> LENGTH: 9
<212> TYPE: PRT
<213> ORGANISM: Homo sapiens

<400> SEQUENCE: 161

Ile Val Ile Arg Ile Ser Pro Glu Val
1               5

<210> SEQ ID NO 162
<211> LENGTH: 9
<212> TYPE: PRT
<213> ORGANISM: Homo sapiens

<400> SEQUENCE: 162

Ser Thr Phe Ala Lys Val Ser Phe Val
1               5

<210> SEQ ID NO 163
<211> LENGTH: 9
<212> TYPE: PRT
<213> ORGANISM: Homo sapiens

<400> SEQUENCE: 163

Tyr Val Met Ala Val Val Asp Asn Ala
1               5

<210> SEQ ID NO 164
<211> LENGTH: 9
<212> TYPE: PRT
<213> ORGANISM: Homo sapiens

<400> SEQUENCE: 164

Val Gln Ile Glu Arg Leu Asp Thr Val
1               5

<210> SEQ ID NO 165
<211> LENGTH: 9
<212> TYPE: PRT
<213> ORGANISM: Homo sapiens

```
<400> SEQUENCE: 165

His Leu Leu Phe Ala Asn Leu Tyr Leu
1               5

<210> SEQ ID NO 166
<211> LENGTH: 9
<212> TYPE: PRT
<213> ORGANISM: Homo sapiens

<400> SEQUENCE: 166

Ser Ile Thr Asn Ala Ile Ala Pro Val
1               5

<210> SEQ ID NO 167
<211> LENGTH: 9
<212> TYPE: PRT
<213> ORGANISM: Homo sapiens

<400> SEQUENCE: 167

Phe Val Phe Cys Gln Gly Phe Leu Ala
1               5

<210> SEQ ID NO 168
<211> LENGTH: 9
<212> TYPE: PRT
<213> ORGANISM: Homo sapiens

<400> SEQUENCE: 168

Val Leu Gln Glu Ala Asp Ile Leu Leu
1               5

<210> SEQ ID NO 169
<211> LENGTH: 9
<212> TYPE: PRT
<213> ORGANISM: Homo sapiens

<400> SEQUENCE: 169

His Met Ile His Trp Asn Ser Thr Leu
1               5

<210> SEQ ID NO 170
<211> LENGTH: 9
<212> TYPE: PRT
<213> ORGANISM: Homo sapiens

<400> SEQUENCE: 170

Ser Ile Val Asn Phe Leu Met Thr Ile
1               5

<210> SEQ ID NO 171
<211> LENGTH: 9
<212> TYPE: PRT
<213> ORGANISM: Homo sapiens

<400> SEQUENCE: 171

Leu Leu Arg Leu Tyr Thr Pro Phe Val
1               5

<210> SEQ ID NO 172
<211> LENGTH: 9
<212> TYPE: PRT
<213> ORGANISM: Homo sapiens

<400> SEQUENCE: 172
```

Met Leu Thr Leu Met Ser Pro Leu Leu
1               5

<210> SEQ ID NO 173
<211> LENGTH: 9
<212> TYPE: PRT
<213> ORGANISM: Homo sapiens

<400> SEQUENCE: 173

Ser Leu Val Met Val Tyr Ala Gly Val
1               5

<210> SEQ ID NO 174
<211> LENGTH: 9
<212> TYPE: PRT
<213> ORGANISM: Homo sapiens

<400> SEQUENCE: 174

Asn Ile Ala Met Thr Leu Pro Thr Val
1               5

<210> SEQ ID NO 175
<211> LENGTH: 9
<212> TYPE: PRT
<213> ORGANISM: Homo sapiens

<400> SEQUENCE: 175

Tyr Leu Asp Leu Ser Pro Asn Asn Leu
1               5

<210> SEQ ID NO 176
<211> LENGTH: 9
<212> TYPE: PRT
<213> ORGANISM: Homo sapiens

<400> SEQUENCE: 176

Ile Val Trp Glu Val Leu Leu Leu Leu
1               5

<210> SEQ ID NO 177
<211> LENGTH: 9
<212> TYPE: PRT
<213> ORGANISM: Homo sapiens

<400> SEQUENCE: 177

Leu Met Ser Met Trp Val Thr Val Ile
1               5

<210> SEQ ID NO 178
<211> LENGTH: 9
<212> TYPE: PRT
<213> ORGANISM: Homo sapiens

<400> SEQUENCE: 178

Ser Leu Thr Phe Leu Phe Phe Met Leu
1               5

<210> SEQ ID NO 179
<211> LENGTH: 9
<212> TYPE: PRT
<213> ORGANISM: Homo sapiens

<400> SEQUENCE: 179

Tyr Phe Leu Pro Ala Ser Phe Pro Ile
1               5

<210> SEQ ID NO 180
<211> LENGTH: 9
<212> TYPE: PRT
<213> ORGANISM: Homo sapiens

<400> SEQUENCE: 180

Ser Leu Phe Leu Phe Leu Val Leu Leu
1               5

<210> SEQ ID NO 181
<211> LENGTH: 9
<212> TYPE: PRT
<213> ORGANISM: Homo sapiens

<400> SEQUENCE: 181

Gly Ile Leu Asn Phe Tyr Met Phe Leu
1               5

<210> SEQ ID NO 182
<211> LENGTH: 9
<212> TYPE: PRT
<213> ORGANISM: Homo sapiens

<400> SEQUENCE: 182

Pro Leu Met Ser Val Val Gln Ser Val
1               5

<210> SEQ ID NO 183
<211> LENGTH: 9
<212> TYPE: PRT
<213> ORGANISM: Homo sapiens

<400> SEQUENCE: 183

Leu Val Met Thr Ser Tyr Ser Ser Val
1               5

<210> SEQ ID NO 184
<211> LENGTH: 9
<212> TYPE: PRT
<213> ORGANISM: Homo sapiens

<400> SEQUENCE: 184

Arg Leu Ile Arg Lys Thr Glu Glu Val
1               5

<210> SEQ ID NO 185
<211> LENGTH: 9
<212> TYPE: PRT
<213> ORGANISM: Homo sapiens

<400> SEQUENCE: 185

Phe Met Tyr Trp Thr Arg Asn Gly Ile
1               5

<210> SEQ ID NO 186
<211> LENGTH: 9
<212> TYPE: PRT
<213> ORGANISM: Homo sapiens

<400> SEQUENCE: 186

Leu Met Gly Gly Thr Val Asp Met Val
1               5

```
<210> SEQ ID NO 187
<211> LENGTH: 9
<212> TYPE: PRT
<213> ORGANISM: Homo sapiens

<400> SEQUENCE: 187

Lys Leu Leu Phe Glu Tyr Leu Ala Leu
1               5

<210> SEQ ID NO 188
<211> LENGTH: 9
<212> TYPE: PRT
<213> ORGANISM: Homo sapiens

<400> SEQUENCE: 188

Ser Leu Leu Leu Ile His Gln Gly Val
1               5

<210> SEQ ID NO 189
<211> LENGTH: 9
<212> TYPE: PRT
<213> ORGANISM: Homo sapiens

<400> SEQUENCE: 189

Leu Leu Gly Ser Leu Val Thr His Ile
1               5

<210> SEQ ID NO 190
<211> LENGTH: 9
<212> TYPE: PRT
<213> ORGANISM: Homo sapiens

<400> SEQUENCE: 190

Leu Leu Asp Tyr Ser Val Pro Val Leu
1               5

<210> SEQ ID NO 191
<211> LENGTH: 9
<212> TYPE: PRT
<213> ORGANISM: Homo sapiens

<400> SEQUENCE: 191

Val Ile Val Gly Asn Ile Tyr Phe Leu
1               5

<210> SEQ ID NO 192
<211> LENGTH: 9
<212> TYPE: PRT
<213> ORGANISM: Homo sapiens

<400> SEQUENCE: 192

Phe Ile Ala Lys Lys Val Thr Gly Ile
1               5

<210> SEQ ID NO 193
<211> LENGTH: 9
<212> TYPE: PRT
<213> ORGANISM: Homo sapiens

<400> SEQUENCE: 193

Ala Leu Leu Tyr Tyr Ser Val Pro Val
1               5

<210> SEQ ID NO 194
<211> LENGTH: 9
```

```
<212> TYPE: PRT
<213> ORGANISM: Homo sapiens

<400> SEQUENCE: 194

Phe Leu Ala Glu Val Pro Asn Arg Leu
1               5

<210> SEQ ID NO 195
<211> LENGTH: 9
<212> TYPE: PRT
<213> ORGANISM: Homo sapiens

<400> SEQUENCE: 195

Lys Leu Leu Ser Lys Tyr Val Pro Val
1               5

<210> SEQ ID NO 196
<211> LENGTH: 9
<212> TYPE: PRT
<213> ORGANISM: Homo sapiens

<400> SEQUENCE: 196

Met Leu His Ser Thr Ser Val Pro Val
1               5

<210> SEQ ID NO 197
<211> LENGTH: 9
<212> TYPE: PRT
<213> ORGANISM: Homo sapiens

<400> SEQUENCE: 197

Arg Leu Gly Glu His Asn Ile Glu Val
1               5

<210> SEQ ID NO 198
<211> LENGTH: 9
<212> TYPE: PRT
<213> ORGANISM: Homo sapiens

<400> SEQUENCE: 198

Leu Leu Phe Glu Phe Leu Phe Phe Ile
1               5

<210> SEQ ID NO 199
<211> LENGTH: 9
<212> TYPE: PRT
<213> ORGANISM: Homo sapiens

<400> SEQUENCE: 199

Ala Leu Leu Gly Ile Ser Phe Phe Ala
1               5

<210> SEQ ID NO 200
<211> LENGTH: 9
<212> TYPE: PRT
<213> ORGANISM: Homo sapiens

<400> SEQUENCE: 200

Asn Leu Trp Gln Leu Phe Phe His Val
1               5

<210> SEQ ID NO 201
<211> LENGTH: 9
<212> TYPE: PRT
<213> ORGANISM: Homo sapiens
```

<400> SEQUENCE: 201

Tyr Met Cys Ser Phe Leu Phe Asn Leu
1               5

<210> SEQ ID NO 202
<211> LENGTH: 9
<212> TYPE: PRT
<213> ORGANISM: Homo sapiens

<400> SEQUENCE: 202

Arg Thr Ala Asp Pro Leu Trp Ala Leu
1               5

<210> SEQ ID NO 203
<211> LENGTH: 9
<212> TYPE: PRT
<213> ORGANISM: Homo sapiens

<400> SEQUENCE: 203

Leu Leu Ser Asp Cys Met Trp Glu Thr
1               5

<210> SEQ ID NO 204
<211> LENGTH: 9
<212> TYPE: PRT
<213> ORGANISM: Homo sapiens

<400> SEQUENCE: 204

Met Ile Leu Gly Ser Leu Leu Tyr Val
1               5

<210> SEQ ID NO 205
<211> LENGTH: 9
<212> TYPE: PRT
<213> ORGANISM: Homo sapiens

<400> SEQUENCE: 205

Val Leu Ala Asp Ala Phe Tyr Gly Ile
1               5

<210> SEQ ID NO 206
<211> LENGTH: 9
<212> TYPE: PRT
<213> ORGANISM: Homo sapiens

<400> SEQUENCE: 206

Tyr Leu Val Thr Gly Val Thr Thr Val
1               5

<210> SEQ ID NO 207
<211> LENGTH: 9
<212> TYPE: PRT
<213> ORGANISM: Homo sapiens

<400> SEQUENCE: 207

Ser Leu Met Ser Val Trp Val Thr Val
1               5

<210> SEQ ID NO 208
<211> LENGTH: 9
<212> TYPE: PRT
<213> ORGANISM: Homo sapiens

<400> SEQUENCE: 208

Leu Met Ile Lys Asp Gln Ile Glu Val
1               5

<210> SEQ ID NO 209
<211> LENGTH: 9
<212> TYPE: PRT
<213> ORGANISM: Homo sapiens

<400> SEQUENCE: 209

Tyr Leu Leu Arg Asp Ser Glu Ser Val
1               5

<210> SEQ ID NO 210
<211> LENGTH: 9
<212> TYPE: PRT
<213> ORGANISM: Homo sapiens

<400> SEQUENCE: 210

Phe Met Asp Ser Phe Val Asn Val Val
1               5

<210> SEQ ID NO 211
<211> LENGTH: 9
<212> TYPE: PRT
<213> ORGANISM: Homo sapiens

<400> SEQUENCE: 211

Phe Leu Met Glu Ala Asp Leu Gly Val
1               5

<210> SEQ ID NO 212
<211> LENGTH: 9
<212> TYPE: PRT
<213> ORGANISM: Homo sapiens

<400> SEQUENCE: 212

Met Leu Asn Pro Leu Ile Tyr Ser Leu
1               5

<210> SEQ ID NO 213
<211> LENGTH: 9
<212> TYPE: PRT
<213> ORGANISM: Homo sapiens

<400> SEQUENCE: 213

Tyr Met Ala Ser Leu Phe Leu Gly Ile
1               5

<210> SEQ ID NO 214
<211> LENGTH: 9
<212> TYPE: PRT
<213> ORGANISM: Homo sapiens

<400> SEQUENCE: 214

Phe Val Trp Phe Ser Val Ala Ala Val
1               5

<210> SEQ ID NO 215
<211> LENGTH: 9
<212> TYPE: PRT
<213> ORGANISM: Homo sapiens

<400> SEQUENCE: 215

Gly Leu Leu Ala Val Ala Phe Leu Val

```
1               5
```

<210> SEQ ID NO 216
<211> LENGTH: 9
<212> TYPE: PRT
<213> ORGANISM: Homo sapiens

<400> SEQUENCE: 216

```
Lys Leu Ala Lys Leu Ala Phe Trp Leu
1               5
```

<210> SEQ ID NO 217
<211> LENGTH: 9
<212> TYPE: PRT
<213> ORGANISM: Homo sapiens

<400> SEQUENCE: 217

```
Leu Leu Ala Gln Glu Leu Leu Pro Leu
1               5
```

<210> SEQ ID NO 218
<211> LENGTH: 9
<212> TYPE: PRT
<213> ORGANISM: Homo sapiens

<400> SEQUENCE: 218

```
Ile Leu Met Lys Ser Phe Leu Ser Val
1               5
```

<210> SEQ ID NO 219
<211> LENGTH: 9
<212> TYPE: PRT
<213> ORGANISM: Homo sapiens

<400> SEQUENCE: 219

```
Thr Leu Leu Asp Ala Leu Tyr Glu Ile
1               5
```

<210> SEQ ID NO 220
<211> LENGTH: 9
<212> TYPE: PRT
<213> ORGANISM: Homo sapiens

<400> SEQUENCE: 220

```
Ala Leu Phe Pro His Pro Gln His Ala
1               5
```

<210> SEQ ID NO 221
<211> LENGTH: 9
<212> TYPE: PRT
<213> ORGANISM: Homo sapiens

<400> SEQUENCE: 221

```
Ser Leu Ile His Val Ala Ala Tyr Ala
1               5
```

<210> SEQ ID NO 222
<211> LENGTH: 9
<212> TYPE: PRT
<213> ORGANISM: Homo sapiens

<400> SEQUENCE: 222

```
Arg Met Met Met Gly Ala Trp Trp Leu
1               5
```

<210> SEQ ID NO 223
<211> LENGTH: 9
<212> TYPE: PRT
<213> ORGANISM: Homo sapiens

<400> SEQUENCE: 223

Tyr Leu Ile Ser Leu Phe Leu Ile Ile
1               5

<210> SEQ ID NO 224
<211> LENGTH: 9
<212> TYPE: PRT
<213> ORGANISM: Homo sapiens

<400> SEQUENCE: 224

Leu Leu Tyr Ser Leu Ala Ala Gly Val
1               5

<210> SEQ ID NO 225
<211> LENGTH: 9
<212> TYPE: PRT
<213> ORGANISM: Homo sapiens

<400> SEQUENCE: 225

Leu Leu Pro Tyr Tyr Val Phe Glu Val
1               5

<210> SEQ ID NO 226
<211> LENGTH: 9
<212> TYPE: PRT
<213> ORGANISM: Homo sapiens

<400> SEQUENCE: 226

Ser Leu Phe Asp Leu Leu Ser Thr Leu
1               5

<210> SEQ ID NO 227
<211> LENGTH: 9
<212> TYPE: PRT
<213> ORGANISM: Homo sapiens

<400> SEQUENCE: 227

Leu Leu Leu Gln Gly Leu Phe Ile Val
1               5

<210> SEQ ID NO 228
<211> LENGTH: 9
<212> TYPE: PRT
<213> ORGANISM: Homo sapiens

<400> SEQUENCE: 228

Met Leu Phe Asp Glu Tyr Gln Gly Leu
1               5

<210> SEQ ID NO 229
<211> LENGTH: 9
<212> TYPE: PRT
<213> ORGANISM: Homo sapiens

<400> SEQUENCE: 229

Ile Leu Phe Ala Asn Leu Tyr Leu Leu
1               5

<210> SEQ ID NO 230

```
<211> LENGTH: 9
<212> TYPE: PRT
<213> ORGANISM: Homo sapiens

<400> SEQUENCE: 230

Gly Leu Glu Glu Tyr Ser Pro Glu Ile
1               5

<210> SEQ ID NO 231
<211> LENGTH: 9
<212> TYPE: PRT
<213> ORGANISM: Homo sapiens

<400> SEQUENCE: 231

Ser Leu Val Ala Ile Ser Pro Trp Val
1               5

<210> SEQ ID NO 232
<211> LENGTH: 9
<212> TYPE: PRT
<213> ORGANISM: Homo sapiens

<400> SEQUENCE: 232

Leu Leu Ala Glu Met Gly Tyr Glu Val
1               5

<210> SEQ ID NO 233
<211> LENGTH: 9
<212> TYPE: PRT
<213> ORGANISM: Homo sapiens

<400> SEQUENCE: 233

Ala Leu Phe Trp Ser Leu Ala Pro Leu
1               5

<210> SEQ ID NO 234
<211> LENGTH: 9
<212> TYPE: PRT
<213> ORGANISM: Homo sapiens

<400> SEQUENCE: 234

Phe Val Leu Ile Val Leu Ser Tyr Val
1               5

<210> SEQ ID NO 235
<211> LENGTH: 9
<212> TYPE: PRT
<213> ORGANISM: Homo sapiens

<400> SEQUENCE: 235

Gln Leu Phe Leu Phe Thr Trp Ser Leu
1               5

<210> SEQ ID NO 236
<211> LENGTH: 9
<212> TYPE: PRT
<213> ORGANISM: Homo sapiens

<400> SEQUENCE: 236

Lys Leu Leu Glu Ser Leu Thr Pro Leu
1               5

<210> SEQ ID NO 237
<211> LENGTH: 9
<212> TYPE: PRT
```

-continued

```
<213> ORGANISM: Homo sapiens

<400> SEQUENCE: 237

Val Leu Asp Glu Tyr Phe Ser Arg Val
1               5

<210> SEQ ID NO 238
<211> LENGTH: 9
<212> TYPE: PRT
<213> ORGANISM: Homo sapiens

<400> SEQUENCE: 238

Ser Leu Gln Asp Gln Gly Asp Tyr Val
1               5

<210> SEQ ID NO 239
<211> LENGTH: 9
<212> TYPE: PRT
<213> ORGANISM: Homo sapiens

<400> SEQUENCE: 239

Lys Leu Ala Phe Trp Leu Leu Ala Val
1               5

<210> SEQ ID NO 240
<211> LENGTH: 9
<212> TYPE: PRT
<213> ORGANISM: Homo sapiens

<400> SEQUENCE: 240

Phe Leu Phe Ser Val Leu Leu Phe Val
1               5

<210> SEQ ID NO 241
<211> LENGTH: 9
<212> TYPE: PRT
<213> ORGANISM: Homo sapiens

<400> SEQUENCE: 241

Phe Ile Asn Glu Leu Val Leu Phe Ile
1               5

<210> SEQ ID NO 242
<211> LENGTH: 9
<212> TYPE: PRT
<213> ORGANISM: Homo sapiens

<400> SEQUENCE: 242

Val Leu Ser Lys Val Ile Glu Ala Val
1               5

<210> SEQ ID NO 243
<211> LENGTH: 9
<212> TYPE: PRT
<213> ORGANISM: Homo sapiens

<400> SEQUENCE: 243

Ser Met Gln Asp Cys Ala Phe Pro Leu
1               5

<210> SEQ ID NO 244
<211> LENGTH: 9
<212> TYPE: PRT
<213> ORGANISM: Homo sapiens
```

<400> SEQUENCE: 244

Arg Ile Tyr Asp Glu Val Phe Glu Leu
1               5

<210> SEQ ID NO 245
<211> LENGTH: 9
<212> TYPE: PRT
<213> ORGANISM: Homo sapiens

<400> SEQUENCE: 245

Val Ile Met Ser Gln Tyr Leu Glu Leu
1               5

<210> SEQ ID NO 246
<211> LENGTH: 9
<212> TYPE: PRT
<213> ORGANISM: Homo sapiens

<400> SEQUENCE: 246

Ala Leu Leu Thr Phe Gly Pro Leu Val
1               5

<210> SEQ ID NO 247
<211> LENGTH: 9
<212> TYPE: PRT
<213> ORGANISM: Homo sapiens

<400> SEQUENCE: 247

Thr Met Leu Asn Gln Leu Tyr Gln Leu
1               5

<210> SEQ ID NO 248
<211> LENGTH: 9
<212> TYPE: PRT
<213> ORGANISM: Homo sapiens

<400> SEQUENCE: 248

Leu Leu Gln Cys Tyr Ala Phe Arg Ala
1               5

<210> SEQ ID NO 249
<211> LENGTH: 9
<212> TYPE: PRT
<213> ORGANISM: Homo sapiens

<400> SEQUENCE: 249

Ala Leu Ala Arg Leu Pro Ala Leu Val
1               5

<210> SEQ ID NO 250
<211> LENGTH: 9
<212> TYPE: PRT
<213> ORGANISM: Homo sapiens

<400> SEQUENCE: 250

Phe Leu Ser Ser Ile Glu Leu Leu Ile
1               5

<210> SEQ ID NO 251
<211> LENGTH: 9
<212> TYPE: PRT
<213> ORGANISM: Homo sapiens

<400> SEQUENCE: 251

```
Ser Leu Arg Glu Phe Ser Asn Phe Leu
1               5
```

<210> SEQ ID NO 252
<211> LENGTH: 9
<212> TYPE: PRT
<213> ORGANISM: Homo sapiens

<400> SEQUENCE: 252

```
Ala Leu Lys Tyr Leu Leu His Leu Val
1               5
```

<210> SEQ ID NO 253
<211> LENGTH: 9
<212> TYPE: PRT
<213> ORGANISM: Homo sapiens

<400> SEQUENCE: 253

```
Val Leu Met Glu Ser Val Trp Asn Met
1               5
```

<210> SEQ ID NO 254
<211> LENGTH: 9
<212> TYPE: PRT
<213> ORGANISM: Homo sapiens

<400> SEQUENCE: 254

```
Leu Val Met Phe Arg Asp Val Ala Val
1               5
```

<210> SEQ ID NO 255
<211> LENGTH: 9
<212> TYPE: PRT
<213> ORGANISM: Homo sapiens

<400> SEQUENCE: 255

```
Ala Ser Val Glu Cys Ile Ser Pro Val
1               5
```

<210> SEQ ID NO 256
<211> LENGTH: 9
<212> TYPE: PRT
<213> ORGANISM: Homo sapiens

<400> SEQUENCE: 256

```
Gln Met Val Asp Glu Leu Glu Ala Val
1               5
```

<210> SEQ ID NO 257
<211> LENGTH: 9
<212> TYPE: PRT
<213> ORGANISM: Homo sapiens

<400> SEQUENCE: 257

```
Leu Val Ser Ser Ser Arg Trp Leu Val
1               5
```

<210> SEQ ID NO 258
<211> LENGTH: 9
<212> TYPE: PRT
<213> ORGANISM: Homo sapiens

<400> SEQUENCE: 258

```
Ser Leu Phe Ser Tyr His Cys Trp Leu
1               5
```

<210> SEQ ID NO 259
<211> LENGTH: 9
<212> TYPE: PRT
<213> ORGANISM: Homo sapiens

<400> SEQUENCE: 259

Asp Leu Leu Gly Leu Thr Phe Arg Ile
1               5

<210> SEQ ID NO 260
<211> LENGTH: 9
<212> TYPE: PRT
<213> ORGANISM: Homo sapiens

<400> SEQUENCE: 260

Ala Ile Leu Gly Phe Thr Ser Pro Val
1               5

<210> SEQ ID NO 261
<211> LENGTH: 9
<212> TYPE: PRT
<213> ORGANISM: Homo sapiens

<400> SEQUENCE: 261

Val Leu Ser Trp Val Ser Phe Trp Ile
1               5

<210> SEQ ID NO 262
<211> LENGTH: 9
<212> TYPE: PRT
<213> ORGANISM: Homo sapiens

<400> SEQUENCE: 262

Val Ile Met Arg Val Asp Phe Asn Val
1               5

<210> SEQ ID NO 263
<211> LENGTH: 9
<212> TYPE: PRT
<213> ORGANISM: Homo sapiens

<400> SEQUENCE: 263

Ala Leu Trp Asp Leu Val Gln Phe Ala
1               5

<210> SEQ ID NO 264
<211> LENGTH: 9
<212> TYPE: PRT
<213> ORGANISM: Homo sapiens

<400> SEQUENCE: 264

Tyr Leu Ile Ser Leu Phe Leu Ile Ile
1               5

<210> SEQ ID NO 265
<211> LENGTH: 9
<212> TYPE: PRT
<213> ORGANISM: Homo sapiens

<400> SEQUENCE: 265

Tyr Met Asn Pro Tyr Gln Leu Asn Ala
1               5

<210> SEQ ID NO 266
<211> LENGTH: 9
<212> TYPE: PRT
<213> ORGANISM: Homo sapiens

<400> SEQUENCE: 266

Phe Thr Leu Ser Leu Ala Met Phe Leu
1               5

<210> SEQ ID NO 267
<211> LENGTH: 9
<212> TYPE: PRT
<213> ORGANISM: Homo sapiens

<400> SEQUENCE: 267

Met Leu Tyr Gly Arg Ile Gly Tyr Ile
1               5

<210> SEQ ID NO 268
<211> LENGTH: 9
<212> TYPE: PRT
<213> ORGANISM: Homo sapiens

<400> SEQUENCE: 268

Ile Leu Ile Ala Ala Ile Leu Glu Leu
1               5

<210> SEQ ID NO 269
<211> LENGTH: 9
<212> TYPE: PRT
<213> ORGANISM: Homo sapiens

<400> SEQUENCE: 269

Ser Leu Leu Pro Phe Ala Asn Glu Thr
1               5

<210> SEQ ID NO 270
<211> LENGTH: 9
<212> TYPE: PRT
<213> ORGANISM: Homo sapiens

<400> SEQUENCE: 270

Phe Leu Leu Ala Lys Val Ile Asn Ala
1               5

<210> SEQ ID NO 271
<211> LENGTH: 9
<212> TYPE: PRT
<213> ORGANISM: Homo sapiens

<400> SEQUENCE: 271

Arg Leu Ala Tyr Leu Asp Tyr Tyr Leu
1               5

<210> SEQ ID NO 272
<211> LENGTH: 9
<212> TYPE: PRT
<213> ORGANISM: Homo sapiens

<400> SEQUENCE: 272

Arg Leu Ala Asn Gln Ile Pro Phe Ile
1               5

<210> SEQ ID NO 273
<211> LENGTH: 9

```
<212> TYPE: PRT
<213> ORGANISM: Homo sapiens

<400> SEQUENCE: 273

Cys Leu Gly Ser Leu Leu Ser His Val
1               5

<210> SEQ ID NO 274
<211> LENGTH: 9
<212> TYPE: PRT
<213> ORGANISM: Homo sapiens

<400> SEQUENCE: 274

Phe Leu Phe Phe Ile Tyr Leu Leu Val
1               5

<210> SEQ ID NO 275
<211> LENGTH: 9
<212> TYPE: PRT
<213> ORGANISM: Homo sapiens

<400> SEQUENCE: 275

Ser Met Val Asp Gly Met Trp Gln Ala
1               5

<210> SEQ ID NO 276
<211> LENGTH: 9
<212> TYPE: PRT
<213> ORGANISM: Homo sapiens

<400> SEQUENCE: 276

Arg Ile Val Glu Ser Tyr Phe Met Leu
1               5

<210> SEQ ID NO 277
<211> LENGTH: 9
<212> TYPE: PRT
<213> ORGANISM: Homo sapiens

<400> SEQUENCE: 277

Asn Ile Phe Ala Ile Leu Gln Ser Val
1               5

<210> SEQ ID NO 278
<211> LENGTH: 9
<212> TYPE: PRT
<213> ORGANISM: Homo sapiens

<400> SEQUENCE: 278

Leu Met Leu Arg Arg Thr Glu Ser Val
1               5

<210> SEQ ID NO 279
<211> LENGTH: 9
<212> TYPE: PRT
<213> ORGANISM: Homo sapiens

<400> SEQUENCE: 279

Ile Leu Ser Gly Leu Ala Asn Met Val
1               5

<210> SEQ ID NO 280
<211> LENGTH: 9
<212> TYPE: PRT
<213> ORGANISM: Homo sapiens
```

<400> SEQUENCE: 280

Ser Met His Trp Gln Asn Asp Ser Val
1               5

<210> SEQ ID NO 281
<211> LENGTH: 9
<212> TYPE: PRT
<213> ORGANISM: Homo sapiens

<400> SEQUENCE: 281

Phe Leu Leu Gln Ala Asn Phe Ile Val
1               5

<210> SEQ ID NO 282
<211> LENGTH: 9
<212> TYPE: PRT
<213> ORGANISM: Homo sapiens

<400> SEQUENCE: 282

Thr Leu Met Ser Pro Pro Leu Gly Leu
1               5

<210> SEQ ID NO 283
<211> LENGTH: 9
<212> TYPE: PRT
<213> ORGANISM: Homo sapiens

<400> SEQUENCE: 283

Ser Ile Met Lys Ala Met Ile Pro Leu
1               5

<210> SEQ ID NO 284
<211> LENGTH: 9
<212> TYPE: PRT
<213> ORGANISM: Homo sapiens

<400> SEQUENCE: 284

Leu Leu Val Gly Ile Asn Gln Ala Leu
1               5

<210> SEQ ID NO 285
<211> LENGTH: 9
<212> TYPE: PRT
<213> ORGANISM: Homo sapiens

<400> SEQUENCE: 285

Phe Ala Leu Cys Leu Ser Leu Met Val
1               5

<210> SEQ ID NO 286
<211> LENGTH: 9
<212> TYPE: PRT
<213> ORGANISM: Homo sapiens

<400> SEQUENCE: 286

Trp Leu Leu Thr Arg Arg Ile Phe Leu
1               5

<210> SEQ ID NO 287
<211> LENGTH: 9
<212> TYPE: PRT
<213> ORGANISM: Homo sapiens

<400> SEQUENCE: 287

Cys Met Leu Asp Ile Phe Val Leu Ile
1               5

<210> SEQ ID NO 288
<211> LENGTH: 9
<212> TYPE: PRT
<213> ORGANISM: Homo sapiens

<400> SEQUENCE: 288

Ile Val Trp Glu Val Leu Phe Leu Leu
1               5

<210> SEQ ID NO 289
<211> LENGTH: 9
<212> TYPE: PRT
<213> ORGANISM: Homo sapiens

<400> SEQUENCE: 289

Phe Leu Gln Met Cys Asn Leu Pro Ile
1               5

<210> SEQ ID NO 290
<211> LENGTH: 9
<212> TYPE: PRT
<213> ORGANISM: Homo sapiens

<400> SEQUENCE: 290

Phe Leu Phe Gln Asp Leu Ala Ile Thr
1               5

<210> SEQ ID NO 291
<211> LENGTH: 9
<212> TYPE: PRT
<213> ORGANISM: Homo sapiens

<400> SEQUENCE: 291

Asn Leu Leu Lys Gly Phe Tyr Thr Ala
1               5

<210> SEQ ID NO 292
<211> LENGTH: 9
<212> TYPE: PRT
<213> ORGANISM: Homo sapiens

<400> SEQUENCE: 292

Tyr Leu Tyr Thr Ala Asp Thr Gly Leu
1               5

<210> SEQ ID NO 293
<211> LENGTH: 9
<212> TYPE: PRT
<213> ORGANISM: Homo sapiens

<400> SEQUENCE: 293

Leu Leu Ser Pro Glu Asp Trp Gly Leu
1               5

<210> SEQ ID NO 294
<211> LENGTH: 9
<212> TYPE: PRT
<213> ORGANISM: Homo sapiens

<400> SEQUENCE: 294

Thr Met Ser Leu Asn Ile Ile Thr Val

```
1               5

<210> SEQ ID NO 295
<211> LENGTH: 9
<212> TYPE: PRT
<213> ORGANISM: Homo sapiens

<400> SEQUENCE: 295

Gly Leu Ala Asp Phe Ala Asp Asn Leu
1               5

<210> SEQ ID NO 296
<211> LENGTH: 9
<212> TYPE: PRT
<213> ORGANISM: Homo sapiens

<400> SEQUENCE: 296

Ile Leu Leu Pro Ile Arg Val Leu Leu
1               5

<210> SEQ ID NO 297
<211> LENGTH: 9
<212> TYPE: PRT
<213> ORGANISM: Homo sapiens

<400> SEQUENCE: 297

Leu Leu Thr Arg Arg Ile Phe Leu Val
1               5

<210> SEQ ID NO 298
<211> LENGTH: 9
<212> TYPE: PRT
<213> ORGANISM: Homo sapiens

<400> SEQUENCE: 298

Phe Ser Val Leu Leu Phe Val Ala Val
1               5

<210> SEQ ID NO 299
<211> LENGTH: 9
<212> TYPE: PRT
<213> ORGANISM: Homo sapiens

<400> SEQUENCE: 299

Ser Met Met Ser Tyr Glu Arg Ser Met
1               5

<210> SEQ ID NO 300
<211> LENGTH: 9
<212> TYPE: PRT
<213> ORGANISM: Homo sapiens

<400> SEQUENCE: 300

Val Leu Cys Asn Gly Leu Val Leu Leu
1               5

<210> SEQ ID NO 301
<211> LENGTH: 9
<212> TYPE: PRT
<213> ORGANISM: Homo sapiens

<400> SEQUENCE: 301

Leu Ile Ala Ala Ile Leu Glu Leu Val
1               5
```

<210> SEQ ID NO 302
<211> LENGTH: 9
<212> TYPE: PRT
<213> ORGANISM: Homo sapiens

<400> SEQUENCE: 302

Leu Met Ala Asn Gly Phe Asp Asn Val
1               5

<210> SEQ ID NO 303
<211> LENGTH: 9
<212> TYPE: PRT
<213> ORGANISM: Homo sapiens

<400> SEQUENCE: 303

Leu Leu Gly Ile Ser Phe Phe Ala Leu
1               5

<210> SEQ ID NO 304
<211> LENGTH: 9
<212> TYPE: PRT
<213> ORGANISM: Homo sapiens

<400> SEQUENCE: 304

Gln Leu Ile Asp Gly Lys Val Thr Val
1               5

<210> SEQ ID NO 305
<211> LENGTH: 9
<212> TYPE: PRT
<213> ORGANISM: Homo sapiens

<400> SEQUENCE: 305

Ala Leu Ile Gln Val Gln Ala Thr Val
1               5

<210> SEQ ID NO 306
<211> LENGTH: 9
<212> TYPE: PRT
<213> ORGANISM: Homo sapiens

<400> SEQUENCE: 306

Phe Leu Val Arg Asn Asn Val Leu Leu
1               5

<210> SEQ ID NO 307
<211> LENGTH: 9
<212> TYPE: PRT
<213> ORGANISM: Homo sapiens

<400> SEQUENCE: 307

Leu Ile Ile Asp Ser Asn Leu Gly Val
1               5

<210> SEQ ID NO 308
<211> LENGTH: 9
<212> TYPE: PRT
<213> ORGANISM: Homo sapiens

<400> SEQUENCE: 308

Tyr Leu His Ser Ile Trp His Val Leu
1               5

<210> SEQ ID NO 309

```
<211> LENGTH: 9
<212> TYPE: PRT
<213> ORGANISM: Homo sapiens

<400> SEQUENCE: 309

Thr Ile Val Leu Ala Leu Met Tyr Val
1               5

<210> SEQ ID NO 310
<211> LENGTH: 9
<212> TYPE: PRT
<213> ORGANISM: Homo sapiens

<400> SEQUENCE: 310

Val Leu Thr Ser Leu Pro Ala Leu Ala
1               5

<210> SEQ ID NO 311
<211> LENGTH: 9
<212> TYPE: PRT
<213> ORGANISM: Homo sapiens

<400> SEQUENCE: 311

Ile Leu Pro Asn Arg Thr Val Leu Val
1               5

<210> SEQ ID NO 312
<211> LENGTH: 9
<212> TYPE: PRT
<213> ORGANISM: Homo sapiens

<400> SEQUENCE: 312

Lys Leu Ser Cys Ala Ser Ile Lys Val
1               5

<210> SEQ ID NO 313
<211> LENGTH: 9
<212> TYPE: PRT
<213> ORGANISM: Homo sapiens

<400> SEQUENCE: 313

Met Leu Pro Gly Phe Leu His Arg Leu
1               5

<210> SEQ ID NO 314
<211> LENGTH: 9
<212> TYPE: PRT
<213> ORGANISM: Homo sapiens

<400> SEQUENCE: 314

Ser Leu Gln Thr Ala Val Ala Glu Val
1               5

<210> SEQ ID NO 315
<211> LENGTH: 9
<212> TYPE: PRT
<213> ORGANISM: Homo sapiens

<400> SEQUENCE: 315

His Leu Phe Leu Asp Leu Pro Lys Leu
1               5

<210> SEQ ID NO 316
<211> LENGTH: 9
<212> TYPE: PRT
```

```
<213> ORGANISM: Homo sapiens

<400> SEQUENCE: 316

Gln Leu Ile Asp Gly Ile Leu Tyr Ala
1               5

<210> SEQ ID NO 317
<211> LENGTH: 9
<212> TYPE: PRT
<213> ORGANISM: Homo sapiens

<400> SEQUENCE: 317

Lys Leu Val Asn Gln Ser Tyr Met Met
1               5

<210> SEQ ID NO 318
<211> LENGTH: 9
<212> TYPE: PRT
<213> ORGANISM: Homo sapiens

<400> SEQUENCE: 318

Ser Ile Gly Cys Ala Val Trp Phe Ala
1               5

<210> SEQ ID NO 319
<211> LENGTH: 9
<212> TYPE: PRT
<213> ORGANISM: Homo sapiens

<400> SEQUENCE: 319

Met Leu Leu Glu Ala Leu Tyr Leu Phe
1               5

<210> SEQ ID NO 320
<211> LENGTH: 9
<212> TYPE: PRT
<213> ORGANISM: Homo sapiens

<400> SEQUENCE: 320

Phe Leu Leu Gln Ala Asn Phe Ile Val
1               5

<210> SEQ ID NO 321
<211> LENGTH: 9
<212> TYPE: PRT
<213> ORGANISM: Homo sapiens

<400> SEQUENCE: 321

Met Leu Asp Arg Leu Leu Arg Ala Ile
1               5

<210> SEQ ID NO 322
<211> LENGTH: 9
<212> TYPE: PRT
<213> ORGANISM: Homo sapiens

<400> SEQUENCE: 322

Tyr Ile Leu His Arg Lys Pro Phe Val
1               5

<210> SEQ ID NO 323
<211> LENGTH: 9
<212> TYPE: PRT
<213> ORGANISM: Homo sapiens
```

```
<400> SEQUENCE: 323

Asn Met Asn Gln Cys Thr Asp Val Val
1               5

<210> SEQ ID NO 324
<211> LENGTH: 9
<212> TYPE: PRT
<213> ORGANISM: Homo sapiens

<400> SEQUENCE: 324

Phe Ala Met Tyr Tyr Glu Thr Phe Val
1               5

<210> SEQ ID NO 325
<211> LENGTH: 9
<212> TYPE: PRT
<213> ORGANISM: Homo sapiens

<400> SEQUENCE: 325

Ser Val Ile Tyr Thr Ile Glu Ala Val
1               5

<210> SEQ ID NO 326
<211> LENGTH: 9
<212> TYPE: PRT
<213> ORGANISM: Homo sapiens

<400> SEQUENCE: 326

Ala Leu Leu Leu Ser Thr Thr Asp Val
1               5

<210> SEQ ID NO 327
<211> LENGTH: 9
<212> TYPE: PRT
<213> ORGANISM: Homo sapiens

<400> SEQUENCE: 327

Gly Leu Leu Gln Phe Ser Thr Gly Leu
1               5

<210> SEQ ID NO 328
<211> LENGTH: 9
<212> TYPE: PRT
<213> ORGANISM: Homo sapiens

<400> SEQUENCE: 328

Ala Leu Gln Ala Gly Thr Val Trp Val
1               5

<210> SEQ ID NO 329
<211> LENGTH: 9
<212> TYPE: PRT
<213> ORGANISM: Homo sapiens

<400> SEQUENCE: 329

Gln Val Val Lys Asp Pro Phe Tyr Val
1               5

<210> SEQ ID NO 330
<211> LENGTH: 9
<212> TYPE: PRT
<213> ORGANISM: Homo sapiens

<400> SEQUENCE: 330
```

Lys Val Leu Phe Ile Leu Phe Arg Val
1               5

<210> SEQ ID NO 331
<211> LENGTH: 9
<212> TYPE: PRT
<213> ORGANISM: Homo sapiens

<400> SEQUENCE: 331

Trp Gln Leu Phe Phe His Val Thr Val
1               5

<210> SEQ ID NO 332
<211> LENGTH: 9
<212> TYPE: PRT
<213> ORGANISM: Homo sapiens

<400> SEQUENCE: 332

Tyr Leu Glu Ile Ile Thr Gln Leu Ile
1               5

<210> SEQ ID NO 333
<211> LENGTH: 9
<212> TYPE: PRT
<213> ORGANISM: Homo sapiens

<400> SEQUENCE: 333

Ile Leu His Glu Met Met Glu Glu Ile
1               5

<210> SEQ ID NO 334
<211> LENGTH: 9
<212> TYPE: PRT
<213> ORGANISM: Homo sapiens

<400> SEQUENCE: 334

Ser Thr Ile Ser Ser Ser Phe Ser Val
1               5

<210> SEQ ID NO 335
<211> LENGTH: 9
<212> TYPE: PRT
<213> ORGANISM: Homo sapiens

<400> SEQUENCE: 335

Ser Val Leu Glu Lys Gly Trp Glu Ile
1               5

<210> SEQ ID NO 336
<211> LENGTH: 9
<212> TYPE: PRT
<213> ORGANISM: Homo sapiens

<400> SEQUENCE: 336

Thr Leu Met Pro Asn Ala Ser Asn Leu
1               5

<210> SEQ ID NO 337
<211> LENGTH: 9
<212> TYPE: PRT
<213> ORGANISM: Homo sapiens

<400> SEQUENCE: 337

Gly Ile Tyr Gln Arg Cys Trp Leu Val
1               5

```
<210> SEQ ID NO 338
<211> LENGTH: 9
<212> TYPE: PRT
<213> ORGANISM: Homo sapiens

<400> SEQUENCE: 338

Tyr Leu Lys Phe Asn Ile Ser Leu Ala
1               5

<210> SEQ ID NO 339
<211> LENGTH: 9
<212> TYPE: PRT
<213> ORGANISM: Homo sapiens

<400> SEQUENCE: 339

Leu Leu Arg Asp Phe Glu Ala Thr Leu
1               5

<210> SEQ ID NO 340
<211> LENGTH: 9
<212> TYPE: PRT
<213> ORGANISM: Homo sapiens

<400> SEQUENCE: 340

Lys Val Phe Asn Thr Val Tyr Ser Leu
1               5

<210> SEQ ID NO 341
<211> LENGTH: 9
<212> TYPE: PRT
<213> ORGANISM: Homo sapiens

<400> SEQUENCE: 341

Trp Leu Ser Ser Val Glu Glu Ala Val
1               5

<210> SEQ ID NO 342
<211> LENGTH: 9
<212> TYPE: PRT
<213> ORGANISM: Homo sapiens

<400> SEQUENCE: 342

Thr Leu Asn Ile Asp Leu Phe Pro Ala
1               5

<210> SEQ ID NO 343
<211> LENGTH: 9
<212> TYPE: PRT
<213> ORGANISM: Homo sapiens

<400> SEQUENCE: 343

Gln Leu Val Pro Tyr Ile Ile Asp Leu
1               5

<210> SEQ ID NO 344
<211> LENGTH: 9
<212> TYPE: PRT
<213> ORGANISM: Homo sapiens

<400> SEQUENCE: 344

Met Leu Leu Pro Glu Thr Lys Gly Ile
1               5
```

```
<210> SEQ ID NO 345
<211> LENGTH: 9
<212> TYPE: PRT
<213> ORGANISM: Homo sapiens

<400> SEQUENCE: 345

Val Ile Leu Glu Ile Glu Glu Pro Ala
1               5

<210> SEQ ID NO 346
<211> LENGTH: 9
<212> TYPE: PRT
<213> ORGANISM: Homo sapiens

<400> SEQUENCE: 346

Phe Ile Leu Leu Asn Leu Leu Lys Val
1               5

<210> SEQ ID NO 347
<211> LENGTH: 9
<212> TYPE: PRT
<213> ORGANISM: Homo sapiens

<400> SEQUENCE: 347

Ser Leu Ala Ala Gly Val Pro Val Leu
1               5

<210> SEQ ID NO 348
<211> LENGTH: 9
<212> TYPE: PRT
<213> ORGANISM: Homo sapiens

<400> SEQUENCE: 348

Val Thr Trp Leu Ile Ser Leu Gly Val
1               5

<210> SEQ ID NO 349
<211> LENGTH: 9
<212> TYPE: PRT
<213> ORGANISM: Homo sapiens

<400> SEQUENCE: 349

Arg Leu Tyr Ser Ala Val Cys Ala Leu
1               5

<210> SEQ ID NO 350
<211> LENGTH: 9
<212> TYPE: PRT
<213> ORGANISM: Homo sapiens

<400> SEQUENCE: 350

Met Met Ala Gln Thr Glu Pro Thr Val
1               5

<210> SEQ ID NO 351
<211> LENGTH: 9
<212> TYPE: PRT
<213> ORGANISM: Homo sapiens

<400> SEQUENCE: 351

Leu Leu Phe Glu Tyr Leu Thr Leu Phe
1               5

<210> SEQ ID NO 352
<211> LENGTH: 9
```

<212> TYPE: PRT
<213> ORGANISM: Homo sapiens

<400> SEQUENCE: 352

Gly Leu Phe Ile Val Leu Ile Leu Val
1               5

<210> SEQ ID NO 353
<211> LENGTH: 9
<212> TYPE: PRT
<213> ORGANISM: Homo sapiens

<400> SEQUENCE: 353

Ile Val Ile Cys Ile Ser Pro Glu Val
1               5

<210> SEQ ID NO 354
<211> LENGTH: 9
<212> TYPE: PRT
<213> ORGANISM: Homo sapiens

<400> SEQUENCE: 354

Ser Thr Phe Ala Lys Ala Ser Phe Val
1               5

<210> SEQ ID NO 355
<211> LENGTH: 9
<212> TYPE: PRT
<213> ORGANISM: Homo sapiens

<400> SEQUENCE: 355

Tyr Val Met Ala Val Val Asp Lys Ala
1               5

<210> SEQ ID NO 356
<211> LENGTH: 9
<212> TYPE: PRT
<213> ORGANISM: Homo sapiens

<400> SEQUENCE: 356

Val Gln Ile Glu Arg Leu Asp Ala Val
1               5

<210> SEQ ID NO 357
<211> LENGTH: 9
<212> TYPE: PRT
<213> ORGANISM: Homo sapiens

<400> SEQUENCE: 357

His Ile Leu Phe Ala Asn Leu Tyr Leu
1               5

<210> SEQ ID NO 358
<211> LENGTH: 9
<212> TYPE: PRT
<213> ORGANISM: Homo sapiens

<400> SEQUENCE: 358

Ser Thr Thr Asn Ala Ile Ala Pro Val
1               5

<210> SEQ ID NO 359
<211> LENGTH: 9
<212> TYPE: PRT
<213> ORGANISM: Homo sapiens

<400> SEQUENCE: 359

Phe Val Val Cys Gln Gly Phe Leu Ala
1               5

<210> SEQ ID NO 360
<211> LENGTH: 9
<212> TYPE: PRT
<213> ORGANISM: Homo sapiens

<400> SEQUENCE: 360

Val Leu Gln Ala Ala Asp Ile Leu Leu
1               5

<210> SEQ ID NO 361
<211> LENGTH: 9
<212> TYPE: PRT
<213> ORGANISM: Homo sapiens

<400> SEQUENCE: 361

His Leu Ile His Trp Asn Ser Thr Leu
1               5

<210> SEQ ID NO 362
<211> LENGTH: 9
<212> TYPE: PRT
<213> ORGANISM: Homo sapiens

<400> SEQUENCE: 362

Gly Ile Val Asn Phe Leu Met Thr Ile
1               5

<210> SEQ ID NO 363
<211> LENGTH: 9
<212> TYPE: PRT
<213> ORGANISM: Homo sapiens

<400> SEQUENCE: 363

Leu Leu Arg Leu Ser Thr Pro Phe Val
1               5

<210> SEQ ID NO 364
<211> LENGTH: 9
<212> TYPE: PRT
<213> ORGANISM: Homo sapiens

<400> SEQUENCE: 364

Met Leu Thr Leu Met Ser Pro Pro Leu
1               5

<210> SEQ ID NO 365
<211> LENGTH: 9
<212> TYPE: PRT
<213> ORGANISM: Homo sapiens

<400> SEQUENCE: 365

Ser Leu Val Leu Val Tyr Ala Gly Val
1               5

<210> SEQ ID NO 366
<211> LENGTH: 9
<212> TYPE: PRT
<213> ORGANISM: Homo sapiens

<400> SEQUENCE: 366

Asn Ile Ala Thr Thr Leu Pro Thr Val
1               5

<210> SEQ ID NO 367
<211> LENGTH: 9
<212> TYPE: PRT
<213> ORGANISM: Homo sapiens

<400> SEQUENCE: 367

Tyr Leu Asp Leu Ser Ser Asn Asn Leu
1               5

<210> SEQ ID NO 368
<211> LENGTH: 9
<212> TYPE: PRT
<213> ORGANISM: Homo sapiens

<400> SEQUENCE: 368

Ile Val Trp Glu Val Leu Phe Leu Leu
1               5

<210> SEQ ID NO 369
<211> LENGTH: 9
<212> TYPE: PRT
<213> ORGANISM: Homo sapiens

<400> SEQUENCE: 369

Leu Met Ser Val Trp Val Thr Val Ile
1               5

<210> SEQ ID NO 370
<211> LENGTH: 9
<212> TYPE: PRT
<213> ORGANISM: Homo sapiens

<400> SEQUENCE: 370

Ser Leu Asn Phe Leu Phe Phe Met Leu
1               5

<210> SEQ ID NO 371
<211> LENGTH: 9
<212> TYPE: PRT
<213> ORGANISM: Homo sapiens

<400> SEQUENCE: 371

Tyr Phe Leu Pro Pro Ser Phe Pro Ile
1               5

<210> SEQ ID NO 372
<211> LENGTH: 9
<212> TYPE: PRT
<213> ORGANISM: Homo sapiens

<400> SEQUENCE: 372

Ser Leu Phe Leu Phe Ser Val Leu Leu
1               5

<210> SEQ ID NO 373
<211> LENGTH: 9
<212> TYPE: PRT
<213> ORGANISM: Homo sapiens

<400> SEQUENCE: 373

Gly Ile Leu Asp Phe Tyr Met Phe Leu 1               5

<210> SEQ ID NO 374
<211> LENGTH: 9
<212> TYPE: PRT
<213> ORGANISM: Homo sapiens

<400> SEQUENCE: 374

Pro Leu Met Arg Val Val Gln Ser Val
1               5

<210> SEQ ID NO 375
<211> LENGTH: 9
<212> TYPE: PRT
<213> ORGANISM: Homo sapiens

<400> SEQUENCE: 375

Leu Val Met Thr Ser Tyr Ser Pro Val
1               5

<210> SEQ ID NO 376
<211> LENGTH: 9
<212> TYPE: PRT
<213> ORGANISM: Homo sapiens

<400> SEQUENCE: 376

Arg Leu Ile Ser Lys Thr Glu Glu Val
1               5

<210> SEQ ID NO 377
<211> LENGTH: 9
<212> TYPE: PRT
<213> ORGANISM: Homo sapiens

<400> SEQUENCE: 377

Phe Met Tyr Arg Thr Arg Asn Gly Ile
1               5

<210> SEQ ID NO 378
<211> LENGTH: 9
<212> TYPE: PRT
<213> ORGANISM: Homo sapiens

<400> SEQUENCE: 378

Leu Met Gly Gly Thr Val Asp Thr Val
1               5

<210> SEQ ID NO 379
<211> LENGTH: 9
<212> TYPE: PRT
<213> ORGANISM: Homo sapiens

<400> SEQUENCE: 379

Lys Leu Leu Phe Glu Tyr Leu Thr Leu
1               5

<210> SEQ ID NO 380
<211> LENGTH: 9
<212> TYPE: PRT
<213> ORGANISM: Homo sapiens

<400> SEQUENCE: 380

Ser Val Leu Leu Ile His Gln Gly Val
1               5

```
<210> SEQ ID NO 381
<211> LENGTH: 9
<212> TYPE: PRT
<213> ORGANISM: Homo sapiens

<400> SEQUENCE: 381

Leu Leu Gly Ser Leu Val Thr Arg Ile
 1               5

<210> SEQ ID NO 382
<211> LENGTH: 9
<212> TYPE: PRT
<213> ORGANISM: Homo sapiens

<400> SEQUENCE: 382

Leu Leu Tyr Tyr Ser Val Pro Val Leu
 1               5

<210> SEQ ID NO 383
<211> LENGTH: 9
<212> TYPE: PRT
<213> ORGANISM: Homo sapiens

<400> SEQUENCE: 383

Val Ile Val Gly Lys Ile Tyr Phe Leu
 1               5

<210> SEQ ID NO 384
<211> LENGTH: 9
<212> TYPE: PRT
<213> ORGANISM: Homo sapiens

<400> SEQUENCE: 384

Phe Ile Ala Lys Lys Val Ile Gly Ile
 1               5

<210> SEQ ID NO 385
<211> LENGTH: 31
<212> TYPE: PRT
<213> ORGANISM: Homo sapiens

<400> SEQUENCE: 385

Leu Thr Ile Gln Phe Val Glu Gly Gln Phe Val Asp Ser Tyr Asp Leu
 1               5                  10                  15

Thr Ile Glu Asn Thr Phe Thr Lys Leu Ile Thr Val Asn Gly Gln
             20                  25                  30

<210> SEQ ID NO 386
<211> LENGTH: 31
<212> TYPE: PRT
<213> ORGANISM: Homo sapiens

<400> SEQUENCE: 386

Asp Asp Thr Arg Glu Lys Cys Leu Ile Gln Arg Ser Ser Asn His Ser
 1               5                  10                  15

Phe Trp Thr Pro Lys Ser Ile Lys Thr Arg Arg Cys Ile Phe Lys
             20                  25                  30

<210> SEQ ID NO 387
<211> LENGTH: 31
<212> TYPE: PRT
<213> ORGANISM: Homo sapiens

<400> SEQUENCE: 387
```

```
Lys His Glu Cys Gly Glu Cys Gly Lys Ser Phe Ser Lys Tyr Val Asn
1               5                   10                  15

Phe Ser Asn His Gln Arg Val His Thr Glu Lys Lys His Glu Cys
                20                  25                  30

<210> SEQ ID NO 388
<211> LENGTH: 31
<212> TYPE: PRT
<213> ORGANISM: Homo sapiens

<400> SEQUENCE: 388

Lys Met Ile Ile Trp Phe Pro Asp Met Val Lys Asp Val Ile Gly Asn
1               5                   10                  15

Tyr Lys Lys Trp Cys Arg Ser Ile Leu Arg Arg Thr Ser Leu Ile
                20                  25                  30

<210> SEQ ID NO 389
<211> LENGTH: 31
<212> TYPE: PRT
<213> ORGANISM: Homo sapiens

<400> SEQUENCE: 389

Gly Gly Gln Arg Asp Pro Leu Pro Gly Leu Pro His Leu Arg Arg Ala
1               5                   10                  15

Arg Leu Phe Pro Trp Pro Trp Arg Leu Pro Ala Ala Ala Gln Ala
                20                  25                  30

<210> SEQ ID NO 390
<211> LENGTH: 31
<212> TYPE: PRT
<213> ORGANISM: Homo sapiens

<400> SEQUENCE: 390

Glu Tyr Cys Ser Gly Asn Met Gly Leu Leu Gln Gln Leu Glu Ala Val
1               5                   10                  15

Ile Gly Ile Thr Leu Ile Ala Val Asp Glu Ala His Cys Ile Ser
                20                  25                  30

<210> SEQ ID NO 391
<211> LENGTH: 31
<212> TYPE: PRT
<213> ORGANISM: Homo sapiens

<400> SEQUENCE: 391

Gln Ser Lys Val Ser Ala Lys Glu Val Asn Leu Ser Lys Glu Val Cys
1               5                   10                  15

Thr Asp Val Gln Tyr Lys Asn Asn Lys Ser Tyr Val Ser Lys Ile
                20                  25                  30

<210> SEQ ID NO 392
<211> LENGTH: 31
<212> TYPE: PRT
<213> ORGANISM: Homo sapiens

<400> SEQUENCE: 392

Gly Lys Gly Cys Asp Asn Asn Phe Ile Glu Asp Val Leu Gly Tyr Ser
1               5                   10                  15

Asn Phe Ala Ser Ile Pro Gln Lys Met Thr His Leu Pro Glu Leu
                20                  25                  30

<210> SEQ ID NO 393
```

```
<211> LENGTH: 31
<212> TYPE: PRT
<213> ORGANISM: Homo sapiens

<400> SEQUENCE: 393

Leu Val Arg Glu Phe Leu Ser Arg Lys Gly Leu Lys Lys Thr Cys Ala
1               5                   10                  15

Thr Met Asp Gln Glu Arg Pro Arg Ser Asp Leu Ser Ile Asn Asn
                20                  25                  30

<210> SEQ ID NO 394
<211> LENGTH: 31
<212> TYPE: PRT
<213> ORGANISM: Homo sapiens

<400> SEQUENCE: 394

Tyr Ser Thr Pro Leu Ala Leu Gln Phe Leu Met Thr Ser Pro Met Pro
1               5                   10                  15

Gly Ala Glu Leu Gly Thr Ala Cys Leu Lys Ala Arg Val Ala Leu
                20                  25                  30

<210> SEQ ID NO 395
<211> LENGTH: 31
<212> TYPE: PRT
<213> ORGANISM: Homo sapiens

<400> SEQUENCE: 395

Arg Asp Ser Leu Glu Val Ala Val Gly Val Cys Arg Glu Asp Val Thr
1               5                   10                  15

Gly Ile Thr Asp Arg Ser Lys Met Ser Pro Asp Val Gly Ile Trp
                20                  25                  30

<210> SEQ ID NO 396
<211> LENGTH: 31
<212> TYPE: PRT
<213> ORGANISM: Homo sapiens

<400> SEQUENCE: 396

Asp Arg Asp Leu Leu Cys Arg Gln Ser Pro Lys Cys Ile Ile Ser Ile
1               5                   10                  15

Glu Val Met Ser Ser Met Glu Ile Cys Val Ile Lys Val Glu
                20                  25                  30

<210> SEQ ID NO 397
<211> LENGTH: 31
<212> TYPE: PRT
<213> ORGANISM: Homo sapiens

<400> SEQUENCE: 397

Leu Gln Met Arg Leu Lys Ala Leu Asp Pro Met Met Glu Arg Glu Thr
1               5                   10                  15

Glu Glu Leu Arg Gln Arg Tyr Thr Ala Lys Arg Gln Pro Ile Leu
                20                  25                  30

<210> SEQ ID NO 398
<211> LENGTH: 31
<212> TYPE: PRT
<213> ORGANISM: Homo sapiens

<400> SEQUENCE: 398

Ser Gly Ile Pro Phe Leu Asp Tyr Arg Thr Tyr Ala Glu Arg Ala Ser
1               5                   10                  15
```

```
Phe Pro Gly His Gly Gly Cys Pro Leu Gln Pro Lys Pro Glu Gly
            20                  25                  30
```

<210> SEQ ID NO 399
<211> LENGTH: 31
<212> TYPE: PRT
<213> ORGANISM: Homo sapiens

<400> SEQUENCE: 399

```
Asn Lys Ile Lys Ser Phe Arg Lys Gln Thr Phe Leu Gly Leu Asp Asn
1               5                   10                  15

Leu Glu Tyr Leu Gln Ala Asp Phe Asn Leu Leu Arg Asp Ile Asp
            20                  25                  30
```

<210> SEQ ID NO 400
<211> LENGTH: 31
<212> TYPE: PRT
<213> ORGANISM: Homo sapiens

<400> SEQUENCE: 400

```
Leu Gly Trp Phe Leu Ser Cys Leu Gly Pro Phe Leu Leu Ser Ala Thr
1               5                   10                  15

Leu Leu Val Leu Val Leu Lys Leu Gly Asp Ile Leu Pro Tyr Ser
            20                  25                  30
```

<210> SEQ ID NO 401
<211> LENGTH: 31
<212> TYPE: PRT
<213> ORGANISM: Homo sapiens

<400> SEQUENCE: 401

```
Leu His Glu Gln Val Ala Ser Leu Ile Asp Leu Cys Glu Tyr His Val
1               5                   10                  15

Ser Leu Leu Asp Glu Lys Arg Leu Val Cys Gly Arg Gly Val Pro
            20                  25                  30
```

<210> SEQ ID NO 402
<211> LENGTH: 31
<212> TYPE: PRT
<213> ORGANISM: Homo sapiens

<400> SEQUENCE: 402

```
Cys Arg Asn Tyr Val Arg Arg Val His Val Asp Gln Phe Leu Pro Leu
1               5                   10                  15

Val Gln Leu Pro Ala Gln Leu Arg Pro Gly Asp Gln Ser Asp Ser
            20                  25                  30
```

<210> SEQ ID NO 403
<211> LENGTH: 31
<212> TYPE: PRT
<213> ORGANISM: Homo sapiens

<400> SEQUENCE: 403

```
Tyr Phe Ala Ile Ser Lys Phe Ile Gly Phe Gly Thr Asp Ser Trp Ile
1               5                   10                  15

Tyr Pro Asn Ile Ser Ile Pro Glu His Gly Arg Leu Ser Arg Lys
            20                  25                  30
```

<210> SEQ ID NO 404
<211> LENGTH: 31
<212> TYPE: PRT
<213> ORGANISM: Homo sapiens

```
<400> SEQUENCE: 404

Asp Leu Ile Ser Asp Ile Phe Thr Thr Ile Gly Ser Val Thr Val Thr
1               5                   10                  15

Leu Leu Leu Ile Leu Leu Leu Ala Ile Val Ala Ser Val Val Thr
            20                  25                  30

<210> SEQ ID NO 405
<211> LENGTH: 31
<212> TYPE: PRT
<213> ORGANISM: Homo sapiens

<400> SEQUENCE: 405

Arg Lys Leu Gln Trp Gln Thr Thr Leu Gly His Ala Val Leu Lys Val
1               5                   10                  15

Glu Phe Lys Glu Gly Lys Lys Glu Phe Gln Val Ser Leu Phe Gln
            20                  25                  30

<210> SEQ ID NO 406
<211> LENGTH: 31
<212> TYPE: PRT
<213> ORGANISM: Homo sapiens

<400> SEQUENCE: 406

Ile Tyr Phe Ala Ile Ser Lys Phe Ile Gly Phe Gly Thr Asp Ser Cys
1               5                   10                  15

Val Tyr Pro Asn Ile Ser Ile Pro Glu His Gly Arg Leu Ser Arg
            20                  25                  30

<210> SEQ ID NO 407
<211> LENGTH: 31
<212> TYPE: PRT
<213> ORGANISM: Homo sapiens

<400> SEQUENCE: 407

Ser Leu Ser Val Gln Cys Arg Tyr Glu Lys Glu His Arg Thr Leu Lys
1               5                   10                  15

Lys Phe Trp Cys Arg Pro Pro Gln Ile Leu Arg Cys Asp Lys Ile
            20                  25                  30

<210> SEQ ID NO 408
<211> LENGTH: 31
<212> TYPE: PRT
<213> ORGANISM: Homo sapiens

<400> SEQUENCE: 408

Ser Glu Gly Arg Arg Asp Asn Met Lys Trp Cys Gly Thr Thr Gln Asp
1               5                   10                  15

Tyr Asp Ala Asp Gln Lys Phe Gly Phe Cys Pro Met Ala Ala His
            20                  25                  30

<210> SEQ ID NO 409
<211> LENGTH: 31
<212> TYPE: PRT
<213> ORGANISM: Homo sapiens

<400> SEQUENCE: 409

Ser Glu Glu Ala Ala Thr Trp Arg Gly Arg Phe Gly Pro Ser Leu Ile
1               5                   10                  15

Arg Gly Leu Leu Ala Val Ser Leu Ala Ala Asn Ala Leu Phe Thr
            20                  25                  30
```

-continued

```
<210> SEQ ID NO 410
<211> LENGTH: 31
<212> TYPE: PRT
<213> ORGANISM: Homo sapiens

<400> SEQUENCE: 410

Ser Gln Ala Phe Gln Arg Gln Leu Thr Ala Leu Ile Gly Tyr Asp Ile
1               5                   10                  15

Thr Asp Val Ser Asn Val His Asp Asp Glu Leu Glu Phe Thr Arg
            20                  25                  30

<210> SEQ ID NO 411
<211> LENGTH: 31
<212> TYPE: PRT
<213> ORGANISM: Homo sapiens

<400> SEQUENCE: 411

Ile Ile Lys Pro Asp Pro Pro Glu Gly Val Arg Leu Ser Pro Leu Thr
1               5                   10                  15

Glu Arg Gln Leu Gln Val Gln Trp Glu Pro Pro Gly Ser Trp Pro
            20                  25                  30

<210> SEQ ID NO 412
<211> LENGTH: 31
<212> TYPE: PRT
<213> ORGANISM: Homo sapiens

<400> SEQUENCE: 412

Pro Gly Arg Ala Ala Pro Thr Gly Ser Glu Ala Gln Gly Pro Ser Thr
1               5                   10                  15

Phe Val Arg Met Glu Lys Gly Ile Pro Ala Ser Pro Arg Cys Gly
            20                  25                  30

<210> SEQ ID NO 413
<211> LENGTH: 31
<212> TYPE: PRT
<213> ORGANISM: Homo sapiens

<400> SEQUENCE: 413

Tyr Arg Arg Ser Gln Ile Ser Met Glu Gln Leu Glu Lys Leu Gln Arg
1               5                   10                  15

Thr Leu Phe Ser Thr Glu Glu Glu Pro Ser Lys Leu Leu Val Gln
            20                  25                  30

<210> SEQ ID NO 414
<211> LENGTH: 31
<212> TYPE: PRT
<213> ORGANISM: Homo sapiens

<400> SEQUENCE: 414

Tyr Ala Ile Ile Ser Thr Ser Pro Ser Asn Ala Ala Ala Met Ala Ser
1               5                   10                  15

Ser Thr Ala Val Ser Val Val Ser Asp Ser Ile Lys Val Gln Pro
            20                  25                  30

<210> SEQ ID NO 415
<211> LENGTH: 31
<212> TYPE: PRT
<213> ORGANISM: Homo sapiens

<400> SEQUENCE: 415

Thr Ser Val Val Val Lys Ser Ile Pro Ala Ser Ser Pro Gly Ala Val
1               5                   10                  15
```

-continued

Thr His Ile Met Gln Gln Ala Leu Ser Ser His Thr Ala Phe Thr
            20                  25                  30

<210> SEQ ID NO 416
<211> LENGTH: 31
<212> TYPE: PRT
<213> ORGANISM: Homo sapiens

<400> SEQUENCE: 416

Gly Ser Leu Val Arg Val Ile Gln Arg Ala Gly Leu Val Phe Pro Lys
1               5                   10                  15

Met Glu Ala Tyr Ala Val Ser Pro Gly Arg Met Arg Gln Phe Asp
            20                  25                  30

<210> SEQ ID NO 417
<211> LENGTH: 31
<212> TYPE: PRT
<213> ORGANISM: Homo sapiens

<400> SEQUENCE: 417

Asp Pro Leu Thr Pro Gly Tyr Pro Ala Asn Glu Tyr Ala Tyr Arg His
1               5                   10                  15

Gly Ile Ala Glu Ala Val Gly Leu Pro Ser Ile Pro Val His Pro
            20                  25                  30

<210> SEQ ID NO 418
<211> LENGTH: 31
<212> TYPE: PRT
<213> ORGANISM: Homo sapiens

<400> SEQUENCE: 418

Gln Asn Ile Phe Thr Ala Met Gln Ala Met Ile Arg Ala Met Asp Ser
1               5                   10                  15

Leu Lys Ile Pro Tyr Lys Tyr Glu His Asn Lys Ala His Ala Gln
            20                  25                  30

<210> SEQ ID NO 419
<211> LENGTH: 31
<212> TYPE: PRT
<213> ORGANISM: Homo sapiens

<400> SEQUENCE: 419

Pro Ile Ser Leu Pro Asn His Ala Lys Asn Cys Val Lys Met Gly Met
1               5                   10                  15

Asp Met Cys Glu Ala Ile Lys Lys Val Arg Asp Ala Thr Gly Val
            20                  25                  30

<210> SEQ ID NO 420
<211> LENGTH: 31
<212> TYPE: PRT
<213> ORGANISM: Homo sapiens

<400> SEQUENCE: 420

Ile Ile Lys Phe His Ser Ala Ala Met Asp Glu Lys Val Ile Gly Glu
1               5                   10                  15

Val Val Asp Gln Ala Cys Thr Leu Glu Lys Ala Gln Val Glu Ser
            20                  25                  30

<210> SEQ ID NO 421
<211> LENGTH: 31
<212> TYPE: PRT
<213> ORGANISM: Homo sapiens

<400> SEQUENCE: 421

Leu Lys Arg Leu Gly Lys Thr Lys Trp Asp Ala His Lys Ser Pro Val
1               5                   10                  15

Cys Val Leu Asn Glu Met Met Gln Asn Glu Glu Lys Tyr Glu Lys
            20                  25                  30

<210> SEQ ID NO 422
<211> LENGTH: 31
<212> TYPE: PRT
<213> ORGANISM: Homo sapiens

<400> SEQUENCE: 422

Asp Val Val Ser Lys Met Leu His Val Asp Pro His Gln Arg Leu Met
1               5                   10                  15

Ala Met Gln Val Leu Lys His Pro Trp Val Val Asn Arg Glu Tyr
            20                  25                  30

<210> SEQ ID NO 423
<211> LENGTH: 31
<212> TYPE: PRT
<213> ORGANISM: Homo sapiens

<400> SEQUENCE: 423

Val Thr Met Val Ser Val Leu Glu Asp Leu Ile Gly Lys Leu Thr Ile
1               5                   10                  15

Leu Gln Leu Gln His Leu Phe Met Ile Leu Ala Ser Pro Arg Tyr
            20                  25                  30

<210> SEQ ID NO 424
<211> LENGTH: 31
<212> TYPE: PRT
<213> ORGANISM: Homo sapiens

<400> SEQUENCE: 424

Leu Val Glu Asp Pro Glu Arg Pro Ala Cys Ala Pro Ala Ala Pro Cys
1               5                   10                  15

Leu Gln Met His His Val Ala Gln Val Leu Arg Glu Leu Leu Gly
            20                  25                  30

<210> SEQ ID NO 425
<211> LENGTH: 31
<212> TYPE: PRT
<213> ORGANISM: Homo sapiens

<400> SEQUENCE: 425

Leu Glu Asn Tyr Arg Asn Leu Glu Ala Val Asp Ile Ser Ser Lys Cys
1               5                   10                  15

Met Met Lys Glu Val Leu Ser Thr Gly Gln Gly Asn Thr Glu Val
            20                  25                  30

<210> SEQ ID NO 426
<211> LENGTH: 31
<212> TYPE: PRT
<213> ORGANISM: Homo sapiens

<400> SEQUENCE: 426

Pro Asn Met Asp Tyr Lys Asn Gly Glu His His Ser Pro Ser His Val
1               5                   10                  15

Ile His Asn Tyr Ser Ala Ala Pro Gly Met Phe Asn Ser Ser Leu
            20                  25                  30

<210> SEQ ID NO 427
<211> LENGTH: 31
<212> TYPE: PRT
<213> ORGANISM: Homo sapiens

<400> SEQUENCE: 427

Val Val Lys Leu Arg Asn Ala Gly His Ala Cys Tyr Leu His Lys Pro
1               5                   10                  15

Gln His Phe His Leu Val Leu Leu Ala Phe Leu Asp His Leu Pro
            20                  25                  30

<210> SEQ ID NO 428
<211> LENGTH: 31
<212> TYPE: PRT
<213> ORGANISM: Homo sapiens

<400> SEQUENCE: 428

Leu Asp Met Val Asn Arg Glu Thr Ala His Glu Arg Glu Met Gln Met
1               5                   10                  15

Ala Met Gln Ile Ser Gln Ser Trp Asp Glu Ser Leu Ser Leu Ser
            20                  25                  30

<210> SEQ ID NO 429
<211> LENGTH: 31
<212> TYPE: PRT
<213> ORGANISM: Homo sapiens

<400> SEQUENCE: 429

Asn His Trp Ile Thr Thr Thr Met Asn Leu Lys Pro Leu Ser Gly Leu
1               5                   10                  15

Asp Arg Ala Trp Met Trp Ser Ala Ser Asp Phe Ser Asp Gly Asp
            20                  25                  30

<210> SEQ ID NO 430
<211> LENGTH: 31
<212> TYPE: PRT
<213> ORGANISM: Homo sapiens

<400> SEQUENCE: 430

Gly Glu Phe Val His Asp Asp Val Trp Ala Ile Val Asn Asn Pro Asn
1               5                   10                  15

Val Arg Pro Gly Ala Pro Leu Arg Trp Gly Ile Phe Thr Asn Asp
            20                  25                  30

<210> SEQ ID NO 431
<211> LENGTH: 31
<212> TYPE: PRT
<213> ORGANISM: Homo sapiens

<400> SEQUENCE: 431

Asp Val Ala Trp Ser Pro His Asp Ala Trp Leu Ala Ser Cys Ser Met
1               5                   10                  15

Asp Asn Thr Val Val Ile Trp Asn Ala Val Lys Phe Pro Glu Ile
            20                  25                  30

<210> SEQ ID NO 432
<211> LENGTH: 31
<212> TYPE: PRT
<213> ORGANISM: Homo sapiens

```
<400> SEQUENCE: 432

Lys Phe Glu Asp Ile Lys Asp Trp Ser Asp Leu Val Thr Pro Gln Glu
1               5                   10                  15

Ile Met Gly Ile Phe Ala Lys Pro Asp His Val Lys Met Thr Tyr
                20                  25                  30

<210> SEQ ID NO 433
<211> LENGTH: 31
<212> TYPE: PRT
<213> ORGANISM: Homo sapiens

<400> SEQUENCE: 433

Val Thr Cys Gln Val Arg Lys Phe Tyr Pro Gln Arg Leu Gln Leu Asn
1               5                   10                  15

Trp Leu Glu Asn Gly Asn Val Ser Arg Thr Glu Thr Ala Ser Thr
                20                  25                  30

<210> SEQ ID NO 434
<211> LENGTH: 31
<212> TYPE: PRT
<213> ORGANISM: Homo sapiens

<400> SEQUENCE: 434

Lys Glu Asn Leu Glu Ala Leu Gln Arg Pro Thr Leu Leu His Leu Thr
1               5                   10                  15

His Gly Lys Val Lys Glu Phe Tyr Ser Tyr Gln Asn Glu Ala Val
                20                  25                  30

<210> SEQ ID NO 435
<211> LENGTH: 31
<212> TYPE: PRT
<213> ORGANISM: Homo sapiens

<400> SEQUENCE: 435

Ser Arg Pro Arg Arg Glu Met Ala Ser Pro Pro Ser Pro Leu Ser Glu
1               5                   10                  15

Glu Phe Leu Asp Thr Lys Asp Arg Gln Ala Glu Glu Asp Arg Gln
                20                  25                  30

<210> SEQ ID NO 436
<211> LENGTH: 31
<212> TYPE: PRT
<213> ORGANISM: Homo sapiens

<400> SEQUENCE: 436

Glu Gln Thr Glu Lys Glu Cys Leu Asn Gln Leu Ala Arg Val Thr Pro
1               5                   10                  15

Met Ala Ala Ser Asn Leu Glu Ser Leu Gln Leu Lys Ala Ala Val
                20                  25                  30

<210> SEQ ID NO 437
<211> LENGTH: 31
<212> TYPE: PRT
<213> ORGANISM: Homo sapiens

<400> SEQUENCE: 437

Lys Ala Phe Thr Arg Val Asn Tyr Leu Thr Gln His Gln Lys Ile Tyr
1               5                   10                  15

Thr Gly Glu Lys Pro His Glu Cys Lys Glu Cys Gly Lys Ala Phe
                20                  25                  30
```

```
<210> SEQ ID NO 438
<211> LENGTH: 31
<212> TYPE: PRT
<213> ORGANISM: Homo sapiens

<400> SEQUENCE: 438

Arg Ala Val Ala Ser Gly Val Lys Ala Arg Arg Pro Ser Val Thr Pro
1               5                   10                  15
Leu Val Trp Asp Asp Met Val Arg Asp Leu Pro Glu Asp Gln Leu
            20                  25                  30

<210> SEQ ID NO 439
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Asn Leu Leu Arg Leu Thr Gly
1               5

<210> SEQ ID NO 440
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Asn Leu Leu Arg Leu Thr Gly Trp
1               5

<210> SEQ ID NO 441
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

His Trp Asp Phe Ala Trp Pro Trp
1               5

<210> SEQ ID NO 442
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

His Trp Asp Phe Ala Trp Pro
1               5

<210> SEQ ID NO 443
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 443

Phe Tyr Gln Leu Ala Leu Thr Trp
1               5

<210> SEQ ID NO 444
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Phe Tyr Gln Leu Ala Leu Thr
1               5

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Arg Lys Leu Phe Phe Asn Leu Arg Trp
1               5

<210> SEQ ID NO 446
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Arg Lys Leu Phe Phe Asn Leu Arg
1               5

<210> SEQ ID NO 447
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Phe Phe Arg Lys
1

<210> SEQ ID NO 448
<211> LENGTH: 8
<212> TYPE: PRT
<213> ORGANISM: Gallus gallus

<400> SEQUENCE: 448

Ser Ile Ile Asn Phe Glu Lys Leu
1               5

<210> SEQ ID NO 449
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 449

Ser Ile Ile Asn Phe Glu Lys Leu Phe Phe Arg Lys Asn Leu Leu Arg
1               5                   10                  15

Leu Thr Gly

<210> SEQ ID NO 450
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Asn Leu Leu Arg Leu Thr Gly Phe Phe Arg Lys Ser Ile Ile Asn Phe
1               5                   10                  15

Glu Lys Leu

<210> SEQ ID NO 451
<211> LENGTH: 27
<212> TYPE: PRT
<213> ORGANISM: Artificial Sequence
<220> FEATURE:
<223> OTHER INFORMATION: M5

<400> SEQUENCE: 451

Phe Val Val Lys Ala Tyr Leu Pro Val Asn Glu Ser Phe Ala Phe Thr
1               5                   10                  15

Ala Asp Leu Arg Ser Asn Thr Gly Gly Gln Ala
            20                  25

<210> SEQ ID NO 452
<211> LENGTH: 27
<212> TYPE: PRT
<213> ORGANISM: Artificial Sequence
<220> FEATURE:
<223> OTHER INFORMATION: M12

<400> SEQUENCE: 452

Thr Pro Pro Pro Glu Glu Ala Met Pro Phe Glu Phe Asn Gly Pro Ala
1               5                   10                  15

Gln Gly Asp His Ser Gln Pro Pro Leu Gln Val
            20                  25

<210> SEQ ID NO 453
<211> LENGTH: 27
<212> TYPE: PRT
<213> ORGANISM: Artificial Sequence
<220> FEATURE:
<223> OTHER INFORMATION: M17

<400> SEQUENCE: 453

Val Val Asp Arg Asn Pro Gln Phe Leu Asp Pro Val Leu Ala Tyr Leu
1               5                   10                  15

Met Lys Gly Leu Cys Glu Lys Pro Leu Ala Ser
            20                  25
```

```
<210> SEQ ID NO 454
<211> LENGTH: 27
<212> TYPE: PRT
<213> ORGANISM: Artificial Sequence
<220> FEATURE:
<223> OTHER INFORMATION: M20

<400> SEQUENCE: 454

Phe Arg Arg Lys Ala Phe Leu His Trp Tyr Thr Gly Glu Ala Met Asp
1               5                   10                  15

Glu Met Glu Phe Thr Glu Ala Glu Ser Asn Met
            20                  25

<210> SEQ ID NO 455
<211> LENGTH: 27
<212> TYPE: PRT
<213> ORGANISM: Artificial Sequence
<220> FEATURE:
<223> OTHER INFORMATION: M22

<400> SEQUENCE: 455

Pro Lys Pro Asp Phe Ser Gln Leu Gln Arg Asn Ile Leu Pro Ser Asn
1               5                   10                  15

Pro Arg Val Thr Arg Phe His Ile Asn Trp Asp
            20                  25

<210> SEQ ID NO 456
<211> LENGTH: 27
<212> TYPE: PRT
<213> ORGANISM: Artificial Sequence
<220> FEATURE:
<223> OTHER INFORMATION: M24

<400> SEQUENCE: 456

Thr Ala Val Ile Thr Pro Pro Thr Thr Thr Lys Lys Ala Arg Val
1               5                   10                  15

Ser Thr Pro Lys Pro Ala Thr Pro Ser Thr Asp
            20                  25

<210> SEQ ID NO 457
<211> LENGTH: 27
<212> TYPE: PRT
<213> ORGANISM: Artificial Sequence
<220> FEATURE:
<223> OTHER INFORMATION: M25

<400> SEQUENCE: 457

Ser Thr Ala Asn Tyr Asn Thr Ser His Leu Asn Asn Asp Val Trp Gln
1               5                   10                  15

Ile Phe Glu Asn Pro Val Asp Trp Lys Glu Lys
            20                  25

<210> SEQ ID NO 458
<211> LENGTH: 27
<212> TYPE: PRT
<213> ORGANISM: Artificial Sequence
<220> FEATURE:
<223> OTHER INFORMATION: M27

<400> SEQUENCE: 458

Arg Glu Gly Val Glu Leu Cys Pro Gly Asn Lys Tyr Glu Met Arg Arg
1               5                   10                  15

His Gly Thr Thr His Ser Leu Val Ile His Asp
            20                  25
```

```
<210> SEQ ID NO 459
<211> LENGTH: 27
<212> TYPE: PRT
<213> ORGANISM: Artificial Sequence
<220> FEATURE:
<223> OTHER INFORMATION: M28

<400> SEQUENCE: 459

Asn Ile Glu Gly Ile Asp Lys Leu Thr Gln Leu Lys Lys Pro Phe Leu
1               5                   10                  15

Val Asn Asn Lys Ile Asn Lys Ile Glu Asn Ile
            20                  25

<210> SEQ ID NO 460
<211> LENGTH: 27
<212> TYPE: PRT
<213> ORGANISM: Artificial Sequence
<220> FEATURE:
<223> OTHER INFORMATION: M29

<400> SEQUENCE: 460

Ile Pro Ser Gly Thr Thr Ile Leu Asn Cys Phe His Asp Val Leu Ser
1               5                   10                  15

Gly Lys Leu Ser Gly Gly Ser Pro Gly Val Pro
            20                  25

<210> SEQ ID NO 461
<211> LENGTH: 27
<212> TYPE: PRT
<213> ORGANISM: Artificial Sequence
<220> FEATURE:
<223> OTHER INFORMATION: M30

<400> SEQUENCE: 461

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu
            20                  25

<210> SEQ ID NO 462
<211> LENGTH: 27
<212> TYPE: PRT
<213> ORGANISM: Artificial Sequence
<220> FEATURE:
<223> OTHER INFORMATION: M36

<400> SEQUENCE: 462

Cys Gly Thr Ala Phe Phe Ile Asn Phe Ile Ala Ile Tyr His His Ala
1               5                   10                  15

Ser Arg Ala Ile Pro Phe Gly Thr Met Val Ala
            20                  25

<210> SEQ ID NO 463
<211> LENGTH: 27
<212> TYPE: PRT
<213> ORGANISM: Artificial Sequence
<220> FEATURE:
<223> OTHER INFORMATION: M44

<400> SEQUENCE: 463

Glu Phe Lys His Ile Lys Ala Phe Asp Arg Thr Phe Ala Asn Asn Pro
1               5                   10                  15

Gly Pro Met Val Val Phe Ala Thr Pro Gly Met
            20                  25
```

```
<210> SEQ ID NO 464
<211> LENGTH: 27
<212> TYPE: PRT
<213> ORGANISM: Artificial Sequence
<220> FEATURE:
<223> OTHER INFORMATION: M45

<400> SEQUENCE: 464

Glu Cys Arg Ile Thr Ser Asn Phe Val Ile Pro Ser Glu Tyr Trp Val
1               5                   10                  15

Glu Glu Lys Glu Glu Lys Gln Lys Leu Ile Gln
            20                  25

<210> SEQ ID NO 465
<211> LENGTH: 27
<212> TYPE: PRT
<213> ORGANISM: Artificial Sequence
<220> FEATURE:
<223> OTHER INFORMATION: M46

<400> SEQUENCE: 465

Asn His Ser Gly Leu Val Thr Phe Gln Ala Phe Ile Asp Val Met Ser
1               5                   10                  15

Arg Glu Thr Thr Asp Thr Asp Thr Ala Asp Gln
            20                  25

<210> SEQ ID NO 466
<211> LENGTH: 27
<212> TYPE: PRT
<213> ORGANISM: Artificial Sequence
<220> FEATURE:
<223> OTHER INFORMATION: M47

<400> SEQUENCE: 466

Gly Arg Gly His Leu Leu Gly Arg Leu Ala Ala Ile Val Gly Lys Gln
1               5                   10                  15

Val Leu Leu Gly Arg Lys Val Val Val Arg
            20                  25

<210> SEQ ID NO 467
<211> LENGTH: 27
<212> TYPE: PRT
<213> ORGANISM: Artificial Sequence
<220> FEATURE:
<223> OTHER INFORMATION: M48

<400> SEQUENCE: 467

Ser His Cys His Trp Asn Asp Leu Ala Val Ile Pro Ala Gly Val Val
1               5                   10                  15

His Asn Trp Asp Phe Glu Pro Arg Lys Val Ser
            20                  25

<210> SEQ ID NO 468
<211> LENGTH: 27
<212> TYPE: PRT
<213> ORGANISM: Artificial Sequence
<220> FEATURE:
<223> OTHER INFORMATION: M50

<400> SEQUENCE: 468

Gly Phe Ser Gln Pro Leu Arg Arg Leu Val Leu His Val Val Ser Ala
1               5                   10                  15

Ala Gln Ala Glu Arg Leu Ala Arg Ala Glu Glu
            20                  25
```

```
<210> SEQ ID NO 469
<211> LENGTH: 38
<212> TYPE: PRT
<213> ORGANISM: Artificial Sequence
<220> FEATURE:
<223> OTHER INFORMATION: M27-Jay

<400> SEQUENCE: 469

Arg Glu Gly Val Glu Leu Cys Pro Gly Asn Lys Tyr Glu Met Arg Arg
1               5                   10                  15

His Gly Thr Thr His Ser Leu Val Ile His Asp Phe Phe Arg Lys Asn
            20                  25                  30

Leu Leu Arg Leu Thr Gly
        35

<210> SEQ ID NO 470
<211> LENGTH: 38
<212> TYPE: PRT
<213> ORGANISM: Artificial Sequence
<220> FEATURE:
<223> OTHER INFORMATION: M30-Jay

<400> SEQUENCE: 470

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu Phe Arg Lys Asn
            20                  25                  30

Leu Leu Arg Leu Thr Gly
        35

<210> SEQ ID NO 471
<211> LENGTH: 27
<212> TYPE: PRT
<213> ORGANISM: Artificial Sequence
<220> FEATURE:
<223> OTHER INFORMATION: Wild Type M27

<400> SEQUENCE: 471

Arg Glu Gly Val Glu Leu Cys Pro Gly Asn Lys Tyr Glu Thr Arg Arg
1               5                   10                  15

His Gly Thr Thr His Ser Leu Val Ile His Asp
            20                  25

<210> SEQ ID NO 472
<211> LENGTH: 27
<212> TYPE: PRT
<213> ORGANISM: Artificial Sequence
<220> FEATURE:
<223> OTHER INFORMATION: Wild type M30

<400> SEQUENCE: 472

Pro Ser Lys Pro Ser Phe Gln Glu Phe Val Asp Trp Glu Lys Val Ser
1               5                   10                  15

Pro Glu Leu Asn Ser Thr Asp Gln Pro Phe Leu
            20                  25

<210> SEQ ID NO 473
<211> LENGTH: 20
<212> TYPE: PRT
<213> ORGANISM: Artificial Sequence
<220> FEATURE:
<223> OTHER INFORMATION: Peptide containing phosphorylated serine
      residue
```

```
<220> FEATURE:
<221> NAME/KEY: MOD_RES
<222> LOCATION: (16)..(16)
<223> OTHER INFORMATION: Phosphorylated Serine

<400> SEQUENCE: 473

Asn Leu Leu Arg Leu Thr Gly Phe Phe Arg Lys Gly Leu Leu Gly Ser
1               5                   10                  15

Pro Val Arg Ala
            20

<210> SEQ ID NO 474
<211> LENGTH: 20
<212> TYPE: PRT
<213> ORGANISM: Artificial Sequence
<220> FEATURE:
<223> OTHER INFORMATION: Peptide containing phosphorylated serine
      residue
<220> FEATURE:
<221> NAME/KEY: MOD_RES
<222> LOCATION: (5)..(5)
<223> OTHER INFORMATION: Phosphorylated Serine residue

<400> SEQUENCE: 474

Gly Leu Leu Gly Ser Pro Val Arg Ala Phe Phe Arg Lys Asn Leu Leu
1               5                   10                  15

Arg Leu Thr Gly
            20

<210> SEQ ID NO 475
<211> LENGTH: 20
<212> TYPE: PRT
<213> ORGANISM: Artificial Sequence
<220> FEATURE:
<223> OTHER INFORMATION: Peptide containing phosphorylated serine
      residue
<220> FEATURE:
<221> NAME/KEY: MOD_RES
<222> LOCATION: (15)..(15)
<223> OTHER INFORMATION: Phosphorylated serine residue

<400> SEQUENCE: 475

Asn Leu Leu Arg Leu Thr Gly Phe Phe Arg Lys Arg Val Ala Ser Pro
1               5                   10                  15

Thr Ser Gly Val
            20

<210> SEQ ID NO 476
<211> LENGTH: 20
<212> TYPE: PRT
<213> ORGANISM: Artificial Sequence
<220> FEATURE:
<223> OTHER INFORMATION: Peptide containing phosphorylated serine
      residue
<220> FEATURE:
<221> NAME/KEY: MOD_RES
<222> LOCATION: (4)..(4)
<223> OTHER INFORMATION: Phosphorylated serine residue

<400> SEQUENCE: 476

Arg Val Ala Ser Pro Thr Ser Gly Val Phe Phe Arg Lys Asn Leu Leu
1               5                   10                  15

Arg Leu Thr Gly
            20
```

```
<210> SEQ ID NO 477
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Phe Phe Arg Lys Asn Leu Leu Arg Leu Thr Gly
1               5                   10

<210> SEQ ID NO 478
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Asn Leu Leu Arg Leu Thr Gly Phe Phe Arg Lys
1               5                   10
```

VACCINES FOR TREATMENT AND PREVENTION OF CANCER

RELATED APPLICATIONS

This application claims priority to U.S. provisional patent applications: 62/161,053, filed May 13, 2015; 62/205,591, filed Aug. 14, 2015; 62/257,458, filed Nov. 19, 2015; and 62/307,592, filed Mar. 14, 2016, each of which is incorporated by reference herein in its entirety.

TECHNICAL FIELD

The invention relates to the field of cancer biology, and more specifically to the treatment and inhibition of recurrence using anti-cancer vaccines.

BACKGROUND

Immunotherapies are becoming important tools in the treatment of cancer. One immunotherapy approach involves the use of therapeutic cancer vaccines comprising cancer-specific antigenic peptides that actively educate a patient's immune system to target and destroy cancer cells. However, the generation of such therapeutic cancer vaccines is limited by the availability of cancer-specific antigenic peptides.

Accordingly, there is a need in the art for improved methods of identifying cancer-specific antigenic peptides and for creating effective anti-cancer vaccines comprising these peptides.

SUMMARY OF INVENTION

The instant disclosure provides compositions useful as therapeutic vaccines (e.g., cancer vaccines), and methods of producing such compositions. The compositions disclosed herein generally employ a stress protein and at least one synthetic antigenic peptide comprising a cancer-specific mutation present in a patient's cancer. The methods disclosed herein are particularly advantageous in that they allow for the preparation of therapeutic vaccine (e.g., cancer vaccine) compositions using only trace amounts of a subject's tissue (e.g., single cells or exosomes).

In one aspect, the disclosure provides a first composition comprising at least two different complexes of a purified stress protein bound to an antigenic peptide, wherein the complexes each comprise a different antigenic peptide, wherein each one of the different antigenic peptides comprises one or more mutant MHC-binding epitopes (e.g., human MHC-binding epitopes) from a cancer cell, and wherein the composition comprises no more than 20 (e.g., 1, 2, 3, 4, 5, 6, 7, 8, 9, 10, 11, 12, 13, 14, 15, 16, 17, 18, 19, or 20) different antigenic peptides that contain only wild-type MHC-binding epitopes (e.g., wild-type human MHC-binding epitopes).

In one embodiment, the present invention relates to a first composition comprising at least two different complexes of a purified stress protein bound to an antigenic peptide, wherein the complexes each comprise a different antigenic peptide, wherein each one of the different antigenic peptides comprises one or more mutant MHC-binding epitopes from a cancer cell, and wherein the composition comprises no more than 5 different antigenic peptides that contain only wild-type MHC-binding epitopes.

In certain embodiments, the composition comprises no more than 1, 2, 3, 4, 5, 6, 7, 8, 9, 10, 11, 12, 13, 14, 15, 16, 17, 18, 19, or 20 different antigenic peptides that contain only wild-type MHC-binding epitopes e.g., wild-type MHC-binding epitopes. In certain embodiments, the composition does not comprise any antigenic peptides that contain only wild-type MHC-binding epitopes.

In certain embodiments, the composition comprises no more than 100 (e.g., 2, 3, 4, 5, 6, 7, 8, 9, 10, 11, 12, 13, 14, 15, 16, 17, 18, 19, or 20; e.g., about 20, 25, 30, 40, 50, 55, 60, 65, 70, 75, 80, 85, 90, 95 or 100) different antigenic peptides. In certain embodiments, the composition comprises no more than 2, 3, 4, 5, 6, 7, 8, 9, 10, 11, 12, 13, 14, 15, 16, 17, 18, 19, 20, 25, 30, 40, 50, 55, 60, 65, 70, 75, 80, 85, 90, 95 or 100 different antigenic peptides.

In certain embodiments, each one of the antigenic peptides binds to an MHC molecule with an $IC_{50}$ of 500 nM or less. In certain embodiments, at least one of the antigenic peptides binds to an MHC I molecule with an $IC_{50}$ of 500 nM or less. In certain embodiments, at least one of the antigenic peptides binds to an MHC II molecule with an $IC_{50}$ of 1000 nM or less. In certain embodiments, each one of the antigenic peptides binds to an MHC II molecule with an $IC_{50}$ of 1000 nM or less. In certain embodiments, the MHC molecule is a human MHC molecule.

In certain embodiments, at least one of the antigenic peptides comprises more than one mutant MHC-binding epitope from a cancer cell. In certain embodiments, each one of the antigenic peptides comprises more than one mutant MHC-binding epitope from a cancer cell. In certain embodiments, at least one of the antigenic peptides is capable of binding to more than one distinct MHC molecule with an $IC_{50}$ of less than 500 nM. In certain embodiments, each one of the antigenic peptides is capable of binding to more than one distinct MHC molecule with an $IC_{50}$ of less than 500 nM.

In certain embodiments, at least one of the mutant MHC-binding epitopes is expressed in cancer cells of a subject but not in normal cells of the subject. In certain embodiments, each one of the mutant MHC-binding epitopes is expressed in cancer cells of a single subject but not in normal cells of the subject. In certain embodiments, at least one of the mutant MHC-binding epitopes is expressed at a higher level in cancer cells of a subject relative to normal cells of the subject. In certain embodiments, each one of the mutant MHC-binding epitopes is expressed at a higher level in cancer cells of a subject relative to normal cells of the subject. In certain embodiments, at least one of the mutant MHC-binding epitopes comprises an amino acid mutation or a gene fusion mutation. In certain embodiments, each one of the mutant MHC-binding epitopes comprises an amino acid mutation or a gene fusion mutation. In certain embodiments, the amino acid mutation is an amino acid substitution, deletion or insertion. In certain embodiments, the amino acid mutation is present in a subject's tumor with an allelic frequency of greater than 0.05.

In certain embodiments, at least one of the mutant MHC-binding epitopes comprises a modified amino acid. In certain embodiments, each one of the mutant MHC-binding epitopes comprises a modified amino acid. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In certain embodiments, at least one of the mutant MHC-binding epitopes has a median expression level of greater than 1 Reads Per Kilobase of transcript per Million mapped reads (RPKM) across multiple cancers of the same indication. In certain embodiments, each one of the mutant MHC-binding epitopes has a median expression level of greater than 1 Reads Per Kilobase of transcript per Million mapped reads (RPKM) across multiple cancers of the same indication. In certain embodiments, at least one of the mutant MHC-binding epitopes has an expression level of greater than 10 Normalized Mutation-containing Read Counts (NMRC) in a subject's tumor. In certain embodiments, each one of the mutant MHC-binding epitopes has an expression level of greater than 10 NMRC in a subject's tumor.

In certain embodiments, at least one of the antigenic peptides stimulates a T-cell response against tumor cells expressing the one or more mutant MHC-binding epitopes in a subject to whom the antigenic peptides are administered. In certain embodiments, each one of the antigenic peptides stimulates a T-cell response against tumor cells expressing the one or more mutant MHC-binding epitopes in a subject to whom the antigenic peptides are administered. In certain embodiments, at least one of the antigenic peptides induces the in vitro proliferation of T-cells in peripheral blood mononuclear cells (PBMC) isolated from the subject. In certain embodiments, each one of the antigenic peptides induces the in vitro proliferation of T-cells in peripheral blood mononuclear cells (PBMC) isolated from the subject.

In certain embodiments, at least one of the antigenic peptides does not comprise the entire amino acid sequence of a protein. In certain embodiments, each one of the antigenic peptides does not comprise the entire amino acid sequence of a protein.

In certain embodiments, at least one of the antigenic peptides is 5 to 50 amino acids in length. In certain embodiments, each one of the antigenic peptides is 5 to 50 amino acids in length. In certain embodiments, at least one of the antigenic peptides is 25 to 40 amino acids in length. In certain embodiments, each one of the antigenic peptides is 25 to 40 amino acids in length. In certain embodiments, at least one of the antigenic peptides is 27 to 31 amino acids in length. In certain embodiments, each one of the antigenic peptides is 27 to 31 amino acids in length. In certain embodiments, at least one of the antigenic peptides is 21 to 31 amino acids in length. In certain embodiments, each one of the antigenic peptides is 21 to 31 amino acids in length.

In certain embodiments, at least one of the antigenic peptides has a tumor-specific mutation at about the middle of the amino acid sequence. In certain embodiments, each one of the antigenic peptides has a tumor-specific mutation at about the middle of the amino acid sequence. In certain embodiments, at least one of the antigenic peptides is 27 amino acids in length and has a tumor-specific mutation at position 11, 12, 13, 14, 15, 16, or 17. In certain embodiments, each one of the antigenic peptides is 27 amino acids in length and has a tumor-specific mutation at position 11, 12, 13, 14, 15, 16, or 17. In certain embodiments, at least one of the antigenic peptides is 29 amino acids in length and has a tumor-specific mutation at position 12, 13, 14, 15, 16, 17, or 18. In certain embodiments, each one of the antigenic peptides is 29 amino acids in length and has a tumor-specific mutation at position 12, 13, 14, 15, 16, 17, or 18. In certain embodiments, at least one of the antigenic peptides is 31 amino acids in length and has a tumor-specific mutation at position 13, 14, 15, 16, 17, 18, or 19. In certain embodiments, each one of the antigenic peptides is 31 amino acids in length and has a tumor-specific mutation at position 13, 14, 15, 16, 17, 18, or 19.

In certain embodiments, at least one of the antigenic peptides is a chemically synthesized peptide. In certain embodiments, each one of the antigenic peptides is a chemically synthesized peptide.

In certain embodiments, at least one of the antigenic peptides further comprises a heat shock protein binding sequence. In certain embodiments, each one of the antigenic peptides further comprises a heat shock protein binding sequence. In one preferred embodiment, at least one of the antigenic peptides further comprises a heat shock protein binding sequence at its N- or C-terminus, more preferably at least one of the antigenic peptides further comprises a heat shock protein binding sequence at its C-terminus and/or the heat shock protein binding sequence is linked to the remainder of the antigenic peptide via a peptide linker. In another preferred embodiment, each one of the antigenic peptides further comprises a heat shock protein binding sequence at its N- or C-terminus, more preferably each one of the antigenic peptides further comprises a heat shock protein binding sequence at its C-terminus and/or the heat shock protein binding sequence is linked to the remainder of the antigenic peptide via a peptide linker. In one preferred embodiment, the peptide linker comprises the amino acid sequence FFRK (SEQ ID NO:447). In certain embodiments, the heat shock protein binding sequence is selected from the group consisting of SEQ ID NOs: 439-446. In certain embodiments, the heat shock protein binding sequence is SEQ ID NO: 439.

In certain embodiments, at least one of the antigenic peptides comprises the amino acid sequence of SEQ ID NO:477 at the C-terminus. In certain embodiments, each one of the antigenic peptides comprises the amino acid sequence of SEQ ID NO:477 at the C-terminus.

In certain embodiments, at least one of the antigenic peptides comprises the amino acid sequence of SEQ ID NO:478 at the N-terminus. In certain embodiments, each one of the antigenic peptides comprises the amino acid sequence of SEQ ID NO:478 at the N-terminus.

In certain embodiments, at least one of the antigenic peptides comprises: i) a first portion comprising a tumor-specific mutation; and ii) a second portion comprising the heat shock protein binding sequence and, optionally, a peptide linker. In certain embodiments, each one of the antigenic peptides comprises: i) a first portion comprising a tumor-specific mutation; and ii) a second portion comprising the heat shock protein binding sequence and, optionally, a peptide linker. In certain embodiments, the first portion is 27-31 amino acids in length. In certain embodiments, the first portion is 27 amino acids in length. In certain embodiments, the first portion is 29 amino acids in length. In certain embodiments, the first portion is 31 amino acids in length. In certain embodiments, the first portion has a tumor-specific mutation at about the middle of the amino acid sequence of the first portion. In certain embodiments, the first portion is 27 amino acids in length and has a tumor-specific mutation at position 11, 12, 13, 14, 15, 16, or 17. In certain embodiments, the first portion is 29 amino acids in length and has a tumor-specific mutation at position 12, 13, 14, 15, 16, 17, or 18. In certain embodiments, the first portion is 31 amino acids in length and has a tumor-specific mutation at position 13, 14, 15, 16, 17, 18, or 19. In certain embodiments, the second portion comprises an amino acid sequence selected from the group consisting of SEQ ID NOs: 439-446, 447, 477, and 478. In certain embodiments, at least one of the antigenic peptides is 38 amino acids in length. In certain embodiments, each one of the antigenic peptides is 38 amino acids in length. In certain embodiments, at least one of the antigenic peptides is 40 amino acids in length. In certain embodiments, each one of the antigenic peptides is 40 amino acids in length. In certain embodiments, at least one of the antigenic peptides is 42 amino acids in length. In certain embodiments, each one of the antigenic peptides is 42 amino acids in length.

In certain embodiments, the composition comprises at least 2 (e.g., 2, 3, 4, 5, 6, 7, 8, 9, 10, 11, 12, 13, 14, 15, 16, 17, 18, 19, or 20; e.g., about 20, 25, 30, 40, 50, 55, 60, 65, 70, 75, 80, 85, 90, 95 or 100) different antigenic peptides.

In certain embodiments, the molar ratio of stress protein to antigenic peptide in each complex is at least 1:1 (e.g., about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 49:1, up to 100:1). In certain embodiments, the molar ratio of stress protein to antigenic peptide in each complex is 1:1 or less (e.g., about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:50, down to 1:100 or less).

In certain embodiments, at least one of the antigenic peptides comprises one or more mutant MHC-binding epitopes of MYC, K-RAS, N-RAS, TP53, KDM6A, NPM1, H-RAS, FGFR3, MSH6, TP53, EGFR, PIK3CA, ABL1, CTNNB1, KIT, HNF1A, JAK2, BRAF, IDH1, RET, PDG-FRA, MET, APC, CDC27, CDK4, prostate-specific antigen, alpha-fetoprotein, breast mucin, gp100, g250, p53, MART-I, MAGE, BAGE, GAGE, tyrosinase, Tyrosinase related protein 11, Tyrosinase related protein, or RAD50.

In certain embodiments, at least one of the antigenic peptides comprises an amino acid sequence selected from the group consisting of SEQ ID NOs: 1-478. In certain embodiments, each one of the antigenic peptides comprises an amino acid sequence selected from the group consisting of SEQ ID NOs: 1-478.

In certain embodiments, the stress protein is a recombinant stress protein. In certain embodiments, the stress protein is selected from the group consisting of hsc70, hsp70, hsp90, hsp110, grp170, gp96, calreticulin, a mutant thereof, and combinations of two or more thereof. In certain embodiments, the stress protein is hsc70. In certain embodiments, the stress protein is a human hsc70. In certain embodiments, the stress protein is hsp70. In certain embodiments, the stress protein is a human hsp70. In certain embodiments, the stress protein is non-covalently bound to the antigenic peptide. In certain embodiments, the stress protein is covalently bound to the antigenic peptide. In certain embodiments, the amount of the stress protein in the composition is 10 µg to 600 µg. In certain embodiments, the amount of the stress protein in the composition is 25 µg.

In certain embodiments, when administered to a subject, each one of the complexes is capable of achieving presentation of the one or more mutant MHC-binding epitopes by an MHC molecule on the surface of cells in the subject.

In certain embodiments, the composition further comprises an adjuvant. In certain embodiments, the adjuvant comprises a saponin or an immunostimulatory nucleic acid. In certain embodiments, the adjuvant comprises QS-21. In certain embodiments, the amount of the QS-21 in the composition is 10 µg, 25 µg, or 50 µg.

In another aspect, the disclosure provides a method of making an antigenic peptide comprising one or more mutant MHC-binding epitopes (e.g., human MHC-binding epitopes) from a cancer cell, the method comprising: (a) determining the sequence of one or more exomes of genomic DNA from cancer cells of a subject; (b) identifying from the exomes one or more non-synonymous mutant alleles that encode mutant proteins, when compared to reference genomic DNA; (c) determining if the mutant alleles identified in step (b) are expressed in the subject's cancer cells; (d) determining the allelic frequency of the mutant alleles identified in step (b); (e) determining one or more MHC types of the subject; (f) selecting a mutant peptide encoded by a mutant allele identified in step (b), wherein the mutant allele has an allelic frequency of greater than 0.05 and is expressed in the subject's cancer cells, and wherein the mutant peptide is predicted to be capable of presentation by at least one of the subject's MHC molecules when administered to the subject; and (g) synthesizing one or more peptides comprising one or more of the peptides selected in step (f), thereby making an antigenic peptide comprising one or more mutant MHC-binding epitopes from a cancer cell.

In certain embodiments, the method further comprises the step of determining the expression level of mRNA containing the mutant alleles identified in step (b).

In certain embodiments, the selection of peptides in step (f) further requires that the mutant allele encoding the mutant peptide has a median expression level of greater than 10 NMRC in the subject's cancer cells. In certain embodiments, the selection of peptides in step (f) further requires that the mutant allele encoding the mutant peptide has a median expression level of greater than 1 RPKM in cancer cells of the same indication in other individuals. In certain embodiments, the selection of peptides in step (f) further requires that the mutant allele encoding the mutant peptide is not expressed in the subject's normal cells. In certain embodiments, the method further comprises the step of determining the binding affinity of the one or more mutant peptides for one or more of the subject's MHC molecules. In certain embodiments, the binding affinity of the one or more mutant peptides for one or more of the subject's MHC molecules is predicted by computer modeling. In certain embodiments, the selection of peptides in step (f) further requires that the one or more mutant peptides encoded by the mutant alleles have an $IC_{50}$ for one or more of the subject's MHC molecules of less than 500 nM. In certain embodiments, the selection of peptides in step (f) further requires that the mutant peptide has an $IC_{50}$ for one or more of the subject's MHC class I molecules of less than 500 nM. In certain embodiments, the selection of peptides in step (f) further requires that the mutant peptides has an $IC_{50}$ for one or more of the subject's MHC class II molecules of less than 1000 nM. In certain embodiments, the selection of peptides in step (f) further requires that the mutant peptide is encoded by a mutant allele that is characteristic of a particular type of cancer. In certain embodiments, the selection of peptides in step (f) further requires that the mutant peptide contains a gene fusion mutation, or an amino acid insertion, deletion, or substitution mutation.

In certain embodiments, the method further comprises the step of ranking the mutant peptides selected in step (f) based upon: (i) the number of predicted MHC-binding epitopes present in the mutant peptides, wherein the higher the number of predicted MHC-binding epitopes in the mutant peptide the higher the ranking; (ii) the $IC_{50}$ of the mutant peptide for binding to the subject's MHC, wherein the lower the $IC_{50}$ the higher the ranking; (iii) the presence or absence of expression of the wild-type equivalent of the mutant peptide in normal cells of the subject, wherein a mutant peptide ranks higher if the wild-type equivalent of the mutant peptide is not expressed in normal cells of the subject; (iv) the stability of binding of the C-terminus of the mutant peptide to an MHC of the subject, wherein the higher the stability the higher the ranking; and/or (v) the predicted kinetics of proteasomal degradation of the mutant peptide, wherein the better a substrate for the proteasome a mutant peptide is predicted to be, the higher the ranking. In certain embodiments, no more than 100 (e.g. 10, 20, 30, 40, 50, 60, 70, 80, 90, or 100) of the highest-ranked peptides are synthesized in step (g).

In certain embodiments, the genomic DNA is isolated from a tumor sample or body fluid from the subject. In certain embodiments, the genomic DNA is isolated from exosomes, or circulating tumor cells obtained from the subject. In certain embodiments, the genomic DNA is circulating tumor cell DNA obtained from the subject.

In certain embodiments, the sequence of the exomes is determined by next generation sequencing. In certain embodiments, the reference genomic DNA is genomic DNA from the subject's normal cells, and wherein the allelic frequency of the mutant alleles is determined in step (d) by next generation sequencing read re-mapping.

In certain embodiments, the expression of non-synonymous mutant alleles is determined in step (c) by next generation sequencing of mRNA isolated from the subject's cancer cells.

In certain embodiments, the mutant alleles identified in step (b) are not single nucleotide polymorphisms (SNPs) found in the subject or in at least 1000 genomes.

In certain embodiments, the synthesized peptides are 5 to 50 amino acids in length. In certain embodiments, the synthesized peptides are 25 to 40 amino acids in length. In certain embodiments, the synthesized peptides are 27 to 31 amino acids in length. In certain embodiments, the synthesized peptides are 21 to 31 amino acids in length.

In certain embodiments, the cancer cells are multiple myeloma or glioblastoma multiforme cells.

In certain embodiments, one or more of the antigenic peptides was made using the methods disclosed herein. In certain embodiments, the present invention relates to a composition comprising antigenic peptides obtainable by a method of the invention. In certain embodiments, all of the antigenic peptides were made using the methods disclosed herein.

In another aspect, provided herein is a first composition of the present invention, for use as a medicament. In another aspect, provided herein is a first composition of the present invention for use in a method for the treatment of cancer.

In another aspect, provided herein is a first composition of the present invention, for use as a therapeutic vaccine.

In another aspect, provided herein is a first composition of the present invention, for use as a cancer vaccine.

In another aspect, provided herein is a first composition of the present invention for use in a method for the treatment of cancer in a subject.

In another aspect, provided herein is a first composition of the present invention for use in a method for the treatment of cancer in a subject comprising administering to the subject an effective amount of a first composition disclosed herein.

In another aspect, provided herein is a first composition of the present invention for use in a method for inducing a cellular immune response to an antigenic peptide.

In another aspect, provided herein is a first composition of the present invention for use in a method for inducing a cellular immune response to an antigenic peptide in a subject with cancer.

In another aspect, provided herein is a first composition of the present invention for use in a method for inducing a cellular immune response to an antigenic peptide in a subject with cancer the method comprising administering to the subject an effective amount of a first composition disclosed herein.

In another aspect, the disclosure provides a method of inducing a cellular immune response to an antigenic peptide in a subject with cancer, the method comprising administering to the subject an effective amount of a first composition disclosed herein. In another aspect, the disclosure provides a method of treating a subject having cancer, the method comprising administering to the subject a therapeutically effective amount of a first composition disclosed herein. The following embodiments apply equally to both of the foregoing methods, as well as to the foregoing compositions for use.

In certain embodiments, one or more of the mutant MHC-binding epitopes were identified as being present in the subject's own cancer cells. In certain embodiments, all of the mutant MHC-binding epitopes were identified as being present in the subject's own cancer cells.

In certain embodiments, an insufficient amount of tumor cells are available from the subject to allow isolation of at least 150 μg of stress protein purified to at least about 65% purity from the tumor cells.

In certain embodiments, the stress protein is selected from the group consisting of hsc70, hsp70, hsp90, hsp110, grp170, gp96, calreticulin, a mutant thereof, and combinations of two or more thereof. In certain embodiments, the stress protein is hsc70. In certain embodiments, the stress protein is a human hsc70. In certain embodiments, the stress protein is hsp70. In certain embodiments, the stress protein is a human hsp70. In certain embodiments, the subject has a tumor with a wet weight of 6 g of less (e.g., 1, 2, 3, 4, 5, 6, 7, 8, 9 or 10 g).

In certain embodiments, the ability of the composition to induce in vitro proliferation of T-cells in peripheral blood mononuclear cells (PBMC) isolated from the subject is determined prior to administration of the composition to the subject. In certain embodiments, the ability of the composition to induce in vitro proliferation of T-cells in peripheral blood mononuclear cells (PBMC) isolated from the subject is determined after administration of the composition to the subject.

In certain embodiments, the composition is administered to the subject in a unit dose comprising 10 μg to 600 μg of stress protein. In certain embodiments, the composition is administered in a unit dose comprising 25 μg of stress protein. In certain embodiments, the composition is administered in a unit dose comprising 240 μg of stress protein.

In certain embodiments, the composition is administered to the subject weekly for four weeks. In certain embodiments, after the four weekly doses, at least 2 further doses of the composition are administered biweekly to the subject. In certain embodiments, at least 6 doses of the composition are administered in total. In certain embodiments, the composition is further administered as a booster three months after the final weekly or biweekly dose. In certain embodiments, the composition is further administered every three months for at least 1 year.

In certain embodiments, the method further comprises administering to the subject lenalidomide, dexamethasone, or cyclophosphamide. In certain embodiments, the method further comprises administering to the subject an indoleamine dioxygenase-1 inhibitor. In certain embodiments, the indoleamine dioxygenase-1 inhibitor comprises 4-amino-N-(3-chloro-4-fluorophenyl)-N'-hydroxy-1,2,5-oxadiazole-3-carboximidamide.

In certain embodiments, the method further comprises administering to the subject a checkpoint antibody. In certain embodiments, the checkpoint antibody is selected from the group consisting of anti-GITR, anti-OX40, anti-PD-1, anti-CTLA-4, anti-TIM-3, and anti-LAG-3.

In certain embodiments, the first composition for use further comprises administering to the subject lenalidomide, dexamethasone, or cyclophosphamide. In certain embodiments, the first composition for use further comprises administering to the subject an indoleamine dioxygenase-1 inhibitor. In certain embodiments, the indoleamine dioxygenase-1 inhibitor comprises 4-amino-N-(3-chloro-4-fluorophenyl)-N'-hydroxy-1,2,5-oxadiazole-3-carboximidamide.

In certain embodiments, the first composition for use further comprises administering to the subject a checkpoint antibody. In certain embodiments, the checkpoint antibody is selected from the group consisting of anti-GITR, anti-OX40, anti-PD-1, anti-CTLA-4, anti-TIM-3, and anti-LAG-3.

In certain embodiments, the present invention relates to (a) a first composition of the present invention, and (b) lenalidomide, dexamethasone, or cyclophosphamide, for use as a medicament.

In certain embodiments, the present invention relates to (a) a first composition of the present invention, and (b) lenalidomide, dexamethasone, or cyclophosphamide, for use in a method for inducing a cellular immune response to an antigenic peptide in a subject with cancer.

In certain embodiments, the present invention relates to (a) a first composition of the present invention, and (b) lenalidomide, dexamethasone, or cyclophosphamide, for use in a method for the treatment of cancer.

In certain embodiments, the present invention relates to a composition, kit or kit-of-parts comprising (a) a first composition of the present invention, and (b) lenalidomide, dexamethasone, or cyclophosphamide.

In certain embodiments, the present invention relates to (a) a first composition of the present invention, and (b) an indoleamine dioxygenase-1 inhibitor, for use as a medicament.

In certain embodiments, the present invention relates to (a) a first composition of the present invention, and (b) an indoleamine dioxygenase-1 inhibitor, for use in a method for inducing a cellular immune response to an antigenic peptide in a subject with cancer.

In certain embodiments, the present invention relates to (a) a first composition of the present invention, and (b) an indoleamine dioxygenase-1 inhibitor, for use in a method for the treatment of cancer.

In certain embodiments, the present invention relates to a composition, kit or kit-of-parts comprising (a) a first composition of the present invention, and (b) an indoleamine dioxygenase-1 inhibitor.

In certain embodiments, the present invention relates to (a) a first composition of the present invention, and (b) a checkpoint antibody, for use as a medicament.

In certain embodiments, the present invention relates to (a) a first composition of the present invention, and (b) a checkpoint antibody, for use in a method for inducing a cellular immune response to an antigenic peptide in a subject with cancer.

In certain embodiments, the present invention relates to (a) a first composition of the present invention, and (b) a checkpoint antibody, for use in a method for the treatment of cancer.

In certain embodiments, the present invention relates to a composition, kit or kit-of-parts comprising (a) a first composition of the present invention, and (b) a checkpoint antibody.

In certain embodiments, the method further comprises administering to the subject a second composition comprising at least 2 different complexes of a purified stress protein bound to an antigenic peptide, wherein the complexes each comprise a different antigenic peptide, and wherein each one of the different antigenic peptides comprises one or more mutant MHC-binding epitopes that are frequently found in cancers of the same type as subject's cancer.

In certain embodiments, the second composition comprises at least 2 (e.g., 2, 3, 4, 5, 6, 7, 8, 9, 10, 11, 12, 13, 14, 15, 16, 17, 18, 19, or 20; e.g., about 20, 25, 30, 40, 50, 55, 60, 65, 70, 75, 80, 85, 90, 95 or 100) different antigenic peptides.

In certain embodiments, the stress protein in the second composition is a recombinant stress protein.

In certain embodiments, at least one of the antigenic peptides in the second composition is a chemically synthesized peptide. In certain embodiments, each one of the antigenic peptides in the second composition is a chemically synthesized peptide.

In certain embodiments, the second composition comprises no more than 20 (e.g., 1, 2, 3, 4, 5, 6, 7, 8, 9, 10, 11, 12, 13, 14, 15, 16, 17, 18, 19, or 20) different antigenic peptides that contain only wild-type MHC-binding epitopes. In certain embodiments, the second composition does not comprise any antigenic peptides that contain only wild-type MHC-binding epitopes.

In certain embodiments, the second composition comprises no more than 100 (e.g., 2, 3, 4, 5, 6, 7, 8, 9, 10, 11, 12, 13, 14, 15, 16, 17, 18, 19, or 20; e.g., about 20, 25, 30, 40, 50, 55, 60, 65, 70, 75, 80, 85, 90, 95 or 100) different antigenic peptides.

In certain embodiments, the first composition is administered simultaneously with the second composition. In certain embodiments, the first composition is administered sequentially with the second composition. In certain embodiments, the second composition is administered prior to administration of the first composition.

In certain embodiments, at least one of the antigenic peptides comprises one or more mutant MHC-binding epitopes of MYC, K-RAS, N-RAS, TP53, KDM6A, NPM1, H-RAS, FGFR3, MSH6, TP53, EGFR, PIK3CA, ABL1, CTNNB1, KIT, HNF1A, JAK2, BRAF, IDH1, RET, PDGFRA, MET, APC, CDC27, CDK4, prostate-specific antigen, alpha-fetoprotein, breast mucin, gp100, g250, p53, MART-I, MAGE, BAGE, GAGE, tyrosinase, Tyrosinase related protein 11, Tyrosinase related protein, or RAD50. In certain embodiments, each one of the antigenic peptides comprises one or more mutant MHC-binding epitopes of MYC, K-RAS, N-RAS, TP53, KDM6A, NPM1, H-RAS, FGFR3, MSH6, TP53, EGFR, PIK3CA, ABL1, CTNNB1, KIT, HNF1A, JAK2, BRAF, IDH1, RET, PDGFRA, MET, APC, CDC27, CDK4, prostate-specific antigen, alpha-fetoprotein, breast mucin, gp100, g250, p53, MART-I, MAGE, BAGE, GAGE, tyrosinase, Tyrosinase related protein 11, Tyrosinase related protein, or RAD50. In certain embodiments, the cancer is multiple myeloma or glioblastoma multiforme.

In certain embodiments, the present invention relates to (a) a first composition of the present invention, and (b) a second composition as disclosed herein, for use as a medicament.

In certain embodiments, the present invention relates to (a) a first composition of the present invention, and (b) a second composition as disclosed herein, for use in a method for inducing a cellular immune response to an antigenic peptide in a subject with cancer.

In certain embodiments, the present invention relates to (a) a first composition of the present invention, and (b) a second composition as disclosed herein, for use in a method for the treatment of cancer.

In certain embodiments, the present invention relates to a composition, kit or kit-of-parts comprising (a) a first composition of the present invention, and (b) a second composition described herein.

In certain embodiments, the first composition is administered simultaneously with the second composition. In certain embodiments, the first composition is administered sequentially with the second composition. In certain embodiments, the second composition is administered prior to administration of the first composition.

In another aspect, provided herein is (a) a first composition of the present invention, and (b) a second composition as disclosed herein, for use as a therapeutic vaccine.

In another aspect, provided herein is (a) a first composition of the present invention, and (b) a second composition as disclosed herein, for use as a cancer vaccine.

In certain embodiments of all of the foregoing compositions, compositions for use, and methods, the subject is a human subject.

In certain embodiments of all of the foregoing compositions, compositions for use, and methods, the MHC-binding epitope is a human MHC-binding epitope.

In certain embodiments of all of the foregoing compositions, compositions for use, and methods, the MHC molecule is a human MHC molecule. In another aspect, the invention is directed to immunogenic compositions for immunizing a subject having or suspected of having cancer, comprising a stress protein and at least one of a first peptide derived from the subject's cancer cells, wherein the first peptide is mutant in the subject's cancer cells but not in the subject's normal cells, and wherein the first peptide does not comprise an entire amino acid sequence of a protein. The composition can further comprise an adjuvant. The composition can further comprise at least one of a second peptide derived from mutant proteins selected from the group consisting of MYC, KRAS, N RAS, TP53, KDM6A, NPM1, H-RAS, FGFR3, MSH6, TP53, EGFR, PIK3CA, ABL1, CTNNB1, KIT, HNF1A, JAK2, BRAF, IDH1, RET, PDGFRA, MET, APC, CDC27, CDK4, prostate-specific antigen, alpha-fetoprotein, breast mucin, gp100, g250, p53, MART-I, MAGE, BAGE, GAGE, tyrosinase, Tyrosinase related protein 11, Tyrosinase related protein, and RAD50 (See Warren and Holt, Human Immunology, 2010. 71: p. 245-254, incorporated herein by reference in its entirety); wherein the second peptide does not comprise an entire amino acid sequence of a protein and wherein the first peptide is not a peptide derived from MYC, K-RAS, N-RAS, T53, KDM6A, NPM1, H-RAS, FGFR3, MSH6, TP53, EGFR, PIK3CA, ABL1, CTNNB1, KIT, HNF1A, JAK2, BRAF, IDH1, RET, PDGFRA, MET, APC, CDC27, CDK4, prostate-specific antigen, alpha-fetoprotein, breast mucin, gp100, g250, p53, MART-I, MAGE, BAGE, GAGE, tyrosinase, Tyrosinase related protein 11, Tyrosinase related protein, or RAD50. For example, the at least one second peptide can be derived from mutant K-RAS and comprise at least one of mutations G13D, G12V, G12R, G12D, or G12C. The at least one second peptide can be derived from mutant NPM1 and comprise the W288 fs*12 mutation. The at least one second peptide can be derived from mutant H-RAS and comprise the G12V mutation. The at least one second peptide can be derived from mutant FGFR3 and comprise at least one of mutations Y373C, S249C, R248C, and G697C. The at least one second peptide can be derived from mutant MSH6 and comprise the P1087 fs*5 mutation. The at least one second peptide can be derived from mutant TP53 and comprise at least one of mutations R273H or R248Q. The at least one second peptide can be derived from mutant EGFR and comprise at least one of mutations L858R or E746_A750del. The at least one second peptide can be derived from mutant PIK3CA and comprise at least one of mutations H1047R or E545K. The at least one second peptide can be derived from mutant ABL1 and comprise the T315I mutation. The at least one second peptide can be derived from mutant CTNNB1 and comprise at least one of mutations T41A, S45del, S45F, or S37A. The at least one second peptide can be derived from mutant KIT and comprise the D816V mutation. The at least one second peptide can be derived from mutant HNF1A and comprise the P291 fs*51 mutation. The at least one second peptide can be derived from mutant JAK2 and comprise the V617F mutation. The at least one second peptide can be derived from mutant BRAF and comprise the V600E mutation. The at least one second peptide can be derived from mutant IDH1 and comprise the R132H mutation. The at least one second peptide can be derived from mutant N-RAS and comprise the Q61R or Q61K mutation. The at least one second peptide can be derived from mutant RET and comprise the M918T mutation. The at least one second peptide can be derived from mutant PDGFRA and comprise the D842V mutation. The at least one second peptide can be derived from mutant MET and comprise the Y1253D mutation. The at least one second peptide can be derived from mutant APC and comprise at least one of the T1556 fs*3 or S1341R mutations. The stress protein can be selected from the group consisting of hsc70, hsp70, hsp90, hsp110, grp170, gp96, calreticulin, a mutant thereof, or combinations of two or more thereof. The adjuvant can comprise a saponin or an immunostimulatory nucleic acid. The one of a first peptide can be a post-translationally modified peptide, such as a phosphopeptide. The composition can comprise a plurality of peptides for the at least one of a first peptide derived from the subject's cancer cells. The peptides can be from about 9-11 amino acids to about 27-31 amino acids. The cancer can be, for example, multiple myeloma or glioblastoma. In one embodiment, at least one post-translationally modified residue in the at least one of a first peptide is replaced with a mimetic residue. In another embodiment, at least one phosphorylated residue in the at least one of a first peptide is replaced with a phosphomimetic residue.

In another aspect, the invention is directed to an immunogenic composition comprising a stress protein and at least one of a first peptide derived from the subject's cancer cells, wherein the first peptide is mutant in the subject's cancer cells but not in the subject's normal cells, and wherein the first peptide does not comprise an entire amino acid sequence of a protein, for use as a medicament.

In another aspect, the invention is directed to an immunogenic composition comprising a stress protein and at least one of a first peptide derived from the subject's cancer cells and an adjuvant, wherein the first peptide is mutant in the subject's cancer cells but not in the subject's normal cells, and wherein the first peptide does not comprise an entire amino acid sequence of a protein.

In another aspect, the invention is directed to an immunogenic composition comprising a stress protein and at least one of a first peptide derived from the subject's cancer cells, wherein the first peptide is mutant in the subject's cancer cells but not in the subject's normal cells, and wherein the first peptide does not comprise an entire amino acid sequence of a protein, for use in a method for immunizing a subject having or suspected of having cancer. The composition can further comprise an adjuvant.

In certain embodiments, the present invention relates to a composition, kit or kit-of-parts comprising (a) a first composition of the present invention and (b) an adjuvant. In another preferred embodiment, the present invention relates to a kit comprising a first container containing a first composition of the invention; and a second container containing an adjuvant.

In another aspect, the invention is directed to administering immunogenic compositions of the first aspect to a subject to treat a subject having a cancer. In certain embodiments, the present invention relates to an immunogenic composition, composition, kit or kit-of-parts of the present invention for use in a method for the treatment of cancer in a subject having a cancer. The cancer can be, for example, multiple myeloma or glioblastoma. The method, immunogenic composition, composition, kit or kit-of-parts of the present invention for use can further comprise administering lenalidomide or dexamethasone. Furthermore, cyclophosphamide may also be administered. Or, the method, immunogenic composition, composition, kit or kit-of-parts of the present invention for use may further comprise administering a checkpoint antibody (such as anti-GITR, anti-OX40, anti-PD-1, anti-CTLA-4, anti-TIM-3, and anti-LAG-3) (which may also be a monoclonal antibody). Or, the subject can also be administered an indoleamine dioxygenase-1 inhibitor, such as 4-amino-N-(3-chloro-4-fluorophenyl)-N'-hydroxy-1,2,5-oxadiazole-3-carboximidamide.

In another aspect, the invention is directed to methods of immunizing a subject recovering from a cancer, comprising administering to the subject immunogenic compositions of the first aspect. In certain embodiments, the present invention relates to an immunogenic composition, composition, kit or kit-of-parts of the present invention for use in a method for of immunizing a subject recovering from a cancer. The cancer can be, for example, multiple myeloma or glioblastoma. The method, immunogenic composition, composition, kit or kit-of-parts of the present invention for use can further comprise administering lenalidomide or dexamethasone. Furthermore, cyclophosphamide may also be administered. Or, the method, immunogenic composition, composition, kit or kit-of-parts of the present invention for use may further comprise administering a checkpoint antibody (such as anti-GITR, anti-OX40, anti-PD-1, anti-CTLA-4, anti-TIM-3, and anti-LAG-3) (which may also be a monoclonal antibody).

In another aspect, the invention is directed to kits, comprising the immunogenic composition of the first aspect and instructions for use. Kits can further comprise lenalidomide, dexamethasone, cyclophosphamide, and a checkpoint antibody (such as anti-GITR, anti-OX40, anti-PD-1, anti-CTLA-4, anti-TIM-3, and anti-LAG-3, which may be monoclonal antibodies).

In another aspect the invention is directed to methods of making an immunogenic peptide from a subject suffering from cancer, comprising:
(a) obtaining a sample of the subject's cancer tissue;
(b) sequencing the exomes of the genomic DNA present in the sample;
(c) identifying from the sample non-synonymous somatic mutant alleles that encode mutant proteins when compared to a wild type control;
(d) sequencing mRNA from the sample or a new sample from the subject's cancer tissue to identify those somatic mutations identified in step (c) that appear in mRNA expressed in the cancer;
(e) determining the allelic frequency of the mutant alleles in the sample;
(f) determining the expression level of the mutant alleles in the sample, by, e.g., determining the median expression level of the mutant allele relative to other cancers of the same indication.
(g) determining the subject's MHC type:
(h) selecting one or more mutant peptides encoded by the mutant alleles that:
   1) has an allelic frequency of greater than 0.05;
   2) has a median expression level of greater than 1 RPKM unit across all cancers of the same indication; and
   3) are predicted to bind to one or more of the subjects MHC molecules;
(i) ranking the mutant peptides selected in step (h) by the number of predicted mutations and by IC50 binding to the subject's MHC type; and
(j) synthesizing one or more peptides of about 27-31 amino acids, each peptide comprising one of the peptides ranked in step (i).

In such methods, the wild type control can be healthy tissue or cells isolated from the subject. The one or more peptides can be a phosphopeptide.

In certain embodiments, the present invention relates to a composition comprising immunogenic peptides obtainable by a method of the invention.

In another aspect the invention is directed to methods of identifying an immunogenic peptide from a subject suffering from cancer, comprising:
(a) obtaining a sample of the subject's cancer tissue;
(b) sequencing the exomes of the genomic DNA present in the sample;
(c) identifying from the sample non-synonymous somatic mutant alleles that encode mutant proteins when compared to a wild type control;
(d) sequencing mRNA from the sample or a new sample from the subject's cancer tissue to identify those somatic mutations identified in step (c) that appear in mRNA expressed in the cancer;
(e) determining the allelic frequency of the mutant alleles in the sample;
(f) determining the expression level of the mutant alleles in the sample, by, e.g., determining the median expression level of the mutant allele relative to other cancers of the same indication.
(g) determining the subject's MHC type:
(h) selecting one or more mutant peptides encoded by the mutant alleles that:
   1) has an allelic frequency of greater than 0.05;
   2) has a median expression level of greater than 1 RPKM unit across all cancers of the same indication; and
   3) are predicted to bind to one or more of the subjects MHC molecules;
(i) ranking the mutant peptides selected in step (h) by the number of predicted mutations and by IC50 binding to the subject's MHC type; and
(j) identifying one or more immunogenic peptides of about 27-31 amino acids, each peptide comprising one of the peptides ranked in step (i).

In another aspect, the invention is directed to methods of making immunogenic peptides from a subject suffering from cancer, comprising:
(a) obtaining a sample of the subject's cancer tissue;
(b) purifying from the sample major histocompatibility complex (MHC)-peptide complexes comprised therein;
(c) eluting from the purified MHC-peptide complexes a plurality of peptides comprised therein;
(d) identifying from the plurality of peptides one or more mutant peptides that are found in the sample of the subject's cancer tissue but that are substantially absent from a sample of normal tissue; and
(e) synthesizing one or more peptides, each peptide comprising a mutant peptide identified in step (d) or a mimetic thereof.

In certain embodiments, the present invention relates to a composition comprising immunogenic peptides obtainable by a method of the invention.

In another aspect, the invention is directed to methods of identifying immunogenic peptides from a subject suffering from cancer, comprising:
(a) obtaining a sample of the subject's cancer tissue;
(b) purifying from the sample major histocompatibility complex (MHC)-peptide complexes comprised therein;
(c) eluting from the purified MHC-peptide complexes a plurality of peptides comprised therein;
(d) identifying from the plurality of peptides one or more mutant peptides that are found in the sample of the subject's cancer tissue but that are substantially absent from a sample of normal tissue; and
(e) identifying one or more immunogenic peptides, each peptide comprising a mutant peptide identified in step (d) or a mimetic thereof.

The MHC can be class I or class II MHC. The sample of normal tissue can be isolated from the subject. The at least one mutant peptide identified in step (d) can be a post-translationally modified peptide. The at least one amino acid residue in the at least one mutant peptide identified in step (d) can be post-translationally modified in the subject's cancer tissue but is not post-translationally modified in normal tissue. The post-translationally modified peptide can be phosphorylated. The at least one synthesized peptide in step (e) can comprise at least one mutant peptide identified in step (d). The at least one synthesized peptide in step (e) can comprise a mimetic of at least one mutant peptide identified in step (d). The at least one mutant peptide identified in step (d) can be a phosphorylated peptide and the at least one synthesized peptide in step (e) can be a phosphopeptide mimetic. A phosphorylated residue in the at least one mutant peptide identified in step (d) can be replaced with a non-hydrolyzable analogue in the at least one synthesized peptide in step (e). The one or more mutant peptides can be identified in step (d) by determining the molecular structure of the plurality of peptides from the subject's cancer tissue using mass spectroscopy and comparing the molecular structure of the plurality of peptides with the corresponding peptides found in normal tissue to identify one or more mutant peptides.

The mutant peptide(s) identified in step (d) can be selected for synthesis in step (e) using a method comprising the steps of:
(f) determining the subject's MHC type;
(g) selecting one or more mutant peptides encoded by the mutant alleles that:
1) have an allelic frequency of greater than 0.05;
2) have a median expression level of greater than 1 RPKM unit across all cancers of the same indication; and
3) are predicted to bind to one or more of the subjects MHC molecules;
(h) ranking the mutant peptides selected in step (g) by the number of predicted mutations, by the frequency of the mutant peptides in cancer cells, and/or by IC50 binding to the subject's MHC type.

In certain embodiments, the present invention relates to a composition comprising immunogenic peptides obtainable by a method of the invention.

In another aspect, the invention is directed to immunogenic compositions comprising a stress protein and a first immunogenic peptide that comprises a second immunogenic peptide or a mimetic thereof, wherein the second immunogenic peptide is a fragment of a mutant protein that occurs in cancer cells of a subject having cancer and comprises at least one amino acid residue that is post-translationally modified, wherein the first immunogenic peptide does not comprise the entire amino acid sequence of a naturally-occurring protein. Normal cells of the subject can comprise a normal form of the mutant protein, the normal form of the mutant protein comprising the second immunogenic peptide except that at least one of the amino acid residues that is post-translationally modified in the second immunogenic peptide is not post-translationally modified in the normal form of the mutant protein. The first immunogenic peptide can comprise the second immunogenic peptide except that at least one residue that is post-translationally modified in the second immunogenic peptide is replaced with a mimetic residue in the first immunogenic peptide. The mimetic residue in the first immunogenic peptide can be less labile than the corresponding residue that is post-translationally modified in the second immunogenic peptide. The at least one amino acid residue that is post-translationally modified in the second immunogenic peptide can be phosphorylated. The at least one phosphorylated amino acid residue in the second immunogenic peptide can be selected from the group consisting of phospho-Ser, phospho-Thr, phospho-Tyr, phospho-His, phospho-Arg, and phospho-Lys. The first immunogenic peptide can comprise the second immunogenic peptide except that at least one phosphorylated residue in the second immunogenic peptide is replaced with a phosphomimetic residue in the first immunogenic peptide. The phosphomimetic residue in the first immunogenic peptide can be a non-hydrolyzable analogue of the corresponding phosphorylated residue in the second immunogenic peptide. The peptides can be 8-50 amino acids long, such as 9-11 amino acids or 27-31 amino acids long. The compositions can further comprise at least one of a third immunogenic peptide derived from mutant proteins selected from the group consisting of myc, k-ras, n-ras, tp53, and kdm6A; wherein the third peptide does not comprise an entire amino acid sequence of a protein and wherein the first immunogenic peptide is not a peptide derived from myc, k-ras, n-ras, t53, or kdm6A. The stress protein can be selected from the group consisting of hsc70, hsp70, hsp90, hsp110, grp170, gp96, calreticulin, a mutant thereof, and combinations of two or more thereof, such as combinations including hsc70 and one or more of hsp70, hsp90, hsp110, grp170, gp96, calreticulin, or mutant thereof. The compositions of these aspects can further comprise an adjuvant, such as a saponin or an immunostimulatory nucleic acid. The compositions of these aspects can be used in methods of treating a subject having a cancer, comprising administering to the subject any of these compositions. In a further aspect, the composition is for use as a medicament. In a further aspect, the composition is for use as a therapeutic vaccine. In a further aspect, the composition is for use as a cancer vaccine. In a further aspect, the composition is for use in a method for the treatment of cancer. In a further aspect, the present invention relates to a composition comprising (a) a stress protein and (b) a first immunogenic peptide that comprises a second immunogenic peptide or a mimetic thereof, as described above, and optionally, (c) a third immunogenic peptide as described above and/or an adjuvant.

The present invention relates to a first composition comprising at least two different complexes of a purified stress protein bound to an antigenic peptide, wherein the complexes each comprise a different antigenic peptide, wherein each one of the different antigenic peptides comprises one or more mutant MHC-binding epitopes from a cancer cell, and wherein the composition comprises no more than 5 different antigenic peptides that contain only wild-type MHC-binding epitopes, preferably wherein the composition does not comprise any antigenic peptides that contain only wild-type MHC-binding epitopes and/or wherein the composition comprises no more than 100 different antigenic peptides. In one preferred embodiment, the stress protein is an hsc70, in particular a human hsc70, or an hsp70, in particular a human hsp70. In a further preferred embodiment, the stress protein is non-covalently bound to the antigenic peptide. In another preferred embodiment, the molar ratio of stress protein to antigenic peptide in each complex is 1:1 or less, in particular, the molar ratio of stress protein to antigenic peptide in each complex is 1:2, 1:4, 1:5, 1:10, 1:20, 1:50, or less, such as up to 1:100. In another preferred embodiment, each one of the antigenic peptides in the composition is 5 to 50 amino acids in length, even preferably 25 to 40 amino acids in length, most preferably 27 to 31 amino acids in length. In another preferred embodiment, at least one of the antigenic peptides in the composition of the invention is 21-31 amino acids in length. In another preferred embodiment, each one of the antigenic peptides in the composition is 21 to 31 amino acids in length. In one preferred embodiment, each one of the antigenic peptides of the composition of the invention comprises a heat shock protein binding sequence. In another preferred embodiment, at least one of the mutant MHC-binding epitopes is expressed in cancer cells of a subject but not in normal cells of the subject, preferably each one of the mutant MHC-binding epitopes is expressed in cancer cells of a single subject but not in normal cells of the subject. In another preferred embodiment, at least one of the mutant MHC-binding epitopes is expressed at a higher level in cancer cells of a subject relative to normal cells of the subject.

In another preferred embodiment, the composition of the invention further comprises a pharmaceutically acceptable carrier or excipient and optionally an adjuvant. In one preferred embodiment, the adjuvant comprises a saponin or an immunostimulatory nucleic acid, even more preferably the adjuvant comprises QS-21.

In another aspect, the invention is directed to immunogenic compositions comprising a first immunogenic peptide that comprises a second immunogenic peptide or a mimetic thereof, wherein the second immunogenic peptide is a fragment of a mutant protein that occurs in cancer cells of a subject having cancer and comprises at least one amino acid residue that is post-translationally modified, wherein the first immunogenic peptide does not comprise the entire amino acid sequence of a naturally-occurring protein. Normal cells of the subject can comprise a normal form of the mutant protein, the normal form of the mutant protein comprising the second immunogenic peptide except that at least one of the amino acid residues that is post-translationally modified in the second immunogenic peptide is not post-translationally modified in the normal form of the mutant protein. The first immunogenic peptide can comprise the second immunogenic peptide except that at least one residue that is post-translationally modified in the second immunogenic peptide is replaced with a mimetic residue in the first immunogenic peptide. The mimetic residue in the first immunogenic peptide can be less labile than the corresponding residue that is post-translationally modified in the second immunogenic peptide. The at least one amino acid residue that is post-translationally modified in the second immunogenic peptide can be phosphorylated. The at least one phosphorylated amino acid residue in the second immunogenic peptide can be selected from the group consisting of phospho-Ser, phospho-Thr, phospho-Tyr, phospho-His, phospho-Arg, and phospho-Lys. The first immunogenic peptide can comprise the second immunogenic peptide except that at least one phosphorylated residue in the second immunogenic peptide is replaced with a phosphomimetic residue in the first immunogenic peptide. The phosphomimetic residue in the first immunogenic peptide can be a non-hydrolyzable analogue of the corresponding phosphorylated residue in the second immunogenic peptide. The peptides can be 8-50 amino acids long, such as 9-11 amino acids or 27-31 amino acids long. The compositions can further comprise at least one of a third immunogenic peptide derived from mutant proteins selected from the group consisting of myc, k-ras, n-ras, tp53, and kdm6A; wherein the third peptide does not comprise an entire amino acid sequence of a protein and wherein the first immunogenic peptide is not a peptide derived from myc, k-ras, n-ras, t53, or kdm6A. The compositions of these aspects can further comprise an adjuvant, such as a saponin or an immunostimulatory nucleic acid. The compositions of these aspects can be used in methods of treating a subject having a cancer, comprising administering to the subject any of these compositions. In a further aspect, the composition is for use as a medicament. In a further aspect, the composition is for use as a therapeutic vaccine. In a further aspect, the composition is for use as a cancer vaccine. In a further aspect, the composition is for use in a method for the treatment of cancer. In a further aspect, the present invention relates to a composition comprising (a) a stress protein and (b) a first immunogenic peptide that comprises a second immunogenic peptide or a mimetic thereof, as described above, and optionally, (c) a third immunogenic peptide as described above and/or an adjuvant.

DETAILED DESCRIPTION

Figure 1:
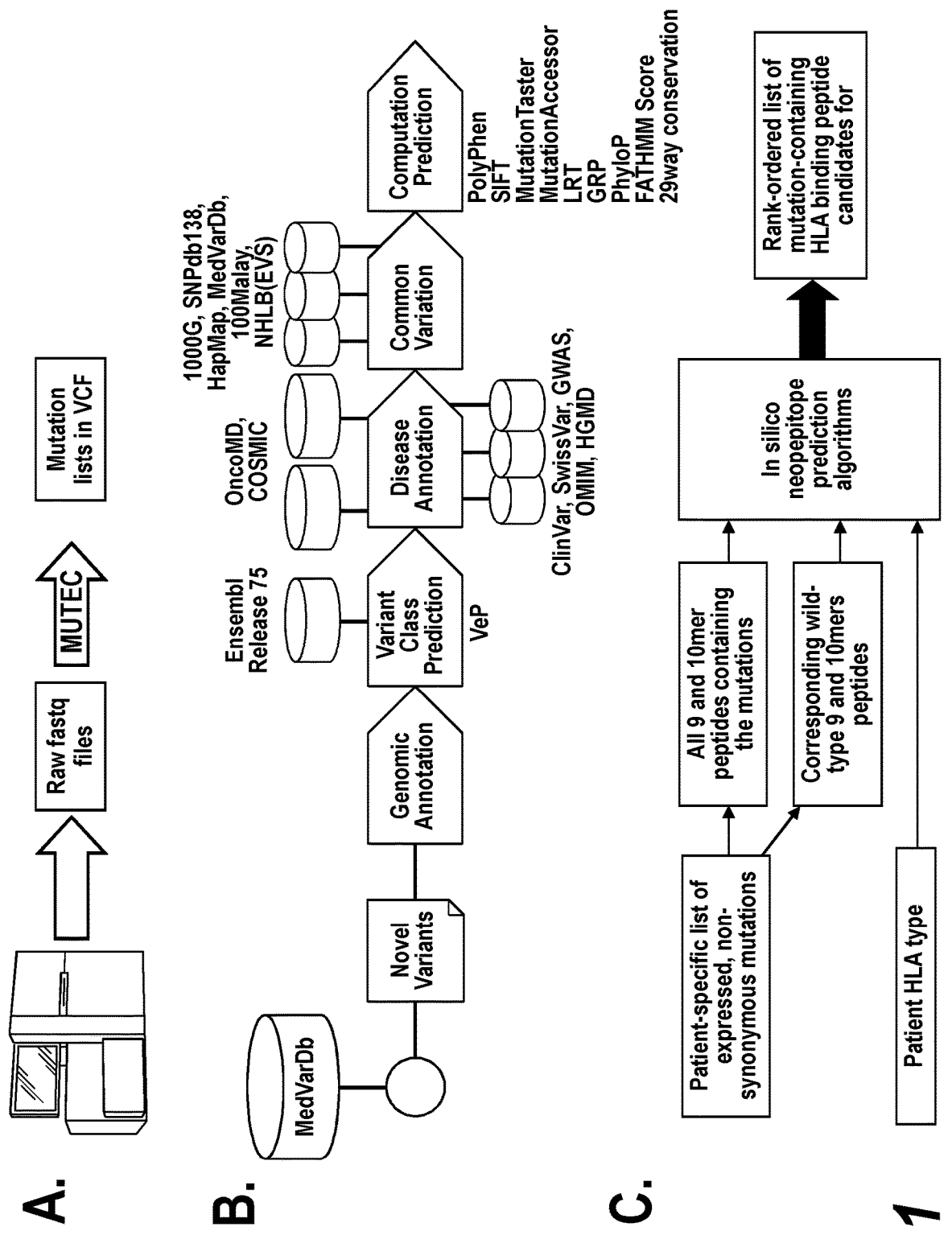
FIG. 1 depicts somatic mutation characterization workflows useful in the methods of the invention. (A) is a schematic illustration of an exemplary method of identifying tumor-specific mutations using the methods disclosed herein. (B) is a schematic illustration of exemplary methods of annotation of a Variant Call Format (VCF) file generated using the methods disclosed herein. MedGenome's Variation and Mutation Annotation Toolkit (VariMAT; Cambridge, Mass.) is used to map single nucleotide variants (SNVs) to the genes. The variant class prediction (missense, nonsense, silent, stop-loss) is performed using Variant Effect Predictor (VeP; Bioinformatics. 2010 Aug. 15; 26(16):2069-70, incorporated herein by reference in its entirety) and somatic variants are identified on the basis of allele frequency in 1000 genome project reported SNPs and indels, and other SNP databases. Disease relevance of each variant is also annotated using data from various databases. (C) is a schematic illustration of the in silico prediction of binding of 9 and 10mer peptide libraries to MHC molecules using NetMHCpan (Immunogenetics. 2009 January; 61(1):1-13; PLoS One. 2007 Aug. 29; 2(8):e796, incorporated herein by reference in its entirety).

The instant disclosure provides compositions useful as therapeutic vaccines (e.g., cancer vaccines), and methods of producing such compositions. The compositions disclosed herein generally employ a stress protein and at least one synthetic antigenic peptide comprising a cancer-specific mutation present in a patient's cancer. The methods disclosed herein are particularly advantageous in that they allow for the preparation of therapeutic vaccine (e.g., cancer vaccine) compositions using only trace amounts of a subject's tissue (e.g., single cells or exosomes).

1. Methods for Identifying Antigenic Peptides

The methods of the invention generally involve the identification of antigenic peptides that comprise one or more mutant MHC-binding epitopes from a cancer cell.

As used herein the term "mutant," in the context of a protein (or peptidic fragment or MHC-binding epitope thereof), refers to a protein (or peptidic fragment or MHC-binding epitope thereof) that contains an amino acid mutation (e.g., substitution, insertion, or deletion) that is found in a subject's disease tissue (e.g., cancer cells) but not in the subject's normal or healthy tissue; a protein (or peptidic fragment or MHC-binding epitope thereof) that contains an amino acid modification (e.g., a post-translational modification, such as phosphorylation) that is found in a subject's disease tissue (e.g., cancer cells) but not in the subject's normal or healthy tissue, or vice versa; a protein (or peptidic fragment or MHC-binding epitope thereof) with different expression profiles in cancer cells as compared with normal or healthy cells (e.g., a protein that is expressed in cancer cells but not in normal cells); or a protein (or peptidic fragment or MHC-binding epitope thereof) that is processed differently in the antigen presentation pathway in the disease tissue (e.g., cancer cells) vs. normal cells, leading to different peptides presented by MHC molecules. Alternatively, in certain embodiments, a mutant protein (or peptidic fragment or MHC-binding epitope thereof) is one that exhibits an elevated level of post-translational modification (e.g., phosphorylation) in cancer cells relative to normal tissue.

In certain embodiments, the present invention relates to a composition comprising immunogenic peptides obtainable by a method of the invention. Mutations that can be present in mutant proteins (or mutant peptidic fragments or mutant MHC-binding epitopes thereof) include, without limitation, amino acid substitution, insertion, or deletion mutations, or gene fusion mutations. As used herein, a "gene fusion mutation" refers to a neo-epitope formed by the breakpoint junction of a protein encoded by a gene fusion (e.g., the BCR-ABL gene fusion breakpoint junction).

As used herein, the term "MHC-binding epitope/epitopes" refers to those epitopes shown to bind an MHC molecule (e.g., a human MHC) by any of the above assays, or predicted to bind an MHC molecule (e.g., a human MHC) by a software program (e.g. SYFPEITHI, Rammensee, et al., Immunogenetics 50, 213-219, 1999, incorporated herein by reference in its entirety). Other methods that can be used include those disclosed in Guan, P. et al., (2003) Applied Bioinformatics, 2: 63-66; Blythe, M. J. et al., (2002) Bioinformatics, 18: 434-439; Flower, D. R. and Doytchinova, I. A. (2002). Applied Bioinformatics, 1: 167-176; Yu, K. et al., (2002) Molecular Medicine, 8: 137-48; Brusic, V. et al., (2002) Immunology and Cell Biology, 80: 280-285; Jung, G. et al., (2001) Biologicals, 29: 179-181 (describes T cell epitope prediction programme EPIPREDICT); Kwok, W. W. et al., (2001) Trends in Immunology, 22: 583-588; Mallios, R. R. (2001) Bioinformatics, 17: 942-948; Romisch, K. (2001). Trends in Biochemical Sciences, 26: 531; Schirle, M. et al., (2001) Journal of Immunological Methods, 257: 1-16; Singh, H. and Raghava, G. P. S. (2001) Bioinformatics, 17: 1236-1237; Andersen, M. H. et al., (2000) Tissue Antigens, 55: 519-531; Buus, S. (1999). Current Opinion in Immunology, 11: 209-213; Mallios, R. R. (1999) Bioinformatics, 15: 432-439; Maffei, A. and Harris, P. E. (1998). Peptides, 19: 179-198; and Vita R. et al., Nucleic Acids Res. 2014 Oct. 9. pii: gku938. [Epub ahead of print] PubMed PMID: 25300482 (describes the immune epitope database (IEDB) 3.0, available at www.iedb.org) (each of which is incorporated herein by reference in its entirety).

As used herein, the term "wild-type" in the context of an MHC-binding epitope, refers to an MHC-binding epitope that has a wild-type amino acid sequence, wild-type post-translational modifications, and is not expressed only in cancer cells or overexpressed in cancer cells relative to normal cells.

In certain embodiments of the methods of the invention, the exomes of the genomic DNA of cancer cells from a subject are sequenced and compared to a non-mutated (wild-type) control (such as non-cancer cells of the subject), and non-synonymous somatic mutant alleles that encode mutant proteins are identified. In certain embodiments, mRNA from the same subject sample, or from a new cancer cell sample from the same subject, is sequenced to identify those somatic mutations that appear in mRNA expressed in the cancer.

In certain embodiments, the expression level of mutant alleles is also determined. In certain embodiments, where the RNA RefSeq data for a gene corresponding to a mutant allele is available, the expression of transcripts of the mutant allele is determined by Normalized Mutation-containing Read Count (NMRC). NMRC is the number of Next Generation Sequencing (NGS) reads obtained from cDNA that contain the mutation divided by the total number of mapped nucleotides multiplied by $10^{10}$ as a normalization factor. As such, NMRC represents the number of reads that contain the mutation normalized to the total number of nucleotides generated in the sequencing experiment. In certain embodiments, mutant alleles with a Normalized Mutation-containing Read Count (NMRC) that is greater than 10 are used to generate antigenic peptides. In certain embodiments, mutant alleles with a Normalized Mutation-containing Read Count (NMRC) that is greater than 1, 2, 3, 4, 5, 6, 7, 8 or 9 are used to generate antigen peptides.

In other embodiments, where RNA RefSeq data is not available, the expression level of the mutant alleles in cancers of the same indication is estimated from publicly available databases (e.g., The Cancer Genome Atlas—Cancer Genome (TCGA: www.cancergenome.nih.gov); The International Cancer Genome Consortium (ICGC: www.icgc.org)) and the median expression of transcripts comprising a mutation is determined based on the Reads Per Kilobase of transcript per Million mapped (RPKM). In RNA-Seq experiments, cDNA fragments are sequenced and mapped back to genes and ideally, individual transcripts. Properly normalized, the RNA-Seq reads, i.e. RPKM, can be used as a measure of relative abundance of transcripts. In certain embodiments, mutant alleles with RPKM reads greater than 1 are used to generate antigen peptides. In certain embodiments, mutant alleles with a RPKM reads greater than 1 are used to generate antigen peptides. In certain embodiments, mutant alleles with RPKM reads greater than 2, 3, 4, 5, 6, 7, 8, 9, or 10 are used to generate antigen peptides.

In certain embodiments, the allelic frequency of mutant alleles is determined. As used herein, the term "allelic frequency" with respect to a mutant allele, is the relative amount (expressed as a fraction or percentage) of a mutant allele relative to other alleles (e.g., wild type alleles) in a sample.

In certain embodiments, the subject's human leukocyte antigen (HLA) type is determined. Any means for determining HLA type can be employed, including sequencing of the DNA of a subject, as disclosed herein.

After identification of mutant alleles that are expressed in a subject's tumor cells, one or more mutant peptides (comprising one or more mutant MHC-binding epitopes) encoded by the mutant alleles are selected based on, for example, having an allelic frequency of greater than 0.05, a median expression level of greater than 1 RPKM unit (e.g., across all cancers of the same indication), and/or a predicted ability to bind to one or more of the subject's HLA molecules. In certain embodiments, the selected mutant peptides are additionally ranked, for example, by the number of predicted mutant MHC-binding epitopes and/or by predicted binding affinity (e.g., IC50) for the subject's HLA type. A mutation characterization workflow useful in the methods of the invention is shown in FIG. 1.

In certain embodiments, one or more antigenic peptides amino acids is synthesized, each peptide comprising one or more of the foregoing selected mutant peptides. Once synthesized, the peptides can be used in the immunogenic compositions of the invention. In certain embodiments, the methods further comprise determining whether the synthesized antigenic peptides are recognized by T cells when presented on a cell surface MHC molecule.

1.1. Next Generation Sequencing

In certain embodiments, the sequence of nucleic acids (e.g., tumor DNA and mRNA) is determined using next-generation sequencing (NGS). NGS is the generic term used to describe a number of different modern sequencing technologies referred to as "highly multiplexed amplicon sequencing." Although the chemistry by which sequence information is generated varies for the different next-generation sequencing platforms, all of them share the common feature of generating sequence data from a very large number of sequencing templates, on which the sequencing reactions are run simultaneously. In general, the data from all of these sequencing reactions are collected using a scanner, and then assembled and analyzed using computers and bioinformatics software programs. The sequencing reactions are performed, read, assembled, and analyzed in a massively parallel or multiplex fashion.

NGS platforms include, without limitation, the 454 FLX™ or 454 TITANIUM™ (Roche), Massively Parallel Signature Sequencing (Lynx Therapeutics); solid-phase, reversible dye-terminator sequencing (SOLEXA™ Genome Analyzer/Illumina), the HELISCOPE™ Single Molecule Sequencer (Helicos Biosciences), and the SOLID™ DNA Sequencer (Life Technologies/Applied Biosystems) instruments), Ion semiconductor sequencing (Ion Torrent); DNA nanoball sequencing (Complete Genomics), nanopore exonuclease sequencing (Oxford Nanopore), PacBio Sequencing Systems built on Single Molecule, Real-Time (SMRT) Sequencing technology (Pacific Biosystems), and DNA sequencing by synthesis (SBS) technology (Intelligent Biosystems).

An exemplary embodiment of NGS includes, for example, solid-phase, reversible dye-terminator sequencing (SOLEXA™ Genome Analyzer/Illumina). Illumina sequencing reads approximately 100-150 bp. Somewhat longer fragments are ligated to generic adaptors and annealed to a slide using the adaptors. PCR is carried out to amplify each read, creating a spot with many copies of the same read. They are then separated into single strands to be sequenced. The slide is flooded with nucleotides and DNA polymerase. These nucleotides are fluorescently labelled, with the color corresponding to the base. They also have a terminator, so that only one base is added at a time. An image is taken of the slide. In each read location, there will be a fluorescent signal indicating the base that has been added. The slide is then prepared for the next cycle. The terminators are removed, allowing the next base to be added, and the fluorescent signal is removed, preventing the signal from contaminating the next image. The process is repeated, adding one nucleotide at a time and imaging in between. Computers are then used to detect the base at each site in each image and these are used to construct a sequence.

Another exemplary embodiment of NGS includes, for example, Roche 454 sequencing. 454 sequencing allows for much longer reads than Illumina. Like Illumina, it does this by sequencing multiple reads at once by reading optical signals as bases are added. As in Illumina, the DNA or RNA is fragmented into shorter reads, in this case up to 1 kb. Generic adaptors are added to the ends and these are annealed to beads, one DNA fragment per bead. The fragments are then amplified by PCR using adaptor-specific primers. Each bead is then placed in a single well of a slide. So each well will contain a single bead, covered in many PCR copies of a single sequence. The wells also contain DNA polymerase and sequencing buffers. The slide is flooded with one of the four NTP species. Where this nucleotide is next in the sequence, it is added to the sequence read. If that single base repeats, then more will be added. So if we flood with Guanine bases, and the next in a sequence is G, one G will be added, however if the next part of the sequence is GGGG, then four Gs will be added. This NTP mix is washed away. The next NTP mix is now added and the process repeated, cycling through the four NTPs. This kind of sequencing generates graphs for each sequence read, showing the signal density for each nucleotide wash. The sequence can then be determined computationally from the signal density in each wash. All of the sequence reads we get from 454 will be different lengths, because different numbers of bases will be added with each cycle.

Another exemplary embodiment of NGS includes, for example, Ion torrent and Ion proton sequencing. Unlike Illumina and Roche's 454, Ion torrent and Ion proton sequencing do not make use of optical signals. Instead, they exploit the fact that addition of a dNTP to a DNA polymer releases an H$^+$ ion. As in other kinds of NGS, the input DNA or RNA is fragmented to a length of ~200 bp. Adaptors are added and one molecule is placed onto a bead. The molecules are amplified on the bead by emulsion PCR. Each bead is placed into a single well of a slide. Like 454, the slide is flooded with a single species of dNTP, along with buffers and polymerase, one NTP at a time. The pH is detected is each of the wells, as each H+ ion released will decrease the pH. The changes in pH allow us to determine if that base, and how many thereof, was added to the sequence read. The dNTPs are washed away, and the process is repeated cycling through the different dNTP species. The pH change, if any, is used to determine how many bases (if any) were added with each cycle.

Descriptions of NGS platforms can also be found in the following: Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; Zhang et al., "The impact of next-generation sequencing on genomics", J Genet Genomics, 2011, 38(3):95-109; Quail et al. (2012). "A tale of three next generation sequencing platforms: comparison of Ion Torrent, Pacific Biosciences and Illumina MiSeq sequencers". BMC Genomics 13 (1): 341; Liu et al. (2012). "Comparison of Next-Generation Sequencing Systems". Journal of Biomedicine and Biotechnology (Hindawi Publishing Corporation) 2012: 1-11; EBI: Next Generation Sequencing Practical Course publically available at the EMBL-EBI web site at www.ebi.ac.uk, each of which is incorporated by reference in its entirety.

1.2. Exome Sequencing and HLA Determination

Sequencing of patient tumor and germline DNA samples can be accomplished using NGS platforms, such as the Illumina HiSeq using whole-exome capture. For example, tumor mutations can now be rapidly and effectively identified in the context of immunotherapy clinical trials, all within weeks of sample acquisition (Br J Cancer, 2014. 111(8): p. 1469-75, incorporated herein by reference in its entirety). Furthermore, the patient HLA type can be simultaneously determined from both standard NGS exome (DNA) and RNA-Seq (RNA) profiling (Genome Med, 2013. 4(12): p. 102; Genome Med, 2012. 4(12): p. 95, each of which is incorporated herein by reference in its entirety). Alternatively HLA type can be determined using appropriate clinical assays or performed by fee-for-service providers. In certain embodiments, nucleic acids can be amplified from a patient's tumor cells (e.g., by polymerase chain reaction (PCR)). This amplification allows for the use of extremely small samples (e.g., single cells or exosomes) and is one advantage of the instant invention over prior art methods of producing immunogenic peptides that rely on harvesting of a patient's own peptides from tumor samples.

1.3. Identifying Non-Synonymous Somatic Mutant Alleles

The nucleotide "reads" from the NGS sequencing are mapped to the human genome. The DNA tumor reads are compared to germline DNA reads to identify and exclude mutations that are germline single nucleotide polymorphisms (SNPs), and a tumor haplotype comprising tumor-specific mutations is statistically identified. Tumor RNA reads overlapping DNA-determined tumor mutations are examined to confirm mutation existence and mutant RNA expression. Local NGS read re-mapping is performed particularly if insertion or deletions or gene fusions are detected. "Read re-mapping" refers to remapping of reads, after an initial alignment (mapping) of the reads to the entire genome, within their local genomic region using a highly sensitive alignment algorithm (a process which is often called local read re-mapping) to eliminate potential spurious false-positive mutation calls. Additionally tumor-specific mutations are evaluated according to the allelic frequency of the DNA mutations in tumors and if the mutation is listed in the COSMIC (Catalogue Of Somatic Mutations In Cancer) database, made publically available by the Wellcome Trust Sanger Institute. The discovery and monitoring for the emergence of additional tumor-specific mutation can be evaluated by testing liquid biopsies, including cell free DNA test (cfDNA; commercially available at Swift Biosciences), circulating tumor cells (CTCs), and circulating exosomal RNA (Exosome Diagnostics).

Data processing is then used to determine if the mutation is transcribed at high levels in the tumor, as shown by RNA-Seq NGS reads, if it occurs in a protein-coding transcript and if the mutation causes a non-synonymous mutation in a protein coding sequence. Other information can also be obtained, although is not necessary for the manufacture of a vaccine, which includes the function and subcellular localization of the mutant protein, the molecular consequences of the protein change, and the expected clinical consequences of the protein change.

1.4. Immunological Characterization and Ranking of Mutation-Containing Peptides

Figure 2:
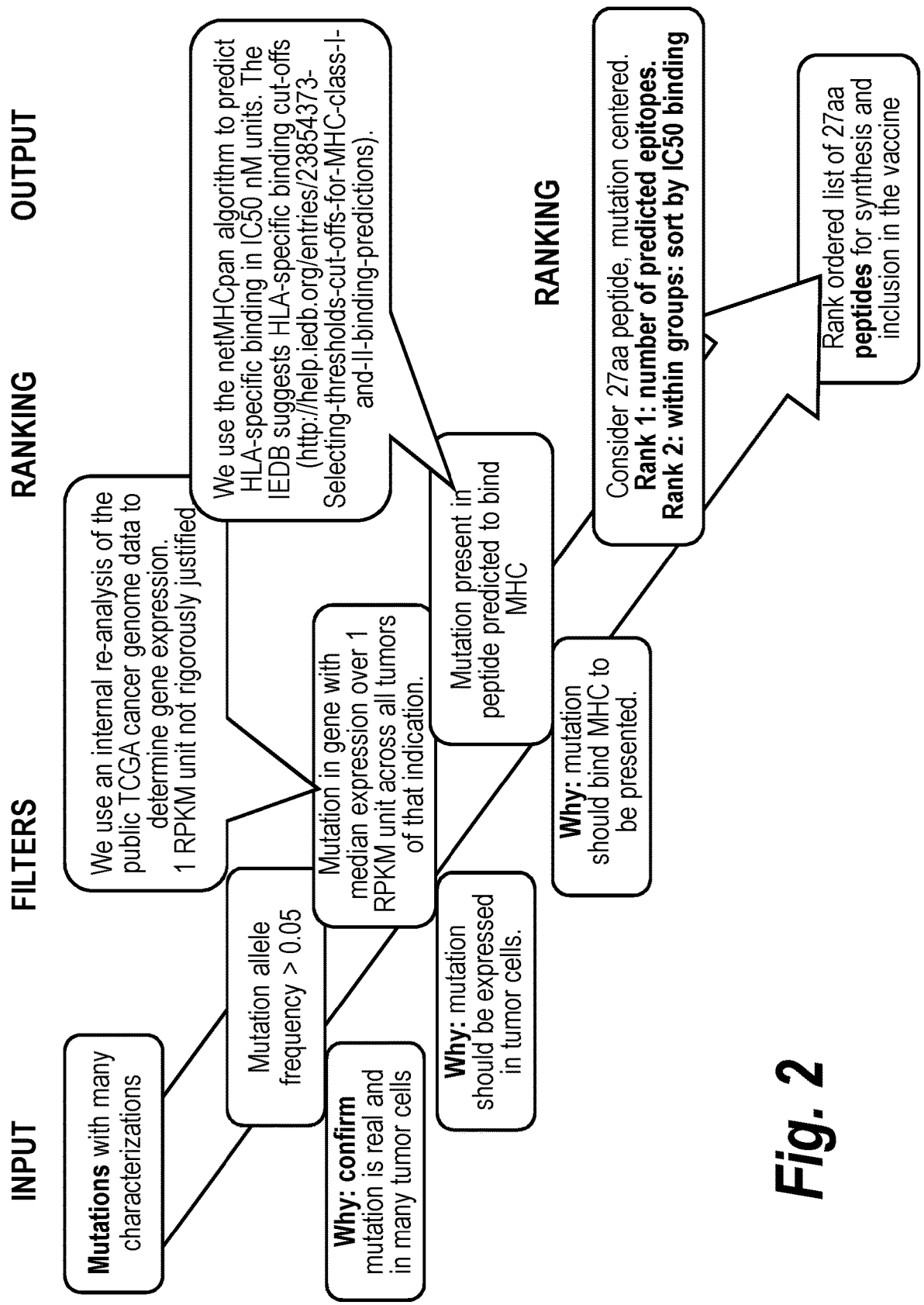
FIG. 2 is a diagram showing a ranking flow to determine those mutations from which to derive peptides for inclusion in the immunogenic compositions of the invention. Tumor mutations are identified (upper left hand corner), and filters are applied to the mutations (proceeding diagonally along the diagonal arrow), including mutation allele frequency of >0.05, a median expression level of, for example, over 1 Reads Per Kilobase of transcript per Million mapped reads (RPKM) units across all tumors of that indication, and then mutation present in peptide predicted to bind to MHC. The peptides that result from the filters are predicted as 27 amino acids, with the mutation centered, and then ranked, first according to number of predicted epitopes and then sorted by IC50 binding to MHC. The higher ranked peptides are synthesized and included in the immunogenic compositions of the invention, such as a vaccine.

In certain embodiments, mutations are characterized using one or more of the characterizations set forth in Table 1. Mutation-containing peptides may also be ranked according to the criteria shown in Table 1, which process is summarized in FIG. 2. Not all the characterizations listed in Table 1 are necessary for ranking the mutation-containing peptides for successful immunogenic composition formulation. For example, in certain embodiments, four characterizations are sufficient. In certain embodiments, five, six or seven characterizations are used for further refinement. In certain embodiments, all the characterizations in Table 1 are used.

TABLE 1

Neo-antigen characterizations (immunological characterization of mutations)

| Characterization | Algorithm | Rationale |
|---|---|---|
| Mutations not found in databases of human-to-human genetic differences ("SNPs") | | Avoid likely non-somatic mutations |
| Mutation DNA zygosity | | Pick mutations in more tumor cells and at high abundance in individual cells |
| "Early mutation" - position on mutation phylogenetic tree | | Pick mutations in more tumor cells (earlier occurrence) |
| Mutations in genes expressed in the specific cancer indication (e.g., GBM) | | Tumor expression |
| Mutations with RNA-Seq support in specific tumor | | Tumor expression |
| Mutant allele expression in specific tumor | | Tumor expression |
| Protein subcellular localization | PSORT (Bioinformatics. 2010 Jul. 1; 26(13): 1608-15*) | MHC class I or II |
| Proteasomal cleavage | NetChop (Immunogenetics., 57(1-2): 33-41, 2005*) | Epitope cleaved by proteasome |
| TAP transport | | |
| pMHC class I binding affinity | netMHCpan (Immunogenetics. 2009 January; 61(1): 1-13*; PLoS One. 2007 Aug. 29; 2(8): e796*) | binds to MHC class I |
| pMHC class II binding affinity | netMHCpan | binds to MHC class II |
| pMHC stability and off rate C terminus stability (Modeling) | NetMHCstab (Immunology. 2014 January; 141(1): 18-26*) | stays on MHC |
| pMHC C-terminus stability | | stays on MHC |
| Large MHC binding "delta" (MUT vs WT) | | escapes tolerance |

TABLE 1-continued

Neo-antigen characterizations (immunological characterization of mutations)

| Characterization | Algorithm | Rationale |
|---|---|---|
| Similar to pathogen HLA ligand | | escapes tolerance |
| Mutation dissimilar to self, bulge | | escapes tolerance |
| Mutation in location accessible to TCR | | escapes tolerance |
| Indel creating non-self peptides | | escapes tolerance |
| Number of epitopes in 27aa peptide | | High utility |

*each of these references is incorporated herein by reference in its entirety 1.5 Identifying Phosphopeptide Mutants In certain embodiments, the mutant peptides identified from a subject's cancer cells are phosphopeptides, where the phosphorylated residue(s) (e.g., Tyr, Ser, Thr, Arg, Lys, and/or His) are not phosphorylated (or to a substantially lesser degree) in the subject's corresponding normal cells. Mutant phosphopeptides can be identified from a patient's cancer cells using any methods known in the art. Suitable methods include, without limitation, those set forth in Meyer et al. J Proteome Res. 2009 July; 8(7):3666-74. doi: 10.1021/pr800937k, and Zarling et al. Proc Natl Acad Sci USA. 2006 Oct. 3; 103(40):14889-94, each of which is incorporated by reference in its entirety. Once suitable mutant peptides have been identified, antigenic phosphopeptides or phosphopeptide mimetics can be synthesized (e.g., as described herein) for use in the therapeutic compositions, compositions for use, and methods of the invention.

2. Antigenic Peptides

In certain embodiments, the compositions disclosed herein comprise complexes of stress proteins bound to different antigenic peptides, each antigenic peptide comprising one or more mutant MHC-binding epitopes from a subject's cancer cell. In particular, in certain embodiments, the present invention relates to a first composition comprising at least two different complexes of a purified stress protein bound to an antigenic peptide, wherein the complexes each comprise a different antigenic peptide, wherein each one of the different antigenic peptides comprises one or more mutant MHC-binding epitopes from a cancer cell, and wherein the composition comprises no more than 5 different antigenic peptides that contain only wild-type MHC-binding epitopes. Mutant MHC-binding epitopes are identified from subjects, such as those suffering, or recovering from, glioblastoma (GBM) or multiple myeloma (MM). Antigenic peptides can be prepared synthetically or by recombinant DNA technology, or can be isolated from natural sources. The antigenic peptides can be used in combination with adjuvants to create compositions that are useful for treatment and/or prevention of cancers, such as GBM or MM. The compositions comprising the antigenic peptides are immunogenic and are effective at eliciting a beneficial immune response against a cancer in a subject.

MHC molecules are classified as either Class I or Class II molecules. Class II MHC molecules are expressed primarily on cells involved in initiating and sustaining immune responses, such as dendritic cells, B lymphocytes, macrophages, etc. Class II MHC molecules are recognized by helper T lymphocytes and induce proliferation of helper T lymphocytes and amplification of the immune response to the particular immunogenic peptide that is displayed. Class I MHC molecules are expressed on almost all nucleated cells and are recognized by cytotoxic T lymphocytes (CTLs), which then destroy the antigen-bearing cells. Cytotoxic T lymphocytes are particularly important in tumor rejection and in fighting viral infections. The CTL recognizes the antigen in the form of a peptide fragment bound to the MHC class I molecules rather than the intact foreign antigen itself. The capacity of peptides to bind MHC molecules can be measured in a variety of different ways, such as by inhibition of antigen presentation (Sette, et al., J. Immunol. 141:3893, 1991, incorporated herein by reference in its entirety), in vitro assembly assays (Townsend, et al., Cell 62:285, 1990), and FACS based assays using mutated cells, such as RMA.S (Melief, et al., Eur. J. Immunol. 21:2963, 1991, incorporated herein by reference in its entirety). MHC-binding epitopes predicted to bind MHC class I molecules are typically between 8 to 11 residues, while MHC-binding epitopes predicted to bind MHC class II molecules are typically in the range of 10 to 20 residues. Accordingly, in certain embodiments, antigenic peptides used in the compositions disclosed herein are between 5-50 amino acids (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 amino acids) in length. In certain embodiments, the antigenic peptides are 5 to 50 amino acids in length. In certain embodiments, the antigenic peptides are 25 to 40, 27 to 31, or 21-31 amino acids in length.

In one embodiment, the invention encompasses antigenic peptides identified by methods of the invention. For example, unique peptides comprising a mutant MHC-binding epitope expressed in tumor cells are identified by mapped RNA-Seq reads. Such identified peptides can also be modified by the addition or deletion of amino acids. For example, several (1, 2, 3, 4, or 5) additional amino acid residues can be added to or removed from either end or both ends of a peptide providing that the antigenicity or immunogenicity of the antigenic peptide is not destroyed. Peptides can also be modified by altering the order or composition of certain residues, for example, residues that are located within a MHC-binding epitope. It can readily be appreciated that certain amino acid residues essential for binding to MHC molecules, e.g., those at critical contact sites or conserved residues in an epitope may generally not be altered without an adverse effect on immunogenic activity.

In certain embodiments, the invention provides antigenic peptides that are variants of the mutant peptides identified using the methods disclosed herein, wherein the amino acid sequence of an antigenic peptide is at least 50%, 60%, 70%, or 80% similar to the originally identified peptide. Preferably, the similarity is 90% and most preferably 95% or higher. The variants can comprise mostly or only conservative substitutions of amino acids relative to the identified amino acid sequence. Preferably few if any of the amino acid substitutions occur within an epitope of a peptide.

Conservative substitutions of amino acids within the sequence may be selected from other members of the class to which the amino acid belongs. By conservative substitutions is meant replacing an amino acid residue with another which is biologically and/or chemically similar, e.g., one hydrophobic residue for another, or one polar residue for another. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such modifications may be made using well known peptide synthesis procedures as described in e.g., Merrifield, Science 232:341-347 (1986), Barany and Merrifield, The Peptides, Gross and Meienhofer, eds. (New York, Academic Press), pp. 1-284 (1979); and Stewart and Young, Solid Phase Peptide Synthesis, (Rockford, Ill., Pierce), 2d Ed. (1984), each of which is incorporated herein by reference in its entirety.

In yet another embodiment, the invention encompasses antigenic peptides that comprise an amino acid sequence that binds to a heat shock protein. Such an amino acid sequence is referred to herein as a "heat shock protein binding sequence." In certain embodiments, the heat shock protein binding sequence binds to a heat shock protein (e.g., hsc70, hsp70, hsp90, hsp110, grp170, gp96, or calreticulin) with a $K_d$ of $10^{-3}$ M, $10^{-4}$ M, $10^{-5}$ M, $10^{-6}$ M, $10^{-7}$ M, $10^{-8}$ M, $10^{-9}$ M, or lower. Heat shock protein binding sequences are typically five to fifteen amino acid residues long and are well known in the art. Such binding sequences are exploited in the present invention to facilitate the non-covalent binding of the segment of peptide that comprises the peptide MHC-binding epitopes of the invention to a heat shock protein, in vitro or in vivo. Many such binding sequences are heterologous to the peptide from which the MHC-binding epitopes are derived. Heterologous shock protein binding sites present in many proteins can be used. Examples of such heat shock protein binding sequences are disclosed in U.S. Pat. Nos. 7,420,037 and 7,309,491, and PCT publication WO 97/06821 corresponding to PCT/US96/13363, Blond-Elguindi, S. et al., "Affinity panning of a library of peptides displayed on bacteriophages reveals the binding specificity of BiP." Cell 75:717-728 (1993); Flynn, G. C. et al., "Peptide binding and release by proteins implicated as catalysts of protein assembly." Science 245:385-390 (1989); Auger, I. et al., "HLA-DR4 and HLA-DR10 motifs that carry susceptibility to rheumatoid arthritis bind 70-kD heat shock proteins." Nature Medicine, 2:306-310 (1996); and Gragerov, A. et al., "Different Specificity of DnaK-peptide binding." J. Molec. Biol. 235:848-854 (1994). Usage of heat shock protein binding sequences is described, e.g., in Moroi et al., Proc. Nat. Acad. Sci. USA 2000, 97:3485, each of which is incorporated herein by reference in its entirety.

One example of a heat shock protein binding sequence useful in the compositions of the invention is a heptameric segment having the sequence: Hy(Trp/X)HyXHyXHy, where Hy represents a hydrophobic amino acid residue, particularly tryptophan, leucine, or phenylalanine, and X is any amino acid. Such heat shock protein binding sequences, or other heat shock protein binding sequences, are preferably present at either one of the ends of an amino acid sequence that comprises the MHC-binding epitope. Optionally, the heat shock protein binding sequence, can be joined to either one of the ends by a short peptide linker that consists of several amino acids (e.g., a tripeptide linker having the sequence: glycine-serine-glycine or phe-phe-arg-lys, as disclosed in U.S. Pat. No. 7,309,491, which is incorporated by reference herein in its entirety). Such antigenic peptides can be synthesized chemically with the amino acid residues of the heat shock protein binding sequence, joined to the rest of the peptide by a peptide bond. Alternatively, such antigenic peptides can be synthesized by recombinant DNA techniques as a fusion peptide. Heat shock protein binding sequences, e.g., high affinity heat shock protein binding sequences, suitable for inclusion in the antigenic peptides disclosed herein include, without limitation, NLLRLTG (SEQ ID NO: 439), NLLRLTGW (SEQ ID NO: 440), HWDFAWPW (SEQ ID NO: 441), HWDFAWP (SEQ ID NO: 442), FYQLALTW (SEQ ID NO: 443), FYQLALT (SEQ ID NO: 444), RKLFFNLRW (SEQ ID NO: 445), and RKLFFNLR (SEQ ID NO: 446).

In certain embodiments, the invention encompasses antigenic peptides that comprise a heat shock protein binding sequence. In some embodiments, the heat shock protein binding sequence is 5 to 15 amino acids in length. Heat shock protein binding sequences suitable for inclusion in the antigenic peptides disclosed herein include, without limitation, NLLRLTG (SEQ ID NO: 439), NLLRLTGW (SEQ ID NO: 440), HWDFAWPW (SEQ ID NO: 441), HWDFAWP (SEQ ID NO: 442), FYQLALTW (SEQ ID NO: 443), FYQLALT (SEQ ID NO: 444), RKLFFNLRW (SEQ ID NO: 445), and RKLFFNLR (SEQ ID NO: 446). In certain embodiments, the heat shock protein binding sequence is NLLRLTG (SEQ ID NO: 439). In some embodiments, the heat shock protein binding sequence is at the C-terminus of the antigenic peptide. In some embodiments, the heat shock protein binding sequence is at the N-terminus of the antigenic peptide. In some embodiments, the heat shock protein binding sequence is in the middle of the antigenic peptide. In certain embodiments, the heat shock protein binding sequence is at either one of the ends of an amino acid sequence that comprises an MHC-binding epitope. In certain embodiments, the heat shock protein binding sequence is joined to either one of the ends of an amino acid sequence that comprises an MHC-binding epitope via a linker. In some embodiments, the linker is a peptide linker. In some embodiments, the linker is 2 to 10 amino acids in length. In some embodiments, the linker is FFRK (SEQ ID NO:447). In certain embodiments, the amino acid sequence that comprises an MHC-binding epitope is 5 to 50 amino acids in length. In certain embodiments, the amino acid sequence that comprises an MHC-binding epitope is 25 to 40 amino acids in length. In certain embodiments, the amino acid sequence that comprises an MHC-binding epitope is 27 to 31 amino acids in length. In certain embodiments, the amino acid sequence that comprises an MHC-binding epitope is 8 to 12 amino acids in length. In certain embodiments, the MHC-binding epitope comprises a phosphorylated residue. In certain embodiments, the MHC-binding epitope comprises a phosphomimetic residue. In certain embodiments, the phosphomimetic residue is a non-hydrolyzable analogue of a phosphorylated residue. In certain embodiments, the amino acid sequence that comprises an MHC-binding epitope is 8 to 12 amino acids in length, and the MHC-binding epitope comprises a phosphorylated residue. In certain embodiments, the amino acid sequence that comprises an MHC-binding epitope is 8 to 12 amino acids in length, and the MHC-binding epitope comprises a phosphomimetic residue. In certain embodiments, the antigenic peptide is 15 to 60 amino acids in length. In certain embodiments, the antigenic peptide is 15 to 40 amino acids in length. In certain embodiments, the antigenic peptide is 30-60 amino acids in length. In certain embodiments, the antigenic peptide is 34-56 amino acids in length, e.g., 34, 35, 36, 37, 38, 39, 40, 41, 42, 43, 44, 45, 46, 47, 48, 49, 50, 51, 52, 53, 54, 55, or 56 amino acids in length, containing an amino acid sequence 27-31 amino acids in length that comprises an MHC-binding epitope; a peptide linker that is 2-10 amino acids in length, e.g., FFRK (SEQ ID NO:447); and a heat shock protein binding sequence that is 5-15 amino acids in length, e.g., NLLRLTG (SEQ ID NO: 439), NLLRLTGW (SEQ ID NO: 440), HWDFAWPW (SEQ ID NO: 441), HWDFAWP (SEQ ID NO: 442), FYQLALTW (SEQ ID NO: 443), FYQLALT (SEQ ID NO: 444), RKLFFNLRW (SEQ ID NO: 445), and RKLFFNLR (SEQ ID NO: 446), wherein the amino acid sequence that comprises an MHC-binding epitope, the peptide linker, and the heat shock protein binding sequence are arranged sequentially N-terminal to C-terminal or C-terminal to N-terminal. In particular embodiments, the antigenic peptide is 38 amino acids in length, containing an amino acid sequence of 27 amino acids in length that comprises an MHC-binding epitope; peptide linker FFRK (SEQ ID NO:447); and heat shock protein binding sequence NLLRLTG (SEQ ID NO: 439), wherein the amino acid sequence that comprises an MHC-binding epitope, the peptide linker, and the heat shock protein binding sequence are arranged sequentially N-terminal to C-terminal or C-terminal to N-terminal. In certain embodiments, the amino acid sequence that comprises an MHC-binding epitope comprises a mutated residue in the middle flanked by two peptides of equal length. In some embodiments, the amino acid sequence that comprises an MHC-binding epitope is 27 amino acids in length and comprises a mutated residue at position 14 flanked by two peptides of 13 amino acids in length. In some embodiments, the amino acid sequence that comprises an MHC-binding epitope is 29 amino acids in length and comprises a mutated residue at position 15 flanked by two peptides of 14 amino acids in length. In some embodiments, the amino acid sequence that comprises an MHC-binding epitope is 31 amino acids in length and comprises a mutated residue at position 16 flanked by two peptides of 15 amino acids in length. In certain embodiments, the antigenic peptide is 15-37 amino acids in length, e.g., 15, 16, 17, 18, 19, 20, 21, 22, 23, 24, 25, 26, 27, 28, 29, 30, 31, 32, 33, 34, 35, 36, or 37 amino acids in length, containing an amino acid sequence 8-12 amino acids in length that comprises an MHC-binding epitope; a peptide linker that is 2-10 amino acids in length, e.g., FFRK (SEQ ID NO:447); and a heat shock protein binding sequence that is 5-15 amino acids in length, e.g., NLLRLTG (SEQ ID NO: 439), NLLRLTGW (SEQ ID NO: 440), HWDFAWPW (SEQ ID NO: 441), HWDFAWP (SEQ ID NO: 442), FYQLALTW (SEQ ID NO: 443), FYQLALT (SEQ ID NO: 444), RKLFFNLRW (SEQ ID NO: 445), and RKLFFNLR (SEQ ID NO: 446), wherein the amino acid sequence that comprises an MHC-binding epitope, the peptide linker, and the heat shock protein binding sequence are arranged sequentially N-terminal to C-terminal or C-terminal to N-terminal. In particular embodiments, the antigenic peptide is 20 amino acids in length, containing an amino acid sequence of 9 amino acids in length that comprises an MHC-binding epitope; peptide linker FFRK (SEQ ID NO:447); and heat shock protein binding sequence NLLRLTG (SEQ ID NO: 439), wherein the amino acid sequence that comprises an MHC-binding epitope, the peptide linker, and the heat shock protein binding sequence are arranged sequentially N-terminal to C-terminal or C-terminal to N-terminal. In certain embodiments, the MHC-binding epitope is an MHC class I-binding epitope. In certain embodiments, the amino acid sequence that comprises an MHC-binding epitope is 8-12 amino acids in length and comprises a phosphorylated residue. In certain embodiments, the amino acid sequence that comprises an MHC-binding epitope is 8-12 amino acids in length and comprises a phosphomimetic residue. In certain embodiments, the phosphomimetic residue is a non-hydrolyzable analogue of a phosphorylated residue.

In one preferred embodiment, each one of the antigenic peptides comprises a heat shock protein binding sequence at its N- or C-terminus, more preferably each one of the antigenic peptides comprises a heat shock protein binding sequence at its C-terminus and/or the heat shock protein binding sequence is linked to the remainder of the antigenic peptide via a peptide linker. In one preferred embodiment, the peptide linker comprises the amino acid sequence FFRK (SEQ ID NO:447).

In certain embodiments, antigenic peptides of the invention comprise the amino acid sequence FFRKNLLRLTG (SEQ ID NO:477) at the C-terminus. In certain embodiments, the antigenic peptides further comprise an amino acid sequence of 27-31 amino acid in length (e.g., 27, 29, or 31 amino acid in length) that comprises a mutant MHC-binding epitope. In certain embodiments, the amino acid sequence comprising the mutant MHC-binding epitope has a tumor-specific mutation at about the middle of the amino acid sequence (e.g., the tumor-specific mutation is at about position 14, 15, and 16 of a 27, 29, or 31 amino acid peptide, respectively).

In certain embodiments, antigenic peptides of the invention comprise the amino acid sequence NLLRLTGFFRK (SEQ ID NO:478) at the N-terminus. In certain embodiments, the antigenic peptides further comprise an amino acid sequence of 27-31 amino acid in length (e.g., 27, 29, or 31 amino acid in length) that comprises a mutant MHC-binding epitope. In certain embodiments, the amino acid sequence comprising the mutant MHC-binding epitope has a tumor-specific mutation at about the middle of the amino acid sequence (e.g., the tumor-specific mutation is at about position 14, 15, and 16 of a 27, 29, or 31 amino acid peptide, respectively).

Included within the scope of the invention are derivatives or analogs of antigenic peptides that are modified during or after translation, e.g., by glycosylation, acetylation, phosphorylation, amidation, or derivatization by known protecting/blocking groups, or proteolytic cleavage. Any of numerous chemical modifications may be carried out by known techniques, including but not limited to, reagents useful for protection or modification of free $NH_2$-groups, free COOH-groups, OH-groups, side groups of Trp-, Tyr-, Phe-, His-, Arg-, or Lys-; specific chemical cleavage by cyanogen bromide, hydroxylamine, BNPS-Skatole, acid, or alkali hydrolysis; enzymatic cleavage by trypsin, chymotrypsin, papain, V8 protease, $NaBH_4$; acetylation, formylation, oxidation, reduction; metabolic synthesis in the presence of tunicamycin; etc.

In certain embodiments, phosphopeptide mimetics are employed, wherein a phosphorylated amino acid residue in an antigenic peptide is replaced with a phosphomimetic group. Non-limiting examples of phosphomimetic groups include O-boranophospho, borono, O-dithiophospho, phosphoramide, H-phosphonate, alkylphosphonate, phosphorothiolate, phosphodithiolate and phosphorofluoridate, any of which may be derivatized on Tyr, Thr, Ser, Arg, Lys, or His residues. In certain embodiments, an Asp or Glu residue is used as a phosphomimetic. Asp or Glu residues can also function as phosphomimetic groups, and be used in place of a phospho-Tyr, phospho-Thr, phospho-Ser, phospho-Arg, phospho-Lys and/or phospho-His residue in a peptide.

2.1. Production of Antigenic Peptides by Chemical Synthesis

Antigenic peptides can be synthesized by standard chemical methods including the use of a peptide synthesizer. Conventional peptide synthesis or other synthetic protocols well known in the art can be used.

Peptides having the amino acid sequence of an antigenic peptide can be synthesized, for example, by solid-phase peptide synthesis using procedures similar to those described by Merrifield, 1963, J. Am. Chem. Soc., 85:2149, incorporated herein by reference in its entirety. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag, each of which is incorporated herein by reference in its entirety).

In addition, peptide analogs and derivatives of antigenic peptides can be chemically synthesized as described supra. If desired, nonclassical amino acids or chemical amino acid analogs can be introduced as a substitution or addition into the peptide sequence. Non-classical amino acids include, but are not limited to, the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, C-α-methyl amino acids, and N-α-methyl amino acids.

Peptides phosphorylated on the side chains of Tyr, Ser, Thr, Arg, Lys, and His can be synthesized in Fmoc solid phase synthesis using the appropriate side chain protected Fmoc-phospho amino acid. In this way, peptides with a combination of phosphorylated and non-phosphorylated Tyr, Ser, Thr, Arg, Lys, and His residues can be synthesized. For example, the method of Staerkaer et al can be applied (1991, Tetrahedron Letters 32: 5389-5392). Other procedures (some for specific amino acids) are detailed in De Bont et al. (1987, Tray. Chim Pays Bas 106: 641, 642), Bannwarth and Trezeciak (1987, Helv. Chim. Acta 70: 175-186), Perich and Johns (1988, Tetrahedron Letters 29: 2369-2372), Kitas et al. (1990, J. Org. Chem. 55:4181-4187), Valerio et al. (1989, Int. J. Peptide Protein Res. 33:428-438), Perich et al. (1991, Tetrahedron Letters 32:4033-4034), Pennington (1994, Meth. Molec. Biol. 35:195-2), and Perich (1997, Methods Enzymol. 289:245-266, each of which is incorporated herein by reference in its entirety).

The phosphopeptide can also be produced by first culturing a cell transformed with the nucleic acid that encodes the amino acid sequence of the basic polypeptide. After producing such a polypeptide by cell culture, the hydroxyl groups of the appropriate amino acid are substituted by phosphate groups using organic synthesis or enzymatic methods with phosphorylation enzymes. For example, in the case of serine-specific phosphorylation, serine kinases can be used.

Phosphopeptide mimetics can also be synthesized, wherein a phosphorylated amino acid residue in an antigenic peptide is replaced with a phosphomimetic group. Non-limiting examples of phosphomimetic groups include O-boranophospho, borono, O-dithiophospho, phosphoramide, H-phosphonate, alkylphosphonate, phosphorothiolate, phosphodithiolate and phosphorofluoridate, any of which may be derivatized on Tyr, Thr, Ser, Arg, Lys, or His residues. In certain embodiments, an Asp or Glu residue is used as a phosphomimetic. Asp or Glu residues can also function as phosphomimetic groups, and be used in place of a phospho-Tyr, phospho-Thr, phospho-Ser, phospho-Arg, phospho-Lys and/or phospho-His residue in a peptide.

Purification of the resulting peptide is accomplished using conventional procedures, such as preparative HPLC using reverse-phase, gel permeation, partition and/or ion exchange chromatography. The choice of appropriate matrices and buffers are well known in the art and so are not described in detail herein.

2.2. Production of Antigenic Peptides Using Recombinant DNA Technology

Antigenic peptides can also be prepared by recombinant DNA methods known in the art. A nucleic acid sequence encoding an antigenic peptide can be obtained by back translation of the amino acid sequence and synthesized by standard chemical methods, such as the use of an oligonucleotide synthesizer. Alternatively, coding information for antigenic peptides can be obtained from DNA templates using specifically designed oligonucleotide primers and PCR methodologies. Variations and fragments of antigenic peptides can be made by substitutions, insertions or deletions that provide for antigenically equivalent molecules. Due to the degeneracy of nucleotide coding sequences, DNA sequences which encode the same or a variation of an antigenic protein may be used in the practice of the present invention. These include, but are not limited to, nucleotide sequences which are altered by the substitution of different codons that encode an antigenically equivalent amino acid residue within the sequence, thus producing a silent or conservative change. The nucleic acid encoding an antigenic peptide can be inserted into an expression vector for propagation and expression in host cells.

As the coding sequence for peptides of the length contemplated herein can be synthesized by chemical techniques, for example, the phosphotriester method of Matteucci et al., J. Am. Chem. Soc. 103:3185 (1981) (incorporated herein by reference in its entirety), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired peptide or fusion protein. A number of such vectors and suitable host systems are now available. For expression of the peptide or fusion proteins, the coding sequence will be provided with operably linked start and stop codons, promoter and terminator regions and usually a replication system to provide an expression vector for expression in the desired cellular host.

An expression construct refers to a nucleotide sequence encoding an antigenic peptide operably linked with one or more regulatory regions which enables expression of the peptide in an appropriate host cell. "Operably-linked" refers to an association in which the regulatory regions and the peptide sequence to be expressed are joined and positioned in such a way as to permit transcription, and ultimately, translation.

The regulatory regions necessary for transcription of the peptide can be provided by the expression vector. A translation initiation codon (ATG) may also be provided if the peptide gene sequence lacking its cognate initiation codon is to be expressed. In a compatible host-construct system, cellular transcriptional factors, such as RNA polymerase, will bind to the regulatory regions on the expression construct to effect transcription of the peptide sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to the peptide gene sequence or to insert the peptide gene sequence into the cloning site of a vector, linkers or adapters providing the appropriate compatible restriction sites may be ligated to the ends of the cDNAs by techniques well known in the art (Wu et al., 1987, Methods in Enzymol 152:343-349, incorporated herein by reference in its entirety). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising an antigenic peptide sequence operably linked with regulatory regions can be directly introduced into appropriate host cells for expression and production of the peptide without further cloning. The expression constructs can also contain DNA sequences that facilitate integration of the DNA sequence into the genome of the host cell, e.g., via homologous recombination. In this instance, it is not necessary to use an expression vector comprising a replication origin suitable for appropriate host cells in order to propagate and express the peptide in the host cells.

A variety of expression vectors may be used including plasmids, cosmids, phage, phagemids or modified viruses. Typically, such expression vectors comprise a functional origin of replication for propagation of the vector in an appropriate host cell, one or more restriction endonuclease sites for insertion of the peptide gene sequence, and one or more selection markers. Expression vectors may be constructed to carry nucleotide sequences for one or more of the antigenic peptides of the invention. The expression vector must be used with a compatible host cell which may be derived from a prokaryotic or eukaryotic organism including but not limited to bacteria, yeasts, insects, mammals and humans. Such host cells can be transformed to express one or more antigenic peptides, such as by transformation of the host cell with a single expression vector containing one or more nucleotide sequences encoding any of the antigenic peptides of the invention, or by transformation of the host cell with multiple expression vectors encoding different antigenic peptides of the invention.

In bacterial systems, a number of expression vectors may be advantageously selected to produce antigenic peptides. For example, when a large quantity of such a protein is to be produced, such as for the generation of pharmaceutical compositions, vectors that direct the expression of high levels of fusion protein products that are readily purified may be desirable. Such vectors include the *E. coli* expression vector pUR278 (Ruther et al., 1983, EMBO J. 2, 1791, incorporated herein by reference in its entirety), in which the peptide coding sequence may be ligated individually into the vector in frame with the lac Z coding region so that a fusion protein is produced; pIN vectors (Inouye and Inouye, 1985, Nucleic Acids Res. 13, 3101-3109; Van Heeke and Schuster, 1989, J. Biol. Chem 264, 5503-5509, each of which is incorporated herein by reference in its entirety); and the like. pGEX vectors may also be used to express these peptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the antigenic peptide can be released from the GST moiety.

Alternatively, for long term, high yield production of properly processed peptide complexes, stable expression in mammalian cells is preferred. Cell lines that stably express peptide complexes may be engineered by using a vector that contains a selectable marker. By way of example, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while peptide is expressed continuously.

The recombinant cells may be cultured under standard conditions of temperature, incubation time, optical density and media composition. However, conditions for growth of recombinant cells may be different from those for expression of the antigenic peptides. Modified culture conditions and media may also be used to enhance production of the peptides. For example, recombinant cells containing peptides with their cognate promoters may be exposed to heat or other environmental stress, or chemical stress. Any techniques known in the art may be applied to establish the optimal conditions for producing peptide complexes.

In one embodiment of the invention, a codon encoding methionine is added at the 5' end of the nucleotide sequence encoding an antigenic peptide to provide a signal for initiation of translation of the peptide. This methionine may remain attached to the antigenic peptide, or the methionine may be removed by the addition of an enzyme or enzymes that can catalyze the cleavage of methionine from the peptide. For example, in both prokaryotes and eukaryotes, N-terminal methionine is removed by a methionine aminopeptidase (MAP) (Tsunasawa et al., 1985, J. Biol. Chem. 260, 5382-5391, incorporated herein by reference in its entirety). Methionine aminopeptidases have been isolated and cloned from several organisms, including *E. coli*, yeast, and rat.

The peptide may be recovered from the bacterial, mammalian, or other host cell types, or from the culture medium, by known methods (see, for example, Current Protocols in Immunology, vol. 2, chapter 8, Coligan et al. (ed.), John Wiley & Sons, Inc.; Pathogenic and Clinical Microbiology: A Laboratory Manual by Rowland et al., Little Brown & Co., June 1994, incorporated herein by reference in its entirety).

3. Heat Shock Proteins and Methods of Use 3.1. Heat Shock Proteins

Heat shock proteins, which are also referred to interchangeably herein as stress proteins, useful in the practice of the instant invention can be selected from among any cellular protein that is capable of binding other proteins or peptides and capable of releasing the bound proteins or peptides in the presence of adenosine triphosphate (ATP) or under acidic conditions. The intracellular concentration of such protein may increase when a cell is exposed to a stressful stimulus. In addition to those heat shock proteins that are induced by stress, the HSP60, HSP70, HSP90, HSP100, sHSPs, and PDI families also include proteins that are related to stress-induced HSPs in sequence similarity, for example, having greater than 35% amino acid identity, but whose expression levels are not altered by stress. Therefore it is contemplated that the definition of stress protein or heat shock protein (HSP) embraces other proteins, mutants, analogs, and variants thereof having at least 35% (e.g., at least 40, 45, 50, 55, 60, 65, 70, 75, 80, 85, 90, 95, or 99%) amino acid identity with members of these families whose expression levels in a cell are enhanced in response to a stressful stimulus.

In addition to the major HSP families described supra, an endoplasmic reticulum resident protein, calreticulin, has also been identified as yet another heat shock protein useful for eliciting an immune response when complexed to antigenic molecules (Basu and Srivastava, 1999, J. Exp. Med. 189:797-202; incorporated herein by reference in its entirety). Other stress proteins that can be used in the invention include grp78 (or BiP), protein disulfide isomerase (PDI), hsp110, and grp170 (Lin et al., 1993, Mol. Biol. Cell, 4:1109-1119; Wang et al., 2001, J. Immunol., 165:490-497, each of which is incorporated herein by reference in its entirety). Many members of these families were found subsequently to be induced in response to other stressful stimuli including nutrient deprivation, metabolic disruption, oxygen radicals, hypoxia and infection with intracellular pathogens. (See Welch, May 1993, Scientific American 56-64; Young, 1990, Annu. Rev. Immunol. 8:401-420; Craig, 1993, Science 260:1902-1903; Gething, et al., 1992, Nature 355:33-45; and Lindquist, et al., 1988, Annu. Rev. Genetics 22:631-677, each of which is incorporated herein by reference in its entirety). It is contemplated that HSPs/stress proteins belonging to all of these families can be used in the practice of the invention. In certain embodiments, a stress protein encompasses any chaperone protein that facilitates peptide-MHC presentation. Suitable chaperone proteins include, but are not limited to, ER chaperones, e.g., tapasin (e.g., human tapasin).

The major HSPs can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch, et al., 1985, J. Cell. Biol. 101:1198-1211, incorporated herein by reference in its entirety). In contrast, hsp90 and hsp60 proteins are abundant at normal temperatures in most, but not all, mammalian cells and are further induced by heat (Lai, et al., 1984, Mol. Cell. Biol. 4:2802-10; van Bergen en Henegouwen, et al., 1987, Genes Dev. 1:525-31, each of which is incorporated herein by reference in its entirety).

In various embodiments, nucleotide sequences encoding heat shock protein within a family or variants of a heat shock protein can be identified and obtained by hybridization with a probe comprising nucleotide sequence encoding an HSP under conditions of low to medium stringency.

By way of example, procedures using such conditions of low stringency are as follows (see also Shilo and Weinberg, 1981, Proc. Natl. Acad. Sci. USA 78:6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for signal detection. If necessary, filters are washed for a third time at 65-68° C. before signal detection. Other conditions of low stringency which may be used are well known in the art (e.g., as used for cross-species hybridizations).

Where HSPs are used, peptide-binding fragments of HSPs and functionally active derivatives, analogs, and variants of HSPs can also be used. The term "HSP peptide-binding fragment" is used to refer to a polypeptide that comprises a domain that is capable of becoming noncovalently associated with a peptide to form a complex and eliciting an immune response, but that is not a full-length HSP. The term "variant of HSPs" refers to a polypeptide that is capable of becoming noncovalently associated with a peptide to form a complex and eliciting an immune response, but that shares a high degree of sequence similarity with a HSP. To determine a region of identity between two amino acid sequences or nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877 (each of which is incorporated herein by reference in its entirety). Such an algorithm is incorporated into the NBLAST and XBLAST programs of Altschul, et al., 1990, J. Mol. Biol. 215:403-410 (incorporated herein by reference in its entirety). BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used. Another example of a mathematical algorithm utilized for the comparison of sequences is the algorithm of Myers and Miller, 1988, CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In one embodiment, for example, hsp70 and hsc70 peptide-binding domain derivatives and analogs can be designed. By computer modeling the three dimensional structure of the Hsp70 peptide-binding site, variants of members of the hsp70 family including hsc70 variants can be designed in which amino acid residues not involved in peptide binding or structurally important determinants may be substituted for the wild-type residues.

In a specific embodiment, an HSP peptide-binding fragment of the invention comprises a peptide-binding domain that is contiguous on its N-terminal side with a variable number of amino acids that naturally flank the peptide-binding domain on the N-terminal side and that is contiguous on the C-terminal side with a variable number of amino acids that naturally flank the peptide-binding domain on the C-terminal side, See for example, the peptide-binding fragments of HSPs disclosed in United States patent publication US 2001/0034042 (incorporated herein by reference in its entirety).

Amino acid sequences and nucleotide sequences of naturally occurring HSPs are generally available in sequence databases, such as GenBank. For example, *Homo sapiens* heat shock protein HSP70 (Heat Shock 70 kDa Protein 1A) has the following identifiers HGNC: 5232; Entrez Gene: 3303; Ensembl: ENSG00000204389; OMIM: 140550; UniProtKB: P08107 and NCBI Reference Sequence: NM_005345.5. Computer programs, such as Entrez, can be used to browse the database, and retrieve any amino acid sequence and genetic sequence data of interest by accession number. These databases can also be searched to identify sequences with various degrees of similarities to a query sequence using programs, such as FASTA and BLAST, which rank the similar sequences by alignment scores and statistics. Such nucleotide sequences of non-limiting examples of HSPs that can be used for preparation of the HSP peptide-binding fragments of the invention are as follows: human Hsp70, Genbank Accession No. NM_005345, Sargent et al., 1989, Proc. Natl. Acad. Sci. U.S.A., 86:1968-1972; human Hsc70: Genbank Accession Nos. P11142, Y00371; human Hsp90, Genbank Accession No. X15183, Yamazaki et al., Nucl. Acids Res. 17:7108; human gp96: Genbank Accession No. X15187, Maki et al., 1990, Proc. Natl. Acad Sci., 87: 5658-5562; human BiP: Genbank Accession No. M19645; Ting et al., 1988, DNA 7: 275-286; human Hsp27, Genbank Accession No. M24743; Hickey et al., 1986, Nucleic Acids Res. 14:4127-45; mouse Hsp70: Genbank Accession No. M35021, Hunt et al., 1990, Gene, 87:199-204; mouse gp96: Genbank Accession No. M16370, Srivastava et al., 1987, Proc. Natl. Acad. Sci., 85:3807-3811; and mouse BiP: Genbank Accession No. U16277, Haas et al., 1988, Proc. Natl. Acad. Sci. U.S.A., 85: 2250-2254 (each of these references is incorporated herein by reference in its entirety). Due to the degeneracy of the genetic code, the term "HSP nucleic acid sequence" refers not only to the naturally occurring nucleotide sequence but also encompasses all the other degenerate DNA sequences that encode the HSP.

The HSPs in pharmaceutical preparations can be prepared by purification from tissues, or by recombinant DNA techniques. HSPs can be purified from tissues in the presence of ATP or under acidic conditions (pH 1 to pH 6.9), for subsequent in vitro complexing to one or more antigenic peptides. See Peng, et al., 1997, J. Immunol. Methods, 204:13-21; Li and Srivastava, 1993, EMBO J. 12:3143-3151 (each of these references is incorporated herein by reference in its entirety). "Purified" stress proteins or heat shock proteins are substantially free of materials that are associated with the proteins in a cell, in a cell extract, in a cell culture medium, or in an individual.

Using the defined amino acid or cDNA sequences of a given HSP or a peptide-binding domains thereof, one can make a genetic construct which is transfected into and expressed in a host cell. The recombinant host cells may contain one or more copies of a nucleic acid sequence comprising a sequence that encodes an HSP or a peptide-binding fragment, operably linked with regulatory region(s) that drives the expression of the HSP nucleic acid sequence in the host cell. Recombinant DNA techniques can be readily utilized to generate recombinant HSP genes or fragments of HSP genes, and standard techniques can be used to express such HSP gene fragments. Any nucleic acid sequence encoding an HSP peptide-binding domain, including cDNA and genomic DNA, can be used to prepare the HSPs or peptide-binding fragments of the invention. An HSP gene fragment containing the peptide-binding domain can be inserted into an appropriate cloning vector and introduced into host cells so that many copies of the gene sequence are generated. A large number of vector-host systems known in the art may be used such as, but not limited to, bacteriophages such as lambda derivatives, or plasmids such as pBR322, pUC plasmid derivatives, the Bluescript vectors (Stratagene) or the pET series of vectors (Novagen). Any technique for mutagenesis known in the art can be used to modify individual nucleotides in a DNA sequence, for purpose of making amino acid substitution(s) in the expressed peptide sequence, or for creating/deleting restriction sites to facilitate further manipulations.

The HSPs or peptide-binding fragments may be expressed as fusion proteins to facilitate recovery and purification from the cells in which they are expressed. For example, the HSP or fragment may contain a signal sequence leader peptide to direct its translocation across the endoplasmic reticulum membrane for secretion into culture medium. Further, the HSP or fragment may contain an affinity label fused to any portion of the HSP or fragment not involved in binding antigenic peptide, such as for example, the carboxyl terminal. The affinity label can be used to facilitate purification of the protein, by binding to an affinity partner molecule. A variety of affinity labels known in the art may be used, such as the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience, incorporated herein by reference in its entirety), glutathione S-transferase (GST; Smith, 1993, Methods Mol. Cell Bio. 4:220-229, incorporated herein by reference in its entirety), the *E. coli* maltose binding protein (Guan et al., 1987, Gene 67:21-30, incorporated herein by reference in its entirety), and various cellulose binding domains (U.S. Pat. Nos. 5,496,934; 5,202,247; 5,137,819; Tomme et al., 1994, Protein Eng. 7:117-123, each of which is incorporated herein by reference in its entirety), etc.

Such recombinant HSPs or fragments can be assayed for antigenic peptide binding activity (see for example, Klappa et al., 1998, EMBO J., 17:927-935, incorporated herein by reference in its entirety) for their ability to elicit an immune response. It is preferred that the recombinant HSP produced in the host cell or library cell is of the same species as the intended recipient of the immunogenic composition. Recombinant human HSP is most preferred.

In one embodiment, the HSP isolated from tissue is a mixture of different HSPs, for example, hsp70 and hsc70. Pharmaceutical compositions can comprise purified human hsc70 produced by recombinant DNA methods, for example using human hsc70 sequence as described in Dworniczak and Mirault, Nucleic Acids Res. 15:5181-5197 (1987) and Genbank accession no. P11142 and/or Y00371 (each of which is incorporated herein by reference in its entirety). In certain embodiments, Hsp70 sequences are as described in Hunt and Morimoto Proc. Natl. Acad. Sci. U.S.A. 82 (19), 6455-6459 (1985) and Genbank accession no. PODMV8 and/or M11717 (each of which is incorporated herein by reference in its entirety).

In other embodiments, the stress protein is a mutated stress protein which has an affinity for a target antigenic peptide that is greater than a native stress protein. Such mutated stress proteins can be useful when an antigenic peptide is phosphorylated or is a phosphopeptide mimetic (such as non-hydrolyzable analogs) or has some other post-translational modification.

In a preferred embodiment of compositions of the present invention, the stress protein is selected from the group consisting of hsc70, hsp70, hsp90, hsp110, grp170, gp96, calreticulin, a mutant thereof, and combinations of two or more thereof. In one preferred embodiment, the stress protein is an hsc70, even more preferably a human hsc70. In another preferred embodiment, the stress protein is an hsp70, even more preferably is a human hsp70. The stress protein may be bound to the antigenic peptide non-covalently or covalently. In a preferred embodiment, the stress protein is non-covalently bound to the antigenic peptide. In one preferred embodiment, the amount of the stress protein in the composition is 10 µg to 600 µg, such as 25 µg.

3.2. Preparation of Heat Shock Protein-Peptide Complexes

Described are exemplary methods for complexing in vitro a HSP with a population of antigenic peptides for preparing compositions of the invention described herein. The complexing reaction can result in the formation of a covalent bond between a HSP and a peptide. The complexing reaction can result in the formation of a non-covalent association between a HSP and a peptide. In various embodiments, the complexes formed in vitro are optionally purified. Purified complexes of heat shock proteins and antigenic peptides are substantially free of materials that are associated with such complexes in a cell, or in a cell extract. Where purified heat shock proteins and purified antigenic peptides are used in an in vitro complexing reaction, the term "purified" complexes of heat shock proteins and antigenic peptides do not exclude a composition that also comprises free HSP and peptides not in complexes. In a preferred embodiment of compositions of the present invention, the stress protein is selected from the group consisting of hsc70, hsp70, hsp90, hsp110, grp170, gp96, calreticulin, a mutant thereof, and combinations of two or more thereof. In one preferred embodiment, the stress protein is an hsc70, even more preferably a human hsc70. In another preferred embodiment, the stress protein is an hsp70, even more preferably is a human hsp70. The stress protein may be bound to the antigenic peptide non-covalently or covalently. In a preferred embodiment, the stress protein is non-covalently bound to the antigenic peptide. In one preferred embodiment, the amount of the stress protein in the composition is 10 µg to 600 µg, such as 25 µg.

Prior to complexing, HSPs can be pretreated with ATP or exposed to acidic conditions to remove any peptides that may be non-covalently associated with the HSP of interest. Acidic conditions are any pH levels in the range pH 1 to pH 6.9, including the ranges pH 1-pH 2, pH 2-pH 3, pH 3-pH 4, pH 4-pH 5, pH 5-pH 6, and pH 6-pH 6.9. When the ATP procedure is used, excess ATP is removed from the preparation by the addition of apyranase as described by Levy, et al., 1991, Cell 67:265-274 (incorporated herein by reference in its entirety). When acidic conditions are used, the buffer is readjusted to neutral pH by the addition of pH modifying reagents. The molar ratio of total antigenic peptides, or of any one peptide, to HSP can be any ratio from 0.01:1 to 100:1, including but not limited to 0.01:1, 0.02:1, 0.05:1. 0.1:1. 0.2:1, 0.5:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 49:1, up to 100:1. In one embodiment of a composition of the invention, the molar ratio of stress protein to antigenic peptide in each complex can be in the range of 1:0.01 to 1:100. In certain embodiments of a composition of the invention, the molar ratio of stress protein to antigenic peptide in each complex is at least 1:1 (e.g., about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 49:1, up to 100:1), In certain embodiments of a composition of the invention, the molar ratio of stress protein to antigenic peptide in each complex is 1:1 or less (e.g., 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:50, down to 1:100 or less). A preferred, exemplary protocol for the noncovalent complexing of a population of peptides to an HSP in vitro is discussed below.

The population of antigenic peptides can comprise a mixture of the different antigenic peptide species of the invention. Then, the mixture is incubated with the pretreated HSP for from 15 minutes to 3 hours at from 4° to 50° C. in a suitable binding buffer, such as phosphate buffered saline pH 7.4, or a buffer containing 20 mM sodium phosphate, pH 7.2, 350 mM NaCl, 3 mM $MgCl_2$ and 1 mM phenyl methyl sulfonyl fluoride (PMSF). Any buffer may be used that is compatible with the HSP. The preparations are then optionally purified by centrifugation through a Centricon 10 assembly (Millipore; Billerica, Mass.) to remove any unbound peptide. The non-covalent association of the proteins/peptides with the HSPs can be assayed by High Performance Liquid Chromatography (HPLC) or Mass Spectrometry (MS). In certain embodiments, tumor-specific antigenic peptides of the invention are 27 amino acids in length ("27mers") with an average molecular weight of ~3,000 daltons. Assuming the molecular weight of HSP70 is 70,000 daltons, the following material will be required to generate complexes of tumor-specific antigenic peptides and HPS70 in quantities sufficient to treat a cancer patient. Assuming in one embodiment a 240 µg dose of HSP70 is intended to be administered 12 times to a patient, approximately 3 mg HSP70 is required. If, in one embodiment, ten 27mer peptides are complexed with the HSP70 the total quantity of peptide required for the complexing reaction is 124 µg (12.4 µg each peptide), assuming a 1:1 molar ratio of total peptide:protein. If a 4:1 molar ratio of total peptide:protein is preferred, then 494 µg total peptide is required. In certain embodiments, the HSP70 species is recombinant human Hsc70 (rhHsc70). In certain embodiments, the HSP70 species is recombinant human Hsp70 (rhHsp70). In certain embodiments, rhHsc70 is incubated for 60 minutes with the mixture of antigenic peptides at 37° C. in a binding buffer comprising 2.7 mM Sodium Phosphate Dibasic, 1.5 mM Potassium Phosphate Monobasic, 150 mM NaCl, pH 7.2. An exemplary alternative binding buffer comprises 9% sucrose in potassium phosphate buffer, or 20 mM sodium phosphate buffer pH 7.5, 0.5M NaCl, 3 mM $MgCl_2$ and 1 mM ADP. The HSP70-peptide binding incubation mixture can optionally be centrifuged one or more times if necessary, through a Centricon 10 assembly (Millipore) to remove any unbound peptide.

In certain embodiments, a 25 μg dose of HSP70 is administered 12 times to a patient, requiring a total of 300 μg HSP70. If in one embodiment where ten 27mer peptides are complexed with the HSP70, the total quantity of peptide required for the complexing reaction is 12.9 μg (1.29 μg each peptide), assuming a 1:1 molar ratio of total peptide:protein. If a 4:1 molar ratio of total peptide:protein is preferred, then 51.6 μg total peptide is required It will be appreciated that the above described quantities of HSP70 and peptides are the minimum exemplary quantities needed for administration of vaccine to a patient and that extra material may be produced for the purposes of satisfying quality control tests and certain regulatory requirements.

In certain embodiments, the HSP70-peptide complexes are mixed with QS-21 adjuvant at bedside just prior to administration to a patient. In certain embodiments, the dose of QS-21 is 50 μg.

In cases where fewer or more than 10 peptides are complexed with HSP70, the quantity of peptide is scaled accordingly to maintain the preferred total peptide:protein molar ratio of 1:1, 4:1 or 10:1 as the case may be. Similarly, if it is desirable to use peptides shorter or longer than 27 amino acids in length for complexing to HSP70, the molecular weight of each peptide will be calculated and the quantity of each peptide scaled accordingly to maintain the preferred total peptide:protein molar ratio of 1:1, 4:1 or 10:1.

Alternatively, for producing non-covalent complexes of gp96 or hsp90 to peptides, the molecular weight of each protein is calculated and the total anticipated dosing requirement for a given patient is determined. In one example, assuming 12 doses of gp96-peptide complexes are to be administered to a patient and the dose of gp96 is 25 μg, then 300 μg total protein is required. If, in one embodiment, where ten 27mer peptides are complexed with the gp96, the total quantity of peptide required for the complexing reaction is 9.4 μg (0.94 μg each peptide), assuming a 1:1 molar ratio of total peptide:protein (in this case, gp96). If a 4:1 molar ratio of total peptide:protein is preferred, then 37.5 μg total peptide is required. Binding buffer may be similar to that described for HSP70-peptide binding reactions.

Following complexing with peptides, immunogenic HSP complexes can optionally be assayed using, for example, the mixed lymphocyte target cell assay (MLTC) described below. In certain embodiments, the complexes are measured by enzyme-linked immunospot (ELISPOT) assay (Taguchi T, et al., J Immunol Methods 1990; 128: 65-73, incorporated herein by reference in its entirety). Once HSP-peptide complexes have been isolated and diluted, they can be optionally characterized further in animal models using the administration protocols and excipients discussed below.

As an alternative to making non-covalent complexes of HSPs and peptides, the antigenic peptides can be covalently attached to HSPs.

HSPs can be covalently coupled to peptides by chemical crosslinking. Chemical crosslinking methods are well known in the art. For example, glutaraldehyde crosslinking may be used. Glutaraldehyde crosslinking has been used for formation of covalent complexes of peptides and HSPs (see Barrios et al., 1992, Eur. J. Immunol. 22: 1365-1372, incorporated herein by reference in its entirety). 1-2 mg of HSP-peptide complex is cross-linked in the presence of 0.002% glutaraldehyde for 2 hours. Glutaraldehyde is removed by dialysis against phosphate buffered saline (PBS) overnight (Lussow et al., 1991, Eur. J. Immunol. 21: 2297-2302, incorporated herein by reference in its entirety). Alternatively, a HSP and peptides can be cross-linked by ultraviolet (UV) crosslinking under conditions known in the art.

Complexes of HSP and antigenic peptides from separate covalent and/or non-covalent complexing reactions can optionally be combined to form a composition before administration to a subject.

Any number of different complexes of a stress protein bound to an antigenic peptide can be included in a single composition, as disclosed herein. In certain embodiments, the compositions comprise no more than 100 different antigenic peptides, (e.g., 2, 3, 4, 5, 6, 7, 8, 9, 10, 11, 12, 13, 14, 15, 16, 17, 18, 19, or 20 antigenic peptides; e.g., about 20, 25, 30, 40, 50, 55, 60, 65, 70, 75, 80, 85, 90, 95 or 100 antigenic peptides.

In certain embodiments, the compositions include antigenic peptides that contain only wild-type MHC-binding epitopes. In certain embodiments, the compositions comprise no more than 20 (e.g., 1, 2, 3, 4, 5, 6, 7, 8, 9, 10, 11, 12, 13, 14, 15, 16, 17, 18, 19, or 20) different antigenic peptides that contain only wild-type MHC-binding epitopes. In certain embodiments, the compositions do not comprise any antigenic peptides that contain only wild-type MHC-binding epitopes.

4. Pharmaceutical Compositions

The compositions of the present disclosure encompasses pharmaceutical compositions comprising compositions of the invention described herein comprising complexes of stress proteins bound to different antigenic peptides either alone as the active ingredient or in combination with one or more adjuvants, for the prevention and treatment of a cancer, such as multiple myeloma (MM). Such pharmaceutical compositions are useful as vaccine formulations, in particular cancer vaccine formulations. The vaccine formulation may be prepared by any method that results in a stable, sterile, preferably injectable formulation.

In certain embodiments, the compositions comprising complexes of stress protein/antigenic peptide complexes are in admixture with one or more adjuvants. Many different adjuvants can be used with the compositions disclosed herein. The composition(s) and adjuvant(s) may be mixed together in the same fluid volume, and the composition(s) can comprise one or more adjuvant(s).

A variety of adjuvants may be employed, including, for example, systemic adjuvants and mucosal adjuvants. A systemic adjuvant is an adjuvant that can be delivered parenterally. Systemic adjuvants include adjuvants that create a depot effect, adjuvants that stimulate the immune system and adjuvants that do both. An adjuvant that creates a depot effect is an adjuvant that causes the antigen to be slowly released in the body, thus prolonging the exposure of immune cells to the antigen. This class of adjuvants includes alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

Other adjuvants stimulate the immune system, for instance, cause an immune cell to produce and secrete cytokines or IgG. This class of adjuvants includes immunostimulatory nucleic acids, such as CpG oligonucleotides; saponins purified from the bark of the *Q. saponaria* tree, such as QS-21; poly[di(carboxylatophenoxy)phosphazene (PCPP polymer; Virus Research Institute, USA); RNA mimetics such as polyinosinic:polycytidylic acid (poly I:C) or poly I:C stabilized with poly-lysine (poly-ICLC [Hiltonol®; Oncovir, Inc.]; derivatives of lipopolysaccharides (LPS) such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Other systemic adjuvants are adjuvants that create a depot effect and stimulate the immune system. These compounds have both of the above-identified functions of systemic adjuvants. This class of adjuvants includes but is not limited to ISCOMs (Immuno stimulating complexes which contain mixed saponins, lipids and form virus-sized particles with pores that can hold antigen; CSL, Melbourne, Australia); AS01 which is a liposome based formulation containing MPL and QS-21 (GlaxoSmithKline, Belgium); AS02 (GlaxoSmithKline, which is an oil-in-water emulsion containing MPL and QS-21: GlaxoSmithKline, Rixensart, Belgium); AS04 (GlaxoSmithKline, which contains alum and MPL; GSK, Belgium); AS15 which is a liposome based formulation containing CpG oligonucleotides, MPL and QS-21 (GlaxoSmithKline, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

The mucosal adjuvants useful according to the invention are adjuvants that are capable of inducing a mucosal immune response in a subject when administered to a mucosal surface in conjunction with complexes of the invention. Mucosal adjuvants include CpG nucleic acids (e.g. PCT published patent application WO 99/61056, incorporated herein by reference in its entirety), bacterial toxins: e.g., Cholera toxin (CT), CT derivatives including but not limited to CT B subunit (CTB); CTD53 (Val to Asp); CTK97 (Val to Lys); CTK104 (Tyr to Lys); CTD53/K63 (Val to Asp, Ser to Lys); CTH54 (Arg to His); CTN107 (His to Asn); CTE114 (Ser to Glu); CTE112K (Glu to Lys); CTS61F (Ser to Phe); CTS 106 (Pro to Lys); and CTK63 (Ser to Lys), Zonula occludens toxin (zot), *Escherichia coli* heat-labile enterotoxin, Labile Toxin (LT), LT derivatives including but not limited to LT B subunit (LTB); LT7K (Arg to Lys); LT61F (Ser to Phe); LT112K (Glu to Lys); LT118E (Gly to Glu); LT146E (Arg to Glu); LT192G (Arg to Gly); LTK63 (Ser to Lys); and LTR72 (Ala to Arg), Pertussis toxin, PT. including PT-9K/129G; Toxin derivatives (see below); Lipid A derivatives (e.g., monophosphoryl lipid A, MPL); Muramyl Dipeptide (MDP) derivatives; bacterial outer membrane proteins (e.g., outer surface protein A (OspA) lipoprotein of *Borrelia burgdorferi*, outer membrane protein of *Neisseria meningitidis*); oil-in-water emulsions (e.g., MF59; aluminum salts (Isaka et al., 1998, 1999); and Saponins (e.g., QS-21, e.g., QS-21 Stimulon®, Antigenics LLC, Lexington, Mass.), ISCOMs, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micelle-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)] phosphazene (PCPP polymer; Virus Research Institute, USA) and *Leishmania* elongation factor (Corixa Corporation, Seattle, Wash.).

The compositions of the invention described herein, comprising complexes of stress proteins and antigenic peptides may be combined with an adjuvant in several ways. For example, different peptides may be mixed together first to form a mixture and then complexed with stress proteins and/or an adjuvant or adjuvants to form a composition. As another example, different antigenic peptides may be complexed individually with a stress protein and/or an adjuvant or adjuvants, and the resulting batches of stress protein/ antigenic peptide/adjuvant complexes may then be mixed to form a composition. The adjuvant can be administered prior to, during, or following administration of the compositions comprising complexes of stress protein and antigenic peptides. Administration of the adjuvant and the compositions comprising complexes of stress protein and antigenic peptides can be at the same or different administration sites. In certain embodiments, the antigenic peptides of the invention are complexed with heat shock proteins. Antigenic peptide-HSP complexes can be covalent or non-covalent.

Adjuvant(s) that can be added to the compositions disclosed herein include, for example, saponins, and immunostimulatory nucleic acids. In specific embodiments, the second adjuvant added to the composition comprising HSPs and the antigenic peptides is QS-21.

The concentration of the peptides at which the efficacy of a vaccine formulation of the invention is optimized can be determined using standard methods known to one skilled in the art, e.g., determined by the antibody or T-cell response to the peptide-stress protein mixture or complex relative to a control formulation, e.g., a formulation comprising the peptide or stress protein alone.

The amount of stress protein/antigenic peptide complex and optionally adjuvants used in the pharmaceutical compositions may vary depending on the chemical nature and the potency of the antigenic peptides, stress proteins, and adjuvants. Typically, the starting concentration of antigenic peptides, stress proteins, and adjuvants in the vaccine formulation is the amount that is conventionally used for eliciting the desired immune response, using the conventional routes of administration, e.g., intramuscular injection. The concentration of the antigenic peptides, stress proteins, and adjuvants is then adjusted, e.g., by dilution using a diluent, in the pharmaceutical compositions of the invention so that an effective protective immune response is achieved as assessed using standard methods known in the art.

Pharmaceutical compositions can be optionally prepared as lyophilized product, which may then be formulated for oral administration or reconstituted to a liquid form for parenteral administration.

Pharmaceutical compositions of the invention can additionally be formulated to contain other agents as pharmaceutically acceptable carriers or excipients including bulking agents, stabilizing agents, buffering agents, sodium chloride, calcium salts, surfactants, antioxidants, chelating agents, other excipients, and combinations thereof.

Bulking agents are preferred in the preparation of lyophilized formulations of the vaccine composition. Such bulking agents form the crystalline portion of the lyophilized product and may be selected from the group consisting of mannitol, glycine, alanine, and hydroxyethyl starch (HES).

Stabilizing agents may be selected from the group consisting of sucrose, trehalose, raffinose, and arginine. These agents are preferably present in amounts between 1-4%. Sodium chloride can be included in the present formulations preferably in an amount of 100-300 mM, or if used without the aforementioned bulking agents, can be included in the formulations in an amount of between 300-500 mM NaCl. Calcium salts include calcium chloride, calcium gluconate, calcium glubionate, or calcium gluceptate.

Buffering agents can be any physiologically acceptable chemical entity or combination of chemical entities which have a capacity to act as buffers, including but not limited to histidine, potassium phosphate, TRIS [tris-(hydroxymethyl)-aminomethane], BIS-Tris Propane (1,3-bis-[tris-(hydroxymethyl)methylamino]-propane), PIPES [piperazine-N,N'-bis-(2-ethanesulfonic acid)], MOPS [3-(N-morpholino)ethanesulfonic acid], HEPES (N-2-hydroxyethylpiperazine-N'-2-ethanesulfonic acid), MES [2-(N-morpholino)ethanesulfonic acid], and ACES (N-2-acetamido-2-aminoethanesulfonic acid). Typically, the buffering agent is included in a concentration of 10-50 mM. Specific examples of base buffers include (i) PBS; (ii) 10 mM $KPO_4$, 150 mM NaCl; (iii) 10 mM HEPES, 150 mM NaCl; (iv) 10 mM imidazole, 150 mM NaCl; and (v) 20 mM sodium citrate. Excipients that can be used include (i) glycerol (10%, 20%); (ii) Tween 50 (0.05%, 0.005%); (iii) 9% sucrose; (iv) 20% sorbitol; (v) 10 mM lysine; or (vi) 0.01 mM dextran sulfate.

Surfactants, if present, are preferably in a concentration of 0.1% or less, and may be chosen from the group including but not limited to polysorbate 20, polysorbate 80, pluronic polyols, and BRIJ 35 (polyoxyethylene 23 laurel ether). Antioxidants, if used, must be compatible for use with a pharmaceutical preparation, and are preferably water soluble. Suitable antioxidants include homocysteine, glutathione, lipoic acid, 6-hydroxy-2,5,7,8-tetramethylchroman-2-carboxylic acid (Trolox), methionine, sodium thio sulfate, platinum, glycine-glycine-histidine (tripeptide), and butylatedhydroxytoluene (BHT). Chelating agents should preferably bind metals such as copper and iron with greater affinity than calcium, if a calcium salt is being used in the composition. A preferred chelator is deferoxamine.

Many formulations known in the art can be used. For example, U.S. Pat. No. 5,763,401 describes a therapeutic formulation, comprising 15-60 mM sucrose, up to 50 mM NaCl, up to 5 mM calcium chloride, 65-400 mM glycine, and up to 50 mM histidine. In some embodiments, the therapeutic formulation is a solution of 9% sucrose in potassium phosphate buffer.

U.S. Pat. No. 5,733,873 (incorporated herein by reference in its entirety) discloses formulations which include between 0.01-1 mg/ml of a surfactant. This patent discloses formulations having the following ranges of excipients: polysorbate 20 or 80 in an amount of at least 0.01 mg/ml, preferably 0.02-1.0 mg/ml; at least 0.1 M NaCl; at least 0.5 mM calcium salt; and at least 1 mM histidine. More particularly, the following specific formulations are also disclosed: (1) 14.7-50-65 mM histidine, 0.31-0.6 M NaCl, 4 mM calcium chloride, 0.001-0.02-0.025% polysorbate 80, with or without 0.1% PEG 4000 or 19.9 mM sucrose; and (2) 20 mg/ml mannitol, 2.67 mg/ml histidine, 18 mg/ml NaCl, 3.7 mM calcium chloride, and 0.23 mg/ml polysorbate 80.

The use of low or high concentrations of sodium chloride has been described, for example U.S. Pat. No. 4,877,608 (incorporated herein by reference in its entirety) teaches formulations with relatively low concentrations of sodium chloride, such as formulations comprising 0.5 mM-15 mM NaCl, 5 mM calcium chloride, 0.2 mM-5 mM histidine, 0.01-10 mM lysine hydrochloride and up to 10% maltose, 10% sucrose, or 5% mannitol.

U.S. Pat. No. 5,605,884 (incorporated herein by reference in its entirety) teaches the use of formulations with relatively high concentrations of sodium chloride. These formulations include 0.35 M-1.2 M NaCl, 1.5-40 mM calcium chloride, 1 mM-50 mM histidine, and up to 10% sugar such as mannitol, sucrose, or maltose. A formulation comprising 0.45 M NaCl, 2.3 mM calcium chloride, and 1.4 mM histidine is exemplified.

International Patent Application WO 96/22107 (incorporated herein by reference in its entirety) describes formulations which include the sugar trehalose, for example formulations comprising: (1) 0.1 M NaCl, 15 mM calcium chloride, 15 mM histidine, and 1.27 M (48%) trehalose; or (2) 0.011% calcium chloride, 0.12% histidine, 0.002% TRIS, 0.002% Tween 80, 0.004% PEG 3350, 7.5% trehalose; and either 0.13% or 1.03% NaCl.

U.S. Pat. No. 5,328,694 (incorporated herein by reference in its entirety) describes a formulation which includes 100-650 mM disaccharide and 100 mM-1.0 M amino acid, for example (1) 0.9 M sucrose, 0.25 M glycine, 0.25 M lysine, and 3 mM calcium chloride; and (2) 0.7 M sucrose, 0.5 M glycine, and 5 mM calcium chloride.

5. Methods of Use

The compositions disclosed herein, comprise complexes of a stress protein bound to an antigenic peptide, for treating and/or preventing cancers, for example, multiple myeloma. The compositions can be used to make medicaments and vaccines for use by individuals or subjects in whom treatment or prevention of cancer is desired. In various embodiments, such individual or subject is an animal, preferably a mammal, a non-human primate, and most preferably human. The term "animal" includes companion animals, such as cats and dogs; zoo animals; wild animals, including deer, foxes and raccoons; farm animals, livestock and fowl, including horses, cattle, sheep, pigs, turkeys, ducks, and chickens, and laboratory animals, such as rodents, rabbits, and guinea pigs.

5.1. Treatment of Cancer

The compositions of the invention can be used alone or in combination with other therapies for the treatment of cancer.

Cancers that can be treated using the compositions of the invention include, without limitation, B cell lymphomas (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

In certain embodiments, the cancer is a carcinoma (e.g., an adenocarcinoma), lymphoma, blastoma, melanoma, sarcoma, or leukemia.

In certain embodiments, the cancer is a human sarcoma or carcinoma, e.g., fibrosarcoma, myxosarcoma, liposarcoma, chondrosarcoma, osteogenic sarcoma, chordoma, angio sarcoma, endotheliosarcoma, lymphangiosarcoma, lymphangioendotheliosarcoma, synovioma, mesothelioma, Ewing's tumor, leiomyo sarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (e.g., metastatic), hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma.

In certain embodiments, the cancer is an acute lymphocytic leukemia or acute myelocytic leukemia (e.g., myeloblastic, promyelocytic, myelomonocytic, monocytic and erythroleukemia); chronic leukemia (chronic myelocytic (granulocytic) leukemia or chronic lymphocytic leukemia); Hodgkin's disease; non-Hodgkin's disease; acute myeloid leukemia; B-cell lymphoma; T-cell lymphoma; anaplastic large cell lymphoma; intraocular lymphoma; follicular lymphoma; small intestine lymphoma; or orsplenic marginal zone lymphoma.

In certain embodiments, the cancer is multiple myeloma, Waldenstrom's macroglobulinemia, heavy chain disease, gastrointestinal stromal tumors, head and/or neck cancer (e.g., squamous cell carcinoma of the hypopharynx, squamous cell carcinoma of the larynx, cell carcinoma of the oropharynx, or verrucous carcinoma of the larynx), endometrial stromal sarcoma, mast cell sarcoma, adult soft tissue sarcoma, uterine sarcoma, merkel cell carcinoma, urothelial carcinoma, melanoma with brain metastases, uveal melanoma, uveal melanoma with liver metastases, non-small cell lung cancer, rectal cancer, or myelodysplastic syndrome.

In certain embodiments, the cancer is prostate cancer, breast cancer, lung cancer, colorectal cancer, melanoma, bronchial cancer, bladder cancer, brain or central nervous system cancer, peripheral nervous system cancer, uterine or endometrial cancer, cancer of the oral cavity or pharynx, non-Hodgkin's lymphoma, thyroid cancer, kidney cancer, biliary tract cancer, small bowel or appendix cancer, salivary gland cancer, thyroid gland cancer, adrenal gland cancer, squamous cell cancer, mesothelioma, osteocarcinoma, thyoma/thymic carcinoma, glioblastoma, myelodysplastic syndrome, soft tissue sarcoma, DIPG, adenocarcinoma, osteosarcoma, chondrosarcoma, leukemia, or pancreatic cancer.

In certain embodiments, the cancer is a squamous cell cancer, small-cell lung cancer, non-small cell lung cancer, gastrointestinal cancer, Hodgkin's lymphoma, non-Hodgkin's lymphoma, pancreatic cancer, glioblastoma, glioma, cervical cancer, ovarian cancer, liver cancer (e.g., hepatic carcinoma and hepatoma), bladder cancer, breast cancer, inflammatory breast cancer, Merkel cell carcinoma, colon cancer, colorectal cancer, stomach cancer, urinary bladder cancer, endometrial carcinoma, myeloma (e.g., multiple myeloma), salivary gland, carcinoma, kidney cancer (e.g., renal cell carcinoma and Wilms' tumors), basal cell carcinoma, melanoma, prostate cancer, vulval cancer, thyroid cancer, testicular cancer, esophageal cancer, serous adenocarcinoma or various types of head and neck cancer. In certain embodiments, the cancer is desmoplastic melanoma, inflammatory breast cancer, thymoma, rectal cancer, anal cancer, or surgically treatable or non-surgically treatable brain stem glioma. In a specific embodiment, the cancer is a solid tumor. In another specific embodiment, the cancer is glioblastoma multiforme. In some embodiments, the glioblastoma multiforme is recurrent. In some embodiments, the glioblastoma multiforme is newly diagnosed. In some embodiments, the glioblastoma multiforme is in a subject having non-methylated MGMT promoters. In some embodiments, the glioblastoma multiforme is refractory to Bevacizumab therapy. In some embodiments, the glioblastoma multiforme is in a subject that has not received Bevacizumab therapy.

In certain embodiments, the cancer is multiple myeloma, glioblastoma, colorectal cancer, hepatocellular carcinoma, sarcoma, head and neck cancer (e.g., head and neck squamous cell carcinoma), breast cancer, lung cancer, and melanoma.

In certain embodiments, the cancer is metastatic.

The compositions of the invention may be administered when a cancer is detected, or prior to or during an episode of recurrence.

Administration can begin at the first sign of cancer or recurrence, followed by boosting doses until at least symptoms are substantially abated and for a period thereafter.

In some embodiments, the compositions can be administered to a subject with cancer who has undergone tumor resection surgery that results in an insufficient amount of resected tumor tissue (e.g., less than 7 g, less than 6 g, less than 5 g, less than 4 g, less than 3 g, less than 2 g, or less than 1 g of resected tumor tissue) for production of a therapeutically effective amount of an autologous cancer vaccine comprising a representative set of antigens collected from the resected tumor tissue. (See, for example, cancer vaccines described in Expert Opin. Biol. Ther. 2009 February; 9(2):179-86; incorporated herein by reference.)

The compositions of the invention can also be used for immunization against recurrence of cancers. Prophylactic administration of a composition to an individual can confer protection against a future recurrence of a cancer.

5.2. Combination Therapy

Combination therapy refers to the use of compositions of the invention with another modality to prevent or treat the cancer. In one embodiment, this additional form of modality is a non-HSP modality, e.g., a modality that does not comprise HSP as a component. This approach is commonly termed combination therapy, adjunctive therapy or conjunctive therapy (the terms are used interchangeably). With combination therapy, additive potency or additive therapeutic effect can be observed. Synergistic outcomes are sought where the therapeutic efficacy is greater than additive. The use of combination therapy can also provide better therapeutic profiles than the administration of the treatment modality, or the compositions of the invention alone. The additive or synergistic effect may allow for a reduction in the dosage and/or dosing frequency of either or both modalities to mitigate adverse effects.

In certain embodiments, a subject is administered a combination of: a first patient-specific composition, that comprises at least two different complexes of a purified stress protein bound (e.g., recombinant stress protein) to an antigenic peptide (e.g., a chemically synthesized antigenic peptide), wherein the complexes each comprise a different antigenic peptide, wherein each one of the different antigenic peptides comprises one or more mutant MHC-binding epitopes present in the subjects cancer cell; and second cancer type-specific composition that comprises at least 2 different complexes of a purified stress protein bound to an antigenic peptide, wherein the complexes each comprise a different antigenic peptide, and wherein each one of the different antigenic peptides comprises one or more mutant MHC-binding epitopes that are frequently found in cancers of the same type as subject's cancer. The first and the second composition can have any one or more of the features of the stress protein/antigenic peptide compositions described herein.

As used herein, the term "frequently found in cancers" refers to one or more mutant MHC-binding epitopes that are found in greater than 5% of cancers.

Any number of different complexes of a stress protein bound to an antigenic peptide can be included in the second composition. In certain embodiments, the compositions comprise no more than 100 different antigenic peptides (e.g., 2, 3, 4, 5, 6, 7, 8, 9, 10, 11, 12, 13, 14, 15, 16, 17, 18, 19, or 20 antigenic peptides; e.g., about 20, 25, 30, 40, 50, 55, 60, 65, 70, 75, 80, 85, 90, 95 or 100 antigenic peptides). In certain embodiments, the second composition comprises at least one antigenic peptide that comprises one or more mutant MHC-binding epitopes of myc, k-ras, n-ras, tp53, or kdm6A found in cancer.

In certain embodiments, the second composition includes antigenic peptides that contain only wild-type MHC-binding epitopes. In certain embodiments, the compositions comprise no more than 20 (e.g., 1, 2, 3, 4, 5, 6, 7, 8, 9, 10, 11, 12, 13, 14, 15, 16, 17, 18, 19, or 20) different antigenic peptides that contain only wild-type MHC-binding epitopes. In certain embodiments, the compositions do not comprise any antigenic peptides that contain only wild-type MHC-binding epitopes.

The first and second stress protein/antigenic peptide compositions can be administered simultaneously or sequentially. In certain embodiments, the second composition is administered prior to administration of the first composition.

In other embodiments, the combination therapy comprises the administration of the compositions of the invention to a subject treated with a treatment modality wherein the treatment modality administered alone is not clinically adequate to treat the subject such that the subject needs additional effective therapy, e.g., a subject is unresponsive to a treatment modality without administering the compositions. Included in such embodiments are methods comprising administering the compositions of the invention to a subject receiving a treatment modality wherein said subject has responded to therapy yet suffers from side effects, relapse, develops resistance, etc. Such a subject might be non-responsive or refractory to treatment with the treatment modality alone. Methods of the invention comprising administration of the compositions of the invention to a subject refractory to a treatment modality alone can improve the therapeutic effectiveness of the treatment modality when administered as contemplated by the methods of the invention. The determination of the effectiveness of a treatment modality can be assayed in vivo or in vitro using methods known in the art. In one embodiment, the compositions of the invention are administered in combination with a second treatment modality comprising a different cancer vaccine.

In one embodiment, a lesser amount of the second treatment modality is required to produce a therapeutic benefit in a subject. In specific embodiments, a reduction of about 10%, 20%, 30%, 40% and 50% of the amount of second treatment modality can be achieved. The amount of second treatment modality, including amounts in a range that does not produce any observable therapeutic benefits, can be determined by dose-response experiments conducted in animal models by methods well known in the art.

In one embodiment, the compositions are administered in combination with a second treatment modality, such as a chemotherapeutic agent. Examples include antineoplastic agents such as: acivicin; aclarubicin; acodazole hydrochloride; acronine; adozelesin; adriamycin; aldesleukin; altretamine; ambomycin; a. metantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; camptothecin; caracemide; carbetimer; carboplatin; carmustine; carubicin hydrochloride; carzelesin; cedefingol; chlorambucil; cirolemycin; cisplatin; cladribine; combretestatin a-4; crisnatol mesylate; cyclophosphamide; cytarabine; dacarbazine; daca (n-[2-(dimethyl-amino)ethyl]acridine-4-carboxamide); dactinomycin; daunorubicin hydrochloride; daunomycin; decitabine; dexormaplatin; dezaguanine; dezaguanine mesylate; diaziquone; docetaxel; dolasatins; doxorubicin; doxorubicin hydrochloride; droloxifene; droloxifene citrate; dromostanolone propionate; duazomycin; edatrexate; eflornithine hydrochloride; ellipticine; elsamitrucin; enloplatin; enpromate; epipropidine; epirubicin hydrochloride; erbulozole; esorubicin hydrochloride; estramustine; estramustine phosphate sodium; etanidazole; ethiodized oil i 131; etoposide; etoposide phosphate; etoprine; fadrozole hydrochloride; fazarabine; fenretinide; floxuridine; fludarabine phosphate; fluorouracil; 5-fdump; flurocitabine; fosquidone; fostriecin sodium; gemcitabine; gemcitabine hydrochloride; gold au 198; homocamptothecin; hydroxyurea; idarubicin hydrochloride; ifosfamide; ilmofosine; interferon alfa-2a; interferon alfa-2b; interferon alfa-nl; interferon alfa-n3; interferon beta-i a; interferon gamma-i b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peploycinsulfate; perfosfamide; pipobroman; pipsulfan; piroxantrone hydrochloride; plicamycin; plomestane; porfimer sodium; porfiromycin; prednimustine; procarbazine hydrochloride; puromycin; puromycin hydrochloride; pyrazofurin; rhizoxin; rhizoxin d; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; strontium chloride sr 89; sulofenur; talisomycin; taxane; taxoid; tecogalan sodium; tegafur; teloxantrone hydrochloride; temoporfin; tenipo side; teroxirone; testolactone; thiamiprine; thioguanine; thiotepa; thymitaq; tiazofurin; tirapazamine; tomudex; top53; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine; vinblastine sulfate; vincristine; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 2-chlorodeoxyadeno sine; 2' deoxyformycin; 9-aminocamptothecin; raltitrexed; N-propargyl-5,8-dideazafolic acid; 2chloro-2'-arabino-fluoro-2'-deoxyadenosine; 2-chloro-2'-deoxyadeno sine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N,N-Bis(2-chloroethyl)-N-nitrosourea (BCNU); N-(2-chloroethyl)-N'cyclohexyl-N-nitro sourea (CCNU); N-(2-chloroethyl)-N'-(trans-4-methylcyclohexyl-N-nitrosourea (MeCCNU); N-(2-chloroethyl)-N-(diethyl)ethylphosphonate-N-nitrosourea (fotemustine); streptozotocin; diacarbazine (DTIC); mitozolomide; temozolomide; thiotepa; mitomycin C; AZQ; adozelesin; cisplatin; carboplatin; ormaplatin; oxaliplatin; C1-973; DWA 2114R; JM216; JM335; Bis (platinum); tomudex; azacitidine; cytarabine; gemcitabine; 6-mercaptopurine; 6-thioguanine; hypoxanthine; teniposide 9-amino camptothecin; topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-hydroxyphenyl) retinamide; 13-cis retinoic acid; 3-methyl TTNEB; 9-cis retinoic acid; fludarabine (2-F-ara-AMP); or 2-chlorodeoxyadeno sine (2-Cda).

Other therapeutic compounds include 20-pi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; episteride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathionc inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives;

palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In some embodiments, indoleamine dioxygenase-1 inhibitors are used, such as 4-amino-N-(3-chloro-4-fluorophenyl)-N'-hydroxy-1,2,5-oxadiazole-3-carboximidamide (WO2006122150).

In another embodiment, the compositions of the invention are used in combination with one or more antibodies, including but not limited to polyclonal antibodies, monoclonal antibodies, chimeric antibodies, antibody fragments, single chain antibodies, and the like. Exemplary antibodies that may be combined with the disclosed compositions include, without limitation, those that are immune checkpoint inhibitors, such as anti-GITR, anti-OX40, anti-PD-1, anti-CTLA-4, anti-TIM-3, and anti-LAG-3. Other immune checkpoint inhibitors include pazopanib, bevacizumab, nivolumab, pembrolizumab/MK-3475, pidilizumab, MEDI0680 (AMP-514), AMP-224; BMS-935559, MEDI4736, MPDL3280A, MSB0010718C, ipilimumab or tremelimumab.

In another embodiment, the compositions of the invention are used in combination with one or more biological response modifiers, for example, cytokines. In one such embodiment, a cytokine is administered to a subject receiving a composition of the invention. In another such embodiment, the compositions of the invention are administered to a subject receiving a chemotherapeutic agent, such as an antiviral agent, antibody, adjuvant, or another biological response modifier, in combination with a cytokine. In various embodiments, one or more cytokine(s) can be used and are selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, TGF-β, IL-15, IL-18, GM-CSF, INF-γ, INF-α, SLC, endothelial monocyte activating protein-2 (EMAP2), MIP-3α, MIP-3β, or an MHC gene, such as HLA-B7. Additionally, other exemplary cytokines include other members of the TNF family, including but not limited to TNF-α-related apoptosis-inducing ligand (TRAIL), TNF-α-related activation-induced cytokine (TRANCE), TNF-α-related weak inducer of apoptosis (TWEAK), CD40 ligand (CD40L), lymphotoxin alpha (LT-α), lymphotoxin beta (LT-β), OX40 ligand (OX40L), Fas ligand (FasL), CD27 ligand (CD27L), CD30 ligand (CD30L), 41BB ligand (41BBL), APRIL, LIGHT, TL1, TNFSF16, TNFSF17, and AITR-L, or a functional portion thereof. See, e.g., Kwon et al., 1999, Curr. Opin. Immunol. 11:340-345 (incorporated herein by reference in its entirety) for a general review of the TNF family. In certain embodiments, the compositions of the invention are administered prior to the treatment modalities.

In other embodiments, the compositions of the invention are used in combination with one or more biological response modifiers which are agonists or antagonists of various ligands, receptors and signal transduction molecules of the immune system. For example, the biological response modifiers, include, but are not limited to, agonists of Toll-like receptors (TLR-2, TLR-7, TLR-8 and TLR-9); LPS; agonists of 41BB, OX40, ICOS, and CD40; and antagonists of Fas ligand, PD1, and CTLA-4. These agonists and antagonists can be antibodies, antibody fragments, peptides, peptidomimetic compounds, polysaccharides, and small molecules.

In certain embodiments, the compositions of the invention can be used in combination with one or more additional adjuvants such as saponins and immunostimulatory nucleic acids.

Quillaja saponins are a mixture of triterpene glycosides extracted from the bark of the tree Quillaja *saponaria*. They have long been recognized as immune stimulators that can be used as vaccine adjuvants, (Campbell, J. B., and Peerbaye, Y. A., Res. Immunol. 143(5):526-530 (1992), which is incorporated herein by reference in its entirety), and a number of commercially available complex saponin extracts have been utilized as adjuvants. Due to its potent adjuvant activity and low toxicity, the saponin, QS-21 (commercially available as the "Stimulon®" adjuvant), has been identified as a useful immunological adjuvant. (Kensil, C. R. et al., "Structural and Immunological Characterization of the Vaccine Adjuvant QS-21," in Vaccine Design: The Subunit and Adjuvant Approach, Powell, M. F. and Newman, M. J. eds., Plenum Press, New York (1995), which is incorporated herein by reference in its entirety). QS-21 is a complex triterpene glycoside of quillaic acid. QS-21 is glycosylated at triterpene carbon 3, triterpene carbon 28, and carbon 5 of the second fatty acyl unit in a fatty acid domain.

In certain embodiments, the disclosed compositions comprise complexes of stress proteins with the antigenic peptides in combination with a saponin. In certain embodiments, the saponin comprises, for example, QS-21 or related compounds, (disclosed in U.S. Pat. Nos. 5,057,540; 5,273,965; 5,443,829; 5,650,398; and 6,524,584, each of which is incorporated herein by reference in its entirety). QS-21 has been further purified using hydrophilic interaction chromatography (HILIC) and resolved into two peaks, QS-21-V1 and QS-21-V2, which have been shown to be chemically different compounds. In C57BL/6 mice immunized with vaccines consisting of ovalbumin and either QS-21, QS-1-V1, or QS-21-V2, both of the individual components QS-21-V1 and QS-21-V2 are comparable in adjuvant effect to the original QS-21 peak (containing a mixture of 3:2 QS-21-V1 and QS-21-V2) for boosting the IgG subclasses IgG1, IgG2b, and IgG2 as well as the total IgG titer (disclosed in U.S. Pat. No. 6,231,859, which is incorporated by reference herein in its entirety).

Many immunostimulatory nucleic acids are oligonucleotides comprising an unmethylated CpG motif, are mitogenic to vertebrate lymphocytes, and are known to enhance the immune response (see Woolridge, et al., 1997, Blood 89:2994-2998, incorporated herein by reference in its entirety). Such oligonucleotides are described in International Patent Publication Nos. WO 01/22972, WO 01/51083, WO 98/40100 and WO 99/61056, as well as U.S. Pat. Nos. 6,207,646, 6,194,388, 6,218,371, 6,239,116, 6,429,199, and 6,406,705 (each of which is incorporated herein by reference in its entirety). Other kinds of immunostimulatory oligonucleotides such as phosphorothioate oligodeoxynucleotides containing YpG- and CpR-motifs have been described by Kandimalla et al. in "Effect of Chemical Modifications of Cytosine and Guanine in a CpG-Motif of Oligonucleotides: Structure-Immunostimulatory Activity Relationships." Bioorganic & Medicinal Chemistry 9:807-813 (2001), which is incorporated herein by reference in its entirety. Also encompassed are immunostimulatory oligonucleotides that lack CpG dinucleotides which when administered by mucosal routes (including low dose administration) or at high doses through parenteral routes, augment antibody responses, often as much as did the CpG nucleic acids, however the response was Th2-biased (IgG1>>IgG2a) (see, for example, United States Patent Publication No. 2001/0044416, which is incorporated herein by reference in its entirety. Methods of determining the activity of immunostimulatory oligonucleotides can be performed as described in the aforementioned patents and publications. Moreover, immunostimulatory oligonucleotides can be modified within the phosphate backbone, sugar, nucleobase and internucleotide linkages in order to modulate the activity. Such modifications are known to those of skill in the art.

In certain embodiments, the disclosure provides compositions comprising complexes of stress proteins with different antigenic peptides having one or more mutant MHC-binding epitopes from a cancer cell in combination with an adjuvant, such as at least one immunostimulatory oligonucleotide or a saponin (e.g., QS-21) in a physiologically acceptable carrier.

In certain embodiments, the compositions can comprise hsp70 complexed with one or more antigenic peptides, combined with QS-21. In certain embodiments, the compositions comprise hsp70 or hsc70 complexed with one or more antigenic peptides, combined with at least one immunostimulatory oligonucleotide. In certain embodiments, the compositions comprise hsp70 or hsc70 complexed with one or more antigenic peptides, combined with QS-21 and at least one immunostimulatory oligonucleotide.

5.3. Dosage

The dosage of compositions disclosed herein, and the dosage of any additional treatment modality such as an adjuvant if combination therapy is to be administered, depends to a large extent on the weight and general state of health of the subject being treated as well as the amount of vaccine composition administered, the frequency of treatment and the route of administration. Amounts effective for this use will also depend on the stage and severity of the disease and the judgment of the prescribing physician, but generally range for the initial immunization (that is, for therapeutic administration) from about 1.0 µg to about 1000 µg (1 mg) (including, for example, 10, 20, 25, 30, 40, 50, 60, 70, 80, 90, 100, 150, 200, 240, 250, 300, 350, 400, 450, 500, 550, 600, 650, 700, 750, 800, 850, 900, 950, or 1000 µg) of any one of the compositions disclosed herein for a 70 kg patient, followed by boosting dosages of from about 1.0 µg to about 1000 µg of the composition (including, for example, 10, 20, 25, 30, 40, 50, 60, 70, 80, 90, 100, 150, 200, 250, 300, 350, 400, 450, 500, 550, 600, 650, 700, 750, 800, 850, 900, 950, or 1000 µg) pursuant to a boosting regimen over weeks to months depending upon the patient's response and condition by measuring specific CTL activity in the patient's blood. Regimens for continuing therapy, including site, dose and frequency may be guided by the initial response and clinical judgment. Dosage ranges and regimens for adjuvants are known to those in the art, see, e.g., Vogel and Powell, 1995, A Compendium of Vaccine Adjuvants and Excipients; M. F. Powell, M. J. Newman (eds.), Plenum Press, New York, pages 141-228.

Preferred adjuvants include QS-21, e.g., QS-21 Stimulon®, and CpG oligonucleotides. Exemplary dosage ranges for QS-21 are 1 µg to 200 µg per administration. In other embodiments, dosages for QS-21 can be 10, 25, and 50 µg per administration.

In certain embodiments the administered amount of compositions comprising heat shock proteins (HSPs) complexed to antigenic peptides, depends on the route of administration and the type of HSPs in the compositions. For example, the amount of HSP in the compositions can range, for example, from 5 to 1000 µg (1 mg) per administration.

In certain embodiments, the administered amount of compositions comprising hsc70-, hsp70- and/or gp96-antigenic peptide complexes is, for example, 5, 10, 20, 25, 30, 40, 50, 60, 70, 80, 90, 100, 200, 250, 300, 400, 500, 600, 700, 750, 800, 900, or 1000 micrograms.

In certain embodiments, the administered amounts of compositions comprising hsc70-, gp96- or hsp70-antigenic peptide complexes are in the range of about 10 to 600 µg per administration and about 5 to 100 µg if the composition is administered intradermally.

In another embodiment, compositions comprising hsc70-, hsp70- and/or gp96-antigenic peptide complexes are administered in an amount ranging from about 5 micrograms to about 600 micrograms, or about 5 micrograms to about 60 micrograms for a human patient. In other embodiments, the administered amount of the compositions can be less than 100 micrograms. In other embodiments, the administered amount of the compositions is about 5 micrograms, 25 micrograms, 50 micrograms, or 240 micrograms. Preferably, the compositions comprising complexes of stress proteins and antigenic peptides are purified.

In certain embodiments, the dosage of the compositions comprising hsp-90 antigenic peptide complexes in a human patient is in the range of about 5 to 1000 micrograms. In certain embodiments, the administered amount of the compositions is 5, 10, 20, 25, 50, 60, 70, 80, 90, 100, 200, 250, 300, 400, 500, 600, 700, 750, 800, 900, or 1000 micrograms. In other embodiments, the dosage of the compositions is 100 micrograms. In certain embodiments, the dosage for intradermal administration of the compositions comprising hsp 90 antigenic peptide complexes ranges from about 5 to 50 µg per administration.

In one embodiment of a therapeutic regimen, a dosage substantially equivalent to that seen to be effective in smaller non-human animals (e.g., mice or guinea pigs) is effective for human administration, optionally subject to a correction factor not exceeding a fifty fold increase, based on the relative lymph node sizes in such mammals and in humans. Specifically, interspecies dose-response equivalence for stress proteins (or HSPs) noncovalently bound to or mixed with antigenic molecules for a human dose is estimated as the product of the therapeutic dosage observed in mice and a single scaling ratio, not exceeding a fifty fold increase.

In another embodiment, dosages of the compositions can be much smaller than the dosages estimated by extrapolation. In one embodiment, the amount of compositions comprising hsc70-antigenic peptide complexes, hsp70-antigenic peptide complexes and/or gp96-antigenic peptide complexes is administered that is, for example, in the range of about 2 microgram to about 150 micrograms for a human patient, the human dosage being the same as used in a 25 g mouse. The dosage for compositions comprising hsp-90 peptide complexes in a human patient is in the range of about 10 to 1,000 micrograms. In another embodiment, the dosage of the compositions is about 20 micrograms.

The doses recited above can be given once or repeatedly, such as daily, every other day, weekly, biweekly, or monthly, for a period up to a year or over a year. Doses are preferably given once every 28 days for a period of about 52 weeks or more.

In one embodiment, the compositions are administered to a subject at reasonably the same time as an additional treatment modality or modalities. This method provides that the two administrations are performed within a time frame of less than one minute to about five minutes, or up to about sixty minutes from each other, for example, at the same doctor's visit.

In another embodiment, the compositions and an additional treatment modality or modalities are administered at exactly the same time.

In yet another embodiment the compositions and an additional treatment modality or modalities are administered in a sequence and within a time interval such that the complexes of the invention and the additional treatment modality or modalities can act together to provide an increased benefit than if they were administered alone.

In another embodiment, the compositions and an additional treatment modality or modalities are administered sufficiently close in time so as to provide the desired therapeutic or prophylactic outcome. Each can be administered simultaneously or separately, in any appropriate form and by any suitable route. In one embodiment, the complexes of the invention and the additional treatment modality or modalities are administered by different routes of administration. In an alternate embodiment, each is administered by the same route of administration. The compositions can be administered at the same or different sites, e.g. arm and leg. When administered simultaneously, the compositions and an additional treatment modality or modalities may or may not be administered in admixture or at the same site of administration by the same route of administration.

In various embodiments, the compositions and an additional treatment modality or modalities are administered less than 1 hour apart, at about 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In other embodiments, the compositions and a vaccine composition are administered 2 to 4 days apart, 4 to 6 days apart, 1 week a part, 1 to 2 weeks apart, 2 to 4 weeks apart, one month apart, 1 to 2 months apart, or 2 or more months apart. In preferred embodiments, the compositions and an additional treatment modality or modalities are administered in a time frame where both are still active. One skilled in the art would be able to determine such a time frame by determining the half-life of each administered component.

In certain embodiments, the compositions are administered to the subject weekly for at least four weeks. In certain embodiments, after the four weekly doses, at least 2 (e.g., 2, 3, 4, 5, 6, 7, 8, 9, 10, 11, 12, 13, 14, 15, 16, 17, 18, 19, or 20) further doses of the compositions are administered biweekly to the subject. In certain embodiments, the compositions administered as a booster three months after the final weekly or biweekly dose. The three monthly booster can be administered for the life of the subject (e.g., at least 1, 2, 3, 4, 5, 6, 7, 8, 9, 10, 11, 12, 13, 14, 15, 16, 17, 18, 19, 20, 25, 30, 40, 50, or more years). In certain embodiments, the total number of doses of the compositions administered to the subject is 1, 2, 3, 4, 5, 6, 7, 8, 9, 10, 11, 12, 13, 14, 15, 16, 17, 18, 19, or 20.

In one embodiment, the compositions and an additional treatment modality or modalities are administered within the same patient visit. In certain embodiments, the compositions are administered prior to the administration of an additional treatment modality or modalities. In an alternate specific embodiment, the compositions are administered subsequent to the administration of an additional treatment modality or modalities.

In certain embodiments, the compositions and an additional treatment modality or modalities are cyclically administered to a subject. Cycling therapy involves the administration of the compositions for a period of time, followed by the administration of a modality for a period of time and repeating this sequential administration. Cycling therapy can reduce the development of resistance to one or more of the therapies, avoid or reduce the side effects of one of the therapies, and/or improve the efficacy of the treatment. In such embodiments, the disclosure contemplates the alternating administration of the compositions followed by the administration of a modality 4 to 6 days later, preferable 2 to 4 days, later, more preferably 1 to 2 days later, wherein such a cycle may be repeated as many times as desired. In certain embodiments, the compositions and the modality are alternately administered in a cycle of less than 3 weeks, once every two weeks, once every 10 days or once every week. In certain embodiments, the compositions are administered to a subject within a time frame of one hour to twenty four hours after the administration of a modality. The time frame can be extended further to a few days or more if a slow- or continuous-release type of modality delivery system is used.

5.4. Routes of Administration

The compositions disclosed herein may be administered using any desired route of administration. Many methods may be used to introduce the compositions described above, including but not limited to, oral, intradermal, intramuscular, intraperitoneal, intravenous, subcutaneous, mucosal, intranasal, intra-tumoral, and intra-lymph node routes. Nonmucosal routes of administration include, but are not limited to, intradermal and topical administration. Mucosal routes of administration include, but are not limited to, oral, rectal and nasal administration. Advantages of intradermal administration include use of lower doses and rapid absorption, respectively. Advantages of subcutaneous or intramuscular administration include suitability for some insoluble suspensions and oily suspensions, respectively. Preparations for mucosal administrations are suitable in various formulations as described below.

Solubility and the site of the administration are factors which should be considered when choosing the route of administration of the compositions. The mode of administration can be varied between multiple routes of administration, including those listed above.

If the compositions are water-soluble, then it may be formulated in an appropriate buffer, for example, phosphate buffered saline or other physiologically compatible solutions, preferably sterile. Alternatively, if a composition has poor solubility in aqueous solvents, then it may be formulated with a non-ionic surfactant such as Tween, or polyethylene glycol. Thus, the compositions may be formulated for administration by inhalation or insufflation (either through the mouth or the nose) or oral, buccal, parenteral, or rectal administration.

For oral administration, the composition may be in liquid form, for example, solutions, syrups or suspensions, or may be presented as a drug product for reconstitution with water or other suitable vehicle before use. Such a liquid preparation may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

The compositions for oral administration may be suitably formulated to be released in a controlled and/or timed manner.

For buccal administration, the compositions may take the form of tablets or lozenges formulated in conventional manner.

The preparation may be formulated for parenteral administration by injection, e.g., by bolus injection or continuous infusion. Formulations for injection may be presented in unit dosage form, e.g., in ampoules or in multi-dose containers, with an added preservative. The preparation may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The preparation may also be formulated in a rectal preparation such as a suppository or retention enema, e.g., containing conventional suppository bases such as cocoa butter or other glycerides.

In addition to the formulations described previously, the preparation may also be formulated as a depot preparation. Such long acting formulations may be administered by implantation (for example, subcutaneously or intramuscularly) or by intramuscular injection. Thus, for example, the preparation may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

For administration by inhalation, the compositions are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

5.5. Patient (Subject) Evaluation

Patients treated with the compositions disclosed herein may be tested for an anti-tumor immune response. In this regard, peripheral blood from patients may be obtained and assayed for markers of anti-tumor immunity. Using standard laboratory procedures, leukocytes may be obtained from the peripheral blood and assayed for frequency of different immune cell phenotypes, HLA subtype, and function of anti-tumor immune cells.

The majority of effector immune cells in the anti-tumor response are $CD8^+$ T cells and thus are HLA class I restricted. Using immunotherapeutic strategies in other tumor types, expansion of CD8+ cells that recognize HLA class I restricted antigens is found in a majority of patients. However, other cell types are involved in the anti-tumor immune response, including, for example, CD4+ T cells, and macrophages and dendritic cells, which may act as antigen-presenting cells. Populations of T cells (CD4+, CD8+, and Treg cells), macrophages, and antigen presenting cells may be determined using flow cytometry. HLA typing may be performed using routine methods in the art, such as methods described in Boegel et al. Genome Medicine 2012, 4:102 (seq2HLA), or using a TruSight® HLA sequencing panel (Illumina, Inc.). The HLA subtype of CD8+ T cells may be determined by a complement-dependent microcytotoxicity test.

To determine if there is an increase in anti-tumor T cell response, an enzyme linked immunospot assay may be performed to quantify the IFNγ-producing peripheral blood mononuclear cells (PBMC). This technique provides an assay for antigen recognition and immune cell function. In some embodiments, subjects who respond clinically to the vaccine may have an increase in tumor-specific T cells and/or IFNγ-producing PBMCs. In some embodiments, immune cell frequency is evaluated using flow cytometry. In some embodiments, antigen recognition and immune cell function is evaluated using enzyme linked immunospot assays.

In some embodiments, a panel of assays may be performed to characterize the immune response generated to HSPPC-96 used alone or given in combination with standard of care (e.g., maximal surgical resection, radiotherapy, and concomitant and adjuvant chemotherapy with temozolomide for glioblastoma multiforme). In some embodiments, the panel of assays includes one or more of the following tests:

whole blood cell count, absolute lymphocyte count, monocyte count, percentage of CD4+CD3+ T cells, percentage of CD8+CD3+ T cells, percentage of CD4+CD25+FoxP3+ regulatory T cells and other phenotyping of PBL surface markers, intracellular cytokine staining to detect proinflammatory cytokines at the protein level, qPCR to detect cytokines at the mRNA level and CFSE dilution to assay T cell proliferation.

In evaluating a subject, a number of other tests may be performed to determine the overall health of the subject. For example, blood samples may be collected from subjects and analyzed for hematology, coagulation times and serum biochemistry. Hematology for CBC may include red blood cell count, platelets, hematocrit, hemoglobin, white blood cell (WBC) count, plus WBC differential to be provided with absolute counts for neutrophils, eosinophils, basophils, lymphocytes, and monocytes. Serum biochemistry may include albumin, alkaline phosphatase, aspartate amino transferase, alanine amino transferase, total bilirubin, BUN, glucose, creatinine, potassium and sodium. Protime (PT) and partial thromboplastin time (PTT) may also be tested. One or more of the following tests may also be conducted: anti-thyroid (anti-microsomal or thyroglobulin) antibody tests, assessment for anti-nuclear antibody, and rheumatoid factor. Urinalysis may be performed to evaluated protein, RBC, and WBC levels in urine. Also, a blood draw to determine histocompatibility leukocyte antigen (HLA) status may be performed.

In some embodiments, radiologic tumor evaluations are performed one or more times throughout a treatment to evaluate tumor size and status. For example, tumor evaluation scans may be performed within 30 days prior to surgery, within 48 hours after surgery (e.g., to evaluate percentage resection), 1 week (maximum 14 days) prior to the first vaccination (e.g., as a baseline evaluation), and approximately every 8 weeks thereafter for a particular duration. MRI or CT imaging may be used. Typically, the same imaging modality used for the baseline assessment is used for each tumor evaluation visit.

6. Kits

Kits are also provided for carrying out the prophylactic and therapeutic methods disclosed herein. The kits may optionally be accompanied by instructions on how to use the various components of the kits.

In a specific embodiment, a kit comprises a first container containing the composition comprising complexes of stress proteins bound to different antigenic peptides, where each antigenic peptide comprises one or more mutant MHC-binding epitopes from a cancer cell; and a second container containing an adjuvant or adjuvants that, when administered before, concurrently with, or after the administration of the peptides in the first container, is effective to induce an immune response against the antigenic peptides. In another embodiment, a kit comprises a first container containing the composition comprising complexes of stress proteins bound to different antigenic peptides, where each antigenic peptide comprises one or more mutant MHC-binding epitopes from a cancer cell; a second container containing an adjuvant or adjuvants; and a third container containing a second treatment modality. In yet another embodiment, the kit comprises a container containing the composition comprising complexes of stress proteins bound to different antigenic peptides, where each antigenic peptide comprises one or more mutant MHC-binding epitopes from a cancer cell and adjuvants in one container, and a second container containing a second treatment modality; or an additional adjuvant, such as a saponin, including but not limited to QS-21, e.g., QS-21 Stimulon® (Antigenics LLC). Additional containers may be present for additional treatment modalities that can be used in combination. In certain embodiments, the compositions in the container are in the form of complexes of heat shock proteins bound to different antigenic peptides where each antigenic peptide comprises one or more mutant MHC-binding epitopes from a cancer cell.

In certain embodiments, the compositions and adjuvants in the container are present in pre-determined amounts effective to treat cancers or prevent their recurrence. If desired, the compositions can be presented in a pack or dispenser device which may contain one or more unit dosage forms of the compositions. The pack may, for example, comprise metal or plastic foil, such as a blister pack. The pack or dispenser device may be accompanied by instructions for administration.

EXAMPLES

Example 1

Identification of Somatic Mutations in Banked Human Multiple Myeloma (MM) Plasma Cell Samples Based on previously annotated RNA and whole exome-sequencing (WES) of over fifty MM samples stored in Mount Sinai Medical Center's Hematological Malignancies Tissue Bank (Miami Beach, Fl.), we have generated lists of non-synonymous mutations for 19 samples. The mutations are computationally characterized, and up to 48 peptides for each of 10 samples are synthesized for testing in immunological assays.

Example 2

Somatic Mutations Identified in Murine MM Tumor Cell Line

We profiled the exome of the immediately available MOPC315, the parental line to MOPC315.BM. Similar to our studies of B16F10 (962 non-synonymous mutations) and CT26 (1,688) and published studies of MC-38 (4,285) and TRAMP-C1 (949), we identified 1,764 non-synonymous somatic point mutations (SNVs) relative to the BALB/c genome. These SNVs occur in 1,539 genes (*Cancer research*. Mar. 1 2012; 72(5):1081-1091; *Nature*. Nov. 27 2014; 515(7528):572-576; *BMC genomics*. 2014; 15:190, each of which is incorporated herein by reference in its entirety). We calculated the potential immunogenicity of MOPC315 mutation-containing peptides. We then applied three filters to identify neo-epitopes that contain features reported to be predictive of immunogenicity or tumor control. These filters were (i) point mutation in the neo-epitope located at position (P3-P7) which is accessible to the T cell receptor as described by Mellman and colleagues (*Nature*. Nov. 27, 2014; 515(7528):572-576); (ii) maximum difference in affinity between predicted neo-epitopes and their normal counterparts as described by Srivastava and colleagues (*The journal of experimental medicine*. Oct. 20 2014; 211(11):2231-2248, incorporated herein by reference in its entirety); and (iii) affinity<150 nM for the H-2Kd, H-2Dd or H-2Ld HLA alleles using the NetMHCpan algorithm.

Example 3

PBMCs of MM Patients Contain T Cells that Recognize Predicted Neo-Epitopes

PBMCs of un-vaccinated MM patients are demonstrated to contain T cells that recognize neo-epitopes identified by next generation sequencing. This demonstration establishes the extent of the mutated tumor antigen recognition at "baseline," setting the stage for Phase 1 clinical testing of (a) vaccine-driven increase in frequency of T cells specific for the various predicted neo-epitopes compared to pre-vaccination baselines and (b) vaccine-driven induction of responses to antigens not recognized at baseline. Peptides containing putative mutated epitopes can be pooled and used to stimulate CD4 and CD8 T cells independently, following processing into naturally selected epitopes by CD4/CD8-depleted PBMC, without the need to predefine alleles of HLA restriction (J. Immunol. Feb. 1 2003; 170(3):1191-1196, incorporated herein by reference in its entirety). Both professional and non-professional antigen presenting cells require uptake and processing of long peptides which ensure that only naturally processed epitopes are presented to T cells, where the mutation may be important for either HLA-binding or T cell recognition. Long peptides are used in this example given based on observations that 1) long peptides facilitate antibody recognition of linear epitopes (Methods Mol. Biol. 2009; 520:11-19, incorporated herein by reference in its entirety); 2) long peptides need to be naturally processed into HLA class I restricted epitopes, often in a proteasome-dependent manner, to be recognized by CD8 T cells (J. Immunol. Feb. 1 2003; 170(3):1191-1196, incorporated herein by reference in its entirety); and 3) long peptides are optimal targets of CD4 T cells (Proc. Natl. Acad. Sci. U.S.A Jul. 9 2003; 100(15):8862-8867, incorporated herein by reference in its entirety).

Basis for Synthesis of Peptides Tested for Recognition in Immunological Assays.

To address both the sub-clonal intra-patient mutation heterogeneity characteristic of MM and the uncertainty in mutation selection, the MM ASV individualized vaccine comprises up to 48 patient- and tumor-specific neo-antigens (Cancer cell. Jan. 13 2014; 25(1):91-101, incorporated herein by reference in its entirety). For most of the patients this comprises all expressed non-synonymous mutations found in their tumor. Analysis of the mutation lists generated from the MM plasma cell samples in Mount Sinai's Hematological Malignancies Tissue Bank is used to identify mutant peptides for synthesis for each sample, up to a maximum of 48. Each peptide consists of a 31mer with the point mutation centered. Long peptides allow for processing by antigen presenting cells (APCs) to generate shorter fragments that may represent either HLA class I or II binding epitopes for up to six alleles that may be expressed in each subject. A pool of long synthetic peptides, each peptide containing a single point mutation, is synthesized along with each peptide's non-mutated counterpart and tested in T cell function assays using bulk autologous PBMCs as a source of T cells and antigen presenting cells. Where possible, the minimal neo-epitope recognized by T cells is defined.

Methods i. Pre-Sensitization

The Hematological Malignancies Tissue Bank holds two green-top tubes, containing ~2-4×10$^7$ PBMCs total, from each MM patient for whom annotated RNA and WES data is available. A single in vitro pre-sensitization is first performed, designed to expand immune responses to neo-epitopes primed in vivo by recognition of malignant cells. Cells are thawed and PBMCs isolated, aliquoted and either used in the pre-sensitization phase or frozen down for later use. For pre-sensitization, 1×10$^7$ are cultured in 24-well plates with pools of 31mer peptides. For patients for whom NGS data reveals ≤48 mutations, long peptides are generated for all mutations and used for sensitization. In cases where >48 mutations are identified, a maximum of 48 peptides are synthesized for sensitization based on random selection of 48 mutations. The size and composition of the peptide pools used for sensitization is determined based on the biochemical characteristics of the various peptides such that solubility of peptides is maintained in the culture plate. The pre-sensitization is carried out for 10-20 days in presence of IL-2 and IL-7. As a positive control, a subset of PBMC is pre-sensitized with recall viral antigens such as CEF peptide pools. Preexisting CD8 T cell responses to peptides are expected to peak around day 10 while CD4 T cells peak around day 20 of culture, and repetitive sampling and functional testing ensures optimal detection.

ii. ELISPOT and Intracellular Cytokine Staining (ICS) Assays

To identify which peptide pools are recognized by autologous T cells, an IFN-γ Enzyme-Linked ImmunoSpot (ELISPOT) assay is then performed with bulk lymphocytes harvested from the pre-sensitization cultures. Autologous EBV-transformed B cells (B-EBV) and/or PHA-expanded T cells (T-APC) are used as antigen presenting cells and pulsed overnight with smaller subpools of the same peptides used for presensitization (alternatively, if target cells are limiting, cell cultures will be divided and sensitized with subpools of peptides). Unstimulated cells serve as a negative control. CEF peptide pool is included as positive control antigens and PHA/PMA-ionomycin is used to assess overall viability and survival of cells. Spots representing IFN-γ secreting lymphocytes is quantified with CTL Immunospot analyzer and software (Shaker Heights, Ohio). To be considered significant, antigen-specific IFN-γ responses must have a spot count of more than 50 out of 50,000 cells and at least three times more than the number of spots obtained with control non-pulsed target cells.

To confirm any observed reactivity and to identify the phenotype (CD4$^+$ or CD8$^+$) of T cells responding to subpools of long peptides in the ELISPOT assay, ICS is performed with remaining cells from the presensitization culture using mAbs for CD8, CD4 and IFN-γ. A positive response will be defined as >0.5% and >3-fold the percentage obtained with control non-pulsed target cells. In some cases, frequencies of antigen-specific T cells may be sufficiently high to allow cryopreservation of cell lines displaying specificity for further analyses.

iii. Specificity of Responding Lymphocytes

Reactivity to one or more pools of neo-epitope containing peptides is identified in the preliminary screen, and those pools are deconvoluted by testing the peptides individually for recognition. To confirm that T cell responses are neo-epitope specific, each mutant peptide are tested alongside its non-mutant (i.e., wild type) counterpart peptide. A presensitization culture followed by ELISPOT assay and ICS, as described above, is used for these experiments.

iv. Identification of Minimal CD8$^+$ T Cell Neo-Epitopes

Depending on the number of 31mer peptides that "pass" the screens described above and the number of PBMCs recovered from the cell bank, a series of assays is performed to identify the minimal T cell neo-epitopes that are recognized. Because HLA class I binding peptides are of a finite size (typically 9, 10 or 11mers) while HLA class II binding peptides may vary considerably in length, minimal epitope identification is focused on class I binding peptides only and thus only on those 31mers that are shown to be recognized by CD8$^+$ T cells in the above described ICS assay. For each positive 31mer, all possible 9, 10 and 11mers are synthesized wherein the point mutation is placed at each position of the putative epitope. The non-mutated counterparts to these short peptides are tested as a control. This requires synthesis of 60 peptides (nine 9mers, ten 10mers and eleven 11mers for each putative neo-epitope and its non-mutated counterpart). The cellular expansion phase is accomplished using the cognate mutant 31mer peptide as stimulating antigen. ELISPOT assays are then performed initially with pools of the short mutant peptides. As described above, the positive pools are then deconvoluted and at this stage may be tested individually for recognition using the counterpart non-mutated peptides as a control. Depending on frequencies observed, it is possible that repeated stimulation in vitro is necessary prior to testing the short peptides on an individual basis for recognition by T cells in the ELISPOT assay. Alternatively, enrichment of antigen-specific T cells is attempted with assays measuring IFN-γ and/or other desirable cytokines that allow sorting of peptide reactive cells and non-specific expansion of monospecific lines with allogeneic feeder and PHA.

Example 4

The Biological Activity of AutoSynVax™ is Tested in One or More Murine MM Models Such as the 5TMM Series or MOPC The biological activity of AutoSynVax™ (ASV™) composition, which comprises HSP complexed with peptides containing cancer neo-epitopes, is tested in the MOPC315.BM murine MM model. MOPC315.BM is a murine malignant plasma cell line syngeneic to BALB/c mice that resembles several features of the human disease. It engrafts bone marrow and causes lytic bone disease when introduced by intravenous injection, and secretes and IgA lambda M-protein that can be measured in serum by ELISA. This model has been used to investigate idiotype vaccine strategies, and a neo-epitope in the hypervariable region of the lambda light chain, peptide 91-101, can elicit robust CD4+ T cell immunity in BALB/c mice. As described above, the parental cell line, MOPC315, was subject to whole exome sequencing and a preliminary list of mutations was identified. In this example, MOPC315.BM is subject to WES to identify and RNAseq to confirm expression of mutations in transcripts. Assuming the number of mutations identified is similar to that seen in the parental line, it is not possible to synthesize all corresponding long peptides for use in the MOPC315.BM ASV surrogate. This is an acknowledged limitation of the model. Instead, a selection of filters is applied to narrow the list of candidate long peptides to a maximum of 48. Each peptide consists of a 31mer with the point mutation centered. The 48 long peptides are complexed to Hsc70 and mixed with QS-21 Stimulon® to generate the surrogate ASV vaccine. Experiments are then conducted to identify optimal dosing for ASV in the BALB/c background and assess immunologic efficacy both alone and in combination with lenalidomide. Experiments sequenced for dose finding, component activity, and combination assessment. The vaccination schedule is based on similar synthetic long peptide based vaccine preparations tested in animal model (Vaccine. Nov. 3 2011; 29(47):8530-8541). Immunogenicity studies are followed by prophylactic tumor protection studies and by therapy studies in combination with lenalidomide.

Methods i. Recombinant Hsc70 and Selection of Long Peptides for Inclusion in MOPC315.BM ASV Surrogate Vaccine Because of the large number of mutations expected to be expressed in MOPC315.BM, an agnostic approach to selection of peptides for inclusion in the surrogate vaccine is not possible. Instead, filters such as the three describe above for the parental line, MOPC315, are applied to enable selection of three groups of 16 peptides each (to be combined to reach a maximum 48 total), representative of all three BALB/c alleles.

ii. Immunogenicity Studies

These experiments identify optimal dosing of the MOPC315.BM surrogate of ASV in the BALB/c background and assess immunologic efficacy both alone and in combination with lenalidomide. Experiments are sequenced for dose finding, vaccine component activity, and combination assessment. The vaccination schedule is based on similar vaccine preparations tested in animal models (Vaccine. Nov. 3 2011; 29(47):8530-8541, incorporated herein by reference in its entirety).

(a) MOPC315.BM ("MOPC") ASV Dose Finding.

Groups of four female BALB/c mice receive escalating doses of ASV by intradermal injection on days 1 and 8. One group receives ASV formulated with peptide containing residues 91-101 from the MOPC lambda light chain idiotype λ2 (Id ASV) as a positive control (The EMBO journal. July 1989; 8(7):1947-1952, incorporated herein by reference in its entirety), and unvaccinated mice serve as negative controls. ASV formulations are 10, 30, or 100 μg of Hsc70 complexed to 48 synthetic 31mer peptides (somatic mutation centered, flanked by naturally occurring residues) at a 1:1 molar ratio of Hsc70 to total peptide mixture. The complex is mixed with 10 μg QS-21 Stimulon® prior to injection in 100 μl total volume sterile saline. 100 μl of whole blood is obtained from each subject by retro-orbital bleed prior to vaccination and at the end of each experiment, and serum is cryopreserved for potential future analysis for humoral immune responses. Subjects are euthanized on day 15, and total splenocytes are recovered by mechanical disruption and ACK buffer lysis of erythrocytes. T cell immunity are assessed by in vitro restimulation and ELISPOT assay as described above. This will establish the in vivo immunogenicity and optimum dose for subsequent experiments.

(b) Vaccine Component Assessment.

The relative contribution of each vaccine component are assessed by vaccinating groups of four test subjects with each component at the optimized dose established in part (a) above.

The vaccination schedule is as described in part (a) above. Groups include MOPC ASV (which includes QS-21 Stimulon®), MOPC ASV without QS-21 Stimulon®, MOPC peptides with QS-21 Stimulon® (but without Hsc70), MOPC peptides alone, MOPC Id ASV or untreated control. Antigen-specific T cell responses are assessed as described.

(c) In Vitro Analysis of Lenalidomide Activity Against MOPC315.BM.

Direct activity of lenalidomide against MOPC315.BM cells is determined in vitro by 8-point dose curve viability assay. Triplicate wells of MOPC315.BM in 96-well plates are co-incubated with lenalidomide at increasing doses, and cell viability is quantified at 40 hrs by Alamar Blue (Life Technologies; Grand Island, N.Y.) fluorescence. Bortezomib at 10 μm serves as a positive control for cytotoxicity. 8-point dose curves are generated by automated aliquots of 10 mM lenalidomide stock solution in DMSO with an HP D3000 dispenser (Hewlett-Packard, Inc.; Palo Alto, Calif.). Lenalidomide and controls are randomly distributed in the plates to eliminate edge effects, and the Alamar Blue fluorescence readout at 40 hrs is deconvoluted prior to analysis. These data provide estimated LD50 concentrations for further analysis. The LD50 are compared with physiologic dose levels from previous vaccination models to identify a target dose that is below the estimated single agent activity level for MOPC315.BM.30-32.

(d) Lenalidomide Activity in Promoting ASV Immune Priming In Vivo.

The activity of lenalidomide in promoting immune priming by MOPC ASV is assessed in the animal model. Groups of test subjects are vaccinated with MOPC ASV or Id ASV administered alone or with lenalidomide at the optimized dose (identified in part (c) above) by intraperitoneal (IP) injection (10 mM DMSO stock diluted in sterile saline). Untreated mice serve as negative control. Immunologic efficacy is assessed as previously described.

(e) Functional Characterization of MOPC ASV-Induced Ag-Specific Immunity.

In order to perform detailed characterization of the cellular immune response to vaccination, cohorts of 10 mice are vaccinated with either MOPC ASV or Id ASV with co-administration of lenalidomide; unvaccinated mice serve as negative controls. Total splenocytes are pooled and CD4 and CD8 T cells are separated by antibody-conjugated magnetic bead sorting and restimulated with total peptide pools. Expanded T cell pools are divided for analysis. The frequency of T cell response to specific neo-epitopes is identified by matrix ELISPOT assays as described above. These populations are functionally characterized by re-stimulation and ICS/flow cytometry for IFN-γ, TNFα, perforin, granzyme, IL-4, and IL-5 expression. Specificity for the mutated neo-epitope repertoire is confirmed by ELISPOT assay using mutated or wild type peptides for stimulation. Epitope-specific T cells is isolated and subcloned by IFN-γ capture.

Cytotoxic activity against MOPC is assessed by LDH (lactate dehydrogenase) release assay; autologous, peptide-pulsed target cells and buffer lysis are positive controls and unpulsed cells are negative controls. Specificity for the MOPC neo-epitope repertoire is assessed by cytotoxicity assays against MOPC or other BALB/c mineral oil-elicited plasma cell lines such as HOPC 1F/12 and RPC5.4 (ATCC; Manassas, Va.). The presence of potential cross-reactive mutations in these cell lines is assessed by WES and analysis as described for MOPC.

iii. Prophylactic Tumor Protection Studies:

(a) Tumor Challenge Optimization.

The number of MOPC315.BM cells is optimized for in vivo modeling by introducing escalating numbers of cells by tail vein injection. Cells are washed in RPMI medium three times and resuspended to deliver the target cell load in 100 μl total volume. 100 μl of whole blood is acquired by retro-orbital bleeding at baseline and seven-day intervals and serum are isolated for IgA ELISA and immunofixation to follow M-spike as a marker of disease progression. Test animals are observed for hind limb paralysis, an indicator of pre-morbid disease burden in the spinal column, and are euthanized at this event. Femurs and spinal columns are recovered at necropsy for decalcification, paraffin embedding, and sectioning for morphology and immunohistochemical (IHC) evaluation of CD138+ plasma cells, CD3+ lymphocytes in marrow. Survival curves are plotted to identify the minimum tumor challenge dose that will result in 100% mortality.

(b) Lenalidomide In Vivo Dose Optimization.

Lenalidomide dosing is optimized to minimize single agent activity against MOPC and maximize co-stimulatory activity with MOPC ASV. Cohorts of 10 mice receive MOPC tumor challenge at the optimized dose. After three days to permit tumor engraftment, test subjects receive weekly intraperitoneal (IP) administration of lenalidomide (10 mM DMSO stock diluted in sterile saline) at three different dose levels centered around the dose identified in (ii)(d) above. Tumor challenged mice without lenalidomide serve as negative controls. Test animals are monitored for IgA level and hind limb paralysis, and tumor burden is confirmed by pathology and IHC of necropsy specimens. Kaplan-Meyer survival curves are generated to identify the maximum lenalidomide dose level that does not significantly prolong survival over background.

(c) Prophylactic Model of MOPC ASV and Lenalidomide Anti-Tumor Immunity.

Cohorts of 12 female BALB/c mice are vaccinated with MOPC ASV+lenalidomide or controls (MOPC Id ASV positive control, lenalidomide alone at optimized dose and untreated mice negative controls) on day 1 and 8, then on day 15 they receive the optimized challenge of MOPC315.BM cells suspended 100 μl sterile saline in the tail vein injection. Untreated, tumor-bearing animals serve as negative controls. Tumor growth is followed by weekly bleeding and IgA ELISA and by physical examination. Animals are euthanized when hind limb paralysis is detected, and when the last negative control subject reaches the pre-morbid milestone all remaining subjects are euthanized. Kaplan-Meyer survival curves are generated for test and untreated control animals. At the termination of each experiment, total splenocytes are recovered for assessment of Ag-specific immunity, epitope specificity, cytotoxicity, and Th phenotype as described above. Necropsy specimens are examined by IHC for tumor burden and T cell infiltration into the bone marrow.

(d) Therapeutic Model of MOPC ASV and Lenalidomide.

Cohorts of test subject receive tumor challenge, and after three days they receive weekly vaccinations with MOPC ASV+lenalidomide or controls as in (iii)(c) above. Tumor growth is followed by IgA ELISA and physical exam, and post-mortem evaluation is performed on splenocytes and bone marrow as described.

Example 5

Production of Phase 1 Appropriate Material for a First in Human Clinical Trial of ASV in Patients with Relapsed MM Patients eligible are those with relapsed MM, and eligible for transplantation following up to four prior treatments. Patients are treated with vaccine in combination with standard of care ImiDs and/or low dose oral Cytoxan. The endpoints include safety, immune response, and signals of additive efficacy of vaccine to the anti-MM therapy. With respect to immune monitoring, a longitudinal biomarker study is conducted to identify immunological responses to the vaccine and track tumor evolution. Blood and potentially bone marrow samples are taken before and after vaccination and assayed for, e.g., neo-epitope-specific T cell phenotype, TCR repertoire and changes in level of expression of mutant genes. Plasma cell exosomes may also be a convenient and useful source for some of these analyses. The studies in support of immune monitoring and tracking of tumor evolution are performed after MM patients are enrolled in the trial and treated with the full course of vaccination.

Methods i. Clinical Trial Design

Safety, feasibility and immunologic response in patients with relapsed multiple myeloma (n=~30) is assessed in a phase I study. The purpose of the study is to evaluate the safety, pharmacokinetics, clinical and immunological response to vaccine. Essential inclusion criteria are: 1) relapsed MM with after at least one, but not more than four, prior treatment regimens, 2) measurable disease (serum M-protein 2 0.5 gm/dL OR involved serum free light chain (sFLC) 2100 mg/L and abnormal sFLC ratio (<0.26 or >1.65) OR urine M-protein 2 200 mg/24 hours), 3) adequate immunologic reserve as demonstrated by peripheral blood absolute lymphocyte count 21000/µl, 4) Hgb 28.0 gm/dL and plt 250,000/µl, and 5) ECOG PS 22. Exclusion criteria are: 1) prior therapy with vaccine immunotherapy for multiple myeloma, 2) history of autoimmune disease, 3) prior allogeneic hematopoietic stem cell transplantation, 4) known HIV or active Hep B or C, and 5) concurrent second malignancy within 5 years except for non-melanoma skin cancer, carcinoma in situ (including superficial bladder cancer), cervical intraepithelial neoplasia, or organ-confined prostate cancer with no evidence of progressive disease.

Patients undergo bone marrow biopsy at screening with tissue acquisition for NGS that is the basis for vaccine production, projected to take eight weeks from delivery of tissue. Enrolled patients receive interim therapy with lenalidomide 25 mg orally daily days 1-21, cyclophosphamide 50 mg orally twice daily and prednisone 20 mg orally daily days 1-7 of each 28-day cycle (cycles 1 and 2). Cyclophosphamide is an alkylating agent that is commonly used in combination with lenalidomide and dexamethasone for multiple myeloma (American journal of hematology. August 2011; 86(8):640-645; British journal of haematology. May 2007; 137(3):268-269). In addition to its direct cytotoxic effects, low dose cyclophosphamide has been shown to decrease the frequency of Tregs and promote a favorable environment for immune priming through dendritic cell maturation and Th1/Th17 T cell phenotypes in animal models and human studies (Cancer immunology, Immunotherapy: CII. May 2013; 62(5):897-908; Blood. Jun. 3 2010; 115(22):4384-4392; Journal of Immunology. Mar. 1 2006; 176(5):2722-2729; Cancer research. Feb. 1 2011; 71(3):661-665; each of which is incorporated herein by reference in its entirety). Early phase clinical trials of metronomic or low dose cyclophosphamide with therapeutic tumor vaccines demonstrated associations with superior immunologic, and in some cases, clinical efficacy (Cancer immunology, immunotherapy: CII. May 2012; 61(5):629-641; Cancer immunology, immunotherapy: *CII*. January 2013; 62(1):171-182; Nature medicine. August 2012; 18(8): 1254-1261, each of which is incorporated herein by reference in its entirety). Therefore, the combination of lenalidomide, low-dose oral cyclophosphamide, and prednisone is a rational choice for interim therapy prior to vaccination with ASV. The triplet combination provides additive effects even in patients who have previously received lenalidomide and dexamethasone. Prednisone is administered only in the first week of each 28-day cycle to ensure that patients entering the vaccine portion of the trial will not have exposure to glucocorticoids for at least three weeks, mitigating the immunosuppressive effects of these agents.

Patients receive ASV by intradermal injection on days 1, 8, 15, and 22 and lenalidomide 25 mg orally daily days 1-21 of 28-day cycle 3, followed by monthly vaccine dosing during each subsequent cycle with concurrent lenalidomide 25 mg orally [P0] on days 1 to 21 of each 28-day cycle (C4 through C12). This constitutes 15 total vaccine administrations over 1 year of treatment. Patients continue to receive low dose cyclophosphamide prior to each vaccination. Once the vaccine portion of the protocol is competed (C12), subjects continue lenalidomide 25 mg orally daily days 1-21 of each 28-day cycle through C12. Protocol-specified dose withholding or reduction for attributable toxicities is allowed for lenalidomide. Clinically-indicated concurrent medications, including thromboprophylaxis, bisphosphonates, and hematopoietic growth factors are allowable. Subjects undergo complete re-staging and immunologic assessment after C12 (end-of-study). Follow up visits continue every 3 months for 24 months to assess PFS.

Immunogenicity, pharmacokinetics (PK), and pharmacodynamics (PD) are evaluated. Safety evaluation includes the frequency, severity, and relationship of adverse events (AEs) and serious AEs with the drug combinations are assessed for up to 60 days after the last dose of study drug. Immunologic assessments will be completed: (1) pre-vaccine, (2) following 4 weekly doses; (3) bi-monthly thereafter or the final study visit. Objective responses (ORs, which include stringent complete response, complete response, very good partial response (VGPR), and PR), disease progression, and relapse are evaluated as a secondary objective and assessed at the end of each cycle or at the study termination visit. Responses are assessed in accordance with the International Myeloma Working Group (IMWG) criteria.

Example 6

MM Neo-Epitopes Derived from a Database

Working with MedGenome (Cambridge, Mass.), we have queried their manually curated database (OncoMD) of somatic mutations in MM identified from published sources and unpublished TCGA and ICGC studies. OncoMD has extensive computational workflows to rapidly process raw NGS fastq files to identify somatic mutations and an annotation engine that combines diverse genomics and bioinformatics data to identify tumor mutation profiles and expression signatures. A summary of the 4505 unique curated mutation data specific to MM is provided in Table 2. Importantly, the database also reports mutations in genes associated with malignant progression in MM (e.g., MYC, KRAS, NRAS, TP53, and KDM6A) which speaks to the fidelity of the curation process in this indication. Most mutations in the curated database occur only once among the 413 samples. This is indicative of the large array of passenger mutations which arise randomly in the genome, and the random nature of the mutations explains why resultant neo-epitopes are largely individually tumor-specific.

TABLE 2

Summary of multiple myeloma mutations present in OncoMD

| Number of studies[1] | Total number of samples[2] | Total number of unique mutations[3] | Median number (range) of genes with non-synonymous somatic mutations[4] | Frequently mutated genes[5] |
|---|---|---|---|---|
| 71 | 413 | 4505 | 38.5 (1-463) | KRAS, NRAS, BRAF FAM46C |

Figure 3:
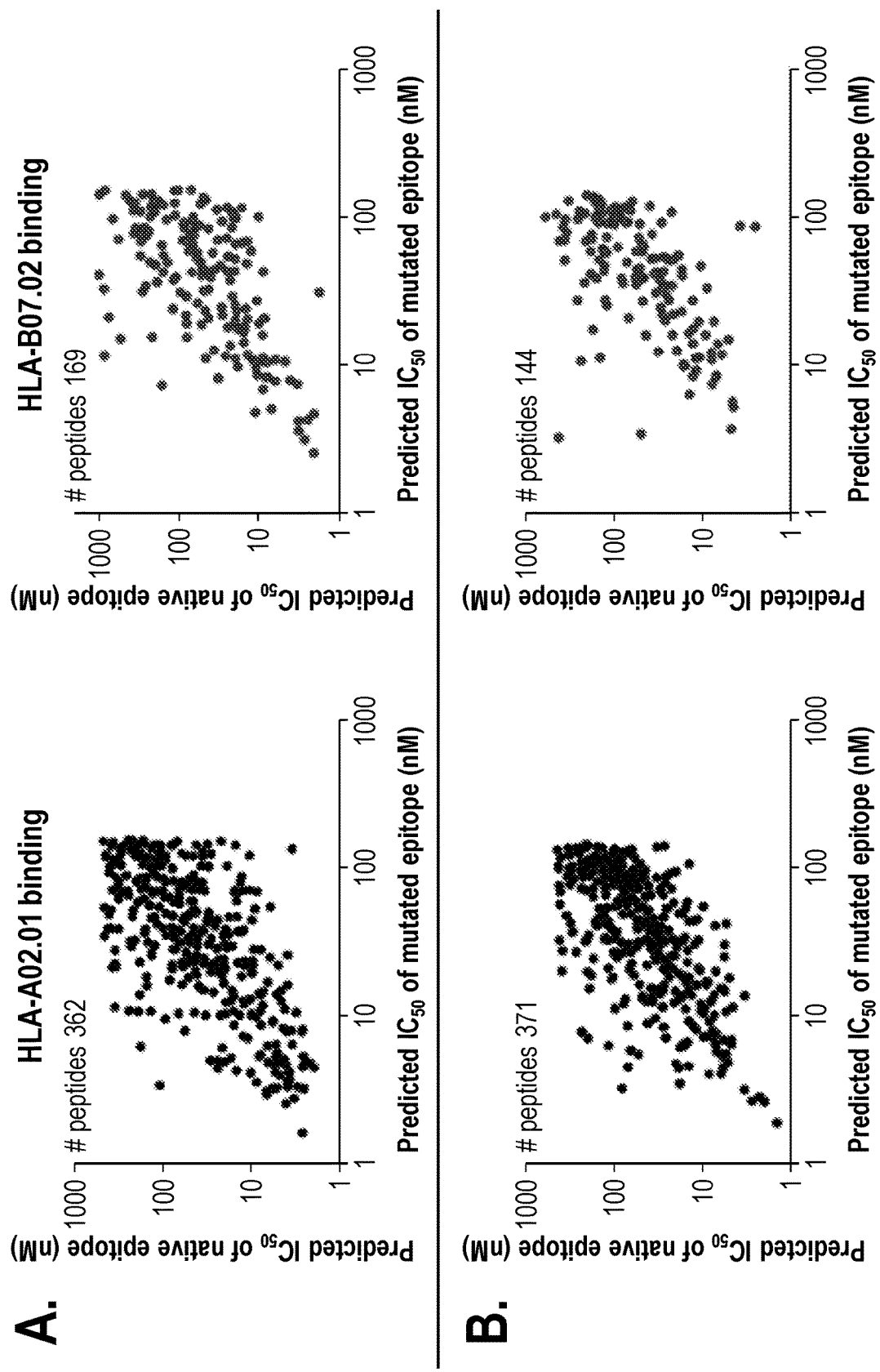
FIG. 3 is a set of scatter plots of neo-epitope 9mer (A) and 10mer (B) peptides and their native counterparts with predicted HLA-A*02:01 and HLA-B*07:02 binding affinity of ≤150 nM.

[1]Six studies reported whole exome and whole genome sequencing and 65 studies reported single or few gene sequencing
[2]Samples that were sequenced.
[3]Unique somatic mutations in genes from all studies (3888 from NGS and 617 from other studies)
[4]Calculated from data reported in six NGS studies
[5]Frequently mutated genes defined as genes mutated in ≥8% samples From the 4505 unique mutations in MM, neo-epitopes and affinities for 12 HLA alleles were predicted using NetMHCpan (FIG. 1). Neo-epitope size was limited to 9 and 10mers. Generally, peptides with $IC_{50}$<150 nM are considered strong to intermediate binders while <500 nM are weak binders. A representative output shows 362 9mers with $IC_{50}$<150 nM and 192 9mers with $IC_{50}$<50 nM were predicted for HLA-A*02:01. Table 3 lists the actual predicted neo-epitopes with $IC_{50}$<50 nM. Scatter plots were generated comparing the affinities of the predicted 9mer and 10mer neo-epitopes to their non-mutated counterparts in the case of HLA-A*02:01 and HLA-B*07:02 for all peptides with $IC_{50}$<150 nM (FIG. 3). In the case of the MM samples curated in OncoMD, similarities in predicted affinities between neo-epitope/normal counterpart pairs are also observed (Table 3 and FIG. 3). In Table 3, peptide sequences are shown in lower case letters, except for the mutated amino acid in the mutant peptide sequence (second column) and the amino acid normally found in the native peptide sequence at the mutated position (sixth column), which are shown in uppercase letters in parentheses.

TABLE 3

| | | Neo-epitopes predicted to bind HLA-A*02:01 | | | | | | | |
|---|---|---|---|---|---|---|---|---|---|
| SEQ ID NO | Mutant peptide sequence | Binding affinity (nM) NetMHC pan | Rank (%) NetMHC pan | SEQ ID NO | Native peptide sequence | Binding affinity (nM) NetMHC pan | Rank(%) NetMHC pan | Gene source | Variant |
| 1. | all(D)ysvpv | 1.66 | 0.01 | 193. | all(Y)ysvpv | 2.80 | 0.05 | MTERFD3 | p.Y293D |
| 2 | flaevp(H)rl | 2.61 | 0.03 | 194. | flaevp(N)rl | 4.26 | 0.12 | PEAK1 | p.N1400H |
| 3. | (M)llskyvpv | 2.82 | 0.05 | 195. | (K)llskyvpv | 3.48 | 0.08 | C9orf125 | p.K156M |
| 4. | ml(L)stsvpv | 2.99 | 0.05 | 196. | ml(H)stsvpv | 7.06 | 0.25 | PTPRZ1 | p.H1237L |
| 5. | rlgeh(I)iev | 3.14 | 0.08 | 197. | rlgeh(N)iev | 7.08 | 0.25 | PRSS1 | p.N77I |
| 6. | llfeflf(L)i | 3.28 | 0.08 | 198. | llfeflf(F)i | 2.70 | 0.05 | TMEM39A | p.F80L |
| 7. | all(D)isffa | 3.30 | 0.08 | 199. | all(G)isffa | 6.07 | 0.20 | KCNQ4 | p.G307D |
| 8. | nlwqlff(Y)v | 3.32 | 0.08 | 200. | nlwqlff(H)v | 5.44 | 0.17 | SEC22A | p.H282Y |
| 9. | ymcs(V)lfnl | 3.36 | 0.08 | 201. | ymcs(F)lfnl | 3.15 | 0.08 | EZH2 | p.F670V |
| 10. | r(M)adplwal | 3.44 | 0.08 | 202. | r(T)adplwal | 112.90 | 3.00 | NEURL | p.T196M |
| 11. | ll(F)dcmwet | 3.62 | 0.08 | 203. | ll(S)dcmwet | 9.19 | 0.40 | HERC1 | p.S1989F |
| 12. | milgsl(I)yv | 3.72 | 0.08 | 204. | milgsl(L)yv | 4.14 | 0.10 | TAS2R1 | p.L135I |
| 13. | vladafy(S)i | 3.75 | 0.10 | 205. | vladafy(G)i | 3.89 | 0.10 | OR13A1 | p.G225S |
| 14. | ylv(A)gvttv | 4.04 | 0.10 | 206. | ylv(T)gvttv | 5.07 | 0.15 | UQCRFS1 | p.T118A |
| 15. | slms(M)wvtv | 4.18 | 0.10 | 207. | slms(V)wvtv | 3.95 | 0.10 | TMEM8B | p.V306M |
| 16. | lmikd(L)iev | 4.19 | 0.10 | 208. | lmikd(Q)iev | 10.66 | 0.50 | DYNC2H1 | p.Q1032L |
| 17. | yllr(H)sesv | 4.23 | 0.12 | 209. | yllr(D)sesv | 5.68 | 0.17 | SH2D1A | p.D33H |
| 18. | fm(N)sfvnvv | 4.26 | 0.12 | 210. | fm(D)sfvnvv | 3.92 | 0.10 | OR8H3 | p.D155N |
| 19. | flmeadlg(M) | 4.55 | 0.12 | 211. | flmeadlg(V) | 2.07 | 0.01 | RASSF4 | p.V264M |
| 20. | mln(P)liysl | 4.72 | 0.12 | 212. | mln(S)liysl | 4.35 | 0.12 | OR5F1 | p.P287S |
| 21. | yma(G)lflgi | 4.74 | 0.15 | 213. | yma(S)lflgi | 4.26 | 0.12 | SCN7A | p.S387G |
| 22. | fvwfsva(G)v | 4.82 | 0.15 | 214. | fvwfsva(A)v | 5.94 | 0.20 | ARHGAP26 | p.A712G |
| 23. | glla(M)aflv | 4.84 | 0.15 | 215. | glla(V)aflv | 5.20 | 0.15 | DOLPP1 | p.V146M |
| 24. | klakl(T)fwl | 4.91 | 0.15 | 216. | klakl(A)fwl | 6.79 | 0.25 | ZNF618 | p.A814T |
| 25. | (F)laqellpl | 4.96 | 0.15 | 217. | (L)laqellpl | 21.24 | 1.00 | FMN1 | p.L116F |
| 26. | ilmk(C)flsv | 4.97 | 0.15 | 218. | ilmk(S)flsv | 4.56 | 0.12 | RAD9A | p.S79C |
| 27. | tlldaly(V)i | 5.03 | 0.15 | 219. | tlldaly(E)i | 2.58 | 0.03 | JRKL | p.E368V |
| 28. | alfphpqh(V) | 5.04 | 0.15 | 220. | alfphpqh(A) | 25.34 | 1.00 | BSX | p.A101V |
| 29. | (F)lihvaaya | 5.06 | 0.15 | 221. | (S)lihvaaya | 30.40 | 1.50 | VWA2 | p.S684F |
| 30. | (G)mmmgawwl | 5.17 | 0.15 | 222. | (R)mmmgawwl | 4.54 | 0.12 | GRID2 | p.R631G |
| 31. | ylislf(P)ii | 5.29 | 0.17 | 223. | ylislf(L)ii | 18.01 | 0.80 | MAS1L | p.L303P |
| 32. | llysl(V)agv | 5.39 | 0.17 | 224. | llysl(A)agv | 8.63 | 0.40 | LPPR5 | p.A72V |
| 33. | llpyyvfe(I) | 5.40 | 0.17 | 225. | llpyyvfe(V) | 2.75 | 0.05 | CDH19 | p.V379I |
| 34. | (R)lfdllstl | 5.41 | 0.17 | 226. | (S)lfdllstl | 5.59 | 0.17 | KIF9 | p.S148R |
| 35. | lllqglf(V)v | 5.56 | 0.17 | 227. | lllqglf(I)v | 8.24 | 0.40 | CDRT15L2 | p.I219V |
| 36. | m(M)fdeyqgl | 5.63 | 0.17 | 228. | m(L)fdeyqgl | 5.28 | 0.15 | FAM114A1 | p.L292M |
| 37. | (L)lfanlyll | 5.69 | 0.17 | 229. | (I)lfanlyll | 5.41 | 0.17 | OR52R1 | p.I277L |
| 38. | gl(Q)eyspei | 6.20 | 0.20 | 230. | gl(E)eyspei | 22.53 | 1.00 | HEMGN | p.E378Q |
| 39. | slvaisp(S)v | 6.35 | 0.25 | 231. | slvaisp(W)v | 6.89 | 0.25 | SERINC5 | p.W251S |
| 40. | llaemgy(K)v | 6.50 | 0.25 | 232. | llaemgy(E)v | 3.66 | 0.08 | SEL1L2 | p.E511K |
| 41. | alfws(F)apl | 6.50 | 0.25 | 233. | alfws(L)apl | 5.54 | 0.17 | SRL | p.L276F |
| 42. | fvlivl(Y)yv | 7.15 | 0.30 | 234. | fvlivl(S)yv | 11.45 | 0.50 | OR10G8 | p.S216Y |
| 43. | qlf(F)ftwsl | 7.38 | 0.30 | 235. | qlf(L)ftwsl | 13.05 | 0.80 | OR13G1 | p.L100F |
| 44. | kll(Q)sltpl | 7.90 | 0.30 | 236. | kll(E)sltpl | 2.84 | 0.05 | LRMP | p.E202Q |
| 45. | vlde(C)fsrv | 7.91 | 0.30 | 237. | vlde(Y)fsrv | 4.19 | 0.10 | AP4S1 | p.Y94C |
| 46. | sl(L)dqgdyv | 8.00 | 0.30 | 238. | sl(Q)dqgdyv | 59.37 | 2.00 | KDR | p.Q635L |
| 47. | kl(T)fwllav | 8.06 | 0.30 | 239. | kl(A)fwllav | 3.72 | 0.08 | ZNF618 | p.A814T |
| 48. | flf(L)vllfv | 8.17 | 0.40 | 240. | flf(S)vllfv | 2.79 | 0.05 | PCDHB4 | p.S703L |
| 49. | fine(M)vlfi | 8.75 | 0.40 | 241. | fine(L)vlfi | 8.20 | 0.40 | OR5K2 | p.L197M |
| 50. | vl(F)kvieav | 8.76 | 0.40 | 242. | vl(S)kvieav | 16.53 | 0.80 | EXOC2 | p.S826F |
| 51. | smqdc(G)fpl | 9.09 | 0.40 | 243. | smqdc(A)fpl | 6.02 | 0.20 | WDR27 | p.A44G |
| 52. | (H)iydevfel | 9.37 | 0.40 | 244. | (R)iydevfel | 6.04 | 0.20 | DNAH17 | p.R459H |
| 53. | v(M)msqylel | 9.66 | 0.40 | 245. | v(I)msqylel | 97.88 | 3.00 | DHX58 | p.I145M |
| 54. | alltf(D)plv | 9.95 | 0.40 | 246. | alltf(G)plv | 9.24 | 0.40 | CTSO | p.G239D |
| 55. | tmlnqly(H)l | 10.11 | 0.40 | 247. | tmlnqly(Q)l | 10.37 | 0.50 | TNRC6C | p.Q1153H |
| 56. | ll(L)cyafra | 10.22 | 0.40 | 248. | ll(Q)cyafra | 34.45 | 1.50 | NEK10 | p.Q436L |
| 57. | ala(H)lpalv | 10.40 | 0.50 | 249. | ala(R)lpalv | 20.66 | 0.80 | LINGO4 | p.R202H |
| 58. | fl(F)sielli | 10.42 | 0.50 | 250. | fl(S)sielli | 10.40 | 0.50 | DIEXF | p.S473F |

TABLE 3-continued

Neo-epitopes predicted to bind HLA-A*02:01

| SEQ ID NO | Mutant peptide sequence | Binding affinity (nM) NetMHC pan | Rank (%) NetMHC pan | SEQ ID NO | Native peptide sequence | Binding affinity (nM) NetMHC pan | Rank(%) NetMHC pan | Gene source | Variant |
|---|---|---|---|---|---|---|---|---|---|
| 59. | sl(C)efsnfl | 10.44 | 0.50 | 251. | sl(R)efsnfl | 70.15 | 2.00 | ARHGAP10 | p.R88C |
| 60. | al(T)yllhlv | 10.62 | 0.50 | 252. | al(K)yllhlv | 46.34 | 1.50 | IKBKAP | p.K879T |
| 61. | vlmesv(C)nm | 10.66 | 0.50 | 253. | vlmesv(W)nm | 3.29 | 0.08 | UBR5 | p.W566C |
| 62. | l(M)mfrdvav | 10.80 | 0.50 | 254. | l(V)mfrdvav | 197.27 | 3.00 | ZFP30 | p.V6M |
| 63. | as(M)ecispv | 10.84 | 0.50 | 255. | as(V)ecispv | 142.95 | 3.00 | SHC3 | p.V475M |
| 64. | (H)mvdeleav | 10.85 | 0.50 | 256. | (Q)mvdeleav | 16.71 | 0.80 | BCR | p.Q765H |
| 65. | lvsss(L)wlv | 10.94 | 0.50 | 257. | lvsss(R)wlv | 249.33 | 4.00 | ARHGEF26 | p.R654L |
| 66. | slfsy(D)cwl | 10.99 | 0.50 | 258. | slfsy(H)cwl | 8.28 | 0.40 | ZDHHC20 | p.H231D |
| 67. | (N)llgltfri | 11.54 | 0.50 | 259. | (D)llgltfri | 359.18 | 4.00 | TRMT2A | p.D396N |
| 68. | ai(V)gftspv | 11.90 | 0.50 | 260. | ai(L)gftspv | 7.82 | 0.30 | THADA | p.L1240V |
| 69. | vlsw(L)sfwi | 12.08 | 0.50 | 261. | vlsw(V)sfwi | 12.64 | 0.80 | GABRG3 | p.V273L |
| 70. | (I)imrvdfnv | 12.45 | 0.50 | 262. | (V)imrvdfnv | 20.27 | 0.80 | PGK2 | p.V19I |
| 71. | alw(N)lvqfa | 12.70 | 0.80 | 263. | alw(D)lvqfa | 4.85 | 0.15 | KLHL1 | p.D265N |
| 72. | ylisl(L)lii | 12.71 | 0.80 | 264. | ylisl(F)lii | 18.01 | 0.80 | MAS1L | p.F302L |
| 73. | y(L)npyqlna | 12.83 | 0.80 | 265. | y(M)npyqlna | 11.69 | 0.50 | CPNE8 | p.M332L |
| 74. | ft(F)slamfl | 13.69 | 0.80 | 266. | ft(L)slamfl | 16.85 | 0.80 | TAS2R14 | p.L193F |
| 75. | mlyg(Q)igyi | 13.90 | 0.80 | 267. | mlyg(R)igyi | 16.62 | 0.80 | LANCL1 | p.R155Q |
| 76. | iliaa(M)lel | 13.93 | 0.80 | 268. | iliaa(I)lel | 8.26 | 0.40 | SLC6A14 | p.I491M |
| 77. | (F)llpfanet | 13.95 | 0.80 | 269. | (S)llpfanet | 189.71 | 3.00 | LATS1 | p.S84F |
| 78. | fllakvin(T) | 14.00 | 0.80 | 270. | fllakvin(A) | 5.46 | 0.17 | SIPA1L3 | p.A803T |
| 79. | (Q)layldyyl | 14.15 | 0.80 | 271. | (R)layldyyl | 8.68 | 0.40 | TLR4 | p.R289Q |
| 80. | (C)lanqipfi | 14.49 | 0.80 | 272. | (R)lanqipfi | 8.10 | 0.40 | MX2 | p.R640C |
| 81. | (S)lgsllshv | 14.53 | 0.80 | 273. | (C)lgsllshv | 28.17 | 1.50 | ATR | p.C1207S |
| 82. | flf(L)iyllv | 14.66 | 0.80 | 274. | flf(F)iyllv | 7.69 | 0.30 | TMEM39A | p.F80L |
| 83. | smvdgmwq(T) | 14.81 | 0.80 | 275. | smvdgmwq(A) | 4.87 | 0.15 | SPHKAP | p.A1061T |
| 84. | rive(F)yfml | 14.97 | 0.80 | 276. | rive(S)yfml | 35.88 | 1.50 | LEPREL1 | p.S544F |
| 85. | nifail(E)sv | 14.98 | 0.80 | 277. | nifail(Q)sv | 17.53 | 0.80 | CDC73 | p.Q254E |
| 86. | lmlr(C)tesv | 15.32 | 0.80 | 278. | lmlr(R)tesv | 39.56 | 1.50 | PLXNC1 | p.R1128C |
| 87. | ilsgl(V)nmv | 15.96 | 0.80 | 279. | ilsgl(A)nmv | 41.43 | 1.50 | TMCO4 | p.A333V |
| 88. | smhwqn(Y)sv | 16.07 | 0.80 | 280. | smhwqn(D)sv | 157.78 | 3.00 | MYO9A | p.D1853Y |
| 89. | (L)llqanfiv | 16.18 | 0.80 | 281. | (F)llqanfiv | 4.11 | 0.10 | CA10 | p.F9L |
| 90. | tlmsp(L)lgl | 16.29 | 0.80 | 282. | tlmsp(P)lgl | 63.13 | 2.00 | CACNA1E | p.P1774L |
| 91. | simk(G)mipl | 16.61 | 0.80 | 283. | simk(A)mipl | 21.51 | 1.00 | CACNA1A | p.A222G |
| 92. | ll(F)ginqal | 17.53 | 0.80 | 284. | ll(V)ginqal | 87.78 | 2.00 | ARMC4 | p.V807F |
| 93. | f(T)lclslmv | 18.13 | 0.80 | 285. | f(A)lclslmv | 53.60 | 1.50 | HTR3E | p.A328T |
| 94. | wlltr(P)ifl | 18.35 | 0.80 | 286. | wlltr(R)ifl | 159.10 | 3.00 | TMEM67 | p.R441P |
| 95. | cmld(M)fvli | 18.85 | 0.80 | 287. | cmld(I)fvli | 22.85 | 1.00 | KCNQ3 | p.I203M |
| 96. | ivwevlf(V)l | 19.32 | 0.80 | 288. | ivwevlf(L)l | 10.33 | 0.40 | CA10 | p.L10V |
| 97. | flq(T)cnlpi | 19.52 | 0.80 | 289. | flq(M)cnlpi | 22.36 | 1.00 | MTX2 | p.M50T |
| 98. | flfqdla(V)t | 19.69 | 0.80 | 290. | flfqdla(I)t | 24.86 | 1.00 | ATP13A4 | p.I940V |
| 99. | nl(F)kgfyta | 19.73 | 0.80 | 291. | nl(L)kgfyta | 30.24 | 1.50 | KRIT1 | p.L540F |
| 100. | ylyt(T)dtgl | 19.78 | 0.80 | 292. | ylyt(A)dtgl | 10.35 | 0.40 | SLX4 | p.A758T |
| 101. | llsp(K)dwgl | 20.24 | 0.80 | 293. | llsp(E)dwgl | 22.22 | 1.00 | ATF6B | p.E25K |
| 102. | tmsln(L)itv | 20.27 | 0.80 | 294. | tmsln(I)itv | 24.29 | 1.00 | DVL2 | p.I265L |
| 103. | gladfad(S)l | 20.45 | 0.80 | 295. | gladfad(N)l | 24.61 | 1.00 | TIAM2 | p.N1560S |
| 104. | illpi(P)vll | 20.80 | 0.80 | 296. | illpi(R)vll | 81.72 | 2.00 | LPCAT2 | p.R69P |
| 105. | lltr(P)iflv | 21.08 | 1.00 | 297. | lltr(R)iflv | 20.68 | 0.80 | TMEM67 | p.R441P |
| 106. | f(L)vllfvav | 21.22 | 1.00 | 298. | f(S)vllfvav | 381.95 | 4.00 | PCDHB4 | p.S703L |
| 107. | (F)mmsyersm | 21.36 | 1.00 | 299. | (S)mmsyersm | 349.98 | 4.00 | SON | p.S1016F |
| 108. | (M)lcnglvll | 21.41 | 1.00 | 300. | (V)lcnglvll | 62.02 | 2.00 | LGR6 | p.V576M |
| 109. | liaa(M)lelv | 21.82 | 1.00 | 301. | liaa(I)lelv | 12.41 | 0.50 | SLC6A14 | p.I491M |
| 110. | lman(R)fdnv | 21.98 | 1.00 | 302. | lman(G)fdnv | 10.07 | 0.40 | ANKS1B | p.G835R |
| 111. | ll(D)isffal | 22.06 | 1.00 | 303. | ll(G)isffal | 82.04 | 2.00 | KCNQ4 | p.G307D |
| 112. | ql(L)dgkvtv | 22.08 | 1.00 | 304. | ql(I)dgkvtv | 29.88 | 1.50 | TUBGCP5 | p.I290L |
| 113. | aliqvq(T)tv | 22.52 | 1.00 | 305. | aliqvq(A)tv | 21.58 | 1.00 | SLC41A1 | p.A187T |
| 114. | flv(W)nnvll | 22.57 | 1.00 | 306. | flv(R)nnvll | 55.99 | 2.00 | TMEM45A | p.R174W |
| 115. | liidsnl(E)v | 22.58 | 1.00 | 307. | liidsnl(G)v | 27.56 | 1.00 | CASP10 | p.G32E |
| 116. | ylhsiwhv(I) | 22.77 | 1.00 | 308. | ylhsiwhv(L) | 15.06 | 0.80 | ACER1 | p.L212I |
| 117. | ti(I)lalmyv | 23.06 | 1.00 | 309. | ti(V)lalmyv | 63.84 | 2.00 | ICAM3 | p.V503I |
| 118. | vltslpal(V) | 23.12 | 1.00 | 310. | vltslpal(A) | 189.59 | 3.00 | DEAF1 | p.A427V |
| 119. | il(S)nrtvlv | 23.33 | 1.00 | 311. | il(P)nrtvlv | 45.72 | 1.50 | PKHD1 | p.P2767S |
| 120. | kl(C)casikv | 23.39 | 1.00 | 312. | kl(S)casikv | 12.43 | 0.50 | OR52N5 | p.S197C |
| 121. | mlpgf(P)hrl | 23.58 | 1.00 | 313. | mlpgf(L)hrl | 10.08 | 0.40 | ACTR10 | p.L316P |
| 122. | sl(H)tavaev | 23.84 | 1.00 | 314. | sl(Q)tavaev | 24.48 | 1.00 | PARD3B | p.Q689H |
| 123. | hlfl(H)lpkl | 24.50 | 1.00 | 315. | hlfl(D)lpkl | 35.84 | 1.50 | MARS | p.D453H |
| 124. | qli(A)gilya | 24.71 | 1.00 | 316. | qli(D)gilya | 6.45 | 0.25 | SF3B1 | p.D894A |
| 125. | klvnqsym(I) | 25.33 | 1.00 | 317. | klvnqsym(M) | 139.45 | 3.00 | ZBBX | p.M82I |
| 126. | si(S)cavwfa | 25.46 | 1.00 | 318. | si(G)cavwfa | 43.82 | 1.50 | ASNSD1 | p.G461S |

TABLE 3-continued

Neo-epitopes predicted to bind HLA-A*02:01

| SEQ ID NO | Mutant peptide sequence | Binding affinity (nM) NetMHCpan | Rank (%) NetMHCpan | SEQ ID NO | Native peptide sequence | Binding affinity (nM) NetMHCpan | Rank(%) NetMHCpan | Gene source | Variant |
|---|---|---|---|---|---|---|---|---|---|
| 127. | mlle(G)lylf | 25.73 | 1.00 | 319. | mlle(A)lylf | 43.76 | 1.50 | EMR2 | p.A621G |
| 128. | f(V)lqanfiv | 25.75 | 1.00 | 320. | f(L)lqanfiv | 4.11 | 0.10 | CA10 | p.L10V |
| 129. | mldrll(S)ai | 26.61 | 1.00 | 321. | mldrll(R)ai | 140.29 | 3.00 | GCNT1 | p.R141S |
| 130. | yilh(Q)kpfv | 26.80 | 1.00 | 322. | yilh(R)kpfv | 57.12 | 2.00 | UNC80 | p.R2266Q |
| 131. | nmnqct(Y)vv | 27.59 | 1.00 | 323. | nmnqct(D)vv | 358.04 | 4.00 | MPRIP | p.D105Y |
| 132. | famy(D)etfv | 27.99 | 1.00 | 324. | famy(Y)etfv | 9.78 | 0.40 | CDH9 | p.Y492D |
| 133. | sviy(I)ieav | 28.00 | 1.00 | 325. | sviy(T)ieav | 79.58 | 2.00 | BBX | p.T489I |
| 134. | all(P)sttdv | 28.09 | 1.50 | 326. | all(L)sttdv | 75.85 | 2.00 | ALK | p.L521P |
| 135. | (V)llqfstgl | 28.41 | 1.50 | 327. | (G)llqfstgl | 25.97 | 1.00 | GPR98 | p.G1704V |
| 136. | alqagtv(G)v | 28.84 | 1.50 | 328. | alqagtv(W)v | 19.91 | 0.80 | ALDH1B1 | p.W469G |
| 137. | qvvk(Y)pfyv | 29.37 | 1.50 | 329. | qvvk(D)pfyv | 236.36 | 4.00 | PKDREJ | p.D829Y |
| 138. | kvlfi(P)frv | 29.51 | 1.50 | 330. | kvlfi(L)frv | 17.34 | 0.80 | WDR81 | p.L264P |
| 139. | wqlff(Y)vtv | 29.65 | 1.50 | 331. | wqlff(H)vtv | 42.90 | 1.50 | SEC22A | p.H282Y |
| 140. | yl(Q)iitqli | 29.80 | 1.50 | 332. | yl(E)iitqli | 128.64 | 3.00 | SLC34A2 | p.E242Q |
| 141. | ilhemm(D)ei | 29.83 | 1.50 | 333. | ilhemm(E)ei | 21.97 | 1.00 | DGKB | p.E204D |
| 142. | stisssf(L)v | 30.44 | 1.50 | 334. | stisssf(S)v | 31.92 | 1.50 | PI4KA | p.S251L |
| 143. | svle(N)gwei | 30.99 | 1.50 | 335. | svle(K)gwei | 51.16 | 1.50 | PKHD1 | p.K3574N |
| 144. | tlmpn(T)snl | 31.00 | 1.50 | 336. | tlmpn(A)snl | 69.88 | 2.00 | ESYT2 | p.A484T |
| 145. | giyq(Q)cwlv | 31.11 | 1.50 | 337. | giyq(R)cwlv | 64.10 | 2.00 | DOK5 | p.R26Q |
| 146. | ylkfni(Y)la | 31.16 | 1.50 | 338. | ylkfni(S)la | 153.61 | 3.00 | ODZ1 | p.S435Y |
| 147. | ll(Q)dfeatl | 31.91 | 1.50 | 339. | ll(R)dfeatl | 240.85 | 4.00 | BMP4 | p.R55Q |
| 148. | kvfnt(I)ysl | 33.08 | 1.50 | 340. | kvfnt(V)ysl | 42.66 | 1.50 | KIAA1586 | p.V253I |
| 149. | w(N)ssveeav | 33.18 | 1.50 | 341. | w(L)ssveeav | 49.34 | 1.50 | EFCAB4B | p.L640M |
| 150. | tlni(N)lfpa | 33.28 | 1.50 | 342. | tlni(D)lfpa | 30.06 | 1.50 | PXDN | p.D1212N |
| 151. | (H)lvpyiidl | 33.67 | 1.50 | 343. | (Q)lvpyiidl | 52.78 | 1.50 | DTX1 | p.Q68H |
| 152. | ml(F)petkgi | 33.69 | 1.50 | 344. | ml(L)petkgi | 77.67 | 2.00 | SLC22A3 | p.L517F |
| 153. | v(M)leieepa | 34.19 | 1.50 | 345. | v(I)leieepa | 472.18 | 5.00 | HHIPL2 | p.I327M |
| 154. | fill(K)llkv | 34.79 | 1.50 | 346. | fill(N)llkv | 21.89 | 1.00 | RHCG | p.N171K |
| 155. | sl(V)agvpvl | 35.13 | 1.50 | 347. | sl(A)agvpvl | 18.96 | 0.80 | LPPR5 | p.A72V |
| 156. | vtwlis(F)gv | 36.02 | 1.50 | 348. | vtwlis(L)gv | 167.21 | 3.00 | ARHGEF6 | p.L14F |
| 157. | rlys(T)vcal | 36.71 | 1.50 | 349. | rlys(A)vcal | 13.36 | 0.80 | RYR3 | p.A1567T |
| 158. | (V)maqteptv | 36.99 | 1.50 | 350. | (M)maqteptv | 14.96 | 0.80 | DOCK10 | p.M644V |
| 159. | llfeyl(A)lf | 37.12 | 1.50 | 351. | llfeyl(T)lf | 37.07 | 1.50 | HARS | p.T310A |
| 160. | glf(V)vlilv | 37.12 | 1.50 | 352. | glf(I)vlilv | 65.90 | 2.00 | CDRT15L2 | p.I219V |
| 161. | ivi(R)ispev | 37.78 | 1.50 | 353. | ivi(C)ispev | 12.80 | 0.80 | PPM1D | p.C374R |
| 162. | stfak(V)sfv | 38.09 | 1.50 | 354. | stfak(A)sfv | 163.49 | 3.00 | CHD9 | p.A1404V |
| 163. | yvmavvd(N)a | 38.15 | 1.50 | 355. | yvmavvd(K)a | 74.62 | 2.00 | MAP1B | p.K1051N |
| 164. | vqierld(T)v | 38.26 | 1.50 | 356. | vqierld(A)v | 37.47 | 1.50 | EDAR | p.A423T |
| 165. | h(L)lfanlyl | 38.44 | 1.50 | 357. | h(I)lfanlyl | 430.92 | 4.00 | OR52R1 | p.I277L |
| 166. | s(I)tnaiapv | 38.48 | 1.50 | 358. | s(T)tnaiapv | 326.75 | 4.00 | MAGEB18 | p.T70I |
| 167. | fv(F)cqgfla | 38.93 | 1.50 | 359. | fv(V)cqgfla | 397.64 | 4.00 | FTSJ3 | p.V196F |
| 168. | vlq(E)adill | 38.97 | 1.50 | 360. | vlq(A)adill | 105.58 | 3.00 | WARS2 | p.A165E |
| 169. | h(M)ihwnstl | 39.06 | 1.50 | 361. | h(L)ihwnstl | 47.40 | 1.50 | CA8 | p.L142M |
| 170. | (S)ivnflmti | 39.35 | 1.50 | 362. | (G)ivnflmti | 82.71 | 2.00 | OR13A1 | p.G225S |
| 171. | llrl(Y)tpfv | 41.26 | 1.50 | 363. | llrl(S)tpfv | 120.30 | 3.00 | GUCY1A2 | p.S383Y |
| 172. | mltlmsp(L)l | 42.47 | 1.50 | 364. | mltlmsp(P)l | 31.20 | 1.50 | CACNA1E | p.P1774L |
| 173. | slv(M)vyagv | 42.82 | 1.50 | 365. | slv(L)vyagv | 59.63 | 2.00 | TMEM194B | p.L282M |
| 174. | nia(M)tlptv | 43.66 | 1.50 | 366. | nia(T)tlptv | 33.17 | 1.50 | DIP2C | p.T1067M |
| 175. | yldls(P)nnl | 43.89 | 1.50 | 367. | yldls(S)nnl | 29.92 | 1.50 | LRRC52 | p.S110P |
| 176. | ivwevl(L)ll | 43.97 | 1.50 | 368. | ivwevl(F)ll | 10.33 | 0.40 | CA10 | p.F9L |
| 177. | lms(M)wvtvi | 43.99 | 1.50 | 369. | lms(V)wvtvi | 62.27 | 2.00 | TMEM8B | p.V306M |
| 178. | sl(T)flffml | 44.14 | 1.50 | 370. | sl(N)flffml | 25.15 | 1.00 | PIGV | p.N123T |
| 179. | yflp(A)sfpi | 45.41 | 1.50 | 371. | yflp(P)sfpi | 140.89 | 3.00 | MORC2 | p.P863A |
| 180. | slflf(L)vll | 45.89 | 1.50 | 372. | slflf(S)vll | 32.05 | 1.50 | PCDHB4 | p.S703L |
| 181. | gil(N)fymfl | 46.05 | 1.50 | 373. | gil(D)fymfl | 10.81 | 0.50 | SI | p.D1193N |
| 182. | plm(S)vvqsv | 46.10 | 1.50 | 374. | plm(R)vvqsv | 128.06 | 3.00 | PRKD2 | p.R383S |
| 183. | lvmtsys(S)v | 46.15 | 1.50 | 375. | lvmtsys(P)v | 18.94 | 0.80 | IFNW1 | p.P18S |
| 184. | rli(R)kteev | 46.30 | 1.50 | 376. | rli(S)kteev | 15.17 | 0.80 | CCDC147 | p.S739R |
| 185. | fmy(W)trngi | 46.35 | 1.50 | 377. | fmy(R)trngi | 228.84 | 4.00 | PDE6A | p.R100W |
| 186. | lmggtvd(M)v | 46.53 | 1.50 | 378. | lmggtvd(T)v | 59.26 | 2.00 | PMPCA | p.T421M |
| 187. | kllfeyl(A)l | 47.06 | 1.50 | 379. | kllfeyl(T)l | 80.21 | 2.00 | HARS | p.T310A |
| 188. | s(L)llihqgv | 48.11 | 1.50 | 380. | s(V)llihqgv | 416.84 | 4.00 | ZNF229 | p.V363L |
| 189. | llgslvt(H)i | 48.64 | 1.50 | 381. | llgslvt(R)i | 96.77 | 3.00 | DNAH17 | p.R459H |
| 190. | ll(D)ysvpvl | 48.97 | 1.50 | 382. | ll(Y)ysvpvl | 44.33 | 1.50 | MTERFD3 | p.Y293D |
| 191. | vivg(N)iyfl | 49.35 | 1.50 | 383. | vivg(K)iyfl | 50.18 | 1.50 | VPS26B | p.K192N |
| 192. | fiakkv(T)gi | 49.52 | 1.50 | 384. | fiakkv(I)gi | 31.73 | 1.50 | TTPAL | p.I209T |

Example 7

Glioblastoma (GLB) Neo-Epitopes

Using the methods disclosed herein, up to 24 peptides of 31 amino acids in length for incorporation into an immunogenic composition (vaccine) were identified for three subjects. Table 4 provides a summary of the data for all three subjects, and Tables 5-7 provide the summary for each of the subjects (patients A, B, and C, respectively).

TABLE 4

| Summary of subject mutations data | | | |
|---|---|---|---|
| GBM patient | A | B | C |
| Mutations in transcripts | 592 | 502 | 1029 |
| Point mutations | 573 | 502 | 1029 |
| Mutations with DNA frequency >10% | 278 | 294 | 553 |
| Mutations causing missense protein change | 61 | 58 | 103 |
| Mutations in genes expressed >0.5 RPKM units | 28 | 31 | 56 |
| Mutations in peptide binding MHC <500 nM | 14 | 13 | 24 |

TABLE 5

Peptides for patient A

| # of epitopes | Minimum binding IC50 (nM) | Chromosome | Coordinate (hg19) | Gene | Ref NT | Mutated NT | Amino acid change | SEQ ID NO | 31 mer (MUT) |
|---|---|---|---|---|---|---|---|---|---|
| 4 | 10.57 | chr7 | 151188043 | RHEB | G | A | p.P37L | 385. | ltiqfvegqfvdsyd(L)tientftklitvngq |
| 3 | 47.55 | chr5 | 37183169 | C5orf42 | A | C | p.I753S | 386. | ddtrekcliqrssnh(S)fwtpksiktrrcifk |
| 2 | 5.39 | chr19 | 58385910 | ZNF814 | C | T | p.S283N | 387. | khecgecgksfskyv(N)fsnhqrvhtekkhec |
| 2 | 6.59 | chr15 | 23931973 | NDN | C | T | p.S131N | 388. | kmiiwfpdmvkdvig(N)ykkwcrsilrrtsli |
| 2 | 304.18 | chrX | 153040426 | PLXNB3 | C | T | p.L976F | 389. | ggqrdplpglphlrrarl(F)pwpwrlpaaaqa |
| 2 | 334.19 | chr8 | 30954361 | WRN | A | T | p.D659V | 390. | eycsgnmgllqqlea(V)igitliavdeahcis |
| 1 | 24.86 | chr2 | 207170555 | ZDBF2 | C | T | p.R435C | 391. | qskvsakevnlskev(C)tdvqyknnksyvski |
| 1 | 71.89 | chr4 | 110454813 | SEC24B | C | G | p.T1217S | 392. | gkgcdnnfiedvlgy(S)nfasipqkmthlpel |
| 1 | 83.82 | chr7 | 30818067 | FAM188B | T | C | p.V28A | 393. | lvreflsrkglkktc(A)tmdqerprsdlsinn |
| 1 | 93 | chr22 | 31011610 | TCN2 | G | C | p.R232P | 394. | ystplalqflmtspm(P)gaelgtaclkarval |
| 1 | 104.98 | chr7 | 99490084 | TRIM4 | A | G | p.M402T | 395. | rdslevavgvcredv(T)gitdrskmspdvgiw |
| 1 | 156.28 | chrX | 99663289 | PCDH19 | G | T | p.L103I | 396. | drdllcrqspkciis(I)evmsssmeicvikve |
| 1 | 280.04 | chr8 | 99468158 | STK3 | A | G | p.I491T | 397. | lqmrlkaldpmmere(T)eelrqrytakrqpil |
| 1 | 337.99 | chrX | 153040425 | PLXNB3 | T | C | p.F1364S | 398. | sgipfldyrtyaera(S)fpghggcplqpkpeg |
| 1 | 369.15 | chr13 | 84455252 | SLITRK1 | C | T | p.D131N | 399. | nkiksfrkqtflgld(N)leylqadfnllrdid |

Ref NT: Reference nucleotide;
Mutated NT: Mutated nucleotide;
# of epitopes: Number of epitopes

TABLE 6

Peptides for patient B

| # of epitopes | Minimum binding IC50 (nM) | Chromosome | Coordinate (hg19) | Gene | Ref NT | Mutated NT | Amino acid change | SEQ ID NO | 31 mer (MUT) |
|---|---|---|---|---|---|---|---|---|---|
| 7 | 3.07 | chr19 | 1047000 | ABCA7 | G | A | p.A470T | 400. | lgwflsclgpfllsa(T)llvlvlklgdilpys |
| 2 | 4.32 | chr9 | 124585045 | TTLL11 | G | C | p.L742V | 401. | lheqvaslidlceyh(V)slldekrlvcgrgvp |
| 2 | 67.75 | chr6 | 44253951 | TC 1E1 | G | A | p.P199L | 402. | crnyvrrvhvdqflp(L)vqlpaqlrpgdqsds |
| 2 | 83.31 | chr2 | 99012639 | CNGA3 | G | A | p.V318I | 403. | yfaiskfigfgtdsw(I)ypnisipehgrlsrk |

TABLE 6-continued

Peptides for patient B

| # of epitopes | Minimum binding IC50 (nM) | Chromosome | Coordinate (hg19) | Gene | Ref NT | Mutated NT | Amino acid change | SEQ ID NO | 31 mer (MUT) |
|---|---|---|---|---|---|---|---|---|---|
| 2 | 99.01 | chr1 | 197446848 | CRB1 | G | A | p.A818T | 404 | dlisdifttigsvtv(T)lllilllaivasvvt |
| 2 | 127.49 | chr13 | 113907496 | CUL4A | C | T | p.A480V | 405 | rklqwqttlghavlk(V)efkegkkefqvslfq |
| 2 | 176.21 | chr2 | 99012638 | CNGA3 | G | C | p.W317C | 406 | iyfaiskfigfgtds(C)vypnisipehgrlsr |
| 2 | 192.37 | chr17 | 72540989 | CD300C | G | T | p.N53K | 407 | slsvqcryekehrtl(K)kfwcrppqilrcdki |
| 2 | 303.07 | chr2 | 216288115 | FN1 | T | C | p.N451D | 408 | segrrdnmkwcgttq(D)ydadqkfgfcpmaah |
| 1 | 7.79 | chr1 | 9673064 | TMEM201 | G | A | p.V528I | 409 | seeaatwrgrfgpsl(I)rgllayslaanalft |
| 1 | 13.28 | chr7 | 106508490 | PIK3CG | G | A | p.V162I | 410 | sqafqrqltaligyd(I)tdvsnvhddeleftr |
| 1 | 64.77 | chr19 | 4234705 | EBI3 | G | A | p.A141T | 411 | iikpdppegvrlspl(T)erqlqvqweppgswp |
| 1 | 104.57 | chr1 | 226924403 | ITPKB | C | T | p.A253T | 412 | pgraaptgseaqgps(T)fvrmekgipasprcg |
| 1 | 116.23 | chr1 | 150235713 | CA14 | G | A | p.G58R | 413 | yrrsqismeqleklq(R)tlfsteeepskllvq |

Ref NT: Reference nucleotide;
Mutated NT: Mutated nucleotide;
# of epitopes: Number of epitopes

TABLE 7

Peptides for patient C

| # of epitopes | Minimum binding IC50 (nM) | Chromosome | Coordinate (hg19) | Gene | REF NT | Mutated NT | Amino acid change | SEQ ID NO | 31 mer (MUT) |
|---|---|---|---|---|---|---|---|---|---|
| 8 | 8.96 | chr22 | 45312231 | PHF21B | G | A | p.P165S | 414 | yaiistspsnaaama(S)staysvvsdsikvqp |
| 3 | 62.52 | chr11 | 76253391 | C11orf30 | A | G | p.I806V | 415 | tsvvyksipasspga(V)thimqqalsshtaft |
| 3 | 66.38 | chr9 | 130652993 | ST6GALNAC6 | G | T | p.N175K | 416 | gslvrviqraglvfp(K)meayayspgrmrqfd |
| 3 | 69.55 | chr11 | 49204779 | FOLH1 | C | T | p.R266H | 417 | dpltpgypaneyayr(H)giaeavglpsipvhp |
| 3 | 91.6 | chr9 | 80537112 | GNAQ | T | A | p.T67S | 418 | qniftamqamiramd(S)lkipykyehnkahaq |
| 3 | 165.15 | chr5 | 7698465 | ADCY2 | C | A | p.L183M | 419 | pislpnhakncvkmg(M)dmceaikkvrdatgv |
| 2 | 12.71 | chr15 | 40916237 | CASC5 | A | G | p.K1259E | 420 | iikfhsaamdekvig(E)vvdqactlekaqves |
| 2 | 33.94 | chr1 | 91403504 | ZNF644 | T | C | p.I1076V | 421 | lkrlgktkwdahksp(V)cvinemmqneekyek |
| 2 | 59.71 | chr6 | 166827373 | RPS6KA2 | G | A | p.T687M | 422 | dvvskmlhvdphqrl(M)amqvlkhpwvvnrey |
| 2 | 96.59 | chr17 | 46058122 | CDK5RAP3 | G | T | p.S145I | 423 | vtmvsvledligklt(I)lqlqhlfmilaspry |
| 2 | 123.51 | chr21 | 45811377 | TRPM2 | C | T | p.R555C | 424 | lvedperpacapaap(C)lqmhhvaqvlrellg |
| 2 | 125.72 | chr19 | 53013839 | ZNF578 | C | T | p.R69C | 425 | lenyrnleavdissk(C)mmkevlstgqgntev |
| 2 | 138.77 | chr4 | 106196951 | TET2 | A | G | p.I1783V | 426 | pnmdykngehhspsh(V)ihnysaapgmfnssl |
| 1 | 21.39 | chr3 | 52014990 | ABHD14A | G | C | p.D258H | 427 | vvklrnaghacylhkpq(H)fhlvllafldhlp |
| 1 | 25.03 | chrX | 133923158 | FAM122B | G | A | p.T78M | 428 | ldmvnretaheremq(M)amqisqswdeslsls |
| 1 | 59.96 | chr2 | 108487837 | RGPD4 | C | T | p.S1126L | 429 | nhwitttmnlkplsg(L)drawmwsasdfsdgd |
| 1 | 90.55 | chr12 | 29936501 | TMTC1 | C | T | p.D62N | 430 | gefvhddvwaivnnp(N)vrpgaplrwgiftnd |
| 1 | 125.65 | chr22 | 19385557 | HIRA | C | T | p.V151M | 431 | dvawsphdawlascs(M)dntvviwnavkfpei |
| 1 | 134 | chr17 | 686559 | RNMTL1 | G | A | p.G111E | 432 | kfedikdwsdlvtpq(E)imgifakpdhvkmty |

TABLE 7-continued

Peptides for patient C

| # of epi-topes | Minimum binding IC50 (nM) | Chromo-some | Coor-dinate (hg19) | Gene | REF NT | Mutated NT | Amino acid change | SEQ ID NO | 31 mer (MUT) |
|---|---|---|---|---|---|---|---|---|---|
| 1 | 167.16 | chr20 | 1584686 | SIRPB1 | G | T | p.T285N | 433. | vtcqvrkfypqrlql(N)wlengnvsrtetast |
| 1 | 172.87 | chr4 | 100504664 | MTTP | T | C | p.I155T | 434. | kenlealqrptllhl(T)hgkvkefysyqneav |
| 1 | 267.11 | chr19 | 55179186 | LILRB4 | G | A | p.G380E | 435. | srprremasppspls(E)efldtkdrqaeedrq |
| 1 | 403.1 | chr3 | 108393016 | DZIP3 | A | C | p.H894P | 436. | eqtekeclnqlarvt(P)maasnleslqlkaav |
| 1 | 429.84 | chr19 | 54080775 | ZNF331 | C | T | p.H321Y | 437. | kaftrvnyltqhqki(Y)tgekpheckecgkaf |
| 1 | 444.61 | chr17 | 80393718 | HEXDC | C | G | p.L109V | 438. | ravasgvkarrpsvtplvwddm(V)rdlpedql |

Ref NT: Reference nucleotide;
Mutated NT: Mutated nucleotide;
# of epitopes: Number of epitopes Example 8

Identification of Cancer-Specific Mutant Peptides

I. Human leukocyte antigen (HLA) proteins corresponding to both major histocompatibility complex (MHC) class I and class II are isolated. Depending on the methods used, HLAs can be isolated with varying levels of specificity using immunoaffinity purification (see e.g., Seward et al. *Mol Cell Proteomics.* 2011 March; 10(3):M110.002477, which is incorporated by reference herein in its entirety). For example, the W6/32 antibody can be used to isolate HLA-A, -B and -C proteins which collectively represent the MHC Class I HLA sub-pool. Similarly, the L243 antibody can be used to isolate HLA-DR proteins. Tissue containing the target HLA-bound peptides is homogenized, and the tissue homogenate is then passed over an immunoaffinity column containing an appropriate antibody against the HLA molecules of interest. Following appropriate washing of column-bound HLA molecules, antibody-bound proteins and their associated peptides are released with low-pH wash. This eluate is ultrafiltered with a low-molecular weight cutoff filter to allow free peptides to flow through separately from proteins. The resulting peptide fraction is then concentrated, transferred to an appropriate solvent system (e.g., solvent A of 0.1% v/v trifluoroacetic acid in water) and then loaded onto a capillary or nano reverse-phase high-performance liquid chromatography (RP-HPLC) column. The column-bound peptides are then eluted using a solvent gradient (for example, 10% to 55% solvent B: 0.1% formic acid in 80% acetonitrile 20% water) over a time course of 90 minutes.

As peptides are eluted during the gradient, they are analyzed by mass spectrometry (MS). Mass spectrometric analysis is typically performed using electro-spray ionization (ESI) and mass analysis on some form of a hybrid tandem mass spectrometer, such as a quadrupole time-of-flight (QTOF) or quadrupole-orbitrap mass spectrometer capable of performing high-accuracy mass measurements of both parent ions and fragments of a molecule under analysis. Such mass spectrometric analysis will typically provide a parent mass of the intact analyte and masses of fragments such that the sequence of the peptide being analyzed is unequivocally defined or nearly so.

Bioinformatics methods are then used to analyze peptide sequences and determine if they correspond to normal (wild-type) or mutant (abnormal) protein sequences. Additionally or alternatively, sequences obtained from diseased tissue are compared to sequences determined by analysis of normal (non-cancer) tissue from the same patient or a suitable control (e.g., a sample from another subject or a database of known peptides from a normal tissue sample). Further analysis is possible by comparison of sequences identified by MS with protein sequences determined by genomic analysis of an individual patient's genome by sequencing of both normal and diseased tissues.

II. In addition to analysis of native, unmodified peptide sequences that correspond directly to normal or abnormal tissues, analysis can also be undertaken for MHC-bound peptides that have been subjected to post-translational modification (PTM) (see e.g., Seward supra; and Drouin et al. *Arthritis Rheum.* 2013 January; 65(1):186-96., which is incorporated by reference herein in its entirety). Such analysis of post-translational modifications can be conducted using accurate precursor mass measurements and collision-induced dissociation (see e.g., Seward supra). Using appropriate software, peptide core sequences and the associated PTM and its location can be identified. The range of PTMs that can be identified include, but are not limited to, oxidized methionine, pyroglutamic acid from amino-terminal glutamine and glutamic acid, and deamidation of glutamine and asparagine. Additional PTMs that can be identified include 0-N-acetylglucosamine at Ser or Thr; acetylation at Lys or the amino terminus; amidation at the carboxyl terminus; Arg to citrulline; S-cysteinylation; S-cysteinylglycine; S-glutathionylation; glycation at Lys or the amino terminus; S-homocysteinylation; 4-hydroxy-5-nonenal at Cys, Lys, or His; malondialdehyde at Lys; methylation at Lys or Arg; oxidation at Cys; and phosphorylation at Ser, Thr, or Tyr. All identifications identified through database searching are optimally manually verified.

III. In addition to analysis of MHC-bound peptides for a range of PTMs, prior fractionation of MHC-bound peptides can be undertaken to enrich the analyzed peptide pool in a specific PTM. For instance, peptides containing a phosphate moiety can be analyzed with this approach (see e.g., Zarling et al. *Proc Natl Acad Sci USA.* 2006 Oct. 3; 103(40):14889-94, herein incorporated by reference in its entirety). Total MHC-bound peptides are isolated in a manner such as that described above. The resulting total peptide pool can then be subjected to methylation to convert carboxylate groups (e.g., C-terminal COOH, and side chain Asp and Glu COOH) to their corresponding methyl esters. The methylated peptide pool is then passed over an $Fe^{3+}$-immobilized metal-affinity chromatography column. Phosphorylated peptides are retained on the column following washing and then eluted with a mild acid wash (e.g., dilute ascorbic acid), which is applied directly to a RP-HPLC column. This phosphopeptide fraction is then eluted through an additional RP-HPLC column with a solvent gradient into a mass spectrometer and analyzed to obtain both parent ion and fragment MS/MS data to allow identification of the core peptide sequence and the location of the phospho-modification.

In a modification of this approach (see e.g., Zarling supra), comparisons of two samples (e.g. normal and diseased tissue, or two different cell lines) can be undertaken in a single analysis. A single sample is divided into two portions and methylated with $d_0$- or $d_4$-methanol resulting in two portions with light and heavy stable isotopic labeling. Samples with different isotopic labels are combined, enriched for phosphopeptides by immobilized metal-affinity chromatography, and analyzed by LC-MS as described above. Signals for phosphopeptides appear in the mass spectrum as doublets separated by 3 m/z units per carboxylate group in the molecule. Phosphopeptides that are unique to one or the other sample appear as singlets.

Data analysis is performed by using a three-dimensional visual representation of the chromatogram available in the Xcalibur software (Thermo Electron Corporation). Peptide sequences are determined by a combination of manual interpretation of MS/MS spectra, accurate mass measurements, and MASCOT Sequence Query (www.matrix-science.com/home.html). Sequences are confirmed by recording MS/MS spectra on the corresponding synthetic peptides. Protein sources for confirmed peptide sequences are obtained by searching the nr and RefSeq databases for human proteins (www.ncbi.nlm.nih.gov/BLAST).

One of ordinary skill in the art would appreciate that the aforementioned techniques can be modified, and that other techniques are known to aid in identifying mutant peptides (e.g., phosphopeptides) useful in the methods and compositions disclosed herein. Suitable methods can be found, for example, in: Meyer et al. *J Proteome Res.* 2009 July; 8(7):3666-74; WO2013177593; WO1992021033; WO2011149909; WO2014036562; WO2015034519; WO2014039675; WO 2014093855; and U.S. Pat. No. 7,026,167, each of which is incorporated by reference herein in its entirety.

Example 9

Tumor-Protective Activity of ASV Compositions in B16.F10 Melanoma

The therapeutic efficacy of an ASV composition containing two predicted neo-epitopes in B16.F10 melanoma, B16-M27 and B16-M30 (Kreiter et al., Nature 520[7549]:692-6 [2015]), was tested in B16.F10 melanoma. The sequences of M27 and M30 are shown in Table 8.

Materials
Corning 175 cm² cell culture flask, Cat#431080, Lot#05415006
FBS, Gemini Bio-Products, Cat 100-106, Lot A96A00Y
PBS, Corning, Catalogue Number 21-040-CV, Lot 21040344
Pen-Strep, Gibco, Catalogue 15140-122, Lot 1665601
L-Glutamine, Gibco, Catalogue 25030-081, Lot 1627656
2 Mercaptoethanol, Gibco, Catalogue 21985-023, Lot 1628448
RPMI1640, Gibco, Catalogue 10-040-CV, Lot 10040609
Complete media composition: 450 ml RPMI-1640, 50 ml FBS, 5 ml Pen-Strep, 5 ml L-Glutamine and 500 ul of 2 Mercaptoethanol.
TrpLE™ Express (Trypsin), Thermo Fisher Methods i. Cell Culture of B16.F10 Cells and Tumor Challenge:

A vial of B16.F10 cells (ATCC; P7) was thawed and resuspended in pre-warmed complete RPMI media in a 15 ml conical tube. The cells were centrifuged at 1500 RPM for four minutes at 25° C. The supernatant was discarded, and the pellet was resuspended in fresh complete media and cultured in a 175 cm2 flask with 50 mL of complete media at 37° C. The cells were observed under a microscope every other day until >80% confluent.

When cells reached >80% confluency, the media was harvested and 10 mL of pre-warmed PBS was added. The PBS was harvested, and then 5 mL of TrpLE™ Express was added to the flask to detach the cells from the surface. The flask was incubated with trypsin for five minutes at 37° C. The trypsin reaction was stopped with fresh 20 mL of complete media. The cell suspension was pipetted up and down using a 10 mL pipet to generate a single-cell suspension. The cells were collected in a 50 mL conical tube and centrifuged at 1500 RPM for four minutes at 25° C. The supernatant was discarded and the cell pellet resuspended in fresh media. The cells were cultured in a ratio of 1:20 in four 175 cm² flasks.

The cells were harvested on the day of injection into mice (C57BL/6; Jackson Laboratories) as described above. The cells were washed twice with serum-free PBS and resuspended in PBS at a concentration of $1.5 \times 10^5$ cells/mL. 100 µl of cells were injected per mouse sub-cutaneously. A total of 60 mice were injected. Measurements of tumor volume (mm³) were obtained every 2-3 days starting on day 12 after tumor challenge.

ii. Preparation of ASV Composition and Therapeutic Groups:

ASV composition was prepared with two 27-mer peptides containing the M27 and M30 melanoma mutations. Mixtures of Hsc70 (Biomay AG) and peptide were prepared in 0.4 mM HEPES, 20 mM KCl at an Hsc70:peptide molar ratio of 1:10, for ASV dosages of 3 µg, 10 µg, or 30 µg in a 200 µL administration per mouse for each of 12 mice per group. Control samples were also prepared as shown for administration of Hsc70 alone (30 µg), peptides alone (6.6 µg each peptide [equivalent to amount present in 30 µg ASV]), and peptides plus poly(I:C) (100 µg each peptide, 50 µg poly [I:C])

For each group, peptide-Hsc70 complexes were individually made for each peptide and then mixed later. Therapeutic groups were as follows:

| Group 1 | 3 µg ASV |
| Group 2 | 10 µg ASV |
| Group 3 | 30 µg ASV |
| Group 4 | 30 µg Hsc70 |
| Group 5 | 6.6 µg each peptide |
| Group 6 | 100 µg each peptide + 50 µg poly(I:C) |

Hsc70-peptide complexes were incubated at 37° C. for 2 hours before preparing aliquots for the three total injections per mouse and freezing the aliquots. For therapeutic group 6, poly(I:C) was added to free peptides just prior to mice injections.

200 ul of the therapeutic dose was injected per mouse sub-cutaneously at the farthest site from the tumor on days 3, 9 and 15 following tumor challenge.

Figure 4:
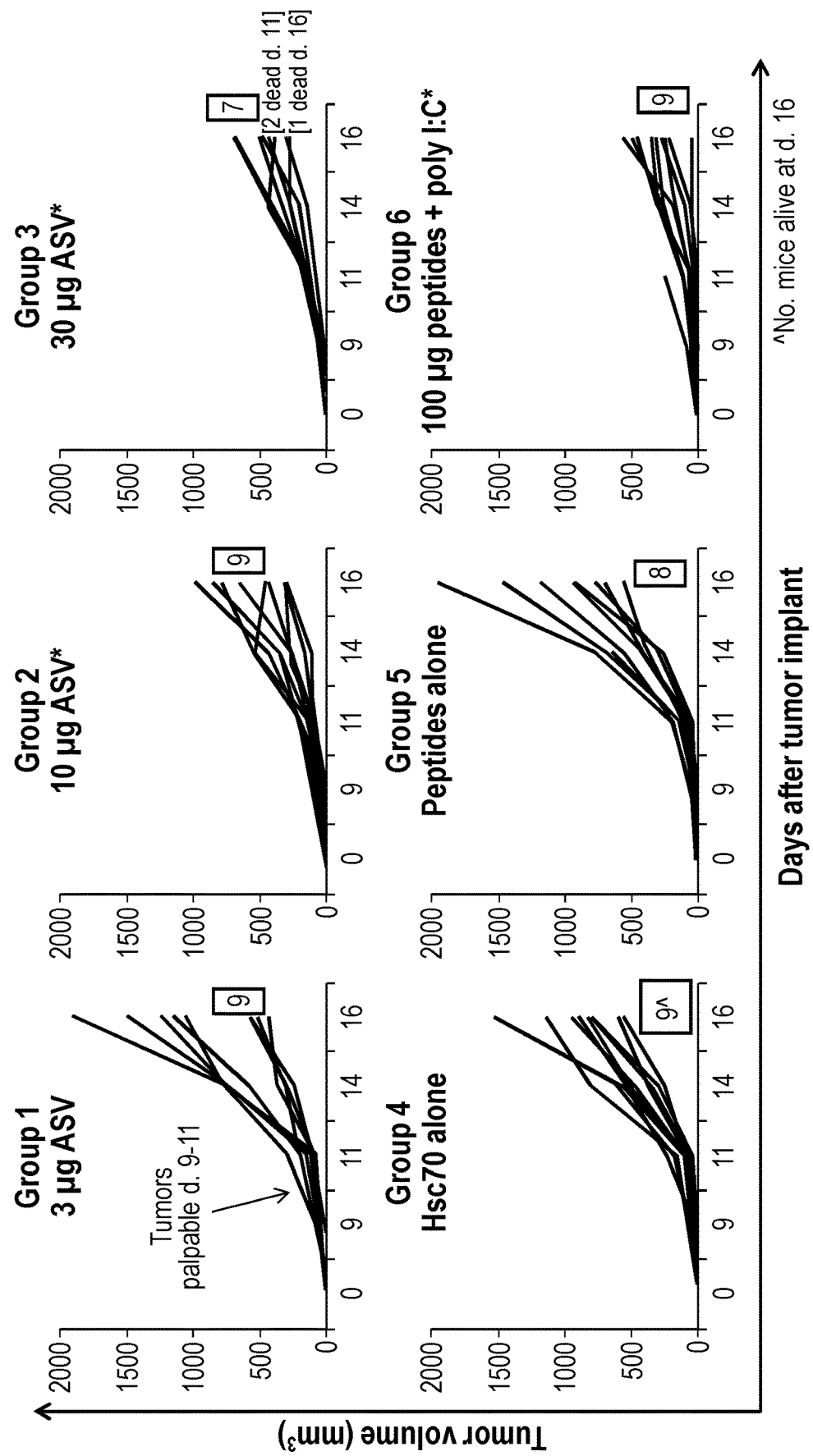
FIG. 4 is a set of tumor growth curves in six groups of C57BL/6 mice after injection with B16.F10 melanoma cells on Day 0, followed by administration on days 3, 9, and 15 of the following: Groups 1-3: 3 µg, 10 µg, and 30 µg, respectively, of compositions comprising Hsc70 complexed with two peptides, B-16-M27 and B-16-M30, containing neoepitopes in B16.F10 melanoma; Group 4: 30 µg Hsc70 alone; Group 5: the peptides alone at an amount equivalent to that in Group 3; and Group 6: 100 µg of each peptide with poly(I:C).
Figure 5:
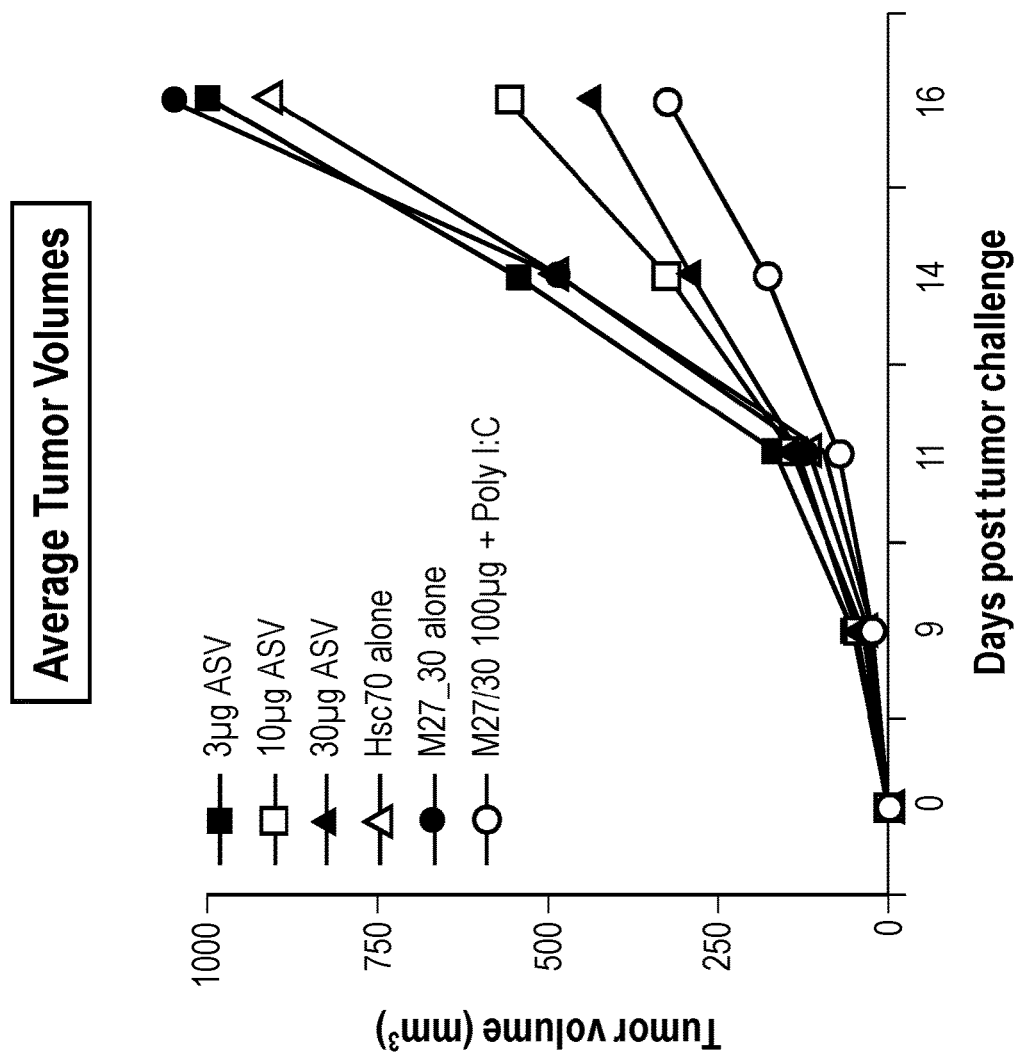
FIG. 5 is a graph showing the average tumor volume after tumor challenge across the groups of mice whose tumor growth curves are depicted in FIG. 4.

Results:

Therapy with ASV at doses of 10 µg and 30 µg per mouse provided significant umor protection relative to therapy with Hsc70 alone (FIG. 4, showing tumor growth curves up to day 16 after tumor cell injection; boxed number at lower right of each plot shows the number of mice still alive at day 16). Specifically, tumors grew at significantly slower rates than negative control groups (Hsc70 or peptides alone) using the "mixed model" test (p<0.005; groups showing significant differences from Hsc70 and peptide-only control groups are shown with an asterisk). Tumor growth rate in mice treated with 10 and 30 µg ASV doses (groups 2 and 3) was not significantly different than in the positive control group (peptides plus poly[I:C]). The average tumor volume across the mice in each therapeutic group is shown in FIG. 5.

Example 10

Testing Different Therapeutic Doses of ASV Composition Comprising Two Neo-Epitopes, with and without QS-21 Stimulon® in B16.F10 Melanoma The therapeutic efficacy of ASV compositions containing the M27 and M30 neo-epitopes described in Example 9 was tested in B16.F10 melanoma in the presence and absence of the saponin adjuvant QS-21 Stimulon® adjuvant. The tumor rejection assay described in Example 9 was repeated in the presence and absence of QS-21 Stimulon®, and in this example, Hsc70-peptide complexes were prepared at Hsc70:peptide molar ratios of 1:20.

Methods:

The methods described in Example 9 were repeated, except that the following ASV compositions and control samples were prepared for administration to seven groups of C57BL/6 mice. Mixtures of Hsc70 and peptide were prepared in 0.4 mM HEPES, 20 mM KCl at an Hsc70:peptide molar ratio of 1:20, for ASV dosages of 3 µg, 10 µg, or 30 µg in a 200 µL administration per mouse for each of 12 mice per group. Control samples were also prepared as shown for administration of Hsc70 alone (30 µg), peptides plus QS-21 Stimulon® (13.3 µg each peptide [equivalent to amount present in 30 µg ASV], no Hsc70), and peptides plus poly(I:C) (100 µg each peptide). The therapeutic groups were as follows:

| | |
|---|---|
| Group 1 | 3 µg ASV |
| Group 2 | 10 µg ASV |
| Group 3 | 30 µg ASV |
| Group 4 | 30 µg ASV + 10 µg QS-21 Stimulon ® |
| Group 5 | 30 µg Hsc70 |
| Group 6 | 13.3 µg each peptide + 10 µg QS-21 Stimulon ® |
| Group 7 | 100 µg each peptide + 50 µg poly(I:C) |

Figure 6:
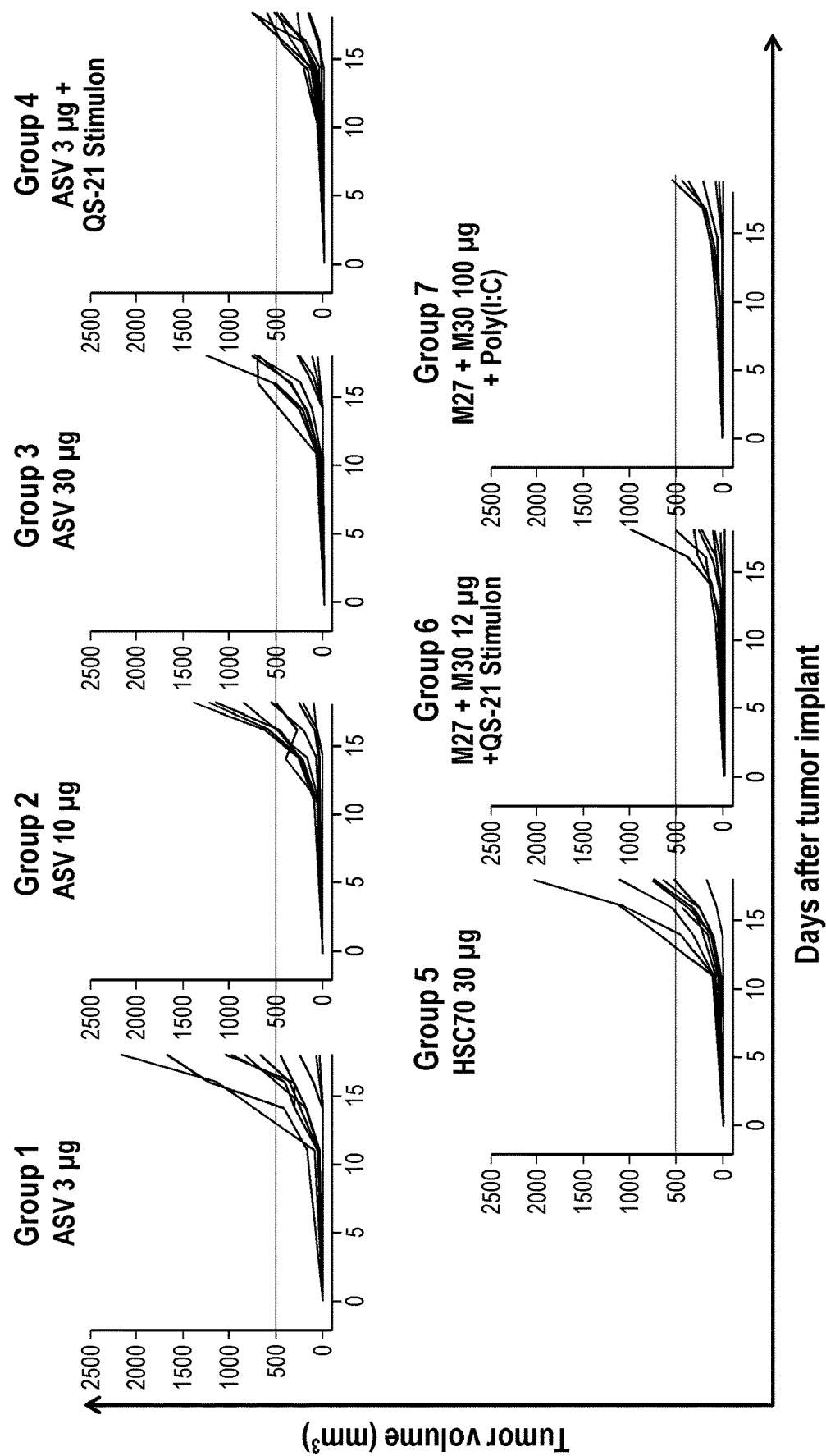
FIG. 6 is a set of tumor growth curves in seven groups of C57BL/6 mice after injection with B16.F10 melanoma cells on Day 0, followed by administration on days 3, 9, and 15 of the following: Groups 1-3: 3 µg, 10 µg, and 30 µg, respectively, of compositions comprising Hsc70 complexed with B-16-M27 and B-16-M30 peptides; Group 4: 30 µg of the same composition as Group 3, with 10 µg QS-21 Stimulon® adjuvant; Group 5: 30 µg Hsc70 alone; Group 6: the peptides alone at an amount equivalent to that in Group 3; and Group 7: 100 µg of each peptide with poly(I:C).
Figure 7:
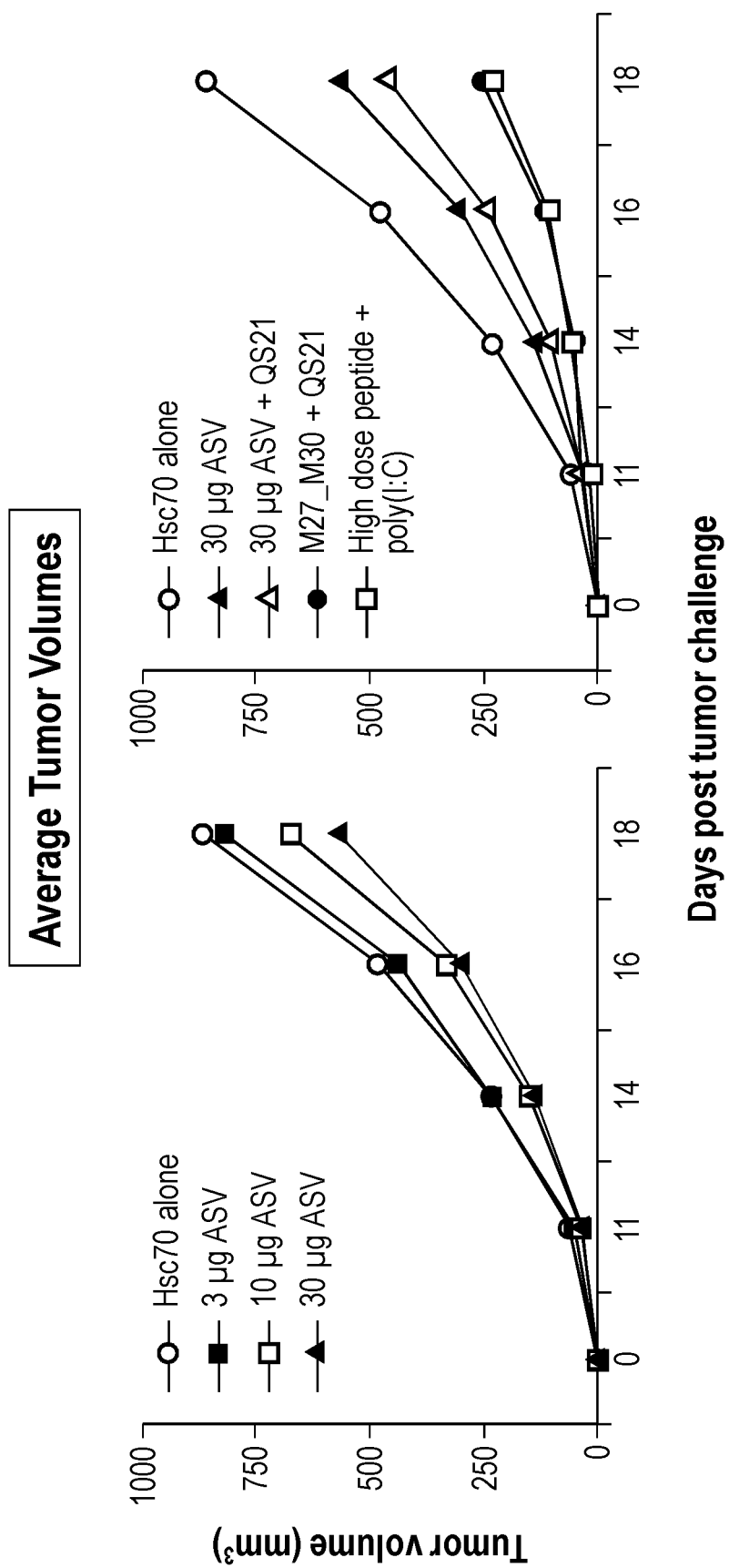
FIG. 7 is a set of graphs showing the average tumor volume after tumor challenge across the groups of mice whose tumor growth curves are depicted in FIG. 6.
Figure 8:
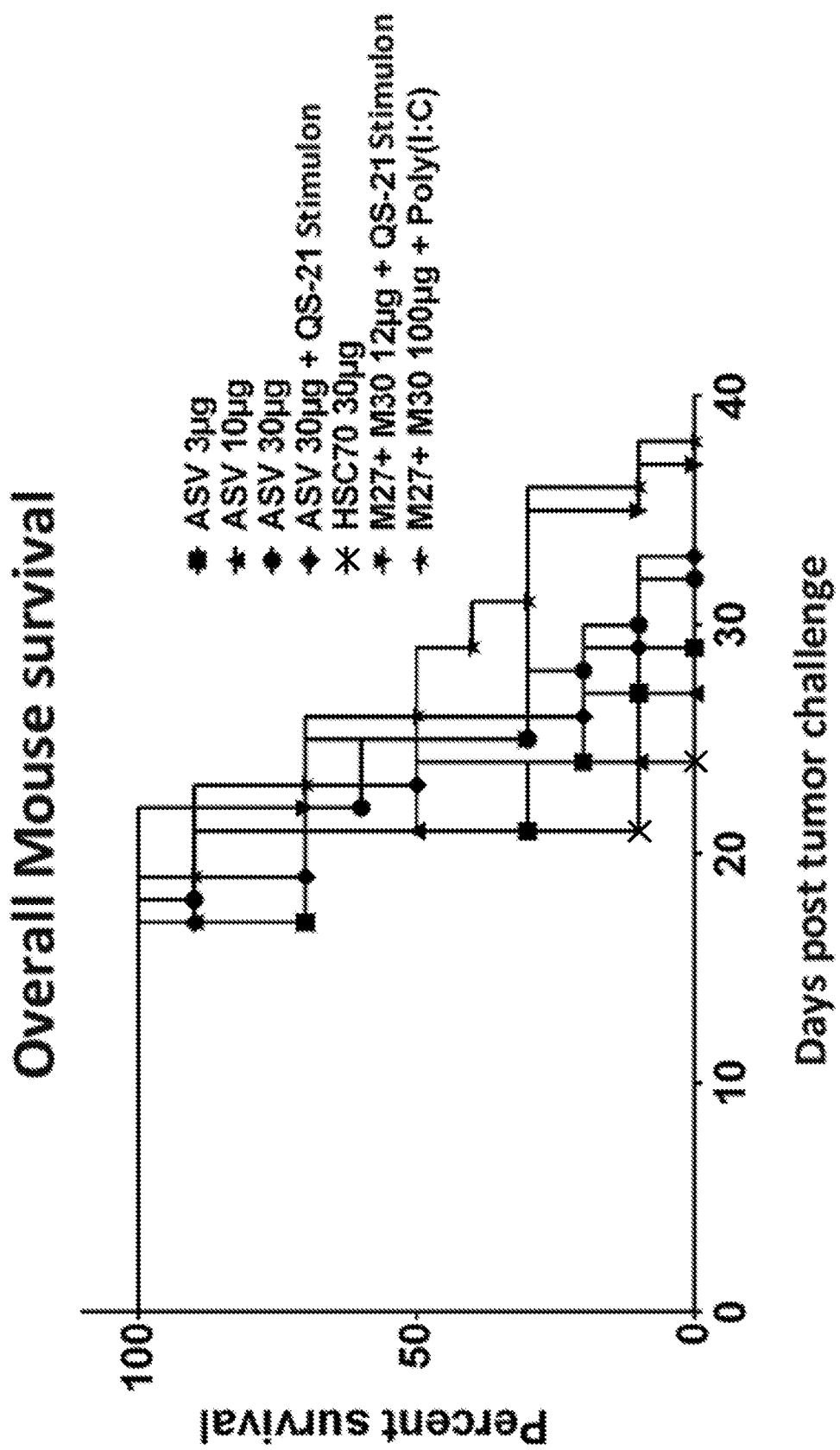
FIG. 8 is a graph showing the percentage survival after tumor challenge in each of the groups of mice whose tumor growth curves are depicted in FIG. 6.

Results:

Therapy with ASV composition at doses of 10 µg, 30 µg, and 30 µg+10 µg QS-21 Stimulon® per mouse provided significant tumor protection relative to therapy with Hsc70 alone (FIG. 6, showing tumor growth up to day 16 after tumor cell injection). Therapy with peptides alone (at the same amount as is present in 30 µg ASV) and QS-21 Stimulon® (group 6) also provided significant protection. The average tumor volume across the mice in each therapeutic group, up to day 18, is shown in FIG. 7. Corresponding effects in survival in the therapeutic groups were observed, with all ASV dosages prolonging survival relative to Hsc70 alone (FIG. 8). Prolonged survival was also observed in the mice treated with peptides alone (at the same amount as is present in 30 µg ASV) and QS-21 Stimulon® (group 6).

Example 11

Analysis of Neo-Epitope Specific T Cell Responses in ASV-Treated Mice

T cell responses to neo-epitopes are analyzed in C57B116 mice following challenge with B16.F10 melanoma tumor cells and treatment with ASV comprising the M27 and M30 B16.F10 neo-epitopes described in Examples 9 and 10. The mice are challenged with tumor cells and administered ASV samples as described in Example 10. At day 22 following tumor challenge, mouse splenocytes are harvested and an ELISPOT assay is performed to probe T cell responses.

Materials:
ACK lysing buffer, Life Technologies, Cat#A10492-01, Lot#1701378
FBS, Gemini Bio-Products, Cat 100-106, Lot A96A00Y
70 micron cell strainer, Corning, Catalogue Number 431751, Lot 111666
PBS, Corning, Catalogue Number 21-040-CV, Lot 21040344
Delicate Operating Scissors 4.75" Straight Sharp/Sharp, Roboz, Catalogue Number RS-6702
BD ELISPOT Plates, Becton, Dickinson & Co, Cat. No. 51-2447KC
BD NA/LE Purified Anti-mouse IFN-γ capture antibody (sterile), Becton, Dickinson & Co, Cat. No. 51-2525KC, Lot. No 5044579, stock concentration 1 mg/mL, diluted 1:200 in sterile PBS for use at a final concentration of 5 µg/mL.
Biotinylated anti-mouse IFN-γ detection antibody, Becton, Dickinson & Co, Cat. No. 51-1818KZ, Lot No. 5044578, stock concentration of 0.5 mg/mL, diluted 1:250 in PBS+10% FBS for a final concentration of 2 µg/mL.
Streptavidin-HRP, Becton, Dickinson & Co, Cat. No. 51-9000209, Lot No. 5163509, 100× stock concentration, diluted 1:100 in PBS+10% FBS for final concentration.
AEC Substrate Set 10 plates, Becton, Dickinson & Co, Cat. No. 551951, Lot No. 6011786, 50× stock concentration; one drop (20 µL) of AEC Chromogen diluted with each 1 mL of AEC Substrate for final working concentration.
Concanavalin A from Canavalia ensiformis cell culture grade (Con A)–5 mg, Sigma Aldrich. Cat. No. C0412-5MG, Lot No. SLBN5209V, diluted to final concentration of 5 µg/mL.
Tween-20, Sigma Aldrich. Cat. No. P5927-500ML, Lot No. 043K01541, diluted in PBS to final concentration of 0.05%.
T cell media (TCM):

| T cell Media (TCM) | Cat# | Supplier | Lot | Volume |
|---|---|---|---|---|
| Corning ™ cellgro ™ RPMI 1640 Medium (Mod.) 1X with L-Glutamine | MT-10-040-CV | Fisher | 10040612 | 500 ml |

| T cell Media (TCM) | Cat# | Supplier | Lot | Volume |
|---|---|---|---|---|
| Gibco ™ Fetal Bovine Serum, Qualified, US Origin, Standard (Sterile-Filtered) | 26-140-079 | Fisher | 1456399 | 55 ml |
| Gibco ™ L-Glutamine (200 mM) (100X) | 25-030-164 | Fisher | 1698934 | 2 ml |
| Gibco ™ Penicillin-Streptomycin (5,000 U/mL) | 15-070-063 | Fisher | 1601706 | 5.5 ml |
| Gibco ™ MEM Non-Essential Amino Acids Solution (100X) | 11-140-050 | Fisher | 1724360 | 3 ml |
| Gibco ™ MEM Amino Acids Solution (50X) | 11-130-051 | Fisher | 1712438 | 3 ml |
| Gibco ™ HEPES (1M) | 15-630-080 | Fisher | 1707767 | 5.5 ml |
| Gibco ™ 2-Mercaptoethanol (55 mM) | 21-985-023 | Fisher | 1733929 | 0.5 ml |

Methods:

At Day −1 (the day before tumor challenge), 50 microliters of the IFN-γ capture antibody is diluted into 10 mL sterile PBS, and 100 microliters of the diluted antibody is added to each well of a 96-well ELISPOT plate. The plate is incubated overnight at 4° C.

The next day (Day 0), the antibody solution is discarded, the plate is washed with complete T-cell media and each well is filled with complete T-cell media (TCM) (containing 10% PBS) to block the plate for at least two hours at room temperature. After two hours, blocking buffer is discarded.

Ten mice are sacrificed and their spleens harvested. The spleens are processed through a 70-micron cell strainer and the red blood cells are lysed using 1 mL ACK lysis buffer per spleen. Complete media is added after a few minutes, the mixture is spun down, and it is resuspended as a single-cell suspension at a concentration of 5 million cells/mL. A naïve mouse is sacrificed and splenocytes are harvested and resuspended in an identical manner. Half of the naïve splenocytes are irradiated for thirty minutes (3000 rads) to function as antigen-presenting cells, and the other half are reserved for use as a control. After irradiation, the cells are resuspended at a concentration of 10 million cells/mL.

The splencoytes from each mouse in complete T-cell media are seeded into each row of the ELISPOT plate with 500,000 cells in 100 microliters TCM. Irradiated splenocytes are partitioned into three groups: the first receives no peptide (negative control), the second is pulsed with 5 μg/mL of peptide M27, and the third is pulsed with 5 μg/mL of peptide M30. These irradiated splenocytes are added at a concentration of 1,000,000 cells in 100 microliters TCM to wells corresponding to each mouse's splenocytes in duplicate for each condition. As a positive control, one well for each mouse is stimulated with Concanavalin A (Con A) at a final concentration of 5 μg/mL. The plate is incubated at 37° C. and 5% CO$_2$ for two days.

After the two-day incubation, the contents of the plate are discarded and the plate is washed twice with 200 μL deionized (DI) water. After washing twice with water, the wells are washed with 200 μL of 0.05% Tween in PBS (PBS-T) three times. After washing, 40 μL of the biotinylated IFN-γ detection antibody is diluted into 10 mL of 10% FBS in PBS, 100 μL of the diluted antibody is added to each well, and the plate is incubated for two hours at room temperature.

After two hours, the antibody solution is discarded and the plate is washed three times with 200 μL of PBS-T. After washing, 100 μL of Strepavidin-HRP is diluted into 9.9 mL of 10% FBS in PBS. 100 μL of the enzyme conjugate solution is added to each well and the plate is incubated for one hour at room temperature.

After the one-hour incubation, the enzyme conjugate solution is discarded and the plate is washed four times with 200 μL of 0.05% Tween in PBS (PBS-T). After the fourth wash, the plate is washed twice with 200 μL of PBS (without Tween). The developer final substrate solution is prepared by diluting ten drops of AEC Chromogen into 10 mL AEC substrate. 100 μL of final substrate solution is added to each well and the reaction is allowed to continue for about 20 minutes (until spots appear, making sure not to overdevelop.) To stop the reaction, the wells are washed with DI water several times. After washing, the plate is thoroughly dried and allowed to dry overnight in the dark. The next day, the plate is analyzed using the CTL ImmunoSpot S6 MacroAnalyzer plate reader (Cellular Technology Limited) and associated software ImmunoSpot 5.1.36.

Example 12

Tumor Protective Activity of Additional ASV Compositions in B16.F10 Melanoma

The therapeutic efficacy of an ASV composition containing 18 predicted neo-epitopes in B16.F10 melanoma was tested in a B16.F10 melanoma mouse model. The 18 peptides were synthesized as long peptides (27mers) (Table 8) and complexed to recombinant human Hsc70 (rhHsc70). The complexes were then tested fof therapeutic efficacy in mice challenged with live B16.F10 tumor cells. A separate cohort of non-tumor bearing C57BL/6 mice was immunized with Hsc70 complexed with two of the 18 peptides (M27 and M309 see Table 8 below) for immunogenicity assessment.

TABLE 8

Synthetic B16.F10 peptides used for in vivo studies

| SEQ ID NO | Amino Acid Sequence * | Name |
|---|---|---|
| 451 | FVVKAYLPVNESFAFTADLRSNTGGQA | M5 |
| 452 | TPPPEEAMPFEFNGPAQGDHSQPPLQV | M12 |
| 453 | VVDRNPQFLDPVLAYLMKGLCEKPLAS | M17 |
| 454 | FRRKAFLHWYTGEAMDEMEFTEAESNM | M20 |
| 455 | PKPDFSQLQRNILPSNPRVTRFHINWD | M22 |
| 456 | TAVITPPTTTTKKARVSTPKPATPSTD | M24 |
| 457 | STANYNTSHLNNDVWQIFENPVDWKEK | M25 |
| 458 | REGVELCPGNKYEMRRHGTTHSLVIHD | M27 |
| 459 | NIEGIDKLTQLKKPFLVNNKINKIENI | M28 |
| 460 | IPSGTTILNCFHDVLSGKLSGGSPGVP | M29 |
| 461 | PSKPSFQEFVDWENVSPELNSTDQPFL | M30 |
| 462 | CGTAFFINFIAIYHHASRAIPFGTMVA | M36 |
| 463 | EFKHIKAFDRTFANNPGPMVVFATPGM | M44 |

TABLE 8-continued

Synthetic B16.F10 peptides used for in vivo studies

| SEQ ID NO | Amino Acid Sequence * | Name |
|---|---|---|
| 464 | ECRITSNFVIPSEYWVEEKEEKQKLIQ | M45 |
| 465 | NHSGLVTFQAFIDVMSRETTDTDTADQ | M46 |
| 466 | GRGHLLGRLAAIVGKQVLLGRKVVVVR | M47 |
| 467 | SHCHWNDLAVIPAGVVHNWDFEPRKVS | M48 |
| 468 | GFSQPLRRLVLHVVSAAQAERLARAEE | M50 |

* The tumor encoded mutated residue at position 14 is indicated in boldface.

Materials and Methods i. Culture of B16.F10 Tumor Cells and Tumor Challenge:

Low passage (P7) B16.F10 cells (ATCC) were harvested from tissue culture, washed in serum-free PBS and re-suspended in PBS at a concentration of $5 \times 10^5$ cells/mL. C57Bl/6 mice shaved on the flank three days earlier were injected subcutaneously in the shaved area with $5 \times 10^4$ cells in 100 µl.

ii. Synthetic B16.F10 Peptides:

Eighteen immunogenic B16.F10 tumor neo-epitopes were synthesized by CS Bio as 27mers with the point mutation centered (Table 8). The peptides were received in powder form and dissolved in 100% DMSO at concentrations ranging from 25-100 mg/ail.

iii. Composition of AutoSynVax Vaccine Surrogate for Treatment of Tumor Bearing Mice:

The frozen stocks of B16.F10 peptides were diluted to working concentration in PBS and then an equimolar pool of the 18 peptides was generated. The peptide pool was mixed with rh-Hsc70 at 1:1 molar ratio of total peptide:protein. Thus, each peptide was represented at 1/18:1 molar ratio. The mixture was incubated for 1 hour at 37° C. and then placed on ice until injection of mice.

iv. Composition of Hsc70-Peptide Complexes for Immunogenicity Studies in Non-Tumor Bearing Mice:

Vaccine material used for immunization of non-tumor bearing mice was prepared by mixing aliquots of rhHsc70 with each of the M27 and M30 B16.F10 peptides at 10:1 molar ratio of peptide:protein. The two complexes were incubated separately for 1 hour at 37° C. and then mixed and placed on ice until injection of mice.

v. Vaccine Administration and Assessment of Tumor Growth Kinetics:

Tumor bearing mice (n=11-12 per group) were treated with 30 or 100 µg (referring to the quantity of Hsc70) AutoSynVax vaccine which was mixed with 10 µg QS-21 Stimulon® adjuvant just prior to injection. As negative controls, two groups of mice were treated with vehicle (PBS) or a mixture of 100 µg Hsc70 and 10 µg QS-21 Stimulon® in the absence of peptides. As a positive control, a group of mice was treated with a pool consisting of a high dose of M22, M27, M30, M44, M48 and M50 peptides (50-100 µg each) mixed with 50 µg poly (I:C) adjuvant. Treatments were administered subcutaneously in 200 µl on the flank diagonally opposite from the tumor on days 3, 9 and 15 after tumor challenge. The size of tumors was assessed using calipers every 2-3 days over 3-4 weeks and tumor volume was plotted as a function of time. Tumor volume was determined using the following formula: $(L \times [W^2]) \div 2$, where L is the length of the longest axis and W is the width of the tumor.

Non-tumor bearing mice were immunized two times at a one week interval with 30 µg Hsc70 complexed to the M27 peptide and the M30 peptide mixed with 10 µg QS-21 Stimulon® adjuvant just prior to injection. Control groups of mice were immunized with (a) 30 µg Hsc70 mixed with 10 µg QS-21 Stimulon® in the absence of peptides or (b) 100 µg each of the two peptides in 50 µg poly (I:C) adjuvant.

vi. Immunogenicity Assessment:

For immunogenicity studies in non-tumor bearing mice, mononuclear cells were prepared from splenocytes after RBC lysis and seeded at $5 \times 10^5$ cells per well of 96-well plate in the presence of 5 µg/ml of each of peptide. As a positive control, splenocytes were stimulated with Concanavalin A (Con A) at a final concentration of 5 µg/mL. The cultures were incubated for 41 hours and MN-γ producing T cells were enumerated using an ELISPOT plate reader (ImmunoSpot 2.0, Cellular Technologies Limited).

Results

Figure 9:
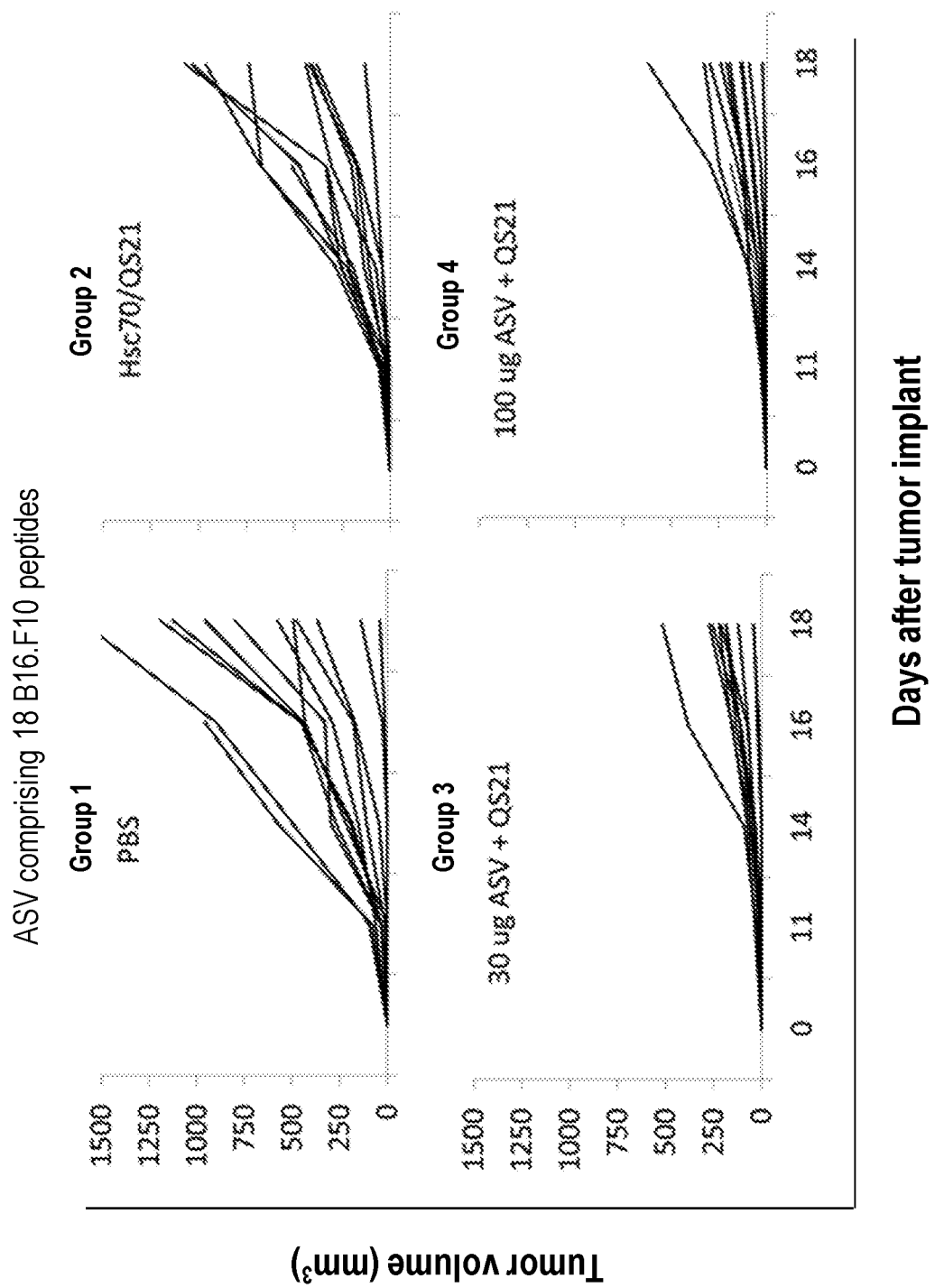
FIG. 9 is a set of tumor growth curves in C57Bl/6 mice (n=11-12/group) injected subcutaneously with $5 \times 10^4$ B16.F10 tumor cells and treated with the indicated agents on days 3, 9 and 15 after tumor challenge. Tumor size was assessed every 2-3 days. Tumor growth kinetics in individual mice are plotted as a function of time. Group 1: PBS alone; Group 2: Hsc70 and QS-21 Stimulon® without peptides; Groups 3 and 4: 30 µg and 100 µg, respectively, of compositions comprising Hsc70 complexed with 18 peptides (M5, M12, M17, M20, M22, M24, M25, M27, M28, M29, M30, M36, M44, M45, M46, M47, M48, and M50) and QS-21 Stimulon® adjuvant.
Figure 10:
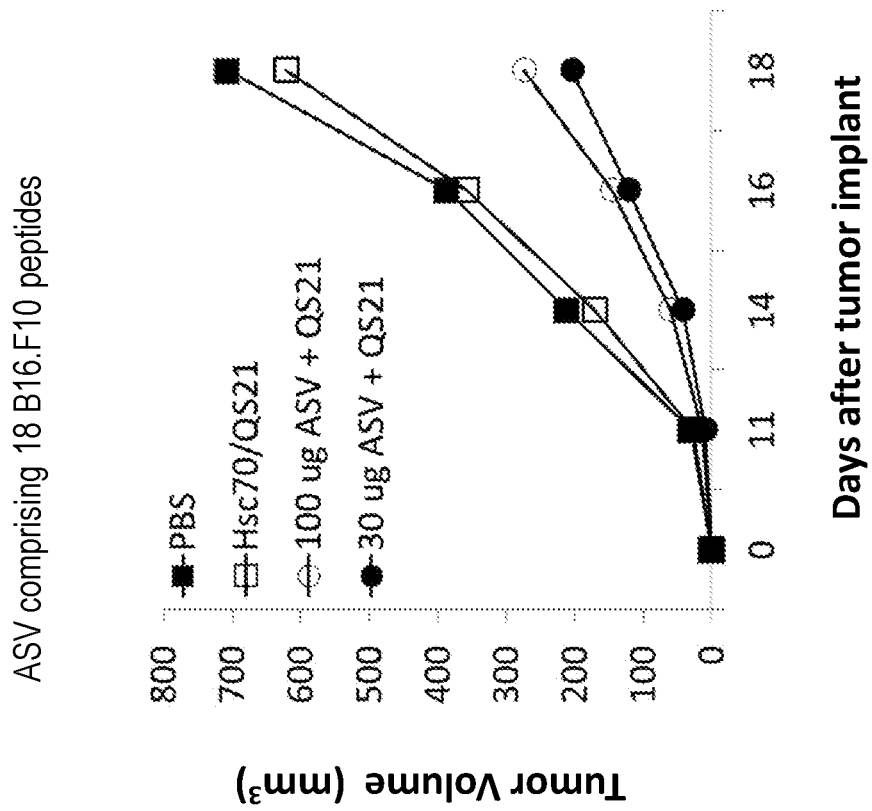
FIG. 10 is a graph showing the mean tumor volume after tumor challenge across the groups of mice whose tumor growth curves are depicted in FIG. 9.

Treatment with 30 or 100 µg AutoSynVax vaccine mixed with QS-21 Stimulon® adjuvant was observed to significantly retard tumor growth in B16.F10 tumor bearing mice when compared with mice treated with PBS or a mixture of Hsc70 and QS-21 Stimulon® without peptides (p<0.01) using linear mixed models testing for a significant treatment-by-time interaction on tumor volume (FIGS. 9 and 10). This degree of tumor growth inhibition achieved was equivalent to that observed with the positive control consisting of the high dose pool of six peptides administered with poly (I:C) adjuvant (not shown). Since only 72 and 240 ng of each of the 18 peptides were present in the 30 and 100 µg AutoSynVax vaccine groups, respectively, compared with 50-100 µg of each of the six peptides administered with poly (I:C), this observation demonstrated the considerable efficiency with which Hsc70 and QS-21 Stimulon® delivered peptides to antigen presenting cells for subsequent processing and presentation to neo-epitope specific T cells.

Figure 11:
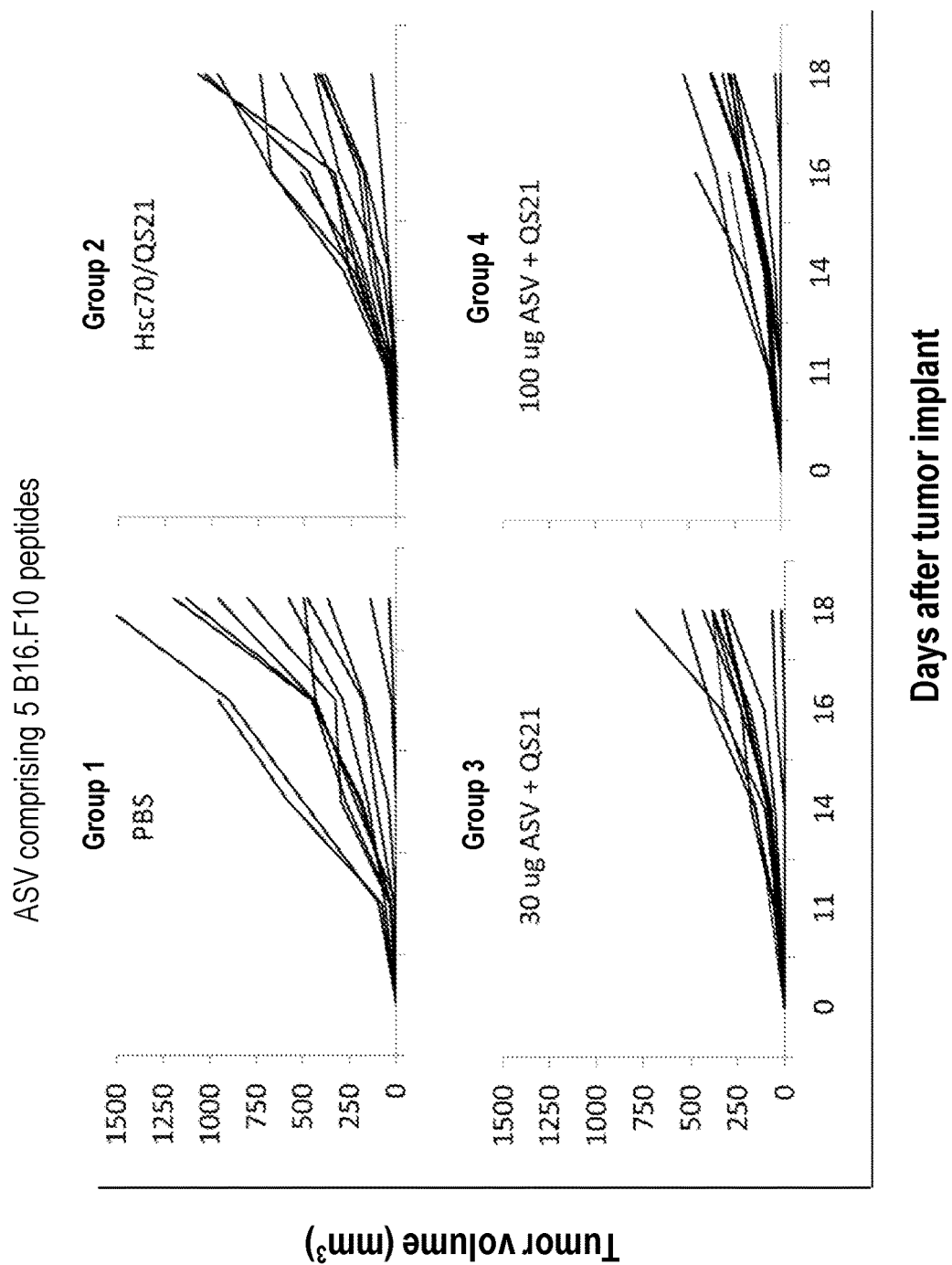
FIG. 11 is a set of tumor growth curves in C57131/6 mice (n=11-12/group) injected subcutaneously with $5 \times 10^4$ B16.F10 tumor cells and treated with the indicated agents on days 3, 9 and 15 after tumor challenge. Tumor size was assessed every 2-3 days. Tumor growth kinetics in individual mice are plotted as a function of time. Group 1: PBS alone; Group 2: Hsc70 and QS-21 Stimulon® without peptides; Groups 3 and 4: 30 µg and 100 µg, respectively, of compositions comprising Hsc70 complexed with 5 peptides (M22, M27, M44, M48, and M50) and QS-21 Stimulon® adjuvant.
Figure 12:
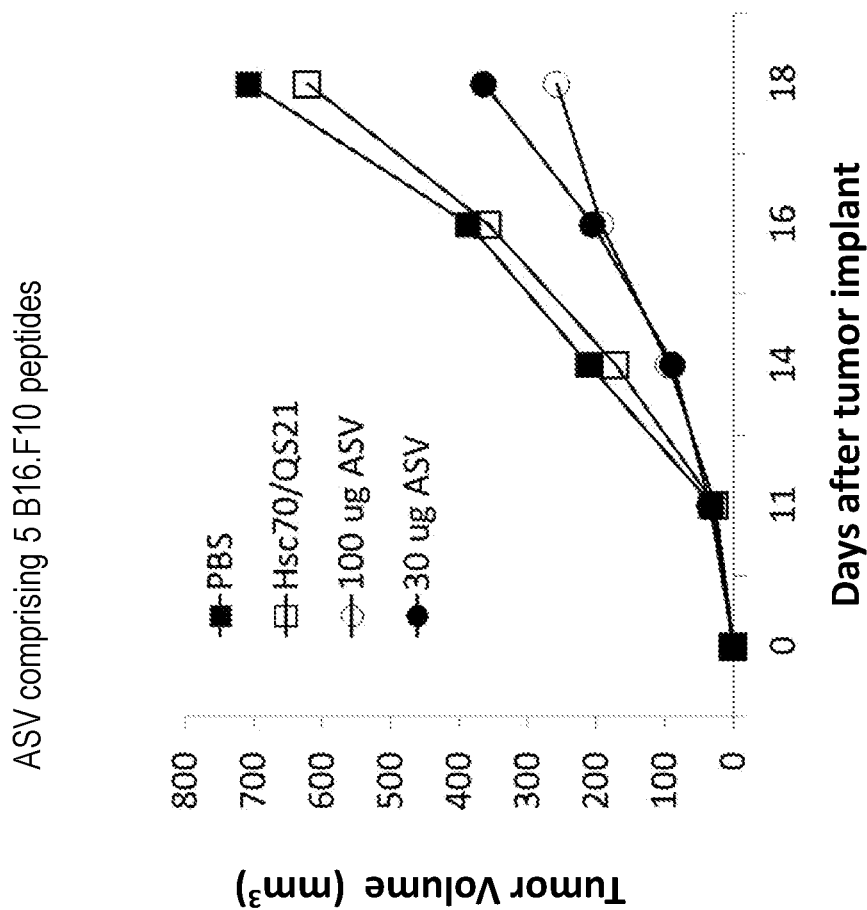
FIG. 12 is a graph showing the mean tumor volume after tumor challenge across the groups of mice whose tumor growth curves are depicted in FIG. 11.

An ASV composition containing five of the 18 peptides, namely M22, M27, M44, M48, and M50, was synthesized and tested in B16.F10 melanoma in a similar study as described above. Similar to the 18-peptide ASV composition, the 5-peptide ASV composition (30 or 100 µg), when administered in combination with QS-21 Stimulon® adjuvant, slowed tumor growth in B16.F10 tumor bearing mice when compared with mice treated with PBS or a mixture of Hsc70 and QS-21 Stimulon® without peptides (FIGS. 11 and 12).

Figure 13:
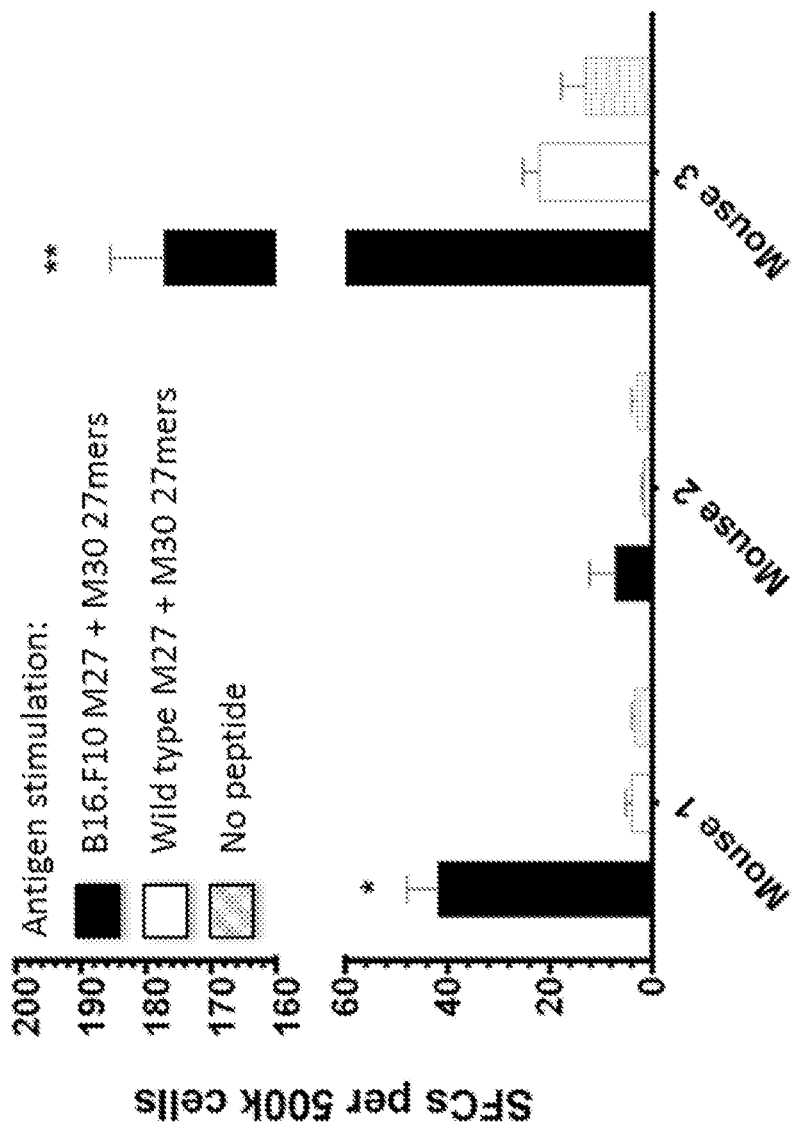
FIG. 13 is a bar graph showing the responses of splenocytes from three mice immunized with Hsc70-M27/M30 peptide complexes in combination with QS-21 Stimulon® adjuvant and cultured with the M27 and M30 B16.F10 27mers, their wild-type counterparts or no peptide. The mean values of IFN-γ spot forming cells (SFCs) per $5 \times 10^{-5}$ splenocytes within each group are shown, Each bar represents technical triplicates from a representative mouse. Statistical significance is measured using a 2-tailed student's t-test (* denotes p<0.05; ** denotes p<0.005).

For the immunogenicity assessment in non-tumor bearing mice, three mice from the Hsc70-M27/M30 B16.F10 peptide complex+QS-21 Stimulon® vaccine group were sacrificed one week after the second immunization to assess whether T cell responses to the peptides could be detected using the IFN-γ ELISPOT assay. A significant response was detected in two of three mice (FIG. 13). A response to the positive control vaccine (M27/M30 peptides in poly (I:C) adjuvant) was also observed in two of three mice while no response was observed in mice immunized with the mixture of Hsc70/QS-21 Stimulon® without peptides (not shown).

Example 13

Figure 14:
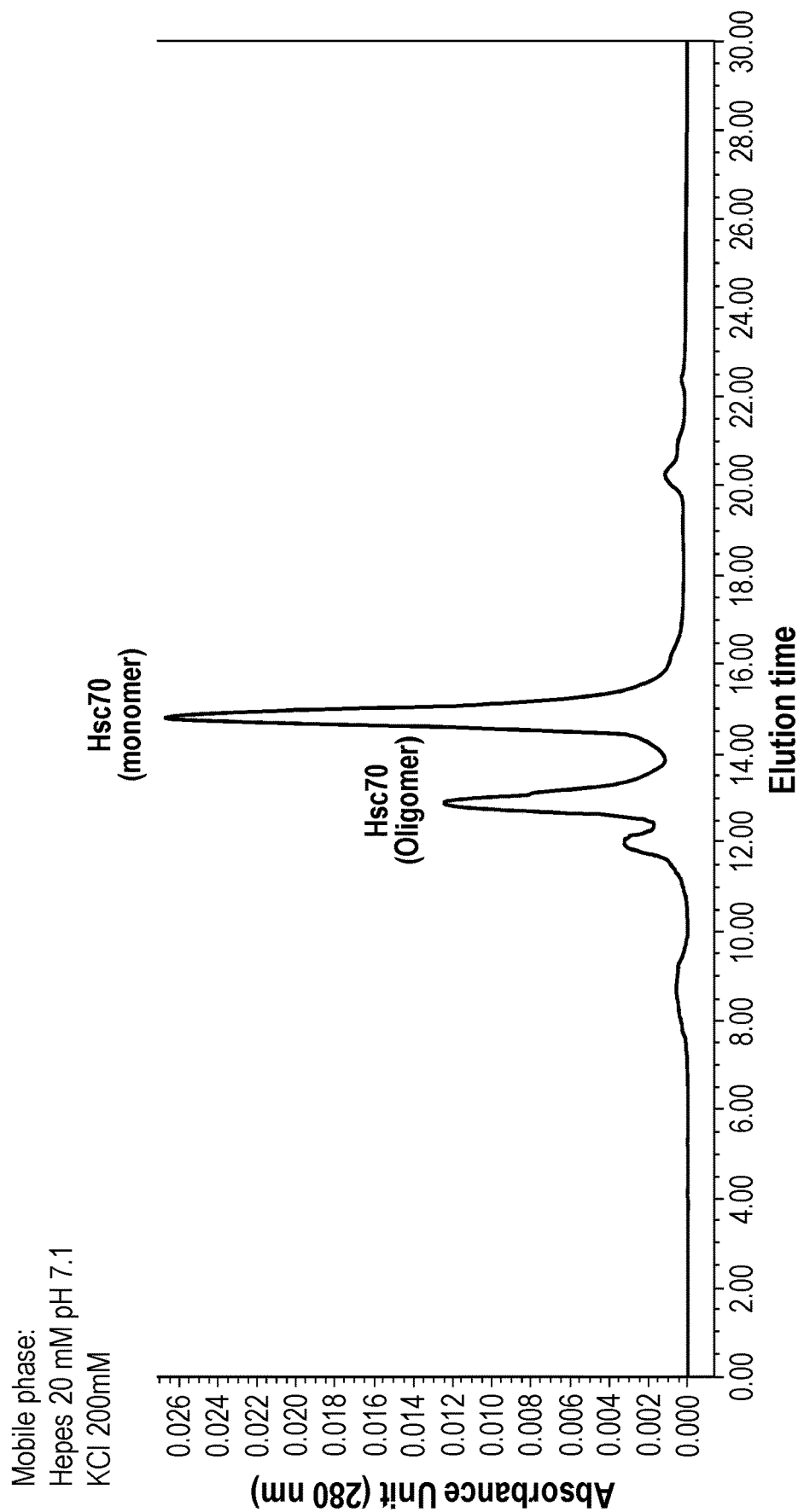
FIG. 14 is a size-exclusion chromatography (SEC) chromatogram of a sample of Hsc70.
Figure 15:
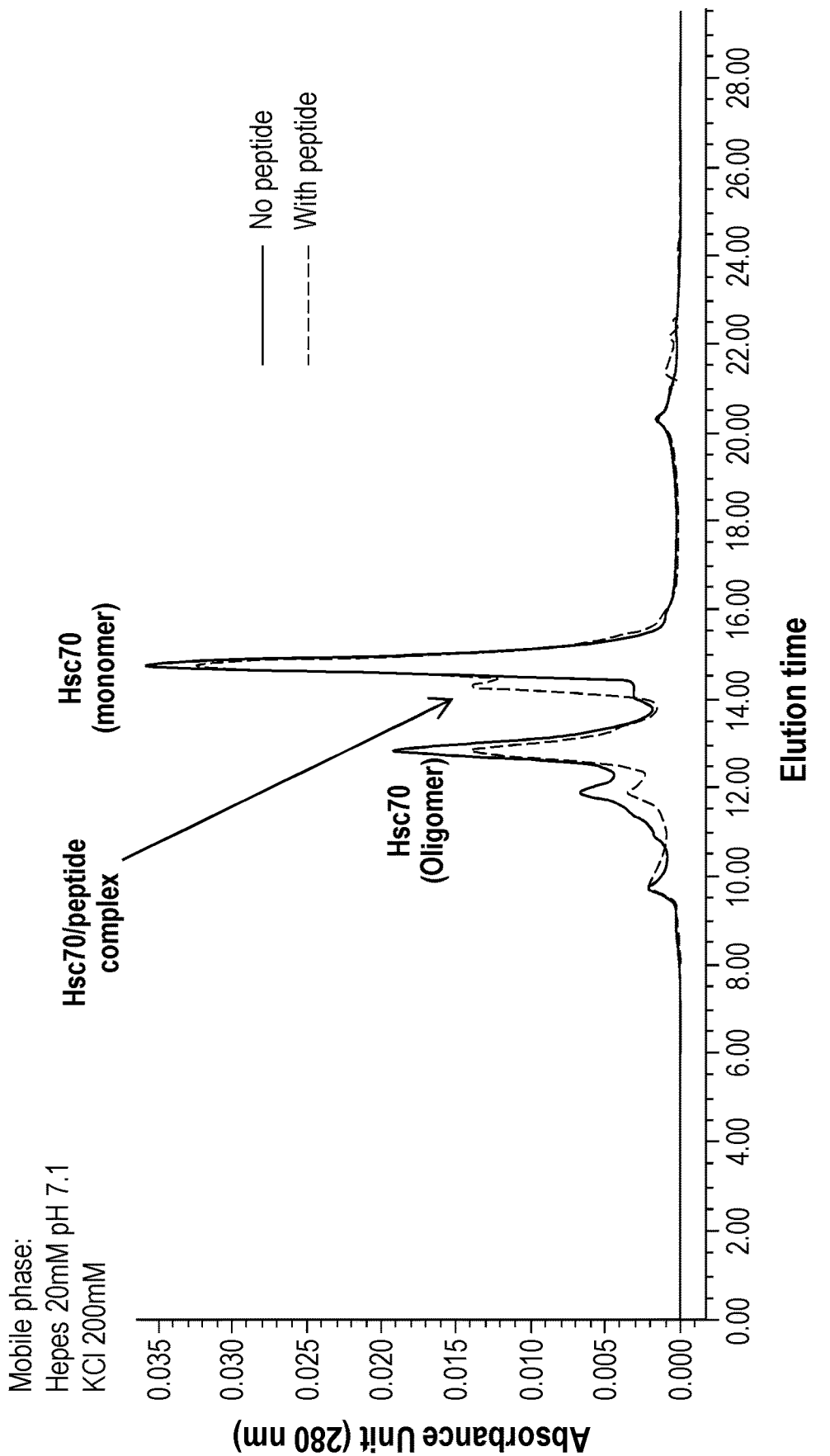
FIG. 15 is a set of superimposed SEC chromatograms of Hsc70 (solid line) and of Hsc70 combined with a substrate peptide (dashed line).

Investigation of Hsc70-Peptide Complex Formation by Size-Exclusion Chromatography Hsc70-peptide complex formation was examined in vitro using size exclusion chromatography (SEC). Hsc70 resolves in two main peaks on a size exclusion column, with one peak corresponding to its monomeric form and the other peak to an oligomeric form (FIG. 14). Hsc70 undergoes a conformational change upon binding peptide (Zhuravleva and Gierasch, P.N.A.S. 112[22]:E2865-73 [2015]), resulting in the appearance of a new peak on the SEC chromatogram that corresponds to the peptide-bound form (FIG. 15). By measuring the surface area of each of the peaks corresponding to the forms of Hsc70 on a chromatogram, the percentage of Hsc70 complexed with a peptide can be determined. The effect of the molar ratio of Hsc70 to peptide on Hsc70-peptide complex formation was determined by combining Hsc70 and a test peptide at Hsc70/peptide molar ratios of 1:4, 1:10, 1:20, and 1:50, and then resolving the resulting mixtures by SEC to determine the extent of complex formation. The peptide used in these experiments was the immunogenic peptide B16-M27 ("M27"), containing a B16-F10 melanoma-specific mutation, as described in Kreiter et al., Nature 520(7549):692-6 (2015) (also described in Examples 9-11). The effect on complex formation of appending a high affinity Hsc70-binding peptide sequence to a chicken ovalbumin peptide having the amino acid sequence SIINFEKL (SEQ ID NO:448), that is highly immunogenic in mice (Zehn et al, Nature 458:211-214 [12 March, 2009]) was also tested. The high affinity Hsc70 binding sequence, NLLRLTG (SEQ ID NO:439) was appended to either the C- or N-terminus of the ovalbumin peptide, and was linked to the ovalbumin peptide by a linker having the sequence FFRK (SEQ ID NO:447), as disclosed in U.S. Pat. No. 7,309,491.

Materials and Methods:

Standard size exclusion chromatography was carried out using 7 μM of recombinant human Hsc70 (Genbank Accession No. P11142.1) (Biomay AG) in a reaction buffer containing 20 mM HEPES and 200 mM KCL in a final volume of 50 μl. Reactions were incubated at 37° C. for 1 or 2 hours and centrifuged 2 min at 13000 RPM. Reaction products (10 μg) were resolved on a TSKgel SuperSW3000, 4 μm particle size, 25 nm pore size gel filtration chromatography column (Tosoh Bioscience). For reactions containing peptide, peptide was included in the reaction mixtures at Hsc70:peptide molar ratios of 1:4, 1:10, 1:20, and 1:50. The percentage of Hsc70 complexed with peptide in each reaction mixture was calculated by measuring the surface area of the appropriate peak.

Figure 16:
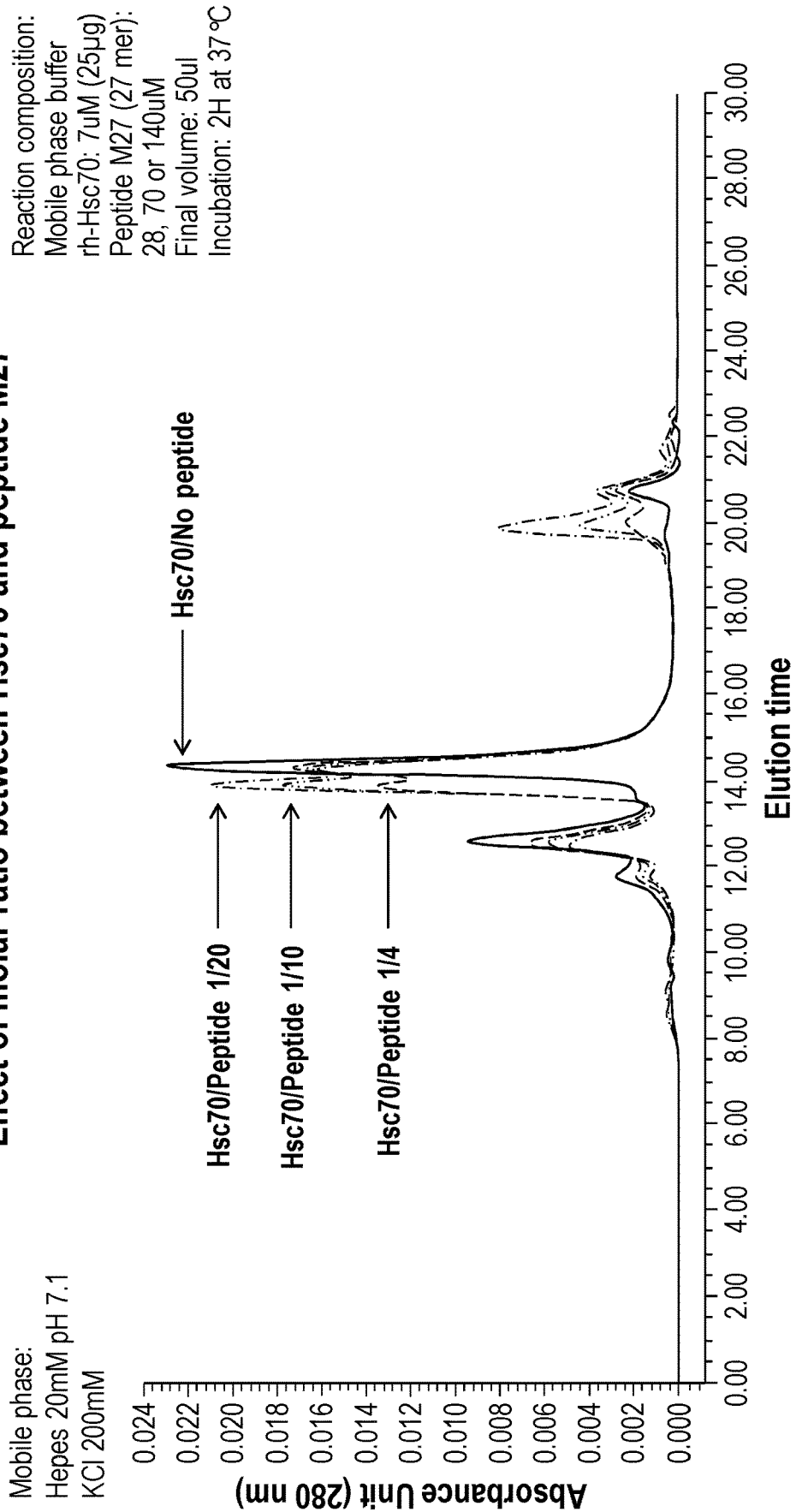
FIG. 16 is a set of superimposed SEC chromatograms of Hsc70 (solid line) and Hsc70-M27-peptide complexes at Hsc70:peptide molar ratios of 1:4 (dashed line), 1:10 (dotted line), and 1:20 (dashed and dotted line).
Figure 17:
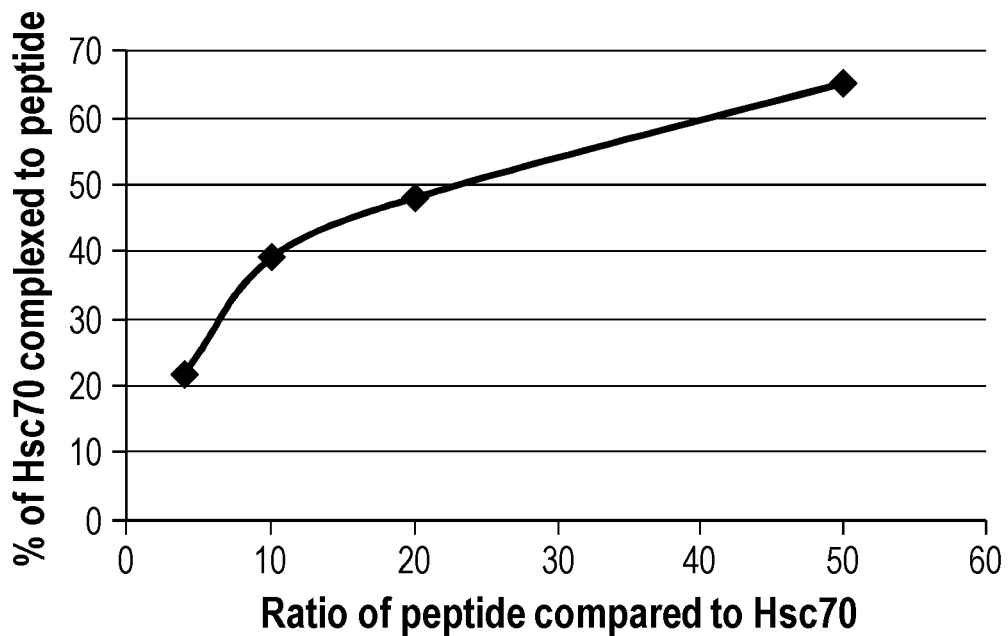
FIG. 17 is a plot of the percentage of Hsc70 that is complexed to M27 peptide as a function of Hsc70:peptide molar ratio.
Figure 18:
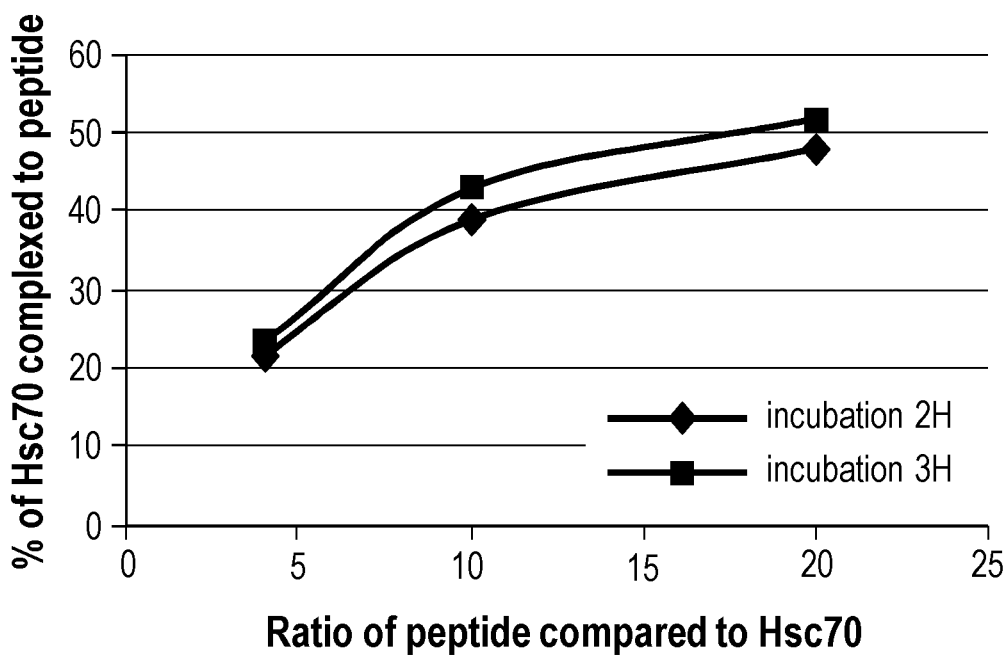
FIG. 18 is a plot of the percentage of Hsc70 that is complexed to M27 peptide as a function of Hsc70:peptide molar ratio after incubation for either 2 or 3 hours at 37 degrees Celsius.

Results:

The percentage of Hsc70 complexed with M27 peptide increased with increasing molar ratio of M27 peptide to Hsc70, as shown in FIG. 16. At an Hsc70:peptide molar ratio of 1:4, only 20% of Hsc70 is bound to M27 peptide, but at a ratio of 1:10, approximately 40% of Hsc70 is complexed. The proportion of Hsc70 complexed progressively increased further at Hsc70:peptide molar ratios of 1:20 (approximately 50%) and 1:50 (approximately 65%) (FIG. 17). When the incubation time was increased from 2 to 3 hours, only a minor increase in the extent of complex formation was observed (FIG. 18).

Figure 19:
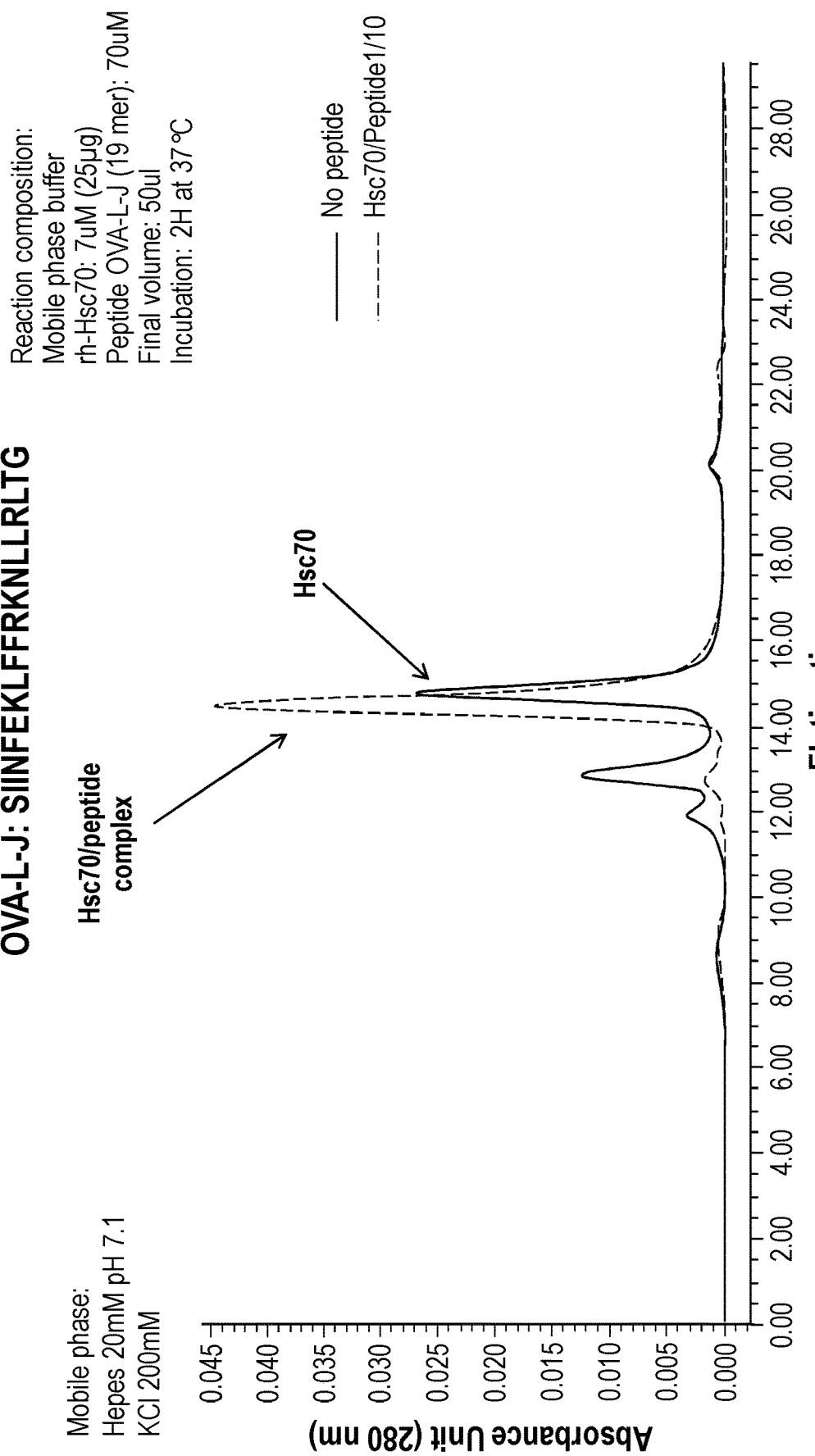
FIG. 19 is a set of superimposed SEC chromatograms of Hsc70 (solid line) and Hsc70 combined at a 1:10 Hsc70:peptide molar ratio with a chicken ovalbumin peptide (SIINFEKL (SEQ ID NO:448)) fused at its C-terminus, via a peptide linker (FFRK (SEQ ID NO:447)), to a high affinity Hsc70 binding sequence (NLLRLTG SEQ ID NO:434) (dashed line).
Figure 20:
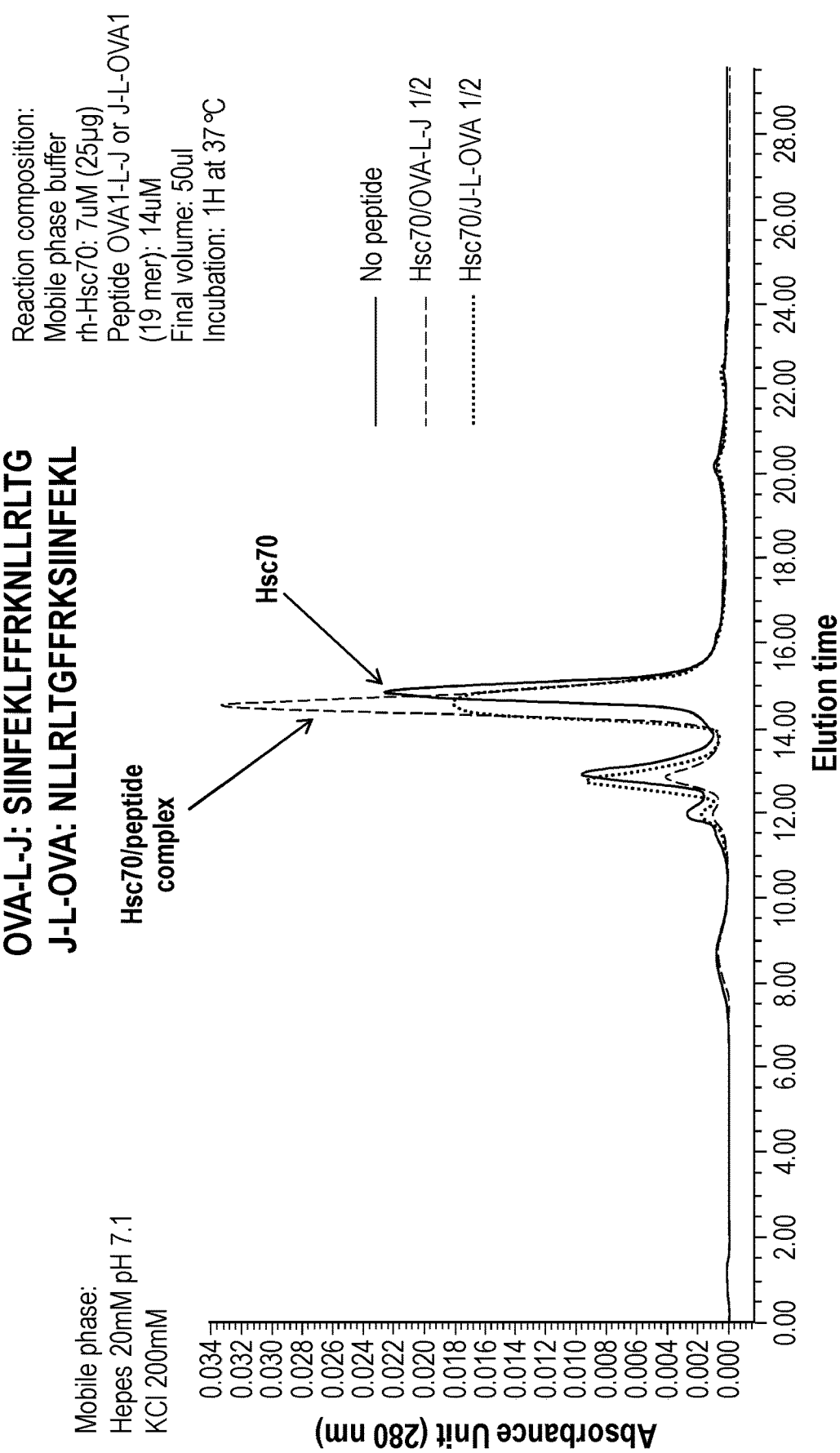
FIG. 20 is a set of superimposed SEC chromatograms of Hsc70 (solid line) and Hsc70 combined at a 1:2 Hsc70:peptide molar ratio with either a chicken ovalbumin peptide (SIINFEKL (SEQ ID NO:448)) fused at its C-terminus, via a peptide linker (FFRK (SEQ ID NO:447)), to a high affinity Hsc70 binding sequence (NLLRLTG (SEQ ID NO: 439)) (dashed line) or the same chicken ovalbumin peptide fused at its N-terminus, via the same peptide linker, to the high affinity Hsc70 binding sequence (dotted line).

When complex formation was analyzed between Hsc70 and the ovalbumin peptide SIINFEKL (SEQ ID NO:448) having the high affinity Hsc70 binding peptide sequence NLLRLTG (SEQ ID NO:439) fused to its C-terminus via the linker FFRK (SEQ ID NO:447), over 90% of Hsc70 was complexed to the peptide (FIG. 19; tested at Hsc70:peptide molar ratio of 1:10; full-length peptide sequence is SIINFEKLFFRKNLLRLTG (SEQ ID NO:449)). The comparative effect of placing the high affinity Hsc70 binding sequence at the N- and C-terminus of the ovalbumin peptide, linked via the FFRK (SEQ ID NO:447) linker in both cases, was also tested. The extent of complex formation was significantly greater with NLLRLTG (SEQ ID NO:439) positioned at the C-terminus as compared to the N-terminus (FIG. 20, showing chromatograms of reaction mixtures with Hsc70:peptide at a molar ratio of 1:2; same result observed at a ratio of 1:5). The sequence of the test peptide with the C-terminal high affinity Hsc70 binding sequence was SIINFEKLFFRKNLLRLTG (SEQ ID NO:449), and the sequence of the test peptide with N-terminal high affinity Hsc70 binding sequence was NLLRLTGFFRKSIINFEKL (SEQ ID NO:450).

Example 14

ASV Compositions Containing High Affinity Hsc70 Binding Peptide Sequence

In this example, ASV compositions containing antigenic peptides linked to a high affinity Hsc70 binding sequence were generated.

Materials and Methods i. B16.F10 Tumor Neo-Epitopes and their Modification with a High Affinity Hsc70 Binding Peptide:

The following four peptides were synthesized to 95% purity (Boston Open Labs, Cambridge, Mass.), representing tumor neo-epitopes of the B16.F10 melanoma cell line, alternatively modified at their C-termini with the addition of a linker sequence FFRK (SEQ ID NO:447) and a high affinity Hsc70 binding peptide NLLRLTG (SEQ ID NO: 439):

M27:
                                               (SEQ ID NO: 458)
REGVELCPGNKYEMRRHGTTHSLVIHD

M30:
                                               (SEQ ID NO: 461)
PSKRSFQEFVDWENVSPELNSTDQPFL

M27-Jav:
                                               (SEQ ID NO: 469)
REGVELCPGNKYEMRRHGTTHSLVIHDFFRKNLLRLTG

M30-Jav:
                                               (SEQ ID NO: 470)
PSKPSFQEFVDWENVSPELNSTDQPFLFFRKNLLRLTG ii. Generation of Hsc70-M27/M30 Peptide Complexes:

The peptides listed above were individually incubated with Hsc70 in PBS at 37° C. f hour to form non-covalent Hsc70-peptide complexes. For M27 and M30, the peptides were added to Hsc70 at a 20:1 molar excess (peptide:Hsc70) while for M27-Jav and M30-Jav, the peptides were added at a 4:1 molar excess. After incubation, the mixtures were diluted 10 times in PBS at 4° C. and concentrated using a 30 kDa MW cut off Millipore® Amicon® centrifugal filter to separate Hsc70-peptide complexes from free, uncomplexed peptide. The retained complexes Hsc70-M27 and Hsc70-M30 were pooled and subsequently analyzed by size exclusion chromatography (SEC) to quantify the proportion of Hsc70 molecules loaded with peptide. Forty-three (43) percent of the Hsc70 molecules were observed to be loaded with the M27/M30 peptides. The same pooling, filtration and SEC analysis steps were followed for the Hsc70-M27-Jay and Hsc70-M30-Jav complexes with the observation that 73% of the Hsc70 molecules were loaded with the peptides.

iii. Vaccine Administration and Immunogenicity Assessment:

C57Bl/6 mice (n=10/group) were inoculated subcutaneously with 5×10⁴ B16.F10 tumor cells in the shaved flank and treated with the following vaccine materials on days 3, 9 and 15 after tumor challenge:

Group 1: 100 µg M27+100 µg M30 mixed with 5 µg QS-21 Stimulon®+5 µg MPL (InvivoGen, San Diego, Calif.) adjuvants Group 2: 30 µg Hsc70 complexed to M27-Jav/M30-Jav Group 3: 30 µg Hsc70 complexed to M27-Jav/M30-Jav mixed with 5 µg QS-21 Stimulon®+5 µg MPL adjuvants Group 4: 30 µg Hsc70 complexed to M27/M30

Group 5: 2.6 µg M27-Jav/M30-Jav (1.3 µg each peptide)

On day 22 after tumor challenge, three mice from each of the above five groups were euthanized and splenocytes were harvested for vaccine immunogenicity assessment. Splenocytes from a naïve C57BL/6 mouse were also harvested as a negative control group in the immunogenicity study.

For the immunogenicity study, mononuclear cells were prepared from splenocytes after RBC lysis and seeded at 5×10⁵ cells per well of 96-well plate in the presence of 5 µg/ml of each of the following peptides.

```
M27:
                                    (SEQ ID NO: 458)
REGVELCPGNKYEMRRHGTTHSLVIHD

M30:
                                    (SEQ ID NO: 461)
PSKPSFQEFVDWENVSPELNSTDQPFL

Wild type M27:
                                    (SEQ ID NO: 471)
REGVELCPGNKYETRRHGTTHSLVIHD Wild type M30:
                                    (SEQ ID NO: 472)
PSKPSFQEFVDWEKVSPELNSTDQPFL
```

As a positive control, splenocytes were stimulated with Concanavalin A (Con A) at a final concentration of 10 µg/mL. The cultures were incubated for 41 hours and IFN-γ producing T cells were enumerated using an ELISPOT plate reader (ImmunoSpot 2.0, Cellular Technologies Limited).

Results

Figure 21:
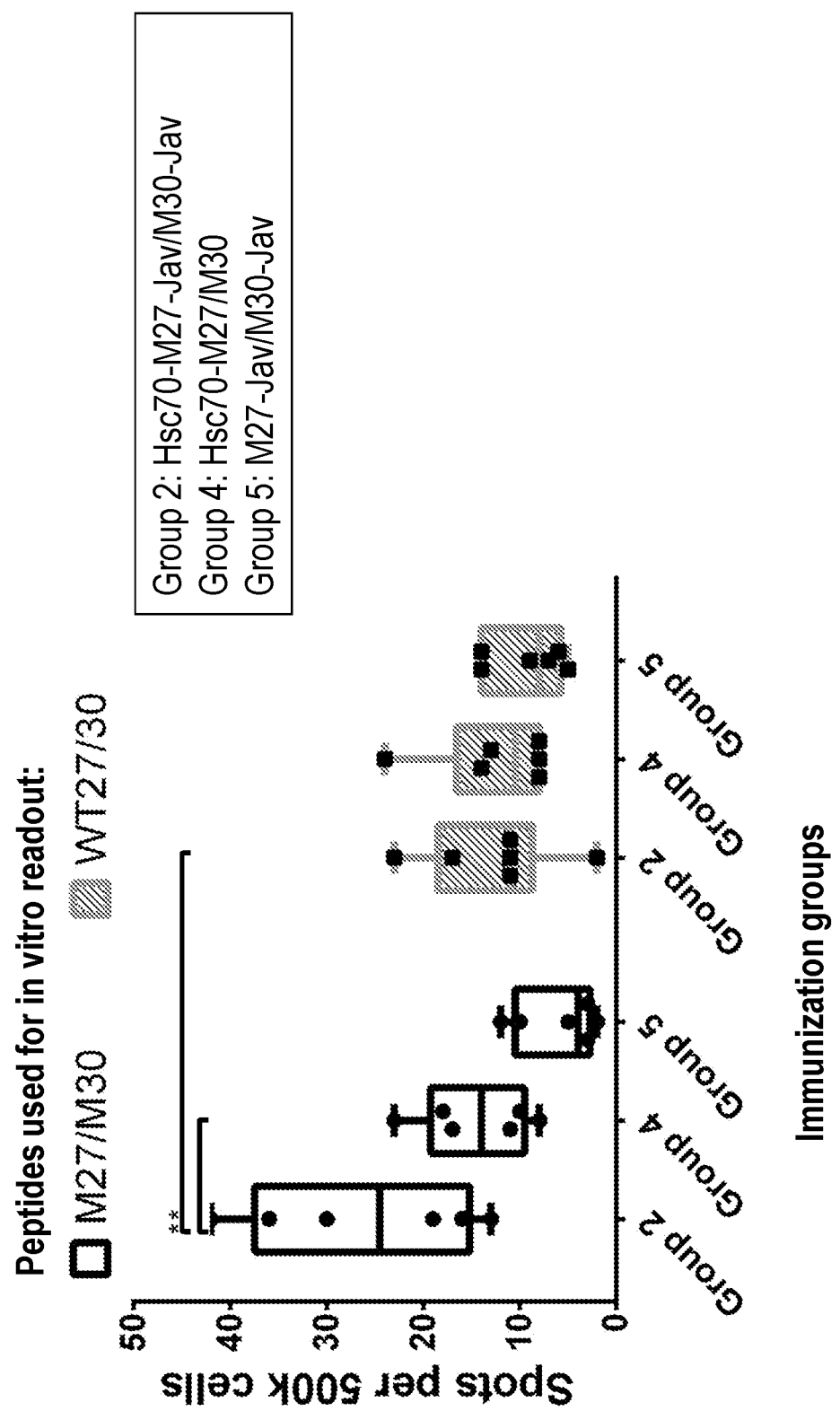
FIG. 21 is a graph showing IFN-γ responses of splenocytes isolated from mice immunized with Hsc70-peptide complexes or peptides alone. The data are displayed using box-and-whisker plots in which the first and third quartiles are at the ends of the box, the median is indicated with a horizontal line in the interior of the box, and the maximum and minimum are at the ends of the whiskers. Each dot represents a single well of the ELISPOT plate onto which splenocytes of each of three mice were seeded in duplicate.
**Statistically significant using a two-way ANOVA test (p-value<0.05).

As shown in FIG. 21, splenocytes isolated from mice immunized with 30 µg Hsc70 complexed to M27-Jav/M30-Jav (Group 2) secreted significantly more IFN-γ upon exposure to a mixture of the mutant M27 and M30 peptides compared to exposure to the same peptides containing wild type residues at position 14 (p-value<0.05 by two-way ANOVA). Addition of QS-21 Stimulon® and MPL adjuvants to this Hsc70-peptide complex (Group 3) did not result in enhancement of the response (not shown). Immunization with a high dose of the M27 and M30 mutant peptides in QS-21 Stimulon®/MPL adjuvants (Group 1) elicited significant IFN-γ production (not shown).

IFN-γ secretion by splenocytes of mice immunized with 30 µg Hsc70 complexed to M27-Jav/M30-Jav (Group 2) and stimulated with the mutant M27 and M30 peptides was significantly greater than the response of splenocytes of mice immunized with 30 µg Hsc70 complexed to M27/M30 peptides that did not contain the high affinity HSP70 binding sequence (Group 4) (p-value<0.05 by two-way ANOVA). These data demonstrate enhanced immunogenicity of complexes of Hsc70 and tumor neo-epitopes containing a high affinity Hsc70 binding domain relative to complexes of Hsc70 and tumor neo-epitopes lacking such a high affinity Hsc70 binding domain.

Minimal IFN-γ secretion was observed in mice immunized with the M27-Jav and M30-Jav peptides in the absence of Hsc70 (Group 5) Similarly, IFN-γ secretion was not observed from splenocytes of naïve (unimmunized) mice exposed to the M27/M30 mutant or wild type peptides.

It is notable that complexes between Hsc70 and the M27/M30 peptides not containing a high affinity Hsc70 binding domain did not elicit an antigen-specific immune response in this study (FIG. 21) while such complexes did in an earlier experiment (FIG. 13). Without being bound by the theory, the difference may be explained by the presence of QS-21 Stimulon® adjuvant in the earlier study but not in the present one.

Example 15

ASV Compositions Containing Phosphopeptide Epitopes

Four peptides (Table 9) containing a phosphorylated serine residue were synthesized to 95% purity (GenScript, Cambridge, Mass.). The peptides comprise HLA-A*02:01 binding epitopes of the CDC25 or IRS-2 antigen modified at either their C-termini or N-termini with the addition of a linker sequence FFRK (SEQ ID NO:447) and a high affinity HSP binding peptide sequence NLLRLTG (SEQ ID NO: 439). These peptides were individually incubated with Hsc70 in PBS at 37° C. for 1 hour at a 4:1 molar excess (peptide:Hsc70) to form non-covalent Hsc70-peptide complexes. After incubation, the complexes were analyzed by SEC to quantify the proportion of Hsc70 molecules loaded with peptide. The results are shown in Table 9.

TABLE 9

Synthetic phosphopeptide epitopes linked to high affinity HSP binding sequence

| Peptide sequence | SEQ ID NO | Percentage of Hsc70 loaded with peptide |
|---|---|---|
| CDC25 antigen (HLA-A*02:01 binding epitope underlined): | | |
| NLLRLTGFFRKGLLG{pSer}PVRA | 473 | 41 |
| GLLG{pSer}PVRAFFRKNLLRLTG | 474 | 74 |
| IRS-2 antigen (HLA-A*02:01 binding epitope underlined): | | |
| NLLRLTGFFRKRVA{pSer}PTSGV | 475 | 34 |
| RVA{pSer}PTSGVFFRKNLLRLTG | 476 | 75 |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

What is claimed:

1. A composition comprising at least two different complexes of a purified stress protein bound to an antigenic peptide, wherein each complex comprises a different antigenic peptide comprising:
   a) an N-terminal portion of 21-31 amino acids in length comprising at least one mutant MHC binding epitope from a cancer cell; and
   b) a C-terminal portion of 11 amino acids in length comprising a heat shock protein binding sequence, wherein the amino acid sequence of the C-terminal portion consists of the amino acid sequence of SEQ ID NO: 477;
   wherein at least one of the antigenic peptides in the composition comprises a tumor-specific missense mutation.

2. The composition of claim 1, wherein the N-terminal portion of at least one of the antigenic peptides is 27-31 amino acids in length.

3. The composition of claim 1, wherein the N-terminal portion of at least one of the antigenic peptides is 27-31 amino acids in length and the tumor-specific missense mutation is at amino position 11, 12, 13, 14, 15, 16, 17, 18, or 19 of the N-terminal portion.

4. The composition of claim 1, wherein the stress protein is selected from the group consisting of hsc70, hsp70, hsp90, hsp110, grp170, gp96, calreticulin, and combinations of two or more thereof.

5. The composition of claim 4, wherein the stress protein is hsc70.

6. The composition of claim 1, wherein the amount of stress protein in the composition is about 10 µg-600 µg.

7. The composition of claim 6, wherein the amount of stress protein in the composition is about 240 µg.

8. The composition of claim 1, wherein the molar ratio of stress protein to antigenic peptide in the composition is selected from the group consisting of about 1:1, 1:2, 1:4, 1:5, 1:10, 1:20, and 1:50.

9. The composition of claim 8, wherein the molar ratio of stress protein to antigenic peptide in the composition is about 1:1.

10. The composition of claim 1, wherein the composition comprises at least 5 different antigenic peptides.

11. The composition of claim 1, wherein the composition comprises at least 10 different antigenic peptides.

12. The composition of claim 1, wherein the composition comprises at least 20 different antigenic peptides.

13. The composition of claim 1, further comprising an adjuvant.

14. The composition of claim 13, wherein the adjuvant comprises a saponin or an immunostimulatory nucleic acid.

15. The composition of claim 13, wherein the adjuvant comprises QS-21.

16. The composition of claim 13, wherein the adjuvant comprises about 1 µg-200 µg of QS-21.

17. The composition of claim 13, wherein the adjuvant comprises about 10 µg, 25 µg, or 50 µg of QS-21.

18. The composition of claim 13, wherein the adjuvant comprises about 50 µg of QS-21.

19. The composition of claim 18, wherein the amount of stress protein in the composition is about 240 pg.

20. The composition of claim 19, wherein the molar ratio of stress protein to antigenic peptide in the composition is about 1:1.

21. A method of inducing a T cell response in a subject to a mutant MHC binding epitope from a cancer cell, the method comprising administering to the subject an effective amount of the composition of claim 1, such that a T cell response to at least one mutant MHC binding epitope in the composition is induced.

* * * * *

UNITED STATES PATENT AND TRADEMARK OFFICE
CERTIFICATE OF CORRECTION

| | |
|---|---|
| PATENT NO. | : 10,568,948 B2 |
| APPLICATION NO. | : 15/154543 |
| DATED | : February 25, 2020 |
| INVENTOR(S) | : Levey et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 389 days.

Signed and Sealed this
Twenty-fourth Day of November, 2020

Andrei Iancu
*Director of the United States Patent and Trademark Office*